United States Patent
Sircar et al.

(10) Patent No.: US 7,312,221 B2
(45) Date of Patent: Dec. 25, 2007

(54) INHIBITORS OF MACROPHAGE MIGRATION INHIBITORY FACTOR AND METHODS FOR IDENTIFYING THE SAME

(75) Inventors: Jagadish Sircar, San Diego, CA (US); Sunil Kumar K C, San Diego, CA (US); Wenbin Ying, San Diego, CA (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

(21) Appl. No.: 11/593,190

(22) Filed: Nov. 3, 2006

(65) Prior Publication Data
US 2007/0054922 A1 Mar. 8, 2007

Related U.S. Application Data

(62) Division of application No. 10/778,884, filed on Feb. 13, 2004, now Pat. No. 7,173,036.

(60) Provisional application No. 60/448,427, filed on Feb. 14, 2003.

(51) Int. Cl.
*A61K 31/496* (2006.01)
(52) U.S. Cl. .................................. 514/253.07; 544/363
(58) Field of Classification Search ..................... None
See application file for complete search history.

(56) References Cited

U.S. PATENT DOCUMENTS

| | | | |
|---|---|---|---|
| 4,284,768 A | 8/1981 | Santilli | |
| 4,299,814 A | 11/1981 | Brandt et al. | |
| 4,683,202 A | 7/1987 | Mullis | |
| 4,708,937 A | 11/1987 | Remold | |
| 5,246,869 A | 9/1993 | Potter et al. | |
| 5,328,990 A | 7/1994 | Wistow | |
| 5,350,687 A | 9/1994 | Odink et al. | |
| 5,352,660 A | 10/1994 | Pawson | |
| 5,411,882 A | 5/1995 | Odink et al. | |
| 5,530,101 A | 6/1996 | Queen et al. | |
| 5,597,708 A | 1/1997 | Holder et al. | |
| 5,650,295 A | 7/1997 | Li et al. | |
| 5,656,596 A | 8/1997 | Monard et al. | |
| 5,656,737 A | 8/1997 | Wistow | |
| 5,683,887 A | 11/1997 | Bucala et al. | |
| 5,700,447 A | 12/1997 | Bucala et al. | |
| 5,702,920 A | 12/1997 | Odink et al. | |
| 5,733,524 A | 3/1998 | Bucala et al. | |
| 5,733,546 A | 3/1998 | Bucala et al. | |
| 5,733,933 A | 3/1998 | Bucala et al. | |
| 5,780,615 A | 7/1998 | Bucala et al. | |
| 5,801,200 A | 9/1998 | Bucala et al. | |
| 5,821,336 A | 10/1998 | Odink et al. | |
| 5,869,534 A | 2/1999 | Bucala et al. | |
| 5,883,224 A | 3/1999 | Kirkpatrick et al. | |
| 5,919,815 A | 7/1999 | Bradley et al. | |
| 5,986,060 A | 11/1999 | Li et al. | |
| 6,028,081 A | 2/2000 | Sada et al. | |
| 6,030,615 A | 2/2000 | Bucala et al. | |
| 6,080,407 A | 6/2000 | Bucala et al. | |

(Continued)

FOREIGN PATENT DOCUMENTS

AU 592753 A 11/1985

(Continued)

OTHER PUBLICATIONS

Abe et al. 1993. "Induction of Vascular Endothelial Tubular Morphogenesis by Human Glioma Cells." *J. Clin. Invest.* 92:54.

(Continued)

*Primary Examiner*—Emily Bernhardt
(74) *Attorney, Agent, or Firm*—Knobbe, Martens, Olson & Bear, LLP

(57) ABSTRACT

Inhibitors of MIF are provided which have utility in the treatment of a variety of disorders, including the treatment of pathological conditions associated with MIF activity. The inhibitors of MIF have the following structures:

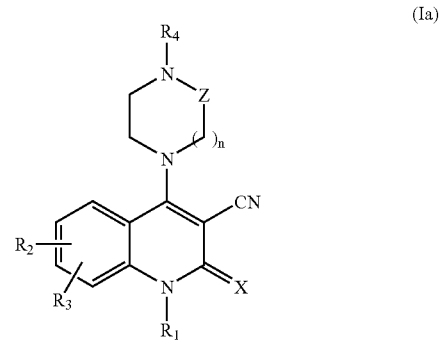

(Ia)

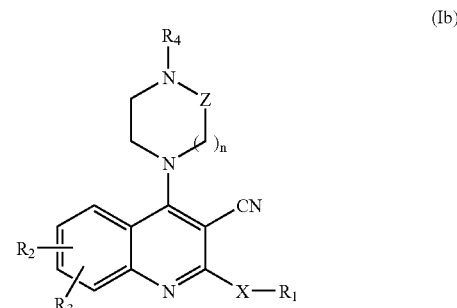

(Ib)

including stereoisomers, prodrugs and pharmaceutically acceptable salts thereof, wherein n, $R_1$, $R_2$, $R_3$, $R_4$, X, and Z are as defined herein. Compositions containing an inhibitor of MIF in combination with a pharmaceutically acceptable carrier are also provided, as well as methods for use of the same.

17 Claims, 3 Drawing Sheets

U.S. PATENT DOCUMENTS

| | | | |
|---|---|---|---|
| 6,214,343 | B1 | 4/2001 | Kink et al. |
| 6,238,874 | B1 | 5/2001 | Jarnagin et al. |
| 6,413,939 | B1 | 7/2002 | Bucala et al. |
| 6,420,188 | B1 | 7/2002 | Bucala et al. |
| 7,084,141 | B2 | 8/2006 | Gaeta et al. |
| 7,105,519 | B2 | 9/2006 | Gaeta et al. |
| 2003/0195194 | A1 | 10/2003 | Gaeta et al. |
| 2004/0019921 | A1 | 1/2004 | Fingerte-Rowson et al. |
| 2004/0204586 | A1 | 10/2004 | Sircar et al. |
| 2005/0124604 | A1 | 6/2005 | Sircar et al. |
| 2006/0094727 | A1 | 5/2006 | Gaeta et al. |

FOREIGN PATENT DOCUMENTS

| | | | |
|---|---|---|---|
| EP | 0020090 | A1 | 12/1980 |
| EP | 0162812 | A1 | 5/1985 |
| EP | 0154454 | A1 | 9/1985 |
| EP | 0263072 | A2 | 4/1988 |
| EP | 0412050 | B1 | 2/1991 |
| EP | 0900789 | A1 | 10/1999 |
| EP | 1424336 | A1 | 6/2004 |
| EP | 1500402 | A1 | 1/2005 |
| WO | WO 80/02287 | A | 10/1980 |
| WO | WO 90/11301 | A | 10/1990 |
| WO | WO 94/20083 | A | 9/1994 |
| WO | WO 94/26307 | A | 11/1994 |
| WO | WO 96/09389 | A2 | 3/1996 |
| WO | WO 96/15242 | A2 | 5/1996 |
| WO | WO 97/29635 | A1 | 8/1997 |
| WO | WO 97/39326 | A2 | 10/1997 |
| WO | WO 97/40159 | A | 10/1997 |
| WO | WO 98/17314 | A1 | 4/1998 |
| WO | WO 99/29894 | A1 | 6/1999 |
| WO | WO 01/32606 | A | 5/2001 |
| WO | WO 02/07720 | A1 | 1/2002 |
| WO | WO 02/067862 | A2 | 9/2002 |
| WO | WO 02/079517 | A1 | 10/2002 |
| WO | WO 03/065979 | A2 | 8/2003 |
| WO | WO 03/104178 | A1 | 12/2003 |
| WO | WO 03/104203 | A1 | 12/2003 |
| WO | WO 2004/060881 | A | 7/2004 |
| WO | WO 2004/076679 | A | 9/2004 |

OTHER PUBLICATIONS

Abe et al. 2001. "Regulation of the CTL Response by Macrophage Migration Inhibitory Factor." *J. Immunol.* 166:747-753.

Archer et al. 1983 "Electrophilic Aromatic Substitution. Part 34. Partial Rate Factors for Detritiation of Dithieno [1,2-b:4,3-b'] benzene, Dithieno[1,2-b:3,4-b'] benzene, and Dithieno [2,1-b:3,4-b']benzene." *J. Chem. Soc. Perkin Trans. II.* 813-819.

Aroca et al. 1991 . "Specificity of dopachrome tautomerase and inhibition by carboxylated indoles." *Biochem. J.* 277:393-397.

Ausubel et al. 1987. *Current Protocols in Molecular Biology.* Ausubel et al.(ed.) John Wiley & Sons, Inc.

Bacher et al. 1998. "MIF Expression in the Rat Brain: Implications for Neuronal Function." *Mol. Med.* 4(4):217-230.

Baugh et al. 2002. "Macrophage migration inhibitory factor," *Crit. Care Med.* 30(1 Suppl.):S27-S35.

Bernhagen et al. 1993. "MIF is a pituitary-derived cytokine that potentiates lethal endotoxaemia." *Nature* 365:756-759.

Bernhagen et al. 1994. "Macrophage migration inhibitory factor is a neuroendocrine mediator of endotoxaemia." *Trends Microbiol.* 2:198-201.

Bernhagen et al. 1995. "The emerging role of MIF in septic shock and infection." *Biotherapy* 8(2):123-7.

Bernhagen et al. 1998. "Regulation of the immune response by macrophage migration inhibitory factor: biological and structural features." *J. Mol. Med.* 76(3-4):151-161.

Bianchi et al. 1999. "Conformational Changes in Human Hepatitis C Virus NS3 Protease upon Binding of Product-Based Inhibitors." *Biochem.* 38(42): 13844-13852.

Blocki et al. 1992. "Rat liver protein linking chemical and immunological detoxification systems" *Nature* 360:269-270.

Blocki et al. 1993. "MIF proteins are theta-class glutathione S-transferase homologs." *Protein Science* 2:2095-2102.

Bone et al. 1987. "A controlled clinical trial of high-dose methylprednisolone in the treatment of severe sepsis and septic shock." N. Eng. J. Med. 317: 653-658.

Bucala. 1994. "MIF, a Previously Unrecognized Pituitary Hormone and Macrophage Cytokine, Is a Pivotal Mediator in Endotoxic Shock." *Circulatory Shock* 44(1):35-39.

Bucala. 1996. "MIF rediscovered; cytokine, pituitary hormone, and glucocorticoid-induced regulator of the immune response." *FASEB J.* 10(14):1607-1613.

Bucala. 1998. "Neuroimmunomodulation by Macrophage Migration Inhibitory Factor (MIF)." *Ann. N.Y. Acad. Sci.* 840:74-82.

Bucala. 2000. "A most interesting factor." *Nature* 408:146-147.

Calandra et al. 1996. "Macrophage Migration Inhibitory Factor: A Counter-Regulator of Glucocorticoid Action and Critical Mediator of Septic Shock." *J. Inflammation* 47:39-51.

Calandra et al. 1994. "The Macrophage is an Important and Previously Unrecognized Source of Macrophage Migration Inhibitory Factor." *J. Exp. Med.* 179:1895-1902.

Calandra et al. 1995. "MIF as a glucocorticoid-induced modulator of cytokine production." *Nature* 377:68-71.

Calandra et al. 1997. "Macrophage Migration Inhibitory Factor (MIF): A Glucocorticoid Counter-Regulator within the Immune System." *Crit. Rev. Immunol.* 17(1):77-88.

Calandra et al. 2000. "Protection from septic shock by neutralization of macrophage migration inhibitory factor." *Nature Medicine* 6(2):164-170.

Carceller et al. 1993. "Synthesis and Structure-Activity Relationships of 1-Acyl-4-((2-methyl-3-pyridyl)cyanomethyl)piperaines as PAF Antagonists." *J. Med. Chem.* 36:2984-2997.

Carvajal et al. 1982. "Cell-Mediated Immunity Against Connective Tissue in Experimental Pulmonary Fibrosis." *Lung* 160(3): 131-40.

Chesney et al. 1999. "An Essential Role for Macrophage Migration Inhibitory Factor (MIF) in Angiogenesis and the Growth of a Murine Lymphoma." *Mol. Med.* 5: 181-191.

Coppola, et al.; Transformation in the 2-Quinolone Series, Journal of Heterocyclic Chemistry, Aug. 1981, vol. 18, No. 5, pp. 917-920.

Dandliker et al. 1970. "Fluorescence polarization in immunochemistry." *Immunochem.* 7:799-828.

Donnelly et al. 1997. "Macrophage migration inhibitory factor: a regulator of glucocorticoid activity with a critical role in inflammatory disease." *Mol. Med. Today* 3(11):502-507.

Donnelly et al. 1997. "Regulatory role for macrophage migration inhibitory factor in acute respiratory distress syndrome." *Nat. Med.* 3(3):320-323.

Durand et al. 1998. "Interaction of methyl green with an oligonucleotide in intramolecular duplex and triplex conformations." *Eur. Biophys. J.* 27(2):147-151.

Ferro et al. 1991. "Antigen induced inhibition of autoimmune response to rat male accessory glands: role of thymocytes on the efferent phase of the suppression." *Autoimmunity* 9(3):193-200.

Florkiewicz et al. 1991a. "Basic Fibroblast Growth Factor Gene Expression." Ann. N.Y. Acad. Sci. 638:109-126.

Florkiewicz et al. 1991b. "Multiple forms of bFGF: differential nuclear and cell surface localization." *Growth Factors* 4:265-275.

Galat et al. 1993. "Purification of macrophage migration inhibitory factor (MIF) from bovine brain cytosol." *Fed. Eur. Biochem. Soc.* 319:233-236.

Garner et al. 2003. "Macrophage Migration Inhibitory Factor (MIF) is a cardiac-derived myocardial depressant factor." *Amer. Jour. Physiol. Heart Circ Physiol.* 285(6):H2500-9. (E-pub Aug. 28, 2003).

Goto et al. 1993. "Synergistic Effects of Vascular Endothelial Growth Factor and Basic Fibroblast Growth Factor on the Proliferation and Cord Formation of Bovine Capillary Endothelial Cells Within Collagen Gels." *Lab. Invest.* 69:508-517.

Harrington et al. 1973. "Macrophage migration from an agarose droplet: development of a micromethod for assay of delayed hypersensitivity." *J. Immunol.* 110:752-759, 1973.

Haugland. 1999. *Handbook of Fluorescent Probes and Research Chemicals- Seventh Ed.*, Molecular Probes, Eugene, OR. Not included, substantially cumulative with Ninth Ed. below.

Haugland. 2002. *Handbook of Fluorescent Probes and Research Chemicals- Ninth Ed.*, Molecular Probes, Eugene, OR.

Hermanowski-Vosatka et al. 1999. "Enzymatically Inactive Macrophage Migration Inhibitory Factor Monoyte Chemotaxis and Random Migration." *Biochemistry* 38:12841-12849.

Huang et al. 2001. "Macrophage Migration Inhibitory Factor Is an Important Mediator in the Pathogenesis of Gastric Inflammation in Rats." *Gastroenterology* 121:619-630.

Huse et al. 1989. "Generation of a Large Combinatorial Library of the Immunoglobin Repertoire in Phage Lambda." *Science* 246:1275-1281.

Johnson et al. 1999. "A kinetic and stereochemical investigation of the role of lysine-32 in the phenylpyruvate tautomerase activity catalyzed by macrophage migration inhibitory factor." *Biochemistry* 38:16024-16033.

Kleifeld et al. 2000. "Spectroscopic Studies of Inhibited Alcohol Dehydrogenase from *Thermoanaerobacter brockii*: Proposed Structure for the Catalytic Intermediate State." *Biochem* 39(26):7702-7711.

Larsen et al. 1974. "Synthesis and Properties of 3-(3-Carboxyphenyl)pyruvic Acid and 3-(3-Carboxyl-4-hydroxyphenyl)pyruvic Acid." *Acta Chem. Scand. B.* 28:92-96.

Leech et al. 1998. "Involvement of macrophage migration inhibitory factor in the evolution of rat adjuvant arthritis." *Arthritis and Rheumatism* 41(5):910-917.

Lukes et al. 1954. "Synthese von α-methylfural." *Collection Czechoslov. Chem. Commun.* 19:609-610.

Lundblad et al. 1996. "Fluorescence Polarization Analysis of Protein-DNA and Protein-Protein Interactions." *Molec. Endocrinol.* 10:607-612.

Meanwell et al. 1993. "Inhibitors of Blood Platelet cAMP Phosphodiesterase. 4. Structural Variation of the Side-Chain Terminus of Water-Soluble 1,3-Dihydro-2*H*-imidazo[4,5-*b*]quinolin-2-one Derivatives." *J. Med. Chem.* 36:3251-3264.

Metz et al. 1997. "Role of Macrophage Migration Inhibitory Factor in Regulation of the Immune Response." *Advances in Immunology* 66:197-223.

Mitchell et al. 1999. "Sustained Mitogen-activated Protein Kinase (MAPK) and Cytoplasmic Phospholipase A2 Activation by Macrophage Migration Inhibitory Factor (MIF)." *J. Biol. Chem.* 274(25):18100-18106.

Monoclonal Anti-human MIF Antibody. Product Information. R&D Systems. Minneapolis, MN, (2001).

Morand et al., Expert Opin. Ther. Patents, vol. 13, pp. 1189-1212 (2003).

Natanson et al. 1994. "Selected Treatment Strategies for Septic Shock Based on Proposed Mechanisms of Pathogenesis." *Annals of Internal Medicine* 120(9):771-783.

Nishihira. 1998. "Novel pathophysiological aspects of macrophage migration inhibitory factor (Review)." *Int. J. Mol. Med* 2(1):17-28.

Ogawa et al. 2000. "An antibody for macrophage migration inhibitory factor suppresses tumour growth and inhibits tumour-associated angiogenesis." *Cytokine* 12(4):309-314.

Okamura et al. 1992. "Model system for tumor angiogenesis—involvement of transforming growth factor-α in tube formation of human microvascular endothelial cells induced by esophageal cancer cells." *Biochem. Biophys. Res. Comm.* 186:1471-1479.

Onodera et al. 2000. "Macrophage Migration Inhibitory Factor Up-regulates Expression of Matrix Metalloproteinases in Synovial Fibroblasts or Rheumatoid Arthritis." *J. Biol. Chem.* 275:444-450.

Pan et al. 2004. "Macrophage migration inhibitory factor deficiency impairs atherosclerosis in low-density lipoprotein receptor-deficient mice." *Circulation -Jour. Amer. Heart Assoc.* 3149-3153.

Perrin. 1926. "Polarisation de la lumiere de fluorescence vie moyenne des molecules dans l'etat excite." *J. Phys. Rad.* 1:390-401 (English Abstract included).

Petrovsky et al. 2002. "Macrophage Migration Inhibitory Factor: A Critical Neurohumoral Mediator." *Front Horm Res. Basel, Karger* 29:83-90.

Product Information. 1990 Cortone Acetate Tablets. Physicians' Desk Reference. Edward R. Barnhart, Publisher. USA, pp. 1341-1342.

Rice, et al. 1998. "Macrophage migration inhibitory factor (MIF): a critical upstream regulator of acute and chronic inflammatory responses." *Ann. Rep. Medicinal Chem.* 243-252.

Riedemann et al., J. Clin. Invest., vol. 112, pp. 460-467 (2003).

Rosengren et al. 1996. "The Immunoregulatory Mediator Macrophage Migration Inhibitory Factor (MIF) Catalyzes a Tautomerization Reaction." *Mol. Med.* 2:143-149.

Rupreht, et al., Murine monoclonal antibodies directed against human recombinant Macrophage Migration Inhibitory Factor, *Pflügers Arch.—Eur. J. Physiol.* (2000) 440 [Suppl]:R78-R80.

Sakaue et al. 1999. "Regulation of Macrophage Migration Inhibitory Factor (MIF) Expression by Glucose and Insulin in Adipocytes In Vitro." *Mol. Med.* 5:361-371.

Sarver et al. 1999. "Thermodynamic and circular dichroism studies differentiate inhibitor interactions with the stromelysin $S_1$-$S_3$ and $S'_1$-$S'_3$ subsites." *Biochim Biophys Acta* 1434(2):304-316.

Scatchard et al. 1949. "The Attractions of Proteins for Small Molecules and Ions." Ann. N.Y. Acad. Sci. 51:660-672.

Scopes. 1987. *Protein Purification: Principles and Practice, Second Edition*. Springer-Verlag. N.Y.

Sprung et al. 1984. "The effects of high-dose corticosteroids in patients with septic shock." *N. Engl. J. Med.* 311: 1137-1143.

Swope et al. 1998. "Direct link between cytokine activity and catalytic site for macrophage migration inhibitory factor." *EMBO J.* 17(13):3534-3541.

Swope et al. 1999. "Macrophage Migration Inhibitory Factor: Cytokine, Hormone, or Enzyme?" *Rev. Physiol. Biochem. Pharmacol.* 139:1-32.

Takahashi et al. 1998. "Involvement of Macrophage Migration Inhibitory Factor (MIF) in the Mechanism of Tumor Cell Growth." *Mol. Med.* 4:707-714.

Takahashi et al. 1999 "Antisense Macrophage Migration Inhibitory Factor (MIF) Prevents Anti-IgM Mediated Growth Arrest and Apoptosis of a Mature B Cell Line by Regulating Cell Cycle Progression." *Microbiol. Immunol.* 43(1)61-67.

Urry. 1969. "Optical Rotation and Biomolecular Conformation." *Spectroscopic Approaches to Biomoleculer Conformation*. American Medical Association Press, Chicago, IL, pp. 33-121.

Waeber et al. 1999. "A Role for the Endocrine and Pro-inflammatory Mediator MIF in the Control of Insulin Secretion During Stress." *Diabetes Met. Res. Rev.* 15(1):47-54.

Ward et al. 1989. "Binding activities of a repertoire of single immunoglobulin variable domains secreted from *Escherichia coli*." *Nature* 341:544-546.

Warren et al. 1995. "Regulation by Vascular Endothelial Growth Factor of Human Colon Cancer Tumorgenesis in a Mouse Model of Experimental Liver Metastasis." *J. Clin. Invest.* 95:1789-1797.

Weir. 1986. *Handbook of Experimental Immunology, Cellular Immunology*. Backwell Scientific, Boston, MA.

Weiser et al. 1985. "Generation of human hybridomas producing migration inhibitory factor (MIF) and of murine hybridomas secreting monoclonal antibodies to human MIF." *Cellular Immunol.* 90:167-178.

Weiser et al. 1989. "Molecular cloning of a cDNA encoding a human macrophage migration inhibitory factor." *Proc. Natl. Acad. Sci. USA*. 86:7522-7526.

Weiser et al. 1991. "Human recombinant migration inhibitory factor activates human macrophages to kill *Leishmania donovani*." J. Immunol. 147:2006-2011.

Winder et al. 1993. "The mouse *brown* (b) locus protein has dopachrome tautomerase activity and is located in lysosomes in transfected fibroblasts." *J. Cell Sci.* 106:153-166.

Winter et al. 1993. "Humanized antibodies." *Immunol. Today* 14(6):243-246.

Wistow et al. 1993. "A macrophage migration inhibitory factor is expressed in the differentiating cells of the eye lens." *Proc. Natl. Acad. Sci. USA* 90:1272-1275.

Wu et al. 1994. "Resonance Energy Transfer: Methods and Applications." *Analytical Biochem.* 218:1-13.

Yang et al. 1998. "Reversal of Established Rat Crescentic Glomerulonephritis by Blockade of Macrophage Migration Inhibitory Factor (MIF): Potential Role of MIF in Regulating Glucocorticoid Production." *Mol. Med* 4(6):413-424.

Zuckerman et al. 1989. "Differential regulation of lipopolysaccharide-induced interleukin 1 and tumour necrosis factor synthesis: effects on endogenous and exogenous glucocorticoids and the role of the pituitary-adrenal axis." *Eur. J. Immunol.* 19:310-305.

INHIBITORS OF MACROPHAGE MIGRATION INHIBITORY FACTOR AND METHODS FOR IDENTIFYING THE SAME

RELATED APPLICATIONS

This application is a division of U.S. application Ser. No. 10/778,884 filed Feb. 13, 2004, now U.S. Pat. No. 7,173,036, which claims the benefit of U.S. Provisional Application No. 60/448,427, filed Feb. 14, 2003.

FIELD OF THE INVENTION

This invention relates generally to inhibitors of macrophage migration inhibitory factor (MIF), methods for identifying MIF inhibitors, and to methods of treating MIF-related disorders by administration of such inhibitors.

BACKGROUND OF THE INVENTION

The lymphokine, macrophage migration inhibitory factor (MIF), has been identified as a mediator of the function of macrophages in host defense and its expression correlates with delayed hypersensitivity, immunoregulation, inflammation, and cellular immunity. See Metz and Bucala, *Adv. Immunol.* 66:197-223, 1997. Macrophage migration inhibitory factors (MIFs), which are between 12-13 kilodaltons (kDa) in size, have been identified in several mammalian and avian species; see, for example, Galat et al., *Fed. Eur. Biochem. Soc.* 319:233-236, 1993; Wistow et al., *Proc. Natl. Acad. Sci. USA* 90:1272-1275, 1993; Weiser et al., *Proc. Natl. Acad. Sci. USA* 86:7522-7526, 1989; Bernhagen et al., *Nature* 365:756-759, 1993; Blocki et al., *Protein Science* 2:2095-2102, 1993; and Blocki et al., *Nature* 360:269-270, 1992. MIF inhibitors are also disclosed in copending U.S. patent application Ser. No. 10/156,650 filed May 24, 2002, the contents of which is hereby incorporated by reference in its entirety.

Although MIF was first characterized as being able to block macrophage migration, MIF also appears to effect macrophage adherence; induce macrophage to express interleukin-1-beta, interleukin-6, and tumor necrosis factor alpha; up-regulate HLA-DR (Human Leucocyte Antigen, d-Related, encoded by the d locus on chromosome 6 and found on lymphoid cells); increase nitric oxide synthase and nitric oxide concentrations; and activate macrophage to kill *Leishmania donovani* tumor cells and inhibit *Mycoplasma avium* growth, by a mechanism different from that effected by interferon-gamma. In addition to its potential role as an immunoevasive molecule, MIF can act as an immunoadjuvant when given with bovine serum albumin or HIV gp120 in incomplete Freunds or liposomes, eliciting antigen induced proliferation comparable to that of complete Freunds. Also, MIF has been described as a glucocorticoid counter regulator and angiogenic factor. As one of the few proteins that is induced and not inhibited by glucocorticoids, it serves to attenuate the immunosuppressive effects of glucocorticoids. As such, it is viewed as a powerful element that regulates the immunosuppressive effects of glucocorticoids. Hence, when its activities/gene expression are over-induced by the administration of excess exogenous glucocorticoids (for example when clinical indicated to suppress inflammation, immunity and the like), there is significant toxicity because MIF itself exacerbates the inflammatory/immune response. See Buccala et al., *Ann. Rep. Med. Chem.* 33:243-252, 1998.

While MIF is also thought to act on cells through a specific receptor that in turn activates an intracellular cascade that includes erk phosphorylation and MAP kinase and upregulation of matrix metalloproteases, c-jun (the protooncogene jun), c-fos (the protooncogene fos) and IL-1 mRNA (see Onodera et al., *J. Biol. Chem.* 275:444-450, 2000), it also possesses endogenous enzyme activity as exemplified by its ability to tautomerize the appropriate substrates (e.g., dopachrome). Further, it remains unclear whether this enzymatic activity mediates the biological response to MIF and the activities of this protein in vitro and in vivo. While site directed mutagenesis of MIF has generated mutants which possess full intrinsic activity, yet fail to possess enzyme activity (Hermanowski-Vosatka et al., *Biochemistry* 38:12841-12849, 1999), Swope et al. have described a direct link between cytokine activity and the catalytic site for MIF (Swope et al., *EMBO J.* 17(13):3534-3541, 1998). Accordingly, it is unclear that strategies to identify inhibitors of MIF activity through inhibition of dopachrome tautomerase alone yields inhibitors of MIF activity of clinical value. The ability to evaluate the inhibition of MIF to its cell surface receptor is also limited since no high affinity receptor is currently known.

The interest in developing MIF inhibitors derives from the observation that MIF is known for its cytokine activity concentrating macrophages at sites of infection, and cell-mediated immunity. Moreover, MIF is known as a mediator of macrophage adherence, phagocytosis, and tumoricidal activity. See Weiser et al., *J. Immunol.* 147:2006-2011, 1991. Hence, the inhibition of MIF results in the indirect inhibition of cytokines, growth factors, chemokines and lymphokines that the macrophage may otherwise bring to a site of inflammation. Human MIF cDNA has been isolated from a T-cell line, and encodes a protein having a molecular mass of about 12.4 kDa with 115 amino acid residues that form a homotrimer as the active form (Weiser et al., *Proc. Natl. Acad. Sci. USA* 86.7522-7526, 1989). While MIF was originally observed in activated T-cells, it has now been reported in a variety of tissues including the liver, lung, eye lens, ovary, brain, heart, spleen, kidney, muscle, and others. See Takahashi et al., *Microbiol. Immunol.* 43(1):61-67, 1999. Another characteristic of MIF is its lack of a traditional leader sequence (i.e., a leaderless protein) to direct classical secretion through the Endoplasmic Reticulum/Golgi (ER/Golgi) pathway.

A MIF inhibitor (and a method to identify MIF inhibitors) that act by neutralizing the cytokine activity of MIF presents significant advantages over other types of inhibitors. For example, the link between tautomerase activity alone and the inflammatory response is controversial. Furthermore, inhibitors that act intracellularly are often toxic by virtue of their action on related targets or the activities of the target inside cells. Small molecule inhibitors of the ligand receptor complex are difficult to identify let alone optimize and develop. The ideal inhibitor of a cytokine like MIF is one that alters MIF itself so that when released from the cell it is effectively neutralized. A small molecule with this activity is superior to antibodies because of the fundamental difference between proteins and chemicals as drugs. MIF inhibitors are disclosed in copending U.S. patent application Ser. No. 10/156,650 filed May 24, 2002.

SUMMARY OF THE INVENTION

As MIF has been identified in a variety of tissues and has been associated with numerous pathological events, there exists a need in the art to identify inhibitors of MIF. There is also a need for pharmaceutical compositions containing such inhibitors, as well as methods relating to the use thereof to treat, for example, immune related disorders or other MIF induced pathological events, such as tumor associated angiogenesis. The preferred embodiments may fulfill these needs, and provide other advantages as well.

In preferred embodiments, inhibitors of MIF are provided that have the following general structures (Ia) and (Ib):

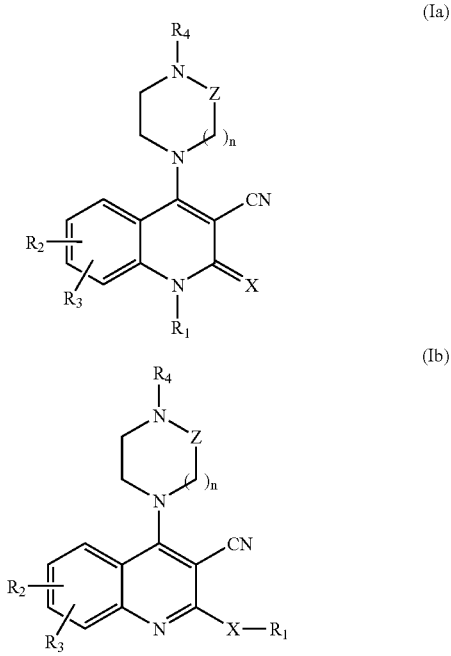

including stereoisomers, prodrugs, and pharmaceutically acceptable salts thereof, wherein n, $R_1$, $R_2$, $R_3$, $R_4$, X, and Z are as defined below.

The MIF inhibitors of preferred embodiments have utility over a wide range of therapeutic applications, and may be employed to treat a variety of disorders, illnesses, or pathological conditions including, but not limited to, a variety of immune related responses, tumor growth (e.g., prostate cancer, and the like), glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, otitis media, Crohn's disease, acute respiratory distress syndrome, delayed-type hypersensitivity, and others. See, e.g., Metz and Bucala (supra); Swope and Lolis, *Rev. Physiol. Biochem. Pharmacol* 139: 1-32, 1999; Waeber et al., *Diabetes M. Res. Rev.* 15(1):47-54, 1999; Nishihira, *Int. J. Mol. Med.* 2(1):17-28, 1998; Bucala, *Ann. N.Y. Acad. Sci.* 840:74-82, 1998; Bernhagen et al., *J. Mol. Med.* 76(3-4):151-161, 1998; Donnelly and Bucala, *Mol. Med. Today* 3(11):502-507, 1997; Bucala et al., *FASEB J.* 10(14):1607-1613, 1996. Such methods include administering an effective amount of one or more inhibitors of MIF as provided by the preferred embodiments, preferably in the form of a pharmaceutical composition, to an animal in need thereof. Accordingly, in another embodiment, pharmaceutical compositions are provided containing one or more inhibitors of MIF of preferred embodiments in combination with a pharmaceutically acceptable carrier and/or diluent.

One strategy of a preferred embodiment characterizes molecules that interact with MIF so as to induce a conformational change in MIF and as such a loss of immunoreactivity to a monoclonal antibody. This change, when identified by screening, identifies small molecule inhibitors of MIF. This particular aspect may be extended to any bioactive polypeptide where loss of immunoreactivity may act as a surrogate for activity (e.g., cytokine activity, enzymatic activity, co-factor activity, or the like).

In a first embodiment, a compound is provided having a structure:

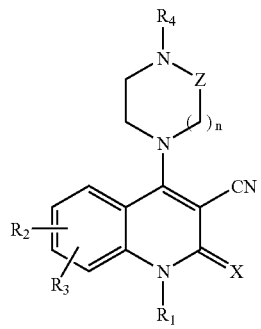

or a stereoisomer, a prodrug, or a pharmaceutically acceptable salt thereof, wherein X is oxygen or sulfur; Z is —$CH_2$— or —C(=O)—; n is 0, 1, or 2, with the proviso that when n is 0, Z is —C(=O); $R_1$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; $R_2$ and $R_3$ are independently selected from the group consisting of halogen, —$R_5$, —$OR_5$, —$SR_5$, and —$NR_5R_6$; $R_4$ is selected from the group consisting of:

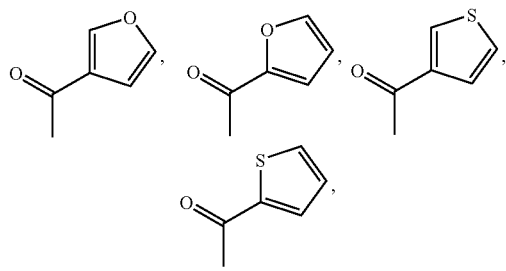

—$CH_2R_7$, —C(=O)$NR_5R_6$, —C(=O)$OR_7$, —C(=O)$R_7$, and $R_8$; $R_5$ and $R_6$ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or R$_5$ and R$_6$ taken together with a nitrogen atom to which they are attached form a heterocycle or substituted heterocycle; R$_7$ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and R$_8$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl.

In an aspect of the first embodiment, a composition is provided comprising the compound of the first embodiment in combination with a pharmaceutically acceptable carrier or diluent.

In an aspect of the first embodiment, a method is provided for treating inflammation in a warm-blooded animal, comprising administering to the animal an effective amount of the compound of the first embodiment.

In an aspect of the first embodiment, a method is provided for treating septic shock in a warm-blooded animal, comprising administering to the animal an effective amount of the compound of the first embodiment.

In an aspect of the first embodiment, a method is provided for treating arthritis in a warm-blooded animal, comprising administering to the animal an effective amount of the compound of the first embodiment.

In an aspect of the first embodiment, a method is provided for treating cancer in a warm-blooded animal, comprising administering to the animal an effective amount of the compound of the first embodiment.

In an aspect of the first embodiment, a method is provided for treating acute respiratory distress syndrome in a warm-blooded animal, comprising administering to the animal an effective amount of the compound of the first embodiment.

In an aspect of the first embodiment, a method is provided for treating an inflammatory disease in a warm-blooded animal, comprising administering to the animal an effective amount of the compound of the first embodiment. The inflammatory disease can include rheumatoid arthritis, osteoarthritis, inflammatory bowel disease, or asthma.

In an aspect of the first embodiment, a method is provided for treating an autoimmune disorder in a warm-blooded animal, comprising administering to the animal an effective amount of the compound of the first embodiment. The autoimmune disorder can include diabetes, asthma, or multiple sclerosis.

In an aspect of the first embodiment, a method is provided for suppressing an immune response in a warm-blooded animal, comprising administering to the animal an effective amount of the compound of the first embodiment.

In an aspect of the first embodiment, a method is provided for decreasing angiogenesis in a warm-blooded animal, comprising administering to the animal an effective amount of the compound of the first embodiment.

In an aspect of the first embodiment, a method is provided for treating a disease associated with excess glucocorticoid levels in a warm-blooded animal, comprising administering to the animal an effective amount of the compound of the first embodiment. The disease can include Cushing's disease.

In an aspect of the first embodiment, a pharmaceutical composition is provided for treating a disease or disorder wherein MIF is pathogenic, the pharmaceutical composition comprising a MIF inhibiting compound according to the first embodiment and a drug for treating the disease or disorder, wherein the drug has no measurable MIF inhibiting activity.

In an aspect of the first embodiment, a pharmaceutical composition is provided for treating a disease or disorder wherein MIF is pathogenic, the pharmaceutical composition comprising a MIF inhibiting compound according to the first embodiment and a drug selected from the group consisting of nonsteroidal anti-inflammatory drugs, anti-infective drugs, beta stimulants, steroids, antihistamines, anticancer drugs, asthma drugs, sepsis drugs, arthritis drugs, and immunosuppresive drugs.

In a second embodiment, a compound is provided having a structure:

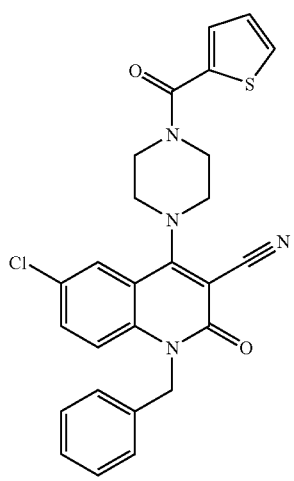

or a stereoisomer, a prodrug, or a pharmaceutically acceptable salt thereof.

In a third embodiment, a method is provided for reducing MIF activity in a patient in need thereof, comprising administering to the patient an effective amount of a compound having the structure:

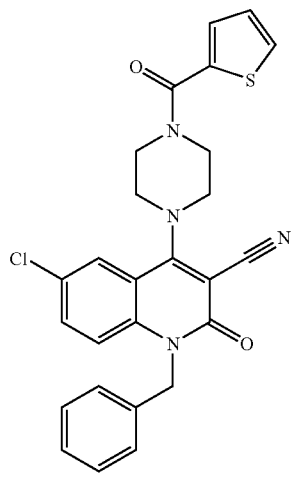

or a stereoisomer, a prodrug, or a pharmaceutically acceptable salt thereof.

In a fourth embodiment, a compound is provided having a structure:

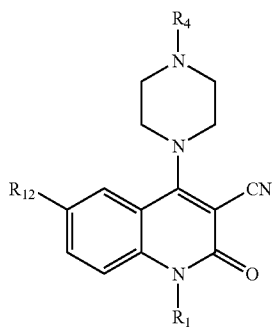

or a stereoisomer, a prodrug, or a pharmaceutically acceptable salt thereof, wherein $R_1$ is selected from the group consisting of:

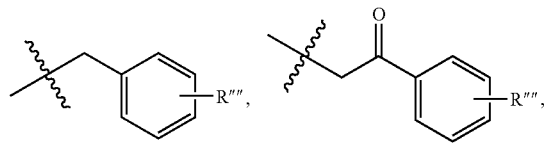

—$CH_2CH_2N(R''')_2$, —$CH_2CH_2NC(O)N(R''')_2$, and —$CH_2COOR'''$; $R_{12}$ is selected from the group consisting of hydrogen, chlorine, fluorine, and methyl; $R_4$ is selected from the group consisting of:

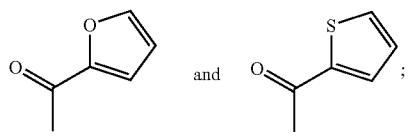

$R'''$ is independently selected from the group consisting of hydrogen, fluorine, chlorine, linear $C_1$-$C_5$ alkyl, and branched $C_1$-$C_5$ alkyl; and $R''''$ is selected from the group consisting of hydrogen, halogen, alkyl, cyano, nitro, —$COOR'''$, —$N(R''')_2$, —$OR'''$, —$NHCOR'''$, and —$OCF_3$.

In a fifth embodiment, a compound is provided having a structure:

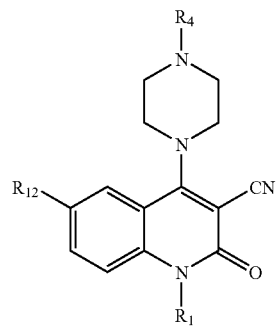

or a stereoisomer, a prodrug, or a pharmaceutically acceptable salt thereof, wherein $R_1$ is selected from the group consisting of:

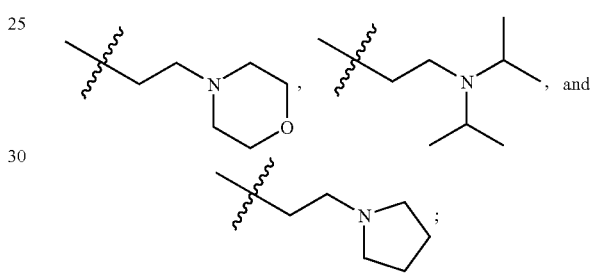

$R_4$ is selected from the group consisting of:

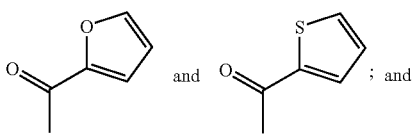

$R_{12}$ is selected from the group consisting of hydrogen, chlorine, fluorine, and methyl.

In a sixth embodiment, a method is provided for reducing MIF activity in a patient in need thereof, comprising administering to the patient an effective amount of a compound having the structure:

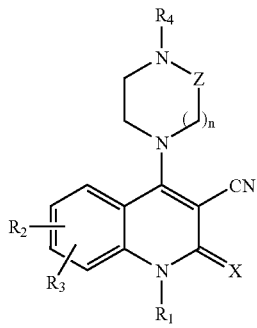

or a stereoisomer, a prodrug, or a pharmaceutically acceptable salt thereof, wherein X is oxygen or sulfur; Z is —CH₂— or —C(=O)—; n is 0, 1, or 2, with the proviso that when n is 0, Z is —C(=O)—; R₁ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyleaakyl, heterocyclearyl, substituted heterocyclearyl, and dialkyl; R₂ and R₃ are independently selected from the group consisting of halogen, —R₅, —OR₅, —SR₅, and —NR₅R₆; R₄ is selected from the group consisting of:

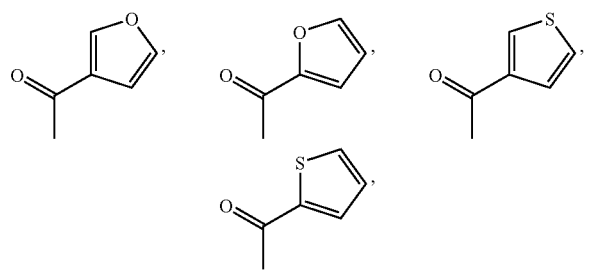

—CH₂R₇, —C(=O)NR₅R₆, —C(=O)OR₇, —C(=O)R₇, and R₈; R₅ and R₆ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or R₅ and R₆ taken together with a nitrogen atom to which they are attached form a heterocycle or substituted heterocycle; R₇ is selected from the group consisting of alkyl, substituted alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, heterocycle, substituted heterocycle, heterocyclealkyl, substituted heterocyclealkyl, heterocyclearyl, substituted heterocyclearyl, and dialkyl.

In a seventh embodiment, a compound is provided having a structure:

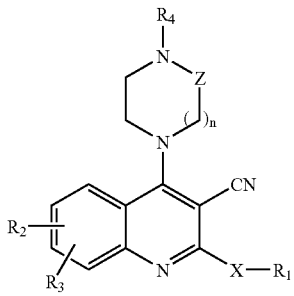

or a stereoisomer, a prodrug, or a pharmaceutically acceptable salt thereof, wherein X is oxygen or sulfur; Z is —CH₂— or —C(=O)—; n is 0, 1, or 2, with the proviso that when n is 0, Z is —C(=O)—; R₁ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; R₂ and R₃ are independently selected from the group consisting of halogen, —R₅, —OR₅, —SR₅, and —NR₅R₆; R₄ is selected from the group consisting of:

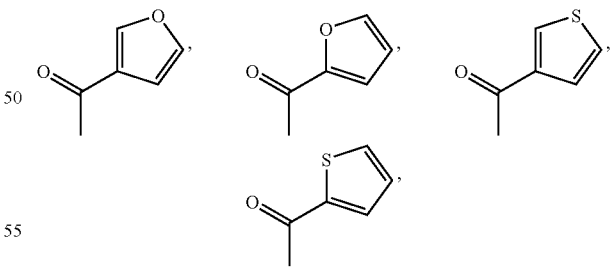

—CH₂R₇, —C(=O)NR₅R₆, —C(=O)OR₇, —C(=O)R₇, and R₈; R₅ and R₆ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; $R_7$ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and $R_8$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl.

In an aspect of the seventh embodiment, a composition is provided comprising the compound of the seventh embodiment in combination with a pharmaceutically acceptable carrier or diluent.

In an aspect of the seventh embodiment, a method is provided for treating inflammation in a warm-blooded animal, comprising administering to the animal an effective amount of the compound of the seventh embodiment.

In an aspect of the seventh embodiment, a method is provided for treating septic shock in a warm-blooded animal, comprising administering to the animal an effective amount of the compound of the seventh embodiment.

In an aspect of the seventh embodiment, a method is provided for treating arthritis in a warm-blooded animal, comprising administering to the animal an effective amount of the compound of the seventh embodiment.

In an aspect of the seventh embodiment, a method is provided for treating cancer in a warm-blooded animal, comprising administering to the animal an effective amount of the compound of the seventh embodiment.

In an aspect of the seventh embodiment, a method is provided for treating acute respiratory distress syndrome in a warm-blooded animal, comprising administering to the animal an effective amount of the compound of the seventh embodiment.

In an aspect of the seventh embodiment, a method is provided for treating an inflammatory disease in a warm-blooded animal, comprising administering to the animal an effective amount of the compound of the seventh embodiment. The inflammatory disease can include rheumatoid arthritis, osteoarthritis, inflammatory bowel disease, or asthma.

In an aspect of the seventh embodiment, a method is provided for treating an autoimmune disorder in a warm-blooded animal, comprising administering to the animal an effective amount of the compound of the seventh embodiment. The autoimmune disorder can include diabetes, asthma, or multiple sclerosis.

In an aspect of the seventh embodiment, a method is provided for suppressing an immune response in a warm-blooded animal, comprising administering to the animal an effective amount of the compound of the seventh embodiment.

In an aspect of the seventh embodiment, a method is provided for decreasing angiogenesis in a warm-blooded animal, comprising administering to the animal an effective amount of the compound of the seventh embodiment.

In an aspect of the seventh embodiment, a method is provided for treating a disease associated with excess glucocorticoid levels in a warm-blooded animal, comprising administering to the animal an effective amount of the compound of the seventh embodiment. The disease can include Cushing's disease.

In an aspect of the seventh embodiment, a pharmaceutical composition is provided for treating a disease or disorder wherein MIF is pathogenic, the pharmaceutical composition comprising a MIF inhibiting compound according to the seventh embodiment and a drug for treating the disease or disorder, wherein the drug has no measurable MIF inhibiting activity.

In an aspect of the seventh embodiment, a pharmaceutical composition is provided for treating a disease or disorder wherein MIF is pathogenic, the pharmaceutical composition comprising a MIF inhibiting compound according to the seventh embodiment and a drug selected from the group consisting of nonsteroidal anti-inflammatory drugs, anti-infective drugs, beta stimulants, steroids, antihistamines, anticancer drugs, asthma drugs, sepsis drugs, arthritis drugs, and immunosuppresive drugs.

In an eighth embodiment, a method is provided for reducing MIF activity in a patient in need thereof, comprising administering to the patient an effective amount of a compound having the structure:

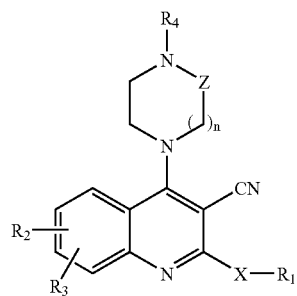

or a stereoisomer, a prodrug, or a pharmaceutically acceptable salt thereof, wherein X is oxygen or sulfur; Z is —CH$_2$— or —C(=O)—; n is 0, 1, or 2, with the proviso that when n is 0, Z is —C(=O)—; $R_1$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; R$_2$ and R$_3$ are independently selected from the group consisting of halogen, —R$_5$, —OR$_5$, —SR$_5$, and —NR$_5$R$_6$; R$_4$ is selected from the group consisting of —CH$_2$R$_7$, —C(=O)NR$_5$R$_6$, —C(=O)OR$_7$, —C(=O)R$_7$, and R$_8$; R$_5$ and R$_6$ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or R$_5$ and R$_6$ taken together with a nitrogen atom to which they are attached form a heterocycle or substituted heterocycle; R$_7$ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and R$_8$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N (CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl.

In a ninth embodiment, a process is provided for preparing a compound of Formula IVa comprising the steps of reacting a compound of Formula I:

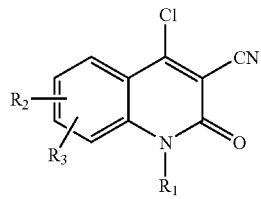

(Formula I)

with a compound of Formula II:

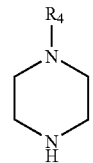

(Formula II)

thereby obtaining a compound of Formula III:

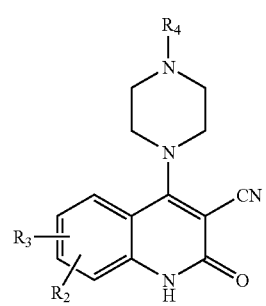

(Formula III)

and reacting the compound of Formula III with a compound of formula X—R$_1$, thereby obtaining a compound of Formula IVa:

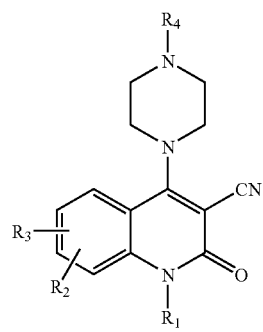

(Formula IVa)

wherein the compound of Formula IVa is suitable for use as a MIF inhibitor, and wherein: R$_2$ and R$_3$ are independently selected from the group consisting of halogen, —R$_5$, —OR$_5$, —SR$_5$, and —NR$_5$R$_6$; R$_4$ is selected from the group consisting of —CH$_2$R$_7$, —C(=O)OR$_7$, —C(=O)R$_7$, R$_8$, and —C(=O)NR$_5$R$_6$; R$_5$ and R$_6$ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N (CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or R$_5$ and R$_6$ taken together with a nitrogen atom to which they are attached form a heterocycle or substituted heterocycle; R₇ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and R₈ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; X is selected from the group consisting of Cl, Br, and I; and R₁ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl.

In a tenth embodiment, a process is provided for preparing a compound of Formula IVb comprising the steps of reacting a compound of Formula I:

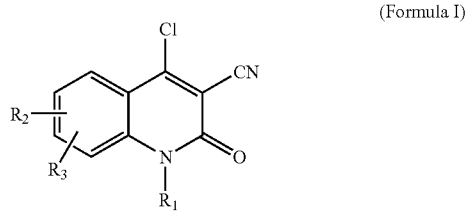

(Formula I)

with a compound of Formula II:

(Formula II)

thereby obtaining a compound of Formula III:

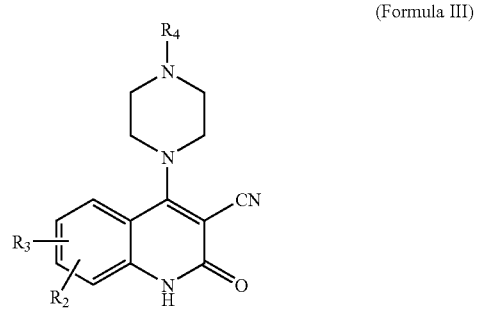

(Formula III)

and reacting the compound of Formula III with a compound comprising X—R₁, wherein X is selected from the group consisting of Cl, Br, and I, and wherein R₁ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH₂)ₓ—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl, wherein x is 2 to 4, thereby obtaining a compound of Formula IVb:

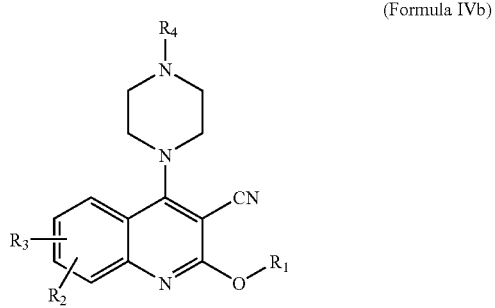

(Formula IVb)

wherein the compound of Formula IVb is suitable for use as a MIF inhibitor.

In an eleventh embodiment, a process is provided for preparing a compound of Formula IVa comprising the steps of reacting a compound of Formula I:

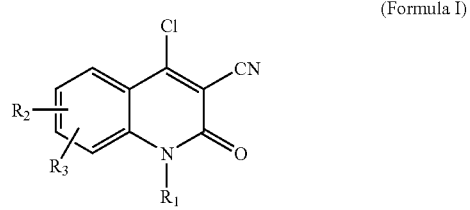

(Formula I)

with piperazine, thereby obtaining a compound of Formula IIIa:

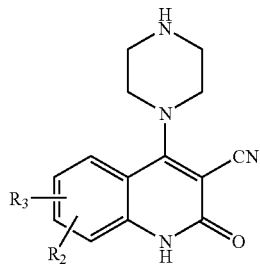

(Formula IIIa)

and thereafter reacting the compound of Formula IIIa with a compound of the formula $R_4$—C(O)—X, thereby obtaining a compound of Formula IVa:

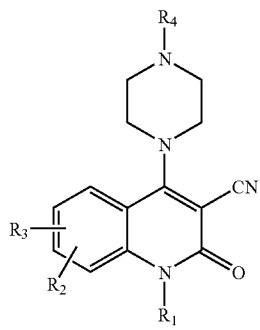

(Formula IVa)

wherein the compound of Formula IVa is suitable for use as a MIF inhibitor, and wherein $R_2$ and $R_3$ are independently selected from the group consisting of halogen, —$R_5$, —$OR_5$, —$SR_5$, and —$NR_5R_6$; $R_4$ is selected from the group consisting of —$CH_2R_7$, —C(=O)$NR_5R_6$, $R_8$, —C(=O)$OR_7$, —C(=O)$R_7$; $R_5$ and $R_6$ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or $R_5$ and $R_6$ taken together with a nitrogen atom to which they are attached form a heterocycle or substituted heterocycle; $R_7$ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and $R_8$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; X is selected from the group consisting of Cl, Br, and I; and $R_1$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl.

In a twelfth embodiment, a process is provided for preparing a compound of Formula IVb comprising the steps of reacting a compound of Formula I:

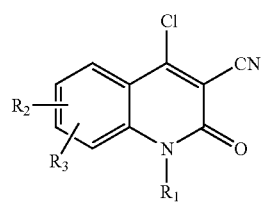

(Formula I)

with piperazine, thereby obtaining a compound of Formula IIIa:

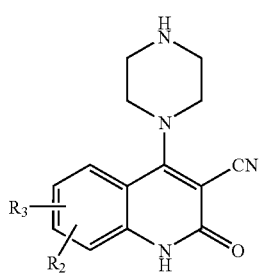

(Formula IIIa)

and thereafter reacting the compound of Formula IIIa with a compound of the formula R$_4$—C(O)—X, thereby obtaining a compound of Formula IVb:

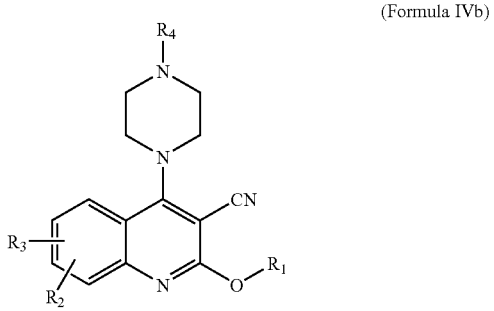

(Formula IVb)

wherein the compound of Formula IVb is suitable for use as a MIF inhibitor, and wherein R$_2$ and R$_3$ are independently selected from the group consisting of halogen, —R$_5$, —OR$_5$, —SR$_5$, and —NR$_5$R$_6$; R$_4$ is selected from the group consisting of —CH$_2$R$_7$, —C(=O)NR$_5$R$_6$, R$_8$, —C(=O)OR$_7$, —C(=O)R$_7$; R$_5$ and R$_6$ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or R$_5$ and R$_6$ taken together with a nitrogen atom to which they are attached form a heterocycle or substituted heterocycle; R$_7$ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N (CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and R$_8$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; X is selected from the group consisting of Cl, Br, and I; and R$_1$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl.

In a thirteenth embodiment, a process is provided for preparing an intermediate compound of Formula I comprising the steps of reacting a compound of Formula Iaa:

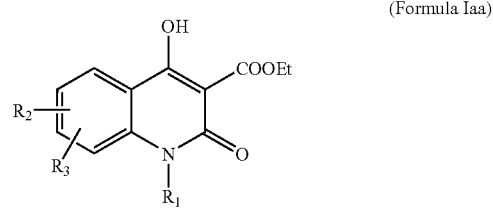

(Formula Iaa)

with cyclohexanamine, thereby obtaining a compound of Formula IIIaa:

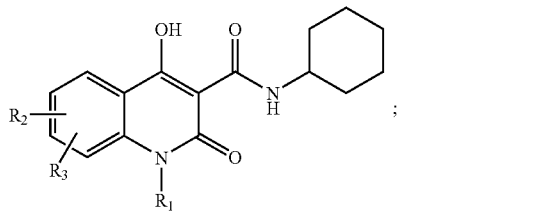

(Formula IIIaa)

reacting the compound of Formula IIIaa with POCl$_3$, thereby obtaining a compound of Formula Ia:

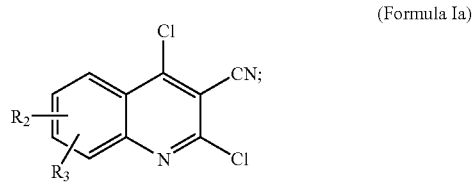

(Formula Ia)

and thereafter reacting the compound of Formula Ia with ammonium acetate in acetic acid, thereby obtaining an intermediate compound of Formula I:

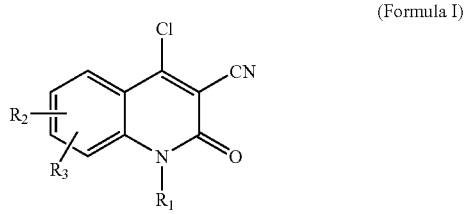

(Formula I)

wherein the compound of Formula I is suitable for use in preparing a MIF inhibitor, and wherein $R_2$ and $R_3$ are independently selected from the group consisting of halogen, —$R_5$, —$OR_5$, —$SR_5$, and —$NR_5R_6$; $R_4$ is selected from the group consisting of —$CH_2R_7$, —$C(=O)NR_5R_6$, —$C(=O)OR_7$, —$C(=O)R_7$, and $R_8$; $R_5$ and $R_6$ are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; or $R_5$ and $R_6$ taken together with a nitrogen atom to which they are attached form a heterocycle or substituted heterocycle; $R_7$ is selected from the group consisting of alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; and $R_8$ is selected from the group consisting of hydrogen, alkyl, substituted alkyl, aryl, substituted aryl, arylalkyl, substituted arylalkyl, heterocycle, substituted heterocycle, heterocyclealkyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, and dialkyl; X is selected from the group consisting of Cl, Br, and I; and $R_1$ is selected from the group consisting of hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, and R'R"N(CH$_2$)$_x$—, wherein x is 2 to 4, and wherein R' and R" are independently selected from the group consisting of hydrogen, alkyl, alkylaryl, substituted alkylaryl, aryl, substituted aryl, arylalkyl, substituted arylalkyl, acylalkyl, acylaryl, substituted acylaryl, heterocycle, substituted heterocycle, heterocyclealkyl, substituted heterocyclealkyl, heterocyclearyl, substituted heterocyclearyl, and dialkyl.

These and other embodiments and aspects thereof will be apparent upon reference to the following detailed description. To this end, various references are set forth herein which describe in more detail certain procedures, compounds and/or compositions, and are hereby incorporated by reference in their entirety.

DETAILED DESCRIPTION OF THE PREFERRED EMBODIMENT

Figure 1:
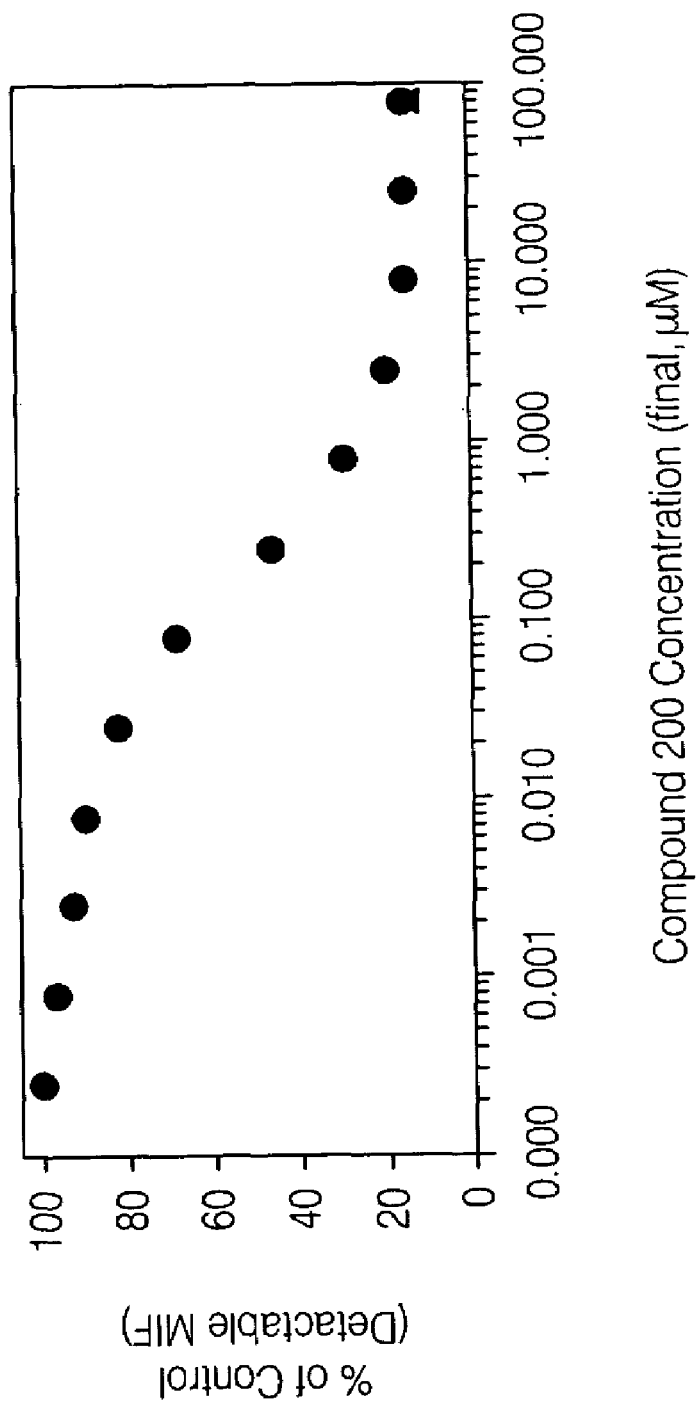
FIG. 1 provides THP-1 Cell Assay data for Compound 200.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

As an aid to understanding the preferred embodiments, certain definitions are provided herein.

The term "MIF activity," as used herein is a broad term and is used in its ordinary sense, including, without limitation, to refer to an activity or effect mediated at least in part by macrophage migration inhibitory factor. Accordingly, MIF activity includes, but is not limited to, inhibition of macrophage migration, tautomerase activity (e.g., using phenylpyruvate or dopachrome), endotoxin induced shock, inflammation, glucocorticoid counter regulation, induction of thymidine incorporation into 3T3 fibroblasts, induction of erk phosphorylation and MAP kinase activity.

The term "export," as used herein is a broad term and is used in its ordinary sense, including, without limitation, to refer to a metabolically active process, which may or may not be energy-dependent, of transporting a translated cellular product to the cell membrane or the extracellular space by a mechanism other than standard leader sequence directed secretion via a canonical leader sequence. Further, "export," unlike secretion that is leader sequence-dependent, is resistant to brefeldin A (i.e., the exported protein is not transported via the ER/Golgi; brefeldin A is expected to have no direct effect on trafficking of an exported protein) and other similar compounds. As used herein, "export" may also be referred to as "non-classical secretion."

The term "leaderless protein," as used herein is a broad term and is used in its ordinary sense, including, without limitation, to refer to a protein or polypeptide that lacks a canonical leader sequence, and is exported from inside a cell to the extracellular environment. Leaderless proteins in the extracellular environment refer to proteins located in the extracellular space, or associated with the outer surface of the cell membrane. Within the context of preferred embodiments, leaderless proteins include naturally occurring proteins, such as macrophage migration inhibitory factor and fragments thereof as well as proteins that are engineered to lack a leader sequence and are exported, or proteins that are engineered to include a fusion of a leaderless protein, or fraction thereof, with another protein.

The term "inhibitor," as used herein is a broad term and is used in its ordinary sense, including, without limitation, to refer to a molecule (e.g., natural or synthetic compound) that can alter the conformation of MIF and/or compete with a monoclonal antibody to MIF and decrease at least one activity of MIF or its export from a cell as compared to activity or export in the absence of the inhibitor. In other words, an "inhibitor" alters conformation and/or activity and/or export if there is a statistically significant change in the amount of MIF measured, MIF activity or in MIF protein detected extracellularly and/or intracellularly in an assay performed with an inhibitor, compared to the assay performed without the inhibitor.

The term "binding agent," as used herein is a broad term and is used in its ordinary sense, including, without limitation, to refer to any molecule that binds MIF, including inhibitors.

In general, MIF inhibitors inhibit the physiological function of MIF, and thus are useful in the treatment of diseases where MIF may be pathogenic.

In certain of the preferred embodiments, inhibitors of MIF are provided that have the following structures (Ia) and (Ib):

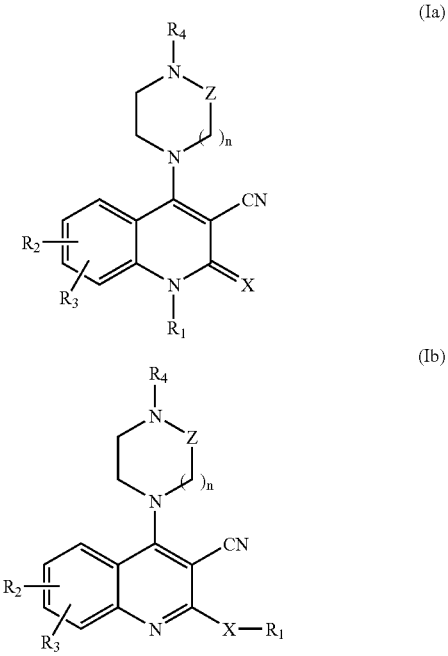

including stereoisomers, prodrugs or pharmaceutically acceptable salts thereof, wherein: X is oxygen or sulfur; Z is —$CH_2$— or —$C(=O)$—; n is 0, 1 or 2, with the proviso that when n is 0, Z is —$C(=O)$—; $R_1$ is hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or R'R"N$(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl; $R_2$ and $R_3$ are the same or different and are independently, halogen, —$R_5$, —$OR_5$, —$SR_5$ or —$NR_5R_6$; $R_4$ is $CH_2R_7$, —$C(=O)NR_5R_6$, —$C(=O)OR_7$, —$C(=O)R_7$ or $R_8$; $R_5$ and $R_6$ are the same or different and are independently hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or R'R"N$(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl; or $R_5$ and $R_6$ taken together with the nitrogen atom to which they are attached form a heterocycle or substituted heterocycle; $R_7$ is alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or R'R"N$(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl; and $R_8$ is hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or R'R"N$(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl.

In preferred embodiments, the groups $R_1$, $R_2$, $R_3$, and $R_4$ are attached to the aromatic ring (as in the case of $R_2$ and $R_3$) or the heteroatom (as in the case of $R_1$ and $R_4$) by a single bond. However, in certain embodiments, $R_1$, $R_2$, $R_3$, and $R_4$ can preferably be attached by a linking group. Preferred linking groups have a carbon backbone, or a carbon backbone wherein one or more of the backbone carbons are substituted with a heteroatom, such as nitrogen, oxygen, or sulfur. Particularly preferred linkages contain ether groups, carboxyl groups, carbonyl groups, sulfide groups, sulfonyl groups, carboxamide groups, sulfonamide groups, alkyl chains, aromatic rings, amine groups, and the like as part of the backbone. Preferred linking groups generally have a backbone of 1, 2, 3, 4, 5, 6, 7, 8, 9, or 10 or more atoms in length. Particularly preferred backbones are of 1, 2, 3, 4, or 5 atoms in length. In a preferred embodiment, methods are provided for reducing MIF activity in a patient in need thereof by administering to the patient an effective amount of a compound having the following structure (Ia) and/or (Ib):

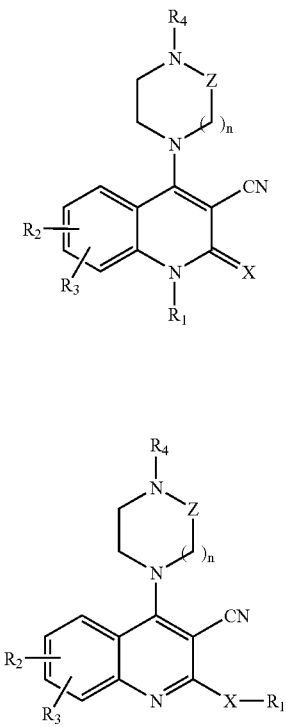

(Ia)

(Ib)

including stereoisomers, prodrugs or pharmaceutically acceptable salts thereof, wherein: X is oxygen or sulfur; Z is —$CH_2$— or —$C(=O)$—; n is 0, 1 or 2, with the proviso that when n is 0, Z is —$C(=O)$—; $R_1$ is hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or $R'R''N(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl; $R_2$ and $R_3$ are the same or different and are independently, halogen, —$R_5$, —$OR_5$, —$SR_5$ or —$NR_5R_6$; $R_4$ is —$CH_2R_7$, —$C(=O)NR_5R_6$, —$C(=O)OR_7$, —$C(=O)R_7$ or $R_8$; $R_5$ and $R_6$ are the same or different and are independently hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or $R'R''N(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl; or $R_5$ and $R_6$ taken together with the nitrogen atom to which they are attached form a heterocycle or substituted heterocycle; $R_7$ is alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or $R'R''N(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl; and $R_8$ is hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, dialkyl, or $R'R''N(CH_2)_x$—, wherein x is 2 to 4, and wherein R' and R" are independently selected from hydrogen, alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, or dialkyl. As used herein, the above terms have the following meanings. The term "alkyl," as used herein is a broad term and is used in its ordinary sense, including, without limitation, to refer to a straight chain or branched, noncyclic or cyclic, unsaturated or saturated aliphatic hydrocarbon containing from one, two, three, four, five, six, seven, eight, nine, or ten carbon atoms, while the term "lower alkyl" has the same meaning as alkyl but contains from one, two, three, four, five, or six carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$cyclopropyl, —$CH_2$cyclobutyl, —$CH_2$cyclopentyl, —$CH_2$cyclohexyl, and the like; while unsaturated cyclic alkyls include cyclopentenyl and cyclohexenyl, and the like. Cyclic alkyls are also referred to as "homocyclic rings" and include di- and poly-homocyclic rings such as decalin and adamantane. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

The term "alkylaryl," as used herein is a broad term and is used in its ordinary sense, including, without limitation, to refer to an aryl having at least one aryl hydrogen atom replaced with an alkyl moiety.

The term "aryl," as used herein is a broad term and is used in its ordinary sense, including, without limitation, to refer to an aromatic carbocyclic moiety such as phenyl or naphthyl.

The term "arylalkyl," as used herein is a broad term and is used in its ordinary sense, including, without limitation, to refer to an alkyl having at least one alkyl hydrogen atom replaced with an aryl moiety, such as benzyl, —CH₂(1 or 2-naphthyl), —CH₂)₂phenyl, —CH₂)₃phenyl, —CH(phenyl)₂, and the like.

The term "heteroaryl," as used herein is a broad term and is used in its ordinary sense, including, without limitation, to refer to an aromatic heterocycle ring of five, six, seven, eight, nine, or ten members and having at least one heteroatom selected from nitrogen, oxygen and sulfur, and containing at least one carbon atom, including both monocyclic and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term "heteroarylalkyl," as used herein is a broad term and is used in its ordinary sense, including, without limitation, to refer to an alkyl having at least one alkyl hydrogen atom replaced with a heteroaryl moiety, such as —CH₂pyridinyl, —CH₂pyrimidinyl, and the like.

The terms "heterocycle" and "heterocycle ring," as used herein, are broad terms and are used in their ordinary sense, including, without limitation, to refer to a five, six, or seven membered monocyclic, or a seven, eight, nine, ten, eleven, twelve, thirteen, or fourteen membered polycyclic, heterocycle ring which is either saturated, unsaturated or aromatic, and which contains one, two, three, or four heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocyclealkyl," as used herein is a broad term and is used in its ordinary sense, including, without limitation, to refer to an alkyl having at least one alkyl hydrogen atom replaced with a heterocycle, such as —CH₂morpholinyl, and the like.

The term "heterocyclearyl," as used herein is a broad term and is used in its ordinary sense, including, without limitation, to refer to an aryl having at least one aryl hydrogen atom replaced with a heterocycle.

The term "acyl," as used herein is a broad term and is used in its ordinary sense, including, without limitation, to refer to a group or radical of the form R—C(O)-L- wherein R is an organic group, including but not limited to alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, or substituted heterocyclearyl, each as herein defined, and L is R as defined above or a single bond. Examples of acyl groups include moieties of formula:

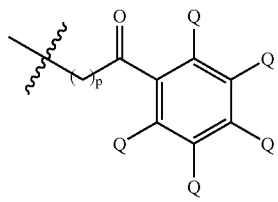

wherein p is an integer selected from 0, 1, 2, 3, 4, 5, 6, 7, 8, 9, 10, and higher integers, and wherein each Q is independently selected from hydrogen and R, wherein R is an organic group, including but not limited to alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, or substituted heterocyclearyl, each as herein defined. In a preferred embodiment, p is 1 and each Q is hydrogen.

The term "arylacyl," as used herein is a broad term and is used in its ordinary sense, including, without limitation, to refer to an acyl group wherein the R group includes an aryl group as herein defined.

The term "alkylacyl," as used herein is a broad term and is used in its ordinary sense, including, without limitation, to refer to an acyl group wherein the R group includes an alkyl as herein defined.

The term "acylalkyl," as used herein is a broad term and is used in its ordinary sense, including, without limitation, to refer to a group or radical of the form R—C(O)-Alk- wherein R is an organic group, including but not limited to alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, each as herein defined, and wherein Alk includes an alkyl moiety.

The term "acylaryl," as used herein is a broad term and is used in its ordinary sense, including, without limitation, to refer to a group or radical of the form R—C(O)-Ary- wherein R is an organic group, including but not limited to alkyl, alkylaryl, substituted alkylaryl, aryl, substituted aryl, arylalkyl, substituted arylalkyl, acylalkyl, substituted acylalkyl, acylaryl, substituted acylaryl, heterocycle, substituted heterocycle, heterocyclealkyl, substituted heterocyclealkyl, heterocyclearyl, substituted heterocyclearyl, each as herein defined, and wherein Ary includes an aryl moiety.

The term "substituted," as used herein is a broad term and is used in its ordinary sense, including, without limitation, to refer to any of the above groups (e.g., alkyl, aryl, arylalkyl, heteroaryl, heteroarylalkyl, heterocycle or heterocyclealkyl) wherein at least one hydrogen atom is replaced with a substituent. In the case of a keto substituent ("—C(═O)—") two hydrogen atoms are replaced. When substituted, "substituents," within the context of preferred embodiment, include halogen, hydroxy, cyano, nitro, sulfonamide, carboxamide, carboxyl, ether, carbonyl, amino, alkylamino, dialkylamino, alkyl, alkoxy, alkylthio, haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(═O)R$_b$, —OR$_a$, —NR$_a$C(═O)NR$_a$R$_b$, —NR$_a$C(═O)OR$_b$—

NR$_a$SO$_2$R$_b$, —OR$_a$, —C(=O)R$_a$—C(=O)OR$_a$, —SH, —SR$_a$, —C(=O)NR$_a$R$_b$, —OC(=O)NR$_a$R$_b$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

The term "halogen," as used herein is a broad term and is used in its ordinary sense, including, without limitation, to refer to fluoro, chloro, bromo and iodo.

The term "haloalkyl," as used herein is a broad term and is used in its ordinary sense, including, without limitation, to refer to an alkyl having at least one hydrogen atom replaced with halogen, such as trifluoromethyl and the like.

The term "alkoxy," as used herein is a broad term and is used in its ordinary sense, including, without limitation, to refer to an alkyl moiety attached through an oxygen bridge (e.g., —O-alkyl) such as methoxy, ethoxy, and the like.

The term "thioalkyl," as used herein is a broad term and is used in its ordinary sense, including, without limitation, to refer to an alkyl moiety attached through a sulfur bridge (e.g., —S-alkyl) such as methylthio, ethylthio, and the like.

The term "alkylsulfonyl," as used herein is a broad term and is used in its ordinary sense, including, without limitation, to refer to an alkyl moiety attached through a sulfonyl bridge (e.g., —SO$_2$-alkyl) such as methylsulfonyl, ethylsulfonyl, and the like.

The terms "alkylamino" and "dialkyl amino" as used herein, are broad terms and are used in their ordinary sense, including, without limitation, to refer to one alkyl moiety or two alkyl moieties, respectively, attached through a nitrogen bridge (for example, —N-alkyl) such as methylamino, ethylamino, dimethylamino, diethylamino, and the like.

The term "hydroxyalkyl," as used herein is a broad term and is used in its ordinary sense, including, without limitation, to refer to an alkyl substituted with at least one hydroxyl group.

The term "mono- or di(cycloalkyl)methyl," as used herein is a broad term and is used in its ordinary sense, including, without limitation, to refer to a methyl group substituted with one or two cycloalkyl groups, such as cyclopropylmethyl, dicyclopropylmethyl, and the like.

The term "alkylcarbonylalkyl," as used herein is a broad term and is used in its ordinary sense, including, without limitation, to refer to an alkyl substituted with a —C(=O)alkyl group.

The term "alkylcarbonyloxyalkyl," as used herein is a broad term and is used in its ordinary sense, including, without limitation, to refer to an alkyl substituted with a —C(=O)Oalkyl group or a —OC(=O)alkyl group.

The term "alkyloxyalkyl," as used herein is a broad term and is used in its ordinary sense, including, without limitation, to refer to an alkyl substituted with an —O-alkyl group.

The term "alkylthioalkyl," as used herein is a broad term and is used in its ordinary sense, including, without limitation, to refer to an alkyl substituted with a —S-alkyl group.

The term "mono- or di(alkyl)amino," as used herein is a broad term and is used in its ordinary sense, including, without limitation, to refer to an amino substituted with one alkyl or with two alkyls, respectively.

The term "mono- or di(alkyl)aminoalkyl," as used herein is a broad term and is used in its ordinary sense, including, without limitation, to refer to an alkyl substituted with a mono- or di(alkyl)amino.

The following numbering schemes are used in the context of preferred embodiments:

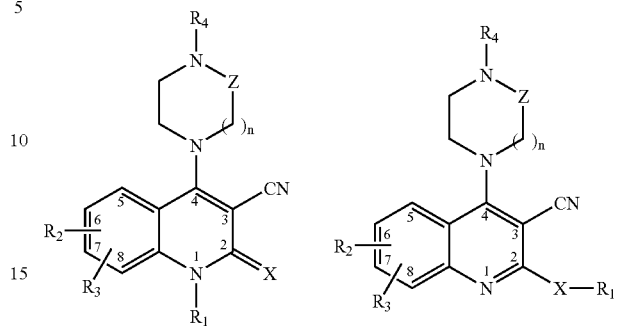

wherein R$_1$, R$_2$, R$_3$, R$_4$, X, Z, and n are as defined above.

Depending upon the Z moiety, representative compounds of preferred embodiments including the following structures (IIa) and (IIb) when Z is methylene (—CH$_2$—) and structures (IIIa) and (IIIb) when Z is carbonyl (—C(=O)—):

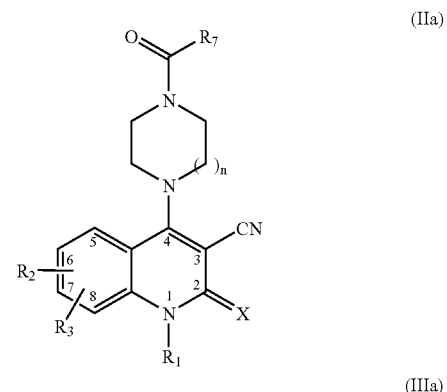

(IIa)

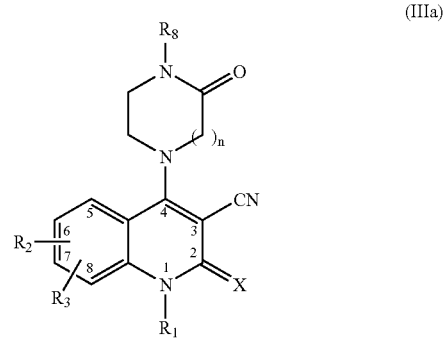

(IIIa)

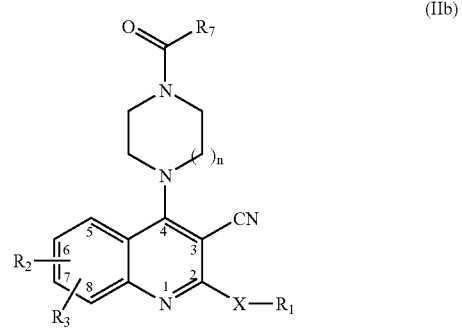

(IIb)

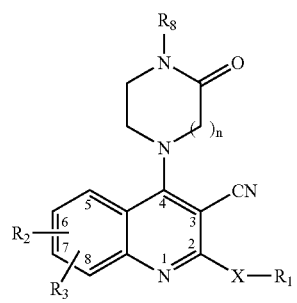
(IIIb)

wherein $R_1$, $R_2$, $R_3$, $R_7$, and $R_8$, X, and n are as defined above.

In further embodiments, n is 0, 1, or 2 as represented by structures (IVa), (IVb), (Va), (Vb), (VIa), and (VIb), respectively:

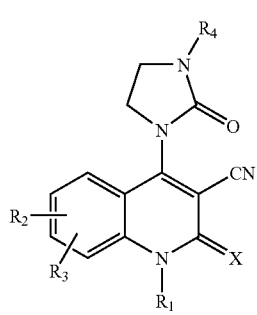
(IVa)

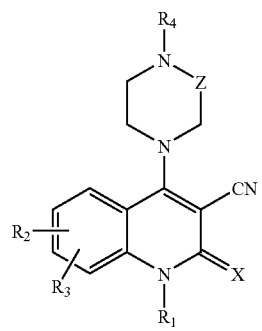
(Va)

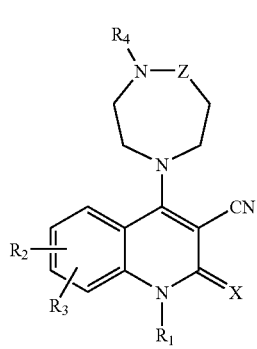
(VIa)

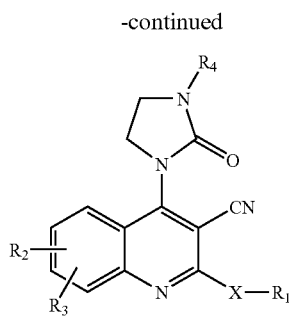
(IVb)

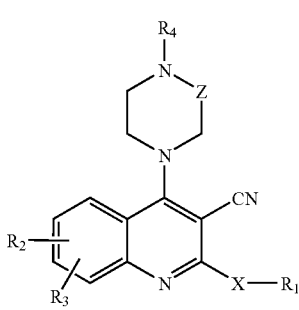
(Vb)

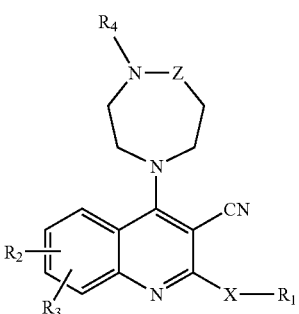
(VIb)

wherein $R_1$, $R_2$, $R_3$, $R_4$, X, and Z are as defined above.

In still further embodiments, compounds of preferred embodiments have the following structures (VIIa) and (VIb) when X is oxygen and structures (VIIIa) and (VIIb) when X is sulfur:

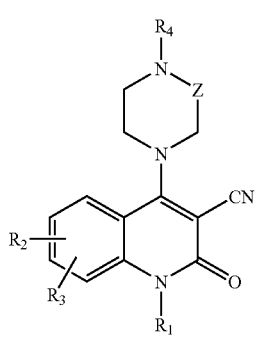
(VIIa)

-continued
(VIIIa)
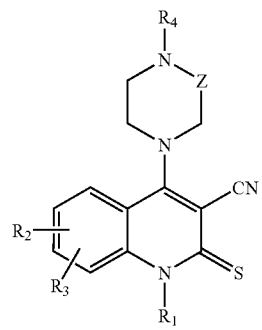
(VIIb)
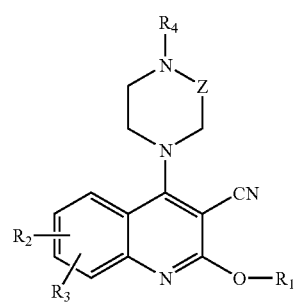
(VIIIb)
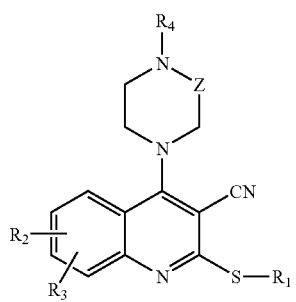
wherein $R_1$, $R_2$, $R_3$, $R_4$, and Z are as defined above.
In a particularly preferred embodiment, the MIF inhibitors are of the structure:
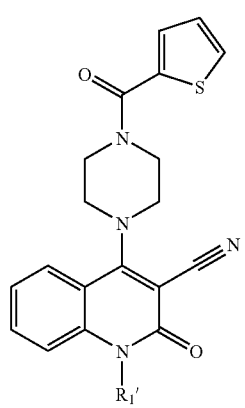
wherein $R_1'$ is selected from moieties of the following formulas:
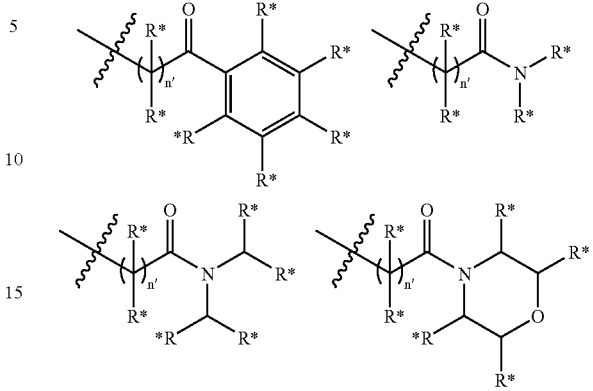
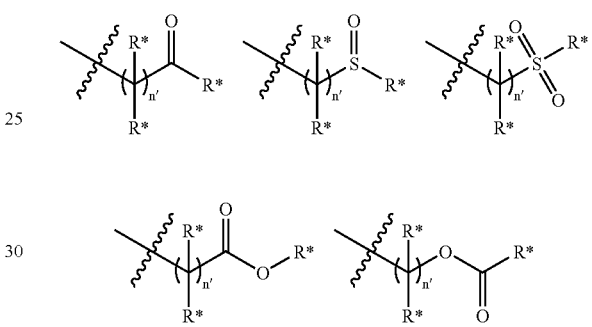
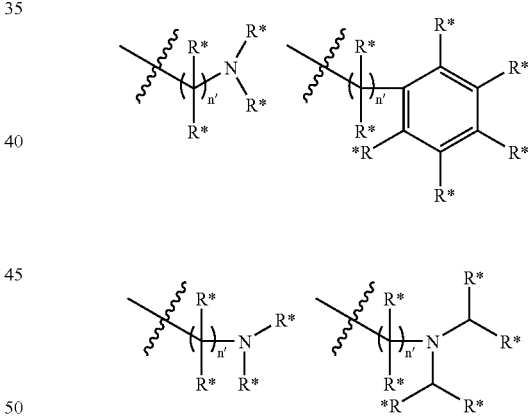
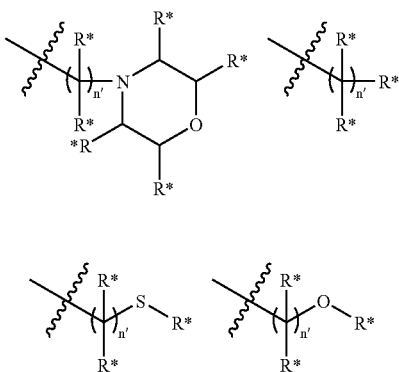

wherein each R* is independently selected from hydrogen, halogen, alkyl, hydroxy, alkyloxy, nitro, amine, nitrile, carboxylic acid, carboxylic acid ester, alkyl amine, $CF_3$, —$OCF_3$, sulfonamide, and carboxamide. In particularly preferred embodiments, each R* in $R_1'$ is hydrogen, as in the following structures:

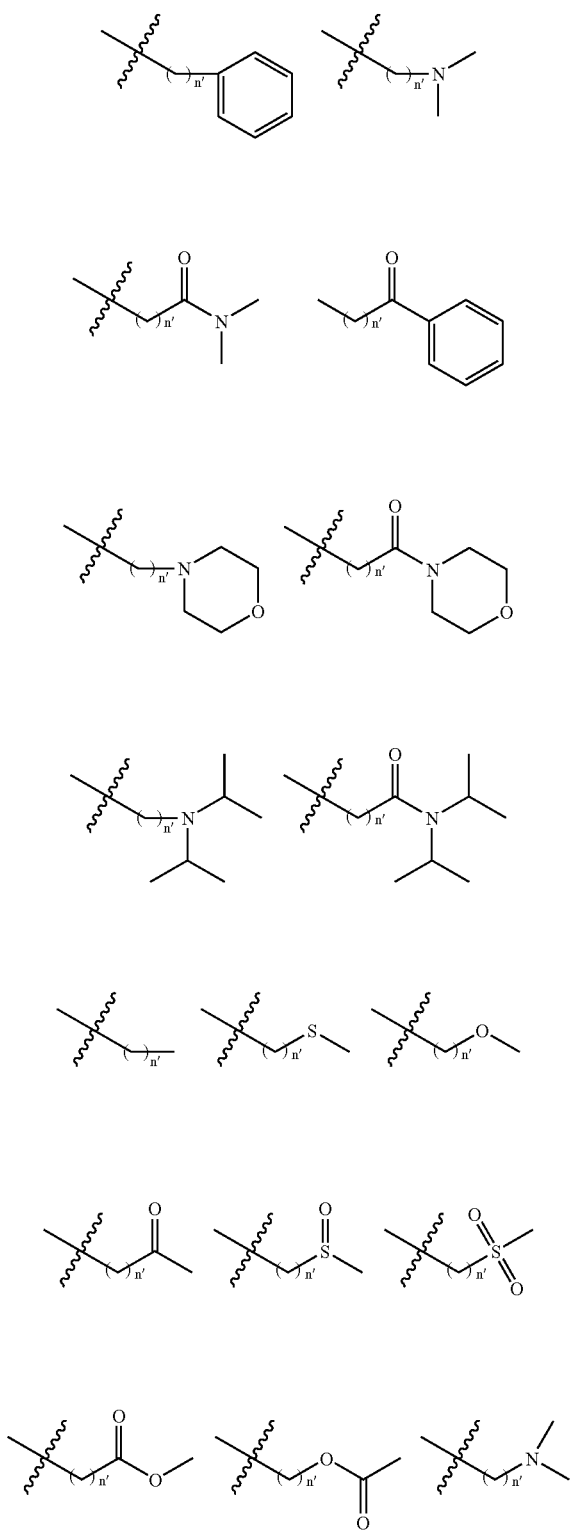

In particularly preferred embodiments, the MIF inhibitors are of the following structures:

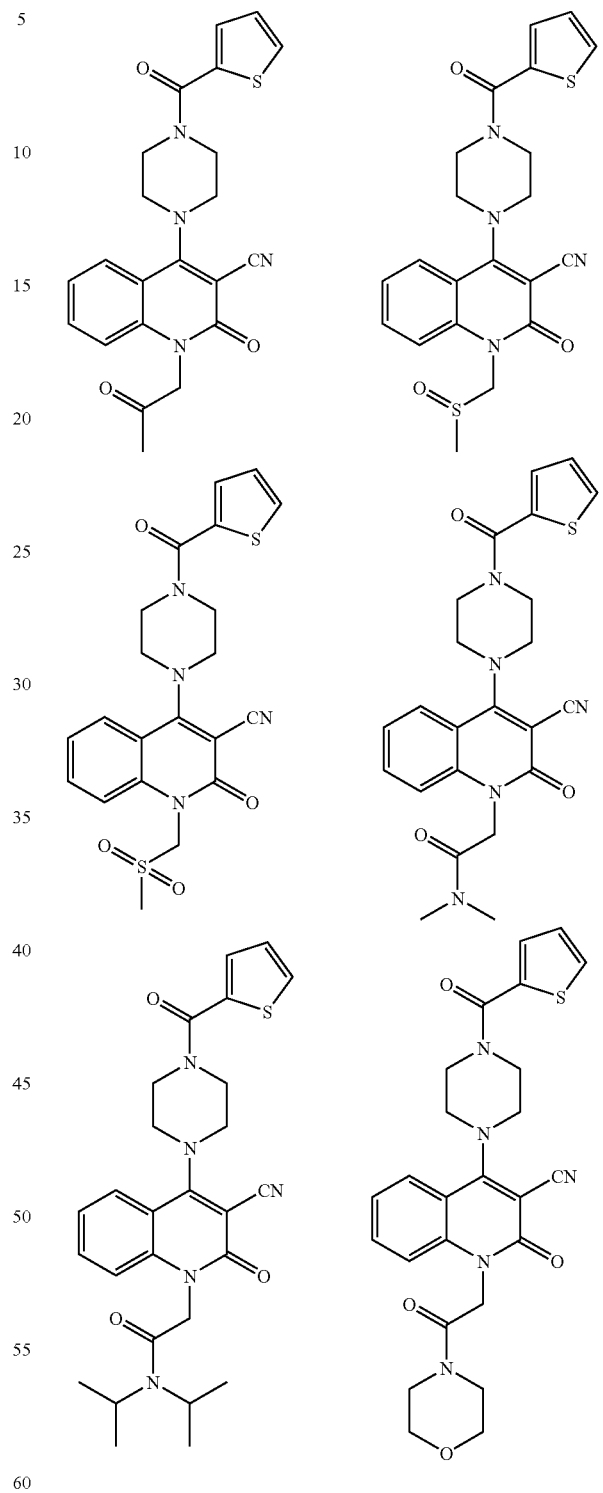

The compounds of preferred embodiments may generally be employed as the free acid or free base. Alternatively, the compounds of preferred embodiments may preferably be in the form of acid or base addition salts. Acid addition salts of the free base amino compounds of preferred embodiments may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts of the free acid may similarly be prepared by methods well known in the art, and may be formed from suitable bases, such as cations chosen from the alkali and alkaline earth metals (e.g., lithium, sodium, potassium, magnesium, barium, or calcium) as well as the ammonium cation. The term "pharmaceutically acceptable salt" of structure (Ia) or (Ib) is intended to encompass any and all acceptable salt forms.

The compounds of structure (Ia) and (Ib) may be prepared according to the organic synthesis techniques known to those skilled in this field, as well as by the representative methods set forth in the Examples.

MIF as a Drug Target

Macrophage migration inhibitory factor (MIF) may be well suited for analysis as a drug target as its activity has been implicated in a variety of pathophysiological conditions. For instance, MIF has been shown to be a significant mediator in both inflammatory responses and cellular proliferation. In this regard, MIF has been shown to play roles as a cytokine, a pituitary hormone, as glucocorticoid-induced immunomodulator, and just recently as a neuroimmunomodulator and in neuronal function. Takahashi et al., *Mol. Med.* 4:707-714, 1998; Bucala, *Ann. N.Y Acad. Sci.* 840:74-82, 1998; Bacher et al., *Mol. Med.* 4(4):217-230, 1998. Further, it has been recently demonstrated that anti-MIF antibodies have a variety of uses, notably decreased tumor growth, along with an observed reduction in angiogenesis. Ogawa et al., *Cytokine* 12(4):309-314, 2000; Metz and Bucala (supra). Accordingly, small molecules that can inhibit MIF have significant value in the treatment of inflammatory responses, reduction of angiogenesis, viral infection, bacterial infection, treatment of cancer (specifically tumorigenesis and apoptosis), treatment of graft versus host disease and associated tissue rejection. A MIF inhibitor may be particularly useful in a variety of immune related responses, tumor growth, glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, inflammatory lung disorders, otitis media, Crohn's disease, acute respiratory distress syndrome, delayed-type hypersensitivity. A MIF inhibitor may also be useful in the treatment of stress and glucocorticoid function disorders, e.g., counter regulation of glucocorticoid action; or overriding of glucocorticoid mediated suppression of arachidonate release (Cys-60 based catalytic MIF oxidoreductase activity or JAB1/CSNS-MIF-interaction based mechanism).

One example of the utility of a MIF inhibitor may be evidenced by the fact that following endotoxin exposure detectable serum concentrations of MIF gradually increase during the acute phase (1-8 hours), peak at 8 hours and persist during the post-acute phase (>8 hours) for up to 20 hours. While not limited to any theory of operation, MIF may likely be produced by activated T-cells and macrophages during the proinflammatory stage of endotoxin-induced shock, e.g., as part of the localized response to infection. Once released by a pro-inflammatory stimulus, e.g., low concentrations of LPS, or by TNF-α and IFN-γ, macrophage-derived MIF may be the probable source of MIF produced during the acute phase of endotoxic shock. Both the pituitary, which releases MIF in response to LPS, and macrophages are the probable source of MIF in the post-acute phase of endotoxic shock, when the infection is no longer confined to a localized site. See, e.g., U.S. Pat. No. 6,080,407, incorporated herein by reference in its entirety and describing these results with anti-MIF antibodies.

As demonstrated herein, inhibitors of preferred embodiments inhibit lethality in mice following LPS challenge and likely attenuate IL-1β and TNF-α levels. Accordingly, a variety of inflammatory conditions may be amenable to treatment with a MIF inhibitor. In this regard, among other advantages, the inhibition of MIF activity and/or release may be employed to treat inflammatory response and shock. Beneficial effects may be achieved by intervention at both early and late stages of the shock response. In this respect, while not limited to any theory or mechanism responsible for the protective effect of MIF inhibition, anti-MIF studies have demonstrated that introduction of anti-MIF antibodies is associated with an appreciable (up to 35-40%) reduction in circulating serum TNF-α levels. This reduction is consistent with the TNF-α-inducing activity of MIF on macrophages in vitro, and suggests that MIF may be responsible, in part, for the extremely high peak in serum TNF-α level that occurs 1-2 hours after endotoxin administration despite the fact that MIF cannot be detected in the circulation at this time. Thus, MIF inhibition therapy may be beneficial at the early stages of the inflammatory response.

MIF also plays a role during the post-acute stage of the shock response, and therefore, offers an opportunity to intervene at late stages where other treatments, such as anti-TNF-α therapy, are ineffective. Inhibition of MIF can protect against lethal shock in animals challenged with high concentrations of endotoxin (i.e., concentrations that induce release of pituitary MIF into the circulation), and in animals challenged with TNF-α. Accordingly, the ability to inhibit MIF and protect animals challenged with TNF indicates that neutralization of MIF during the later, post-acute phase of septic shock may be efficacious.

As evidenced herein, TNF-α and IL-1β levels are correlated at least in some instances to MIF levels. Accordingly, an anti-MIF small molecule may be useful in a variety of TNF-α and/or IL-1β associated disease states including transplant rejection, immune-mediated and inflammatory elements of CNS disease (e.g., Alzheimer's, Parkinson's, multiple sclerosis, and the like), muscular dystrophy, diseases of hemostasis (e.g., coagulopathy, veno occlusive diseases, and the like), allergic neuritis, granuloma, diabetes, graft versus host disease, chronic renal damage, alopecia (hair loss), acute pancreatitis, joint disease, congestive heart failure, cardiovascular disease (restenosis, atherosclerosis), joint disease, and osteoarthritis.

Further, additional evidence in the art has indicated that steroids while potent inhibitors of cytokine production actually increase MIF expression. Yang et al., *Mol. Med.* 4(6): 413-424, 1998; Mitchell et al., *J. Biol. Chem.* 274(25): 18100-18106, 1999; Calandra and Bucala, *Crit. Rev. Immunol.* 17(1):77-88, 1997; Bucala, *FASEB J.* 10(14): 1607-1613, 1996. Accordingly, it may be of particular utility to utilize MIF inhibitors in combination with steroidal therapy for the treatment of cytokine mediated pathophysiological conditions, such as inflammation, shock, and other cytokine-mediated pathological states, particularly in chronic inflammatory states such as rheumatoid arthritis. Such combination therapy may be beneficial even subsequent to the onset of pathogenic or other inflammatory responses. For example, in the clinical setting, the administration of steroids subsequent to the onset of septic shock symptoms has proven of little benefit. See Bone et al., *N. Engl. J. Med.* 317: 653-658, 1987; Spring et al., *N. Engl. J. Med.* 311: 1137-1141, 1984. Combination steroids/MIF inhibition therapy may be employed to overcome this obstacle. Further, one of skill in the art may understand that such therapies may be tailored to inhibit MIF release and/or activity locally and/or systemically.

Assays

The effectiveness of a compound as an inhibitor of MIF may be determined by various assay methods. Suitable inhibitors of preferred embodiments are capable of decreasing one or more activities associated with MIF and/or MIF export. A compound of structure (Ia) or (Ib) or any other structure may be assessed for activity as an inhibitor of MIF by one or more generally accepted assays for this purpose, including (but not limited to) the assays described below.

The assays may generally be divided into three categories, those being, assays which monitor export; those which monitor effector or small molecule binding, and those that monitor MIF activity. However, it should be noted that combinations of these assays are within the scope of the present application. Surprisingly, it appears that epitope mapping of MIF acts as surrogate for biological activity. For example, in one assay, the presence of a candidate inhibitor blocks the detection of export of MIF from cells (e.g., THP-1 cells—a human acute monocytic leukemia cell line) measured using a monoclonal antibody such as that commercially available from R&D systems (Minneapolis, Minn.) whereas a polyclonal antibody demonstrates that MIF is present. Further, cellular based or in vitro assays may be employed to demonstrate that these potential inhibitors inhibit MIF activity. In an alternative, these two assays (i.e., binding and activity assays) may be combined into a singular assay which detects binding of a test compound (e.g., the ability to displace monoclonal antibodies or inhibit their binding) while also affecting MIF activity. Such assays include combining an ELISA type assay (or similar binding assay) with a MIF tautomerism assay or similar functional assay. As one of ordinary skill in the art may readily recognize, the exact assay employed is irrelevant, provided it is able to detect the ability of the compound of interest to bind MIF. In addition, the assay preferably detects the ability of the compound to inhibit a MIF activity because it selects for compounds that interact with biologically active MIF and not inactive MIF.

It should also be understood that compounds demonstrating the ability to inhibit monoclonal antibody binding to biologically active and not inactive MIF (e.g., small molecule inhibited), necessarily indicate the presence of a compound (e.g., a small molecule) that is interacting with MIF either in a fashion which changes the conformation of MIF or blocks an epitope necessary for antibody binding. In other embodiments, MIF inhibitory activity may also be recognized as a consequence of interfering with the formation of a polypeptide complex that includes MIF; disturbing such a complex may result in a conformational change inhibiting detection. Accordingly, the use of assays that monitor conformational changes in MIF, are advantageous when employed either in addition to assays measuring competition between compounds, such as small molecules with mAb or as a replacement of such an assay. A variety of such assays are known in the art and include, calorimetry, circular-dichroism, fluorescence energy transfer, light-scattering, nuclear magnetic resonance (NMR), surface plasmon resonance, scintillation proximity assays (see U.S. Pat. No. 5,246,869), and the like. See also WO02/07720-A1 and WO97/29635-A1. Accordingly, one of skill in the art may recognize that any assay that indicates binding and preferably conformational change or placement near the active site of MIF may be utilized. Descriptions of several of the more complicated proximity assays and conformational assays are set forth below, this discussion is merely exemplary and in no way should be construed as limiting to the type of techniques that may be utilized in preferred embodiments.

In one example, circular dichroism may be utilized to determine candidate inhibitor binding. Circular dichroism (CD) is based in part on the fact that most biological protein macromolecules are made up of asymmetric monomer units, L-amino acids, so that they all possess the attribute of optical activity. Additionally, rigid structures like DNA or an alpha helical polypeptide have optical properties that can be measured using the appropriate spectroscopic system. In fact, large changes in an easily measured spectroscopic parameter can provide selective means to identify conformational states and changes in conformational states under various circumstances, and sometimes to observe the perturbation of single groups in or attached to the macromolecule. Further, CD analysis has been frequently employed to probe the interactions of various macromolecules with small molecules and ligands. See Durand et al., *Eur. Biophys. J.* 27(2):147-151, 1998; Kleifeld et al., *Biochem* 39(26):7702-7711, 2000; Bianchi et al., *Biochem* 38(42):13844-13852, 1999; Sarver et al., *Biochim Biophys Acta* 1434(2):304-316, 1999.

The Pasteur principle states that an optically active molecule must be asymmetric; that is, the molecule and its mirror image cannot be superimposed. Plane polarized light is a combination of left circularly polarized light and right circularly polarized light traveling in phase. The interaction of this light with an asymmetric molecule results in a preferential interaction of one circularly polarized component which, in an absorption region, is seen as a differential absorption (i.e., a dichroism). See Urry, D. W., Spectroscopic Approaches to Biomolecular Conformation, American Medical Association Press, Chicago, Ill., pp. 33-120 (1969); Berova and Woody, Circular Dichroism: Principles and Applications, John Wiley & Sons, N.Y., (2000).

Circular dichroism, then, is an absorptive phenomenon that results when a chromophore interacts with plane polarized light at a specific wavelength. The absorption band can be either negative or positive depending on the differential absorption of the right and left circularly polarized components for that chromophore. Unlike optical rotatory dispersion (ORD) that measures the contributions of background and the chromophore of interest many millimicrons from the region of actual light interaction, CD offers the advantage of measuring optical events at the wavelength at which the event takes place. Circular dichroism, then, is specific to the electronic transition of the chromophore. See Berova and Woody, Circular Dichroism: Principles and Applications, John Wiley & Sons, N.Y., (2000).

Application of circular dichroism to solutions of macromolecules has resulted in the ability to identify conformation states (Berova and Woody, Circular Dichroism: Principles and Applications, John Wiley & Sons, N.Y., (2000)). The technique can distinguish random coil, alpha helix, and beta chain conformation states of macromolecules. In proteins, alpha helical fibrous proteins show absorption curves closely resembling those of alpha helical polypeptides, but in globular proteins of known structure, like lysozyme and ribonuclease, the helical structures are in rather poor agreement with X-ray crystallography work. A further source of difficulty in globular proteins is the prevalence of aromatic chromophores on the molecules around 280 nm. An interesting example of helical changes has been demonstrated using myoglobin and apomyoglobin. After removing the prosthetic group heme, the apoprotein remaining has a residual circular dichroic ellipticity reduced by 25%. This loss of helix is attributable to an uncoiling of 10-15 residues in the molecule. Other non-peptide, optically active chromophores include tyrosine, tryptophan, phenylalanine, and cysteine when located in the primary amino acid sequence of a macromolecule. Examples of non-peptide ellipticities include the disulfide transition in ribonuclease and the cysteine transitions of insulin.

Accordingly, circular dichroism may be employed to screen candidate inhibitors for the ability to affect the conformation of MIF.

In certain embodiments provided herein, MIF-binding agent or inhibitor complex formation may be determined by detecting the presence of a complex including MIF and a detectably labeled binding agent. As described in greater detail below, fluorescence energy signal detection, for example by fluorescence polarization, provides determination of signal levels that represent formation of a MIF-binding agent molecular complex. Accordingly, and as provided herein, fluorescence energy signal-based comparison of MIF-binding agent complex formation in the absence and in the presence of a candidate inhibitor provides a method for identifying whether the agent alters the interaction between MIF and the binding agent. For example, the binding agent may be a MIF substrate, an anti-MIF antibody, or a known inhibitor, while the candidate inhibitor may be the compound to be tested or vice versa.

As noted above, certain preferred embodiments also pertain in part to fluorescence energy signal-based determination of MIF-binding agent complex formation. Fluorescence energy signal detection may be, for example, by fluorescence polarization or by fluorescence resonance energy transfer, or by other fluorescence methods known in the art. As an example of certain other embodiments, the MIF polypeptide may be labeled as well as the candidate inhibitor and may comprise an energy transfer molecule donor-acceptor pair, and the level of fluorescence resonance energy transfer from energy donor to energy acceptor is determined.

In certain embodiments the candidate inhibitor and/or binding agent is detectably labeled, and in particularly preferred embodiments the candidate inhibitor and/or binding agent is capable of generating a fluorescence energy signal. The candidate inhibitor and/or binding agent can be detectably labeled by covalently or non-covalently attaching a suitable reporter molecule or moiety, for example any of various fluorescent materials (e.g., a fluorophore) selected according to the particular fluorescence energy technique to be employed, as known in the art and based upon the methods described herein. Fluorescent reporter moieties and methods for as provided herein can be found, for example in Haugland (1996 *Handbook of Fluorescent Probes and Research Chemicals—Sixth Ed.*, Molecular Probes, Eugene, Oreg.; 1999 *Handbook of Fluorescent Probes and Research Chemicals—Seventh Ed.*, Molecular Probes, Eugene, Oreg., http://www.probes.com/lit/) and in references cited therein. Particularly preferred for use as such a fluorophore in preferred embodiments are fluorescein, rhodamine, Texas Red, AlexaFluor-594, AlexaFluor-488, Oregon Green, BODIPY-FL, and Cy-5. However, any suitable fluorophore may be employed, and in certain embodiments fluorophores other than those listed may be preferred.

As provided herein, a fluorescence energy signal includes any fluorescence emission, excitation, energy transfer, quenching, or dequenching event or the like. Typically a fluorescence energy signal may be mediated by a fluorescent detectably labeled candidate inhibitor and/or binding agent in response to light of an appropriate wavelength. Briefly, and without wishing to be bound by theory, generation of a fluorescence energy signal generally involves excitation of a fluorophore by an appropriate energy source (e.g., light of a suitable wavelength for the selected fluorescent reporter moiety, or fluorophore) that transiently raises the energy state of the fluorophore from a ground state to an excited state. The excited fluorophore in turn emits energy in the form of detectable light typically having a different (e.g., usually longer) wavelength from that preferred for excitation, and in so doing returns to its energetic ground state. The methods of preferred embodiments contemplate the use of any fluorescence energy signal, depending on the particular fluorophore, substrate labeling method and detection instrumentation, which may be selected readily and without undue experimentation according to criteria with which those having ordinary skill in the art are familiar.

In certain embodiments, the fluorescence energy signal is a fluorescence polarization (FP) signal. In certain other embodiments, the fluorescence energy signal may be a fluorescence resonance energy transfer (FRET) signal. In certain other preferred embodiments the fluorescence energy signal can be a fluorescence quenching (FQ) signal or a fluorescence resonance spectroscopy (FRS) signal. (For details regarding FP, FRET, FQ and FRS, see, for example, WO97/39326; WO99/29894; Haugland, *Handbook of Fluorescent Probes and Research Chemicals—6th Ed.*, 1996, Molecular Probes, Inc., Eugene, Oreg., p. 456; and references cited therein.)

FP, a measurement of the average angular displacement (due to molecular rotational diffusion) of a fluorophore that occurs between its absorption of a photon from an energy source and its subsequent emission of a photon, depends on the extent and rate of rotational diffusion during the excited state of the fluorophore, on molecular size and shape, on solution viscosity and on solution temperature (Perrin, 1926 *J. Phys. Rad.* 1:390). When viscosity and temperature are held constant, FP is directly related to the apparent molecular volume or size of the fluorophore. The polarization value is a ratio of fluorescence intensities measured in distinct planes (e.g., vertical and horizontal) and is therefore a dimensionless quantity that is unaffected by the intensity of the fluorophore. Low molecular weight fluorophores, such as the detectably labeled candidate inhibitor and/or binding agent provided herein, are capable of rapid molecular rotation in solution (i.e., low anisotropy) and thus give rise to low fluorescence polarization readings. When complexed to a higher molecular weight molecule such as MIF as provided herein, however, the fluorophore moiety of the substrate associates with a complex that exhibits relatively slow molecular rotation in solution (i.e., high anisotropy), resulting in higher fluorescence polarization readings.

This difference in the polarization value of free detectably labeled candidate inhibitor and/or binding agent compared to the polarization value of MIF:candidate inhibitor and/or binding agent complex may be employed to determine the ratio of complexed (e.g., bound) to free. This difference may also be employed to detect the influence of a candidate agent (i.e., candidate inhibitor) on the formation of such complexes and/or on the stability of a pre-formed complex, for example by comparing FP detected in the absence of an agent to FP detected in the presence of the agent. FP measurements can be performed without separation of reaction components.

As noted above, one aspect of a preferred embodiment utilizes the binding or displacement of a monoclonal antibody, known inhibitor, or other binding agent and/or complex formation of the candidate inhibitor with MIF to provide a method of identifying an inhibitor that alters the activity of MIF. Surprisingly, the inhibitors of preferred embodiments were identified in such a nonconventional manner. In this regard, a class of compounds demonstrated the ability to inhibit/decrease monoclonal antibody binding to a biologically active MIF that is naturally produced from cells while not affecting the antibody's ability to recognize inactive (recombinant) MIF (as is available from commercial sources) and also demonstrated pronounced modulation of MIF activity in vivo. Accordingly, antibody binding may be preferred as a surrogate for enzyme activity, thus eliminating the need to run expensive and complex enzymatic assays on each candidate compound. As those of ordinary skill in the art readily appreciate, the ability to avoid enzymatic assays leads to an assay that may be extremely well suited for high throughput use.

Further, as those of ordinary skill in the art can readily appreciate, such an assay may be employed outside of the MIF context and wherever enzyme or biological activity can be replaced by a binding assay. For example, any enzyme or other polypeptide whose biologically active form is recognized by a monoclonal antibody that does not recognize the inactive form (e.g., small molecule inhibited form) may be preferred. Within the context of an enzyme, the monoclonal antibody may bind the active site, but be displaced by a small molecule. Thus, any small molecule that displaces the antibody may be a strong lead as a potential enzyme inhibitor. As those of skill in the art appreciate, the antibody may recognize an epitope that changes conformation depending on the active state of the enzyme, and that binding of a small molecule such that it precludes antibody binding to this epitope may also act as a surrogate for enzymatic activity even though the epitope may not be at the active site. Accordingly, the type of assay utilized herein may be expanded to be employed with essentially any polypeptide wherein antibody displacement is predictive of activity loss. Thus, in its simplest form any polypeptide, e.g., enzyme and its associated neutralizing antibody may be employed to screen for small molecules that displace this antibody, thereby identifying likely inhibitors.

A MIF-binding agent/candidate inhibitor complex may be identified by any of a variety of techniques known in the art for demonstrating an intermolecular interaction between MIF and another molecule as described above, for example, co-purification, co-precipitation, co-immunoprecipitation, radiometric or fluorimetric assays, western immunoblot analyses, affinity capture including affinity techniques such as solid-phase ligand-counterligand sorbent techniques, affinity chromatography and surface affinity plasmon resonance, NMR, and the like (see, e.g., U.S. Pat. No. 5,352,660). Determination of the presence of such a complex may employ antibodies, including monoclonal, polyclonal, chimeric and single-chain antibodies, and the like, that specifically bind to MIF or the binding agent.

Labeled MIF and/or labeled binding agents/candidate inhibitors can also be employed to detect the presence of a complex. The molecule of interest can be labeled by covalently or non-covalently attaching a suitable reporter molecule or moiety, for example any of various enzymes, fluorescent materials, luminescent materials, and radioactive materials. Examples of suitable enzymes include, but are not limited to, horseradish peroxidase, alkaline phosphatase, β-galactosidase, and acetylcholinesterase. Examples of suitable fluorescent materials include, but are not limited to, umbelliferone, fluorescein, fluorescein isothiocyanate, rhodamine, dichlorotriazinylamine fluorescein, dansyl chloride, phycoerythrin, Texas Red, AlexaFluor-594, AlexaFluor-488, Oregon Green, BODIPY-FL and Cy-5. Appropriate luminescent materials include, but are not limited to, luminol and suitable radioactive materials include radioactive phosphorus [$^{32}$P], iodine [$^{125}$I or $^{131}$I] or tritium [$^{3}$H].

MIF and the binding agent and/or the candidate inhibitor are combined under conditions and for a time sufficient to permit formation of an intermolecular complex between the components. Suitable conditions for formation of such complexes are known in the art and can be readily determined based on teachings provided herein, including solution conditions and methods for detecting the presence of a complex and/or for detecting free substrate in solution.

Association of a detectably labeled binding agent(s) and/or candidate inhibitor(s) in a complex with MIF, and/or binding agent or candidate inhibitor that is not part of such a complex, may be identified according to a preferred embodiment by detection of a fluorescence energy signal generated by the substrate. Typically, an energy source for detecting a fluorescence energy signal is selected according to criteria with which those having ordinary skill in the art are familiar, depending on the fluorescent reporter moiety with which the substrate is labeled. The test solution, containing (a) MIF and (b) the detectably labeled binding agent and/or candidate inhibitor, is exposed to the energy source to generate a fluorescence energy signal, which is detected by any of a variety of well known instruments and identified according to the particular fluorescence energy signal. In preferred embodiments, the fluorescence energy signal is a fluorescence polarization signal that can be detected using a spectrofluorimeter equipped with polarizing filters. In particularly preferred embodiments the fluorescence polarization assay is performed simultaneously in each of a plurality of reaction chambers that can be read using an LJL CRITERION™ Analyst (LJL Biosystems, Sunnyvale, Calif.) plate reader, for example, to provide a high throughput screen (HTS) having varied reaction components or conditions among the various reaction chambers. Examples of other suitable instruments for obtaining fluorescence polarization readings include the POLARSTAR™ (BMG Lab Technologies, Offenburg, Germany), BEACON™ (Panvera, Inc., Madison, Wis.) and the POLARION™ (Tecan, Inc., Research Triangle Park, N.C.) devices.

Determination of the presence of a complex that has formed between MIF and a binding agent and/or a candidate inhibitor may be performed by a variety of methods, as noted above, including fluorescence energy signal methodology as provided herein and as known in the art. Such methodologies may include, by way of illustration and not limitation FP, FRET, FQ, other fluorimetric assays, co-purification, co-precipitation, co-immunoprecipitation, radiometric, western immunoblot analyses, affinity capture including affinity techniques such as solid-phase ligand-counterligand sorbent techniques, affinity chromatography and surface affinity plasmon resonance, circular dichroism, and the like. For these and other useful affinity techniques, see, for example, Scopes, R. K., *Protein Purification: Principles and Practice*, 1987, Springer-Verlag, N.Y.; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California; which are hereby incorporated by reference in their entireties, for details regarding techniques for isolating and characterizing complexes, including affinity techniques. In various embodiments, MIF may interact with a binding agent and/or candidate inhibitor via specific binding if MIF binds the binding agent and/or candidate inhibitor with a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$ to $10^{11} M^{-1}$. Affinities of binding partners can be readily calculated from data generated according to the fluorescence energy signal methodologies described above and using conventional data handling techniques, for example, those described by Scatchard et al., *Ann. N.Y. Acad. Sci.* 51:660 (1949).

For example, in various embodiments where the fluorescence energy signal is a fluorescence polarization signal, fluorescence anisotropy (in polarized light) of the free detectably labeled candidate inhibitor and/or binding agent can be determined in the absence of MIF, and fluorescence anisotropy (in polarized light) of the fully bound substrate can be determined in the presence of a titrated amount of MIF. Fluorescence anisotropy in polarized light varies as a function of the amount of rotational motion that the labeled candidate inhibitor and/or binding agent undergoes during the lifetime of the excited state of the fluorophore, such that the anisotropies of free and fully bound candidate inhibitor and/or binding agent can be usefully employed to determine the fraction of candidate inhibitor and/or binding agent bound to MIF in a given set of experimental conditions, for instance, those wherein a candidate agent is present (see, e.g., Lundblad et al., 1996 *Molec. Endocrinol.* 10:607; Dandliker et al., 1971 *Immunochem.* 7:799; Collett, E., *Polarized Light: Fundamentals and Applications*, 1993 Marcel Dekker, New York).

Certain of the preferred embodiments pertain in part to the use of intermolecular energy transfer to monitor MIF-binding agent complex formation and stability and/or MIF-candidate inhibitor complex formation.

Energy transfer (ET) is generated from a resonance interaction between two molecules: an energy-contributing "donor" molecule and an energy-receiving "acceptor" molecule. Energy transfer can occur when (1) the emission spectrum of the donor overlaps the absorption spectrum of the acceptor and (2) the donor and the acceptor are within a certain distance (for example, less than about 10 nm) of one another. The efficiency of energy transfer is dictated largely by the proximity of the donor and acceptor, and decreases as a power of 6 with distance. Measurements of ET thus strongly reflect the proximity of the acceptor and donor compounds, and changes in ET sensitively reflect changes in the proximity of the compounds such as, for example, association or dissociation of the donor and acceptor.

It is therefore an aspect of a preferred embodiment to provide a method for assaying a candidate MIF inhibitor, in pertinent part, by contacting MIF or an MIF-binding agent complex including one or more ET donor and an ET acceptor molecules, exciting the ET donor to produce an excited ET donor molecule and detecting a signal generated by energy transfer from the ET donor to the ET acceptor. As also provided herein, the method can employ any suitable ET donor molecule and ET acceptor molecule that can function as a donor-acceptor pair.

In certain preferred embodiments, a detectable signal that is generated by energy transfer between ET donor and acceptor molecules results from fluorescence resonance energy transfer (FRET), as discussed above. FRET occurs within a molecule, or between two different types of molecules, when energy from an excited donor fluorophore is transferred directly to an acceptor fluorophore (for a review, see Wu et al., *Analytical Biochem.* 218:1-13, 1994).

In other aspects of preferred embodiments, the ability of a candidate inhibitor to effect MIF export is tested.

The first step of such an assay is performed to detect MIF extracellularly. For this assay, test cells expressing MIF are employed (e.g., THP-1 cells). Either the test cells may naturally produce the protein or produce it from a transfected expression vector. Test cells preferably normally express the protein, such that transfection merely increases expressed levels. Thus, for expression of MIF and IL-1, THP1 cells are preferred. When one is assaying virally-derived proteins, such as HIV tat (a protein released from Human Immunodeficiency Virus infected cells), if the test cells do not "naturally" produce the protein, they may readily be transfected using an appropriate vector, so that the test cells express the desired protein, as those of skill in the art readily appreciate.

Following expression, MIF is detected by any one of a variety of well-known methods and procedures. Such methods include staining with antibodies in conjunction with flow cytometry, confocal microscopy, image analysis, immunoprecipitation of cell cytosol or medium, Western blot of cell medium, ELISA, 1- or 2-D gel analysis, HPLC, or bioassay. A convenient assay for initial screening is ELISA. MIF export may be confirmed by one of the other assays, preferably by immunoprecipitation of cell medium following metabolic labeling. Briefly, cells expressing MIF protein are pulse labeled for 15 minutes with $^{35}$S-methionine and/or $^{35}$S-cysteine in methionine and/or cysteine free medium and chased in medium supplemented with excess methionine and/or cysteine. Media fractions are collected and clarified by centrifugation, such as in a microfuge. Lysis buffer containing 1% NP-40, 0.5% deoxycholate (DOC), 20 mM Tris, pH 7.5, 5 mM ethylene diamine tetraacetic acid (EDTA), 2 mM EGTA, 10 nM phenyl methyl sulforyl fluoride (PMSF), 10 ng/ml aprotinin, 10 ng/ml leupeptin, and 10 ng/ml pepstatin is added to the clarified medium. An antibody to MIF is added and following incubation in the cold, a precipitating second antibody or immunoglobulin binding protein, such as protein A-Sepharose® or Gamma-Bind™-Sepharose®, is added for further incubation. A-Sepharose® is Protein A, an immunoglobulin G (IgG) binding reagent used for measurement and purification of free and cell bound antigens and antibodies, that is available from Pharmacia, Inc. Protein A binds the Fc portion of antibodies (IgG class) without disturbing their binding of antigen. GammaBind™-Sepharose® from Pharmacia, Inc. is Protein G, a binding reagent that binds to the constant region of many types of immunoglobulin G, and can be used to detect, quantify and purify IgG antibodies and antigen/antibody complexes. In parallel, as a control, a cytosolic protein is monitored and an antibody to the cytosolic protein is preferred in immunoprecipitations. Immune complexes are pelleted and washed with ice-cold lysis buffer. Complexes are further washed with ice-cold IP buffer (0.15 M NaCl, 10 mM Na-phosphate, pH 7.2, 1% DOC, 1% NP-40, 0.1% SDS). Immune complexes are eluted directly into SDS-gel sample buffer and electrophoresed in SDS-PAGE. The gel is processed for fluorography, dried and exposed to X-ray film. Alternatively cells can be engineered to produced a MIF that is tagged with a reporter so that the presence of an active MIF can be through the surrogate activity of the reporter.

While not wishing to be bound to theory, it is believed that the present inhibitors function by interacting directly with the naturally produced MIF complex in such a fashion as to alter the protein's conformation enough to block its biological activity. This interaction can be mapped by X-ray crystallography of MIF-compound co-crystals to determine the exact site of interaction. One site localizes to the pocket that is responsible for the tautomerase activity of MIF.

Screening assays for inhibitors of MIF export varies according to the type of inhibitor and the nature of the activity that is being affected. Assays may be performed in vitro or in vivo. In general, in vitro assays are designed to evaluate MIF activity, or multimerization, and in vivo assays are designed to evaluate MIF activity, extracellular, and intracellular localization in a model cell or animal system. In any of the assays, a statistically significant increase or decrease compared to a proper control is indicative of enhancement or inhibition.

One in vitro assay can be performed by examining the effect of a candidate compound on the ability of MIF to inhibit macrophage migration. Briefly, human peripheral blood monocytes are preferred as indicator cells in an agarose-droplet assay system essentially as described by Weiser et al., *Cell. Immunol.* 90:167-178, 1985 and Harrington et al., *J. Immunol.* 110:752-759, 1973. Other assay systems of analyzing macrophage migration may also be employed. Such an assay is described by Hermanowski-Vosatka et al., *Biochem.* 38:12841-12849, 1999.

An alternative in vitro assay is designed to measure the ability of MIF to catalyze tautomerization of the D-isomer of dopachrome (see Rosengren et al., *Mol. Med.* 2:143-149, 1996; Winder et al., *J. Cell Sci.* 106:153-166, 1993; Aroca et al., *Biochem. J.* 277:393-397). Briefly, in this method, D-dopachrome is provided to MIF in the presence and absence of a candidate inhibitor and the ability to catalyze the tautomerization to 5,6-dihydroxyindole-2-carboxylic acid (DHICA) is monitored. However, use of methyl esters of D-dopachrome may be preferred in that a faster reaction rate is observed. Detection of the tautomerization can be performed by any one of a variety of standard methods.

In a similar assay, the ability of MIF to catalyze the tautomerization of phenylpyruvate may be tested (see Johnson et al., *Biochem.* 38(48):16024-16033, 1999). Briefly, in this method, typically ketonization of phenylpyruvate or (p-hydroxyphenyl)pyruvate is followed by spectroscopy. Further, product formation may be verified by treatment of these compounds with MIF and subsequent conversion to malate for $^1$H NMR analysis.

In vivo assays can be performed in cells transfected either transiently or stably with an expression vector containing a MIF nucleic acid molecule, such as those described herein. These cells are preferred to measure MIF activity (e.g., modulation of apoptosis, proliferation, and the like) or extracellular and intracellular localization in the presence or absence of a candidate compound. When assaying for apoptosis, a variety of cell analyses may be employed including, for example, dye staining and microscopy to examine nucleic acid fragmentation and porosity of the cells.

Other assays may be performed in model cell or animal systems, by providing to the system a recombinant or naturally occurring form of MIF or inducing endogenous MIF expression in the presence or absence of test compound, thereby determining a statistically significant increase or decrease in the pathology of that system. For example, LPS can be employed to induce a toxic shock response.

The assays briefly described herein may be employed to identify an inhibitor that is specific for MIF.

In any of the assays described herein, a test cell may express the MIF naturally (e.g., THP-1 cells) or following introduction of a recombinant DNA molecule encoding the protein. Transfection and transformation protocols are well known in the art and include $Ca_2PO_4$-mediated transfection, electroporation, infection with a viral vector, DEAE-dextran mediated transfection, and the like. As an alternative to the proteins described above, chimeric MIF proteins (i.e., fusion of MIF protein with another protein or protein fragment), or protein sequences engineered to lack a leader sequence may be employed. In a similar fashion, a fusion may be constructed to direct secretion, export, or cytosolic retention. Any and all of these sequences may be employed in a fusion construct with MIF to assist in assaying inhibitors. The host cell can also express MIF as a result of being diseased, infected with a virus, and the like. Secreted proteins that are exported by virtue of a leader sequence are well known and include, human chorionic gonadatropin (hCGα), growth hormone, hepatocyte growth factor, transferrin, nerve growth factor, vascular endothelial growth factor, ovalbumin, and insulin-like growth factor. Similarly, cytosolic proteins are well known and include, neomycin phosphotransferase, β-galactosidase, actin and other cytoskeletal proteins, and enzymes, such as protein kinase A or C. The most useful cytosolic or secreted proteins are those that are readily measured in a convenient assay, such as ELISA. The three proteins (leaderless, secreted, and cytosolic) may be co-expressed naturally, by co-transfection in the test cells, or transfected separately into separate host cells. Furthermore, for the assays described herein, cells may be stably transformed or express the protein transiently.

Immunoprecipitation is one such assay that may be employed to determine inhibition. Briefly, cells expressing MIF naturally or from an introduced vector construct are labeled with $^{35}$S-methionine and/or $^{35}$S-cysteine for a brief period of time, typically 15 minutes or longer, in methionine- and/or cysteine-free cell culture medium. Following pulse labeling, cells are washed with medium supplemented with excess unlabeled methionine and cysteine plus heparin if the leaderless protein is heparin binding. Cells are then cultured in the same chase medium for various periods of time. Candidate inhibitors or enhancers are added to cultures at various concentration. Culture supernatant is collected and clarified. Supernatants are incubated with anti-MIF immune serum or a monoclonal antibody, or with anti-tag antibody if a peptide tag is present, followed by a developing reagent such as *Staphylococcus aureus* Cowan strain I, protein A-Sepharose®, or Gamma-bind™ G-Sepharose®. Immune complexes are pelleted by centrifugation, washed in a buffer containing 1% NP-40 and 0.5% deoxycholate, EGTA, PMSF, aprotinin, leupeptin, and pepstatin. Precipitates are then washed in a buffer containing sodium phosphate pH 7.2, deoxycholate, NP-40, and SDS. Immune complexes are eluted into an SDS gel sample buffer and separated by SDS-PAGE. The gel is processed for fluorography, dried, and exposed to x-ray film.

Alternatively, ELISA may be preferred to detect and quantify the amount of MIF in cell supernatants. ELISA is preferred for detection in high throughput screening. Briefly, 96-well plates are coated with an anti-MIF antibody or anti-tag antibody, washed, and blocked with 2% BSA. Cell supernatant is then added to the wells. Following incubation and washing, a second antibody (e.g., to MIF) is added. The second antibody may be coupled to a label or detecting reagent, such as an enzyme or to biotin. Following further incubation, a developing reagent is added and the amount of MIF determined using an ELISA plate reader. The developing reagent is a substrate for the enzyme coupled to the second antibody (typically an anti-isotype antibody) or for the enzyme coupled to streptavidin. Suitable enzymes are well known in the art and include horseradish peroxidase, which acts upon a substrate (e.g., ABTS) resulting in a colorimetric reaction. It is recognized that rather than using a second antibody coupled to an enzyme, the anti-MIF antibody may be directly coupled to the horseradish peroxidase, or other equivalent detection reagent. If desired, cell supernatants may be concentrated to raise the detection level. Further, detection methods, such as ELISA and the like may be employed to monitor intracellular as well as extracellular levels of MIF. When intracellular levels are desired, a cell lysate is preferred. When extracellular levels are desired, media can be screened.

ELISA may also be readily adapted for screening multiple candidate inhibitors or enhancers with high throughput. Briefly, such an assay is conveniently cell based and performed in 96-well plates. Test cells that naturally or stably express MIF are plated at a level sufficient for expressed product detection, such as, about 20,000 cells/well. However, if the cells do not naturally express the protein, transient expression is achieved, such as by electroporation or $Ca_2PO_4$-mediated transfection. For electroporation, 100 µl of a mixture of cells (e.g., 150,000 cells/ml) and vector DNA (5 µg/ml) is dispensed into individual wells of a 96-well plate. The cells are electroporated using an apparatus with a 96-well electrode (e.g., ECM 600 Electroporation System, BTX, Genetronics, Inc.). Optimal conditions for electroporation are experimentally determined for the particular host cell type. Voltage, resistance, and pulse length are the typical parameters varied. Guidelines for optimizing electroporation may be obtained from manufacturers or found in protocol manuals, such as *Current Protocols in Molecular Biology* (Ausubel et al. (ed.), Wiley Interscience, 1987). Cells are diluted with an equal volume of medium and incubated for 48 hours. Electroporation may be performed on various cell types, including mammalian cells, yeast cells, bacteria, and the like. Following incubation, medium with or without inhibitor is added and cells are further incubated for 1-2 days. At this time, culture medium is harvested and the protein is assayed by any of the assays herein. Preferably, ELISA is employed to detect the protein. An initial concentration of 50 µM is tested. If this amount gives a statistically significant reduction of export or reduction of monoclonal Ab detection, the candidate inhibitor is further tested in a dose response.

Alternatively, concentrated supernatant may be electrophoresed on an SDS-PAGE gel and transferred to a solid support, such as nylon or nitrocellulose. MIF is then detected by an immunoblot (see Harlow, *Antibodies: A Laboratory Manual*, Cold Spring Harbor Laboratory, 1988), using an antibody to MIF containing an isotopic or non-isotopic reporter group. These reporter groups include, but are not limited to enzymes, cofactors, dyes, radioisotopes, luminescent molecules, fluorescent molecules, and biotin. Preferably, the reporter group is $^{125}I$ or horseradish peroxidase, which may be detected by incubation with 2,2'-azino-di-3-ethylbenzthiazoline sulfonic acid. These detection assays described above are readily adapted for use if MIF contains a peptide tag. In such case, the antibody binds to the peptide tag. Other assays include size or charge-based chromatography, including HPLC, and affinity chromatography.

Alternatively, a bioassay may be employed to quantify the amount of active MIF present in the cell medium. For example, the bioactivity of the MIF may be measured by a macrophage migration assay. Briefly, cells transfected with an expression vector containing MIF are cultured for approximately 30 hours, during which time a candidate inhibitor or enhancer is added. Following incubation, cells are transferred to a low serum medium for a further 16 hours of incubation. The medium is removed and clarified by centrifugation. A lysis buffer containing protease inhibitors is added to the medium or, in the alternative, cells are lysed and internal levels are determined as follows. Bioactivity of MIF is then measured by macrophage migration assay, isomerase activity, or a proliferation assay. A proliferation assay is performed by adding various amounts of the eluate to cultured quiescent 3T3 cells. Tritiated thymidine is added to the medium and TCA precipitable counts are measured approximately 24 hours later. Reduction of the vital dye MTT is an alternative way to measure proliferation. For a standard, purified recombinant human FGF-2 (fibroblast growth factor 2) may be employed. Other functions may be assayed in other appropriate bioassays available in the art, such as capsular polysaccharides (CPS) induced toxic shock, TSST-1 induced toxic shock, collagen induced arthritis, and the like.

Other in vitro angiogenic assays include bioassays that measure proliferation of endothelial cells within collagen gel (Goto et al., *Lab Invest*. 69:508, 1993), co-culture of brain capillary endothelial cells on collagen gels separated by a chamber from cells exporting the MIF protein (Okamure et al., *B. B. R. C*. 186:1471, 1992; Abe et al., *J. Clin. Invest*. 92:54, 1993), or a cell migration assay (see Warren et al., *J. Clin. Invest*. 95:1789, 1995).

Production of Antibodies

The term "antibody," as used herein is a broad term and is used in its ordinary sense, including, without limitation, to refer to polyclonal, monospecific, and monoclonal antibodies, as well as antigen binding fragments of such antibodies. With regard to an anti-MIF/target antibody of preferred embodiments, the term "antigen" as used herein is a broad term and is used in its ordinary sense, including, without limitation, to refer to a macrophage migration inhibitory factor polypeptide or a target polypeptide, variant, or functional fragment thereof. An anti-MIF/target antibody, or antigen binding fragment of such an antibody, may be characterized as having specific binding activity for the target polypeptide or epitope thereof of at least about $1 \times 10^5$ $M^{-1}$, generally at least about $1 \times 10^6$ $M^{-1}$, and preferably at least about $1 \times 10^8$ $M^{-1}$. Fab, F(ab')$_2$, Fd and Fv fragments of an anti-MIF/target antibody, which retain specific binding activity for a MIF/target polypeptide-specific epitope, are encompassed within preferred embodiments. Of particular interest are those antibodies that bind active polypeptides and are displaced upon binding of an inhibitory small molecule. Those of skill in the art readily appreciate that such displacement can be the result of a conformational change, thus changing the nature of the epitope, competitive binding with the epitope, or steric exclusion of the antibody from its epitope. In one example, the active site of an enzyme may be the epitope for a particular antibody and upon binding of a small molecule at or near the active site, immunoreactivity of the antibody is lost, thereby allowing the use of loss of immunoreactivity with an antibody as a surrogate marker for enzyme activity.

In addition, the term "antibody" as used herein is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. Such non-naturally occurring antibodies may be constructed using solid phase peptide synthesis, may be produced recombinantly, or may be obtained, for example, by screening combinatorial libraries including variable heavy chains and variable light chains (Huse et al., *Science* 246:1275-1281 (1989)). These and other methods of making, for example, chimeric, humanized, CDR-grafted, single chain, and bifunctional antibodies are well known in the art (Winter and Harris, *Immunol. Today* 14:243-246 (1993); Ward et al., *Nature* 341:544-546 (1989); Harlow and Lane, *Antibodies: A Laboratory Manual*, Cold Spring Harbor Laboratory, New York (1992); Borrabeck, *Antibody Engineering*, 2d ed., Oxford Univ. Press (1995); Hilyard et al., *Protein Engineering: A practical approach*, IRL Press (1992)).

In certain preferred embodiments, an anti-MIF/target antibody may be raised using as an immunogen such as, for example, an isolated peptide including the active site region of MIF or the target polypeptide, which can be prepared from natural sources or produced recombinantly, as described above, or an immunogenic fragment of a MIF/target polypeptide (e.g., immunogenic sequences including 8-30 or more contiguous amino acid sequences), including synthetic peptides, as described above. A non-immunogenic peptide portion of a MIF/target polypeptide can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (Harlow and Lane, supra, 1992).

Methods for raising polyclonal antibodies, for example, in a rabbit, goat, mouse, or other mammal, are well known in the art. In addition, monoclonal antibodies may be obtained using methods that are well known and routine in the art (Harlow and Lane, supra, 1992). For example, spleen cells from a target polypeptide-immunized mammal can be fused to an appropriate myeloma cell line such as SP/02 myeloma cells to produce hybridoma cells. Cloned hybridoma cell lines may be screened using a labeled target polypeptide or functional fragment thereof to identify clones that secrete target polypeptide monoclonal antibodies having the desired specificity. Hybridomas expressing target polypeptide monoclonal antibodies having a desirable specificity and affinity may be isolated and utilized as a continuous source of the antibodies, which are useful, for example, for preparing standardized kits. Similarly, a recombinant phage that expresses, for example, a single chain anti-target polypeptide also provides a monoclonal antibody that may be employed for preparing standardized kits.

Applications and Methods Utilizing Inhibitors of MIF

Inhibitors of MIF have a variety of applicable uses, as noted above. Candidate inhibitors of MIF may be isolated or procured from a variety of sources, such as bacteria, fungi, plants, parasites, libraries of chemicals (small molecules), peptides or peptide derivatives and the like. Further, one of skill in the art recognize that inhibition has occurred when a statistically significant variation from control levels is observed.

Given the various roles of MIF in pathology and homeostasis, inhibition of MIF activity or MIF extracellular localization may have a therapeutic effect. For example, recent studies have demonstrated that MIF is a mediator of endotoxemia, where anti-MIF antibodies fully protected mice from LPS-induced lethality. See Bernhagen et al., *Nature* 365:756-759, 1993; Calandra et al., *J. Exp. Med.* 179:1895-1902, 1994; Bernhagen et al., *Trends Microbiol.* 2:198-201, 1994. Further, anti-MIF antibodies have markedly increased survival in mice challenged with gram-positive bacteria that induces septic shock. Bernhagen et al., *J. Mol. Med.* 76:151-161, 1998. Other studies have demonstrated the role of MIF in tumor cell growth and that anti-sense inhibition of MIF leads to resistance to apoptotic stimuli. Takahashi et al., *Mol. Med.* 4:707-714, 1998; Takahashi et al., *Microbiol. Immunol.* 43(1):61-67, 1999. In addition, the finding that MIF is a counterregulator of glucocorticoid action indicates that methods of inhibiting MIF extracellular localization may allow for treatment of a variety of pathological conditions, including autoimmunity, inflammation, endotoxemia, and adult respiratory distress syndrome, inflammatory bowel disease, otitis media, inflammatory joint disease and Crohn's disease. Bernhagen et al., *J. Mol. Med.* 76:151-161, 1998; Calandra et al., *Nature* 377:68-71, 1995; Donnelly et al., *Nat. Med.* 3:320-323, 1997. Because MIF is also recognized to be angiogenic, the inhibition of this cytokine may have anti-angiogenic activity and particular utility in angiogenic diseases that include, but are not limited to, cancer, diabetic retinopathy, psoriasis, angiopathies, fertility, obesity and genetic diseases of glucocorticoid dysfunction like Cushings and Addisons disease.

The inhibitors of MIF activity or export may be employed therapeutically and also utilized in conjunction with a targeting moiety that binds a cell surface receptor specific to particular cells. Administration of inhibitors or enhancers generally follows established protocols. Compositions of preferred embodiments may be formulated for the manner of administration indicated, including for example, for oral, nasal, venous, intracranial, intraperitoneal, subcutaneous, or intramuscular administration. Within other embodiments, the compositions described herein may be administered as part of a sustained release implant. Within yet other embodiments, compositions of preferred embodiments may be formulized as a lyophilizate, utilizing appropriate excipients that provide stability as a lyophilizate, and subsequent to rehydration.

In another embodiment, pharmaceutical compositions containing one or more inhibitors of MIF are provided. For the purposes of administration, the compounds of preferred embodiments may be formulated as pharmaceutical compositions. Pharmaceutical compositions of preferred embodiments comprise one or more MIF inhibitors of preferred embodiments and a pharmaceutically acceptable carrier and/or diluent. The inhibitor of MIF is present in the composition in an amount which is effective to treat a particular disorder, that is, in an amount sufficient to achieve decreased MIF levels or activity, symptoms, and/or preferably with acceptable toxicity to the patient. Preferably, the pharmaceutical compositions of preferred embodiments may include an inhibitor of MIF in an amount from less than about 0.01 mg to more than about 1000 mg per dosage depending upon the route of administration, preferably about 0.025, 0.05, 0.075, 0.1, 0.2, 0.3, 0.4, 0.5, 0.6, 0.7, 0.8, or 0.9 mg to about 65, 70, 75, 80, 85, 90, 95, 100, 125, 150, 175, 200, 225, 250, 300, 350, 375, 400, 425, 450, 500, 600, 700, 800, or 900 mg, and more preferably from about 1, 2, 3, 4, 5, 6, 7, 8, 9, 10, 15, 20, or 25 mg to about 30, 35, 40, 45, 50, 55, or 60 mg. In certain embodiments, however, lower or higher dosages than those mentioned above may be preferred. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, or tablets that contain, in addition to an inhibitor of MIF, diluents, dispersing and surface-active agents, binders, and lubricants. One skilled in this art may further formulate the inhibitor of MIF in an appropriate manner, and in accordance with accepted practices, such as those described in *Remington's Pharmaceutical Sciences*, Gennaro, Ed., Mack Publishing Co., Easton, Pa. 1990.

In addition, prodrugs are also included within the context of preferred embodiments. Prodrugs are any covalently bonded carriers that release a compound of structure (Ia) or (Ib) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structures (Ia) and (Ib) may have chiral centers and may occur as racemates, racemic mixtures and as individual enantiomers or diastereomers. All such isomeric forms are included within preferred embodiments, including mixtures thereof. Furthermore, some of the crystalline forms of the compounds of structures (Ia) and (Ib) may exist as polymorphs, which are included in preferred embodiments. In addition, some of the compounds of structures (Ia) and (Ib) may also form solvates with water or other organic solvents. Such solvates are similarly included within the scope of the preferred embodiments.

In another embodiment, a method is provided for treating a variety of disorders or illnesses, including inflammatory diseases, arthritis, immune-related disorders, and the like. Such methods include administering of a compound of preferred embodiments to a warm-blooded animal in an amount sufficient to treat the disorder or illness. Such methods include systemic administration of an inhibitor of MIF of preferred embodiments, preferably in the form of a pharmaceutical composition. As used herein, systemic administration includes oral and parenteral methods of administration. For oral administration, suitable pharmaceutical compositions of an inhibitor of MIF include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of preferred embodiments can be prepared in aqueous injection solutions that may contain, in addition to the inhibitor of MIF activity and/or export, buffers, antioxidants, bacteriostats, and other additives commonly employed in such solutions.

As mentioned above, administration of a compound of preferred embodiments can be employed to treat a wide variety of disorders or illnesses. In particular, the compounds of preferred embodiments may be administered to a warm-blooded animal for the treatment of inflammation, cancer, immune disorders, and the like.

MIF inhibiting compounds may be used in combination therapies with other pharmaceutical compounds. In preferred embodiments, the MIF inhibiting compound is present in combination with conventional drugs used to treat diseases or conditions wherein MIF is pathogenic or wherein MIF plays a pivotal or other role in the disease process. In particularly preferred embodiments, pharmaceutical compositions are provided comprising one or more MIF inhibiting compounds, including, but not limited to compounds of structures (1a) or (1b), in combination with one or more additional pharmaceutical compounds, including, but not limited to drugs for the treatment of various cancers, asthma or other respiratory diseases, sepsis, arthritis, inflammatory bowel disease (IBD), or other inflammatory diseases, immune disorders, or other diseases or disorders wherein MIF is pathogenic.

In particularly preferred embodiments, one or more MIF inhibiting compounds are present in combination with one or more nonsteroidal anti-inflammatory drugs (NSAIDs) or other pharmaceutical compounds for treating arthritis or other inflammatory diseases. Preferred compounds include, but are not limited to, celecoxib; rofecoxib; NSAIDS, for example, aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In particularly preferred embodiments, one or more MIF inhibiting compounds are present in combination with one or more beta stimulants, inhalation corticosteroids, antihistamines, hormones, or other pharmaceutical compounds for treating asthma, acute respiratory distress, or other respiratory diseases. Preferred compounds include, but are not limited to, beta stimulants, for example, commonly prescribed bronchodilators; inhalation corticosteroids, for example, beclomethasone, fluticasone, triamcinolone, mometasone, and forms of prednisone such as prednisone, prednisolone, and methylprednisolone; antihistamines, for example, azatadine, carbinoxamine/pseudoephedrine, cetirizine, cyproheptadine, dexchlorpheniramine, fexofenadine, loratadine, promethazine, tripelennamine, brompheniramine, cholopheniramine, clemastine, diphenhydramine; and hormones, for example, epinephrine.

In particularly preferred embodiments, one or more MIF inhibiting compounds are present in combination with pharmaceutical compounds for treating IBD, such as azathioprine or corticosteroids, in a pharmaceutical composition.

In particularly preferred embodiments, one or more MIF inhibiting compounds are present in combination with pharmaceutical compounds for treating cancer, such as paclitaxel, in a pharmaceutical composition.

In particularly preferred embodiments, one or more MIF inhibiting compounds are present in combination with immunosuppresive compounds in a pharmaceutical composition. In particularly preferred embodiments, one or more MIF inhibiting compounds are present in combination with one or more drugs for treating an autoimmune disorder, for example, Lyme disease, Lupus (e.g., Systemic Lupus Erythematosus (SLE)), or Acquired Immune Deficiency Syndrome (AIDS). Such drugs may include protease inhibitors, for example, indinavir, amprenavir, saquinavir, lopinavir, ritonavir, and nelfinavir; nucleoside reverse transcriptase inhibitors, for example, zidovudine, abacavir, lamivudine, idanosine, zalcitabine, and stavudine; nucleotide reverse transcriptase inhibitors, for example, tenofovir disoproxil fumarate; non nucleoside reverse transcriptase inhibitors, for example, delavirdine, efavirenz, and nevirapine; biological response modifiers, for example, etanercept, infliximab, and other compounds that inhibit or interfere with tumor necrosing factor; antivirals, for example, amivudine and zidovudine.

In particularly preferred embodiments, one or more MIF inhibiting compounds are present in combination with pharmaceutical compounds for treating sepsis, such as steroids or anti-infective agents. Examples of steroids include corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone. Examples of anti-infective agents include anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscamet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

In the treatment of certain diseases, it may be beneficial to treat the patient with a MIF inhibitor in combination with an anesthetic, for example, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocalne, and phenazopyridine.

EXAMPLES

The inhibitors of MIF of preferred embodiments may be prepared and screened for inhibition of activity or export as described in the following examples.

Example 1

Macrophage Migration Assay

Macrophage migration is measured by using the agarose droplet assay and capillary method as described by Harrington and Stastny et al., *J. Immunol.* 110(3):752-759, 1973. Briefly, macrophage-containing samples are added to hematocrit tubes, 75 mm long with a 1.2 mm inner diameter. The tubes are heat sealed and centrifuged at 100×G for 3 minutes, cut at the cell-fluid interface and imbedded in a drop of silicone grease in Sykes-Moore culture chambers. The culture chambers contain either a control protein (BSA) or samples. Migration areas are determined after 24 and 48 hours of incubation at 37° C. by tracing a projected image of the macrophage fans and measuring the areas of the migration by planimetry.

Alternatively, each well of a 96-well plate is pre-coated with one microliter of liquid 0.8% (w/v) Sea Plaque Agarose in water dispensed onto the middle of each well. The plate is then warmed gently on a light box until the agarose drops are just dry. Two microliters of macrophage containing cell suspensions of up to 25% (v/v) in media (with or without MIF or other controls), containing 0.2% agarose (w/v) and heated to 37° C. is added to the precoated plate wells and cooled to 4° C. for 5 min. Each well is then filled with media and incubated at 37° C. under 5% $CO_2$-95% air for 48 hr. Migration from the agarose droplets is measured at 24 and 48 hr by determining the distance from the edge of the droplet to the periphery of migration.

Migration Assay

Monocyte migration inhibitory activities of recombinant murine and human wild-type and murine mutant MIF are analyzed by use of human peripheral blood mononuclear cells or T-cell depleted mononuclear cells in a modified Boyden chamber format. Calcein AM-labeled monocytes are suspended at 2.5 to $5 \times 10^6$/mL in RPMI 1640 medium (medium for the growth of human leukemia cells in monolayer or suspension cultures, from Roswell Park Memorial Institute), with L-glutamine (without phenol red) and 0.1 mg/mL human serum albumin or bovine serum albumin. An aliquot (200 µL) of cell suspension is added to wells of a U-bottom 96-well culture plate (Costar, Cambridge, Mass.) prewarmed to 37° C. MIF in RPMI 1640 is added to the cell suspension to yield final concentrations of 1, 10, 100, and 1000 ng/mL. The culture plate is placed into the chamber of a temperature-controlled plate reader, mixed for 30 s, and incubated at 37° C. for 10-20 min. During the incubation, 28 µL of prewarmed human monocyte chemotactic protein 1 (MCP-1; Pepro Tech., Inc., Rocky Hill, N.J.) at 10 or 25 ng/mL or RPMI 1640 with 0.1 mg/mL HSA is added to the bottom well of a ChemoTX plate (Neuro Probe Inc., Gaithersburg, Md.; 3 mm well diameter, 5 µM filter pore size). The filter plate is carefully added to the base plate. Treated cell suspensions are removed from the incubator and 30 µL is added to each well of the filter plate. The assembled plate is incubated for 90 min. at 37° C. in a humidified chamber with 5% $CO_2$. Following incubation, the cell suspension is aspirated from the surface of the filter and the filter is subsequently removed from the base plate and washed three times by adding 50 µL of 1×HBSS⁻ (Hanks' Balance Salt Solution in the 1× concentration) to each filter segment. Between washes, a squeegee (NeuroProbe) is employed to remove residual HBSS⁻. The filter is air-dried and then read directly in the fluorescent plate reader, with excitation at 485 nm and emission at 535 nm. Chemotactic or random migration indices are defined as average filter-bound fluorescence for a given set of wells divided by average fluorescence of filters in wells containing neither MCP-1 nor MIF. Titration of fluorescently labeled cells revealed that levels of fluorescence detected in this assay have a linear relationship to cell number (not shown).

Tautomerase Assay

The tautomerization reaction is carried out essentially as described by Rosengren et al., *Mol. Med* 2(1):143-149, 1996. D-dopachrome conversion to 5,6-dihydroxyindole-2-carboxylic acid is assessed. 1 ml sample cuvettes containing 0.42 mM substrate and 1.4 µg of MIF in a sample solution containing 0.1 mM EDTA and 10 mM sodium phosphate buffer, pH 6.0 are prepared and the rate of decrease in iminochrome absorbance is followed at 475 nm. L-dopachrome is employed as a control. In addition, the reaction products can be followed using an HPLC, utilizing a mobile phase including 20 mM $KH_2PO_4$ buffer (pH 4.0) and 15% methanol with a flow rate of 1.2 ml/min. Fluorimetric detection is followed at 295/345 nm.

Alternatively, the tautomerization reaction utilizing phenylpyruvate or (p-hydroxyphenyl)pyruvate is carried out essentially as described by Johnson et al., *Biochem.* 38:16024-16033, 1999. In this version, ketonization of phenylpyruvate is monitored at 288 nm ($\epsilon$=17300 $M^{-1}$ $cm^{-1}$) and the ketonization of (p-hydroxyphenyl)pyruvate is monitored at 300 nm ($\epsilon$=21600 $M^{-1}$ $cm^{-1}$). The assay mixture contains 50 mM $Na_2HPO_4$ buffer (1 mL, pH 6.5) and an aliquot of a solution of MIF sufficiently dilute (0.5-1.0 µL of a 2.3 mg/mL solution, final concentration of 93-186 nM) to yield an initial liner rate. The assay is initiated by the addition of a small quantity (1-3.3 µL) of either phenylpyruvate or (p-hydroxyphenyl)pyruvate from stock solutions made up in ethanol. The crystalline forms of phenylpyruvate and (p-hydroxyphenyl)pyruvate exist exclusively as the enol isomers (Larsen et al., *Acta Chem. Scand. B* 28:92-96, 1974). The concentration of substrate may range from 10 to 150 M, with no significant inhibition of MIF activity by ethanol observed at less than 0.5% v/v.

Immunoprecipitation and Western Blot Analysis

Cell culture experiments are designed to characterize the activity of candidate compounds, MIF expression, trafficking, and export. Cell and conditioned medium fractions are prepared for immunoprecipitation essentially as described previously (Florkiewicz et al., *Growth Factors* 4:265-275, 1991; Florkiewicz et al., *Ann. N.Y. Acad. Sci.* 638:109-126) except that 400 µl of lysis buffer (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) is added to the medium fraction after clarification by centrifugation in a microfuge for 15 minutes. Cell or medium fractions are incubated with monoclonal or polyclonal antibodies to MIF and GammaBind™ G Sepharose® (Pharmacia LKB Biotechnology, Uppsala, Sweden) was added for an additional 30 minutes incubation. Immune complexes are sedimented by microfuge centrifugation, washed three times with lysis buffer, and four times with ice cold immunoprecipitation wash buffer (0.15M NaCl, 0.01 M Na-phosphate pH 7.2, 1% deoxycholate, 1% NP-40, 0.1% sodium dodecyl sulfate). Immune complexes are dissociated directly in SDS gel sample buffer 125 mM Tris, pH 6.8, 4% SDS, 10% glycerol, 0.004% bromphenol blue, 2 mM EGTA, and separated by 12% SDS-PAGE. The gel is processed for fluorography, dried, and exposed to X-ray film at –70° C. When neomycin phosphotransferase is immunoprecipitated, a rabbit anti-NPT antibody (5Prime-3Prime, Boulder, Colo.) was employed.

For Western blot analysis, proteins are transferred from the 12% SDS-PAGE gel to a nitrocellulose membrane (pore size 0.45 µm in cold buffer containing 25 mM 3-[dimethyl(hydroxymethyl)methylamino]-2-hydroxypropane-sulfonic acid, pH 9.5, 20% methanol for 90 minutes at 0.4 amps. For Western blotting analysis, of cell conditioned media, the media was centrifuged (10 minutes at 800 g) and the supernatants concentrated 10-fold by membrane filtration (10 kDa cut-off, Centricon-10 Amicon). Samples were then resolved on 16% SDS Tris-glycin Gel (Novex, San Diego, Calif.) under reducing condition and transferred onto nitrocellulose membrane (Novex) at 20V for 3 hours. Membrane was incubated with rabbit polyclonal anti-rat antibodies (1:1000) (Torrey Pines Biolab, San Diego, Calif.), and then with horseradish peroxidase-conjugate (1:1000)(Pierce, Rockford, Ill.). MIF was visualized by development with chloronaphtnol/$H_2O_2$. Recombinant MIF (2 ng, purchased from R&D systems, Minneapolis) was electrophoresed and transferred as a standard. Membranes are blocked in 10 mM Tris, pH 7.5, 150 mM NaCl, 5 mM $NaN_3$, 0.35% polyoxyethylene-sorbitan monolaurate, and 5% nonfat dry milk (Carnation Co., Los Angeles, Calif.) for 1 hr at room temperature. Membranes are incubated with a monoclonal antibody (Catalog Number MAB289, purchased from R&D Systems, Minneapolis, Minn.) or polyclonal (goat polyclonal serum, R&D Systems cat#AF-289-PB). Following incubation, membranes are washed at room temperature with 10 changes of buffer containing 150 mM NaCl, 500 mM sodium phosphate pH 7.4, 5 mM $NaN_3$, and 0.05% polyoxyethylene-sorbitan monolaurate. When using monoclonal antibodies, membranes are then incubated in blocking buffer containing 1 µg/ml rabbit anti-mouse IgG (H+ L, affinipure, Jackson Immuno Research Laboratories, West Grove, Pa.) for 30 minutes at room temperature. For polyclonal probing, incubation employed rabbit anti-goat (Sigma, Catalog Number G5518). Membranes are subsequently washed in 1 L of buffer described above, and incubated for 1 hr in 100 ml of blocking buffer containing 15 µCi $^{125}$I-protein A (ICN Biochemicals, Costa Mesa, Calif.), and washed with 1 L of buffer. The radiosignal is visualized by autoradiography.

Overnight conditioned media is collected from LPS (10 µg/ml) treated THP-1 cells also treated with varying amounts of candidate compounds and screened by immunoprecipitation with monoclonal or polyclonal antibodies to detect MIF binding. Conditioned media show a significant loss of detectable MIF using the monoclonal antibody in the presence of 10 µM of candidate compounds that is not observed with the polyclonal antibody. This response mirrors the effect of candidate compounds on MIF enzyme activity. Accordingly, monoclonal reactivity acts as a surrogate marker for enzymatic activity.

Varying concentrations of inhibitor analogs are added to LPS stimulated THP-1 cells and allowed to incubate overnight. The following day the amount of immunoreactive MIF detected is evaluated by ELISA. Candidate compounds inhibit the ability of the antibody to recognize MIF.

The ability of candidate compounds to decrease the immunoreactivity of MIF produced by THP-1 cells is determined. THP-1 cells are treated with 10 µg/ml of LPS and 10 µM of the candidate compound is added at various times post-LPS stimulation and immunoreactivity monitored with an anti-MIF monoclonal. Following addition of candidate compounds, immunoreactivity is rapidly lost. The activity of compounds or buffer alone controls on MIF detection is measured when the candidate compounds are initially added at various times to cell cultures and then the corresponding conditioned media samples are processed in a time dependent fashion.

The ability of candidate compounds to modulate antibody recognition of MIF is examined using pre-conditioned media, in the absence of live cells. In this experiment, LPS is added to THP1 cells in culture as describe above. Six hours later, the conditioned media is removed, clarified of cell debris and the amount of MIF determined to be 22 ng/ml. This pre-conditioned media is then divided into two groups. Both groups are incubated at 37° C. for varying periods of time before a candidate compound or buffer alone (control) is added for an additional 30 minutes of incubation at 37° C. The level of detectable MIF is then determined by ELISA using the monoclonal anti-MIF antibody for detection. The rapid loss of MIF specific ELISA signal is dependent upon the presence of the candidate compound. Control levels of MIF do not change. Accordingly, candidate compounds interact with MIF, and block the antibody's ability to subsequently interact with MIF, even in the absence of cells. As this interaction takes place at the catalytic site, or constrains catalytic activity, the loss of immunoreactivity correlates with lost enzymatic activity and/or MIF associated activities.

Extracellular Localization Assay

In order to further assess in vitro activity of candidate compounds to modulate MIF export, mouse macrophage RAW 264.7 cells (a murine macrophage cell line, American Type Culture Collection, Manassas, Va.) are selected.

Raw 264.7 macrophage ($3 \times 10^6$ cells per well) are plated in 12-well tissue culture plates (Costar) and cultured in RPMI/1% heat-inactivated fetal bovine serum (FBS) (Hyclone Laboratories, Logan, Utah). After three hours of incubation at 37° C. in a humidified atmosphere with 5% $CO_2$, nonadherent cells are removed and wells are washed twice with RPMI/1% FBS. Cells are then incubated for 24 hours with LPS (0111:B4) or TSST-1 (Toxic Shock Syndrome Toxin-1, Toxin Technology, Sarasota, Fla.), which are approximately 95% pure and resuspended in pyrogen-free water, at a concentration ranging from 1 pg/ml to 1000 ng/ml (for the dose response experiment). For time-course experiments, conditioned media of parallel cultures are removed at 0.5, 1, 2, 4, 8 and 24 hours intervals after stimulation with 1 ng/ml TSST-1 or LPS. For the inhibition studies, RAW 264.7 cells ($3 \times 10^6$ cells per well) are incubated for 24 hours with 1 ng/ml of LPS (0111:B4) or 1 ng/ml of TSST-1 in the presence of 0.01 μM to 10 μM candidate compound or buffer (as control). The MIF in cell-conditioned media is concentrated on filters and the MIF remaining in the samples is analyzed by Western blotting and MIF band densities are also measured by Stratagene Eagle Eye™.

RAW cells can be induced to express MIF by addition of either 1 ng/ml TSST-1 or LPS and cultured for 24 hours. MIF in conditioned media is measured as described above. Candidate compounds reduce immunodetectable MIF levels in conditioned media in a concentration dependent manner, as compared to cells incubated with buffer only.

Cell Culture, Transfection, and Metabolic Labeling

Target cells obtained from the American Type Culture Collection (ATCC No. CRL 1650) are cultured overnight in a 48-well plate in DMEM (Dulbecco's Modified Eagles Medium) supplemented with 10% fetal bovine serum, 2 mM L-glutamine, 1 mM sodium pyruvate, 100 nM nonessential amino acids, and 50 μg/ml gentamycin. The target cells are then transfected with 2 μg/ml of CsCl-purified plasmid DNA in transfection buffer (140 mM NaCl, 3 mM KCl, 1 mM $CaCl_2$, 0.5 mM $MgCl_2$, 0.9 mM $Na_2HPO_4$, 25 mM Tris, pH 7.4. To each well, 300 μl of the DNA in transfection buffer is added. Cells are incubated for 30 minutes at 37° C., and the buffer is aspirated. Warm medium supplemented with 100 μm chloroquine is added for 1.5 hr. This medium is removed and the cells are washed twice with complete medium. Cells are then incubated for 40-48 hr. The plasmid of interest is co-transfected with pMAMneo (glucocorticoid-inducible mammalian expression vector containing a neomycin-resistant gene, Clontech, Palo Alto, Calif.), which contains the selectable marker neomycin phosphotransferase. When 2 μg of the plasmid of interest are co-transfected with 10 μg of pMAMneo, greater than 70% of transfected cells express both MIF and neo, as determined by immunofluorescence microscopy.

For immunoprecipitation assays the target cells are metabolically pulse-labeled for 15 minutes with 100 μCi of $^{35}$S-methionine and $^{35}$S-cysteine (Trans $^{35}$S-label, ICN Biomedicals, Irvine, Calif.) in 1 ml of methionine and cysteine free DMEM. Following labeling, the cell monolayers are washed once with DMEM supplemented with excess (10 mM) unlabeled methionine and cysteine for 1-2 minutes. Cells are then cultured in 2 ml of this medium for the indicated lengths of time and the cell supernatants are immunoprecipitated for the presence of leaderless protein. For the indicated cultures, chase medium is supplemented with modulator at the indicated concentrations.

Alternatively, for analysis by ELISA, the target cells are washed once with 250 μl of 0.1 M sodium carbonate, pH 11.4, for 1 to 2 minutes and immediately aspirated. A high salt solution may alternatively be preferred. The cells are washed with media containing 0.5% FBS plus 25 μg/ml heparin and then the cells are incubated in this same medium for the indicated lengths of time. For indicated cultures, chase medium is supplemented with a modulator. For cells transfected with vector encoding a protein containing a leader sequence, such as hCG-α or any other non-heparin binding protein, the carbonate wash and heparin containing medium may be omitted.

High Throughput Screening Assay for MIF Inhibitors

The high throughput screening assay for MIF inhibitors is performed in a 96-well format using MIF produced by THP-1 cells and is performed as follows. MIF assays are performed by ELISA as indicated above. THP-1 cells are resuspended to approx. $5 \times 10^6$ cells/ml in RPMI medium containing 20 μg/ml of bacterial LPS and the cells incubated for 18-20 hours. Subsequently cell supernatant is collected and incubated with putative inhibitors. Briefly, a 96-well plate (Costar Number 3590) ELISA plate is coated with a MIF monoclonal antibody (R&D Systems Catalog Number MAB289) at a concentration of 4 μg/ml for two hours at 37° C. Undiluted culture supernate is added to the ELISA plate for a two-hour incubation at room temperature. The wells are then washed, a biotinylated MIF polyclonal antibody (R&D Systems #AF-289-PB) is added followed by Streptavidin-HRP and a chromogenic substrate. The amount of MIF is calculated by interpolation from an MIF standard curve.

HPLC Analysis of Candidate Inhibitors in Serum

Prior to evaluating the affects of any small molecule in vivo, it is desirable to be able to detect, in a quantitative fashion, the compound in a body fluid such as blood. An analytical method was established to first reproducibly detect test compounds, such as MIF inhibitors, and then measure its concentration in biological fluid.

RP-HPLC is performed with a Hewlett-Packard Model HP-1100 unit using Symmetry Shield RP-8 (4.6×75 mm id, Waters, Milford, Mass.). The mobile phase is an isocratic solution of 35% Acetonitrile/water containing 0.1% trifluroacetic acid. Absorbance is monitored at 235 nm. To measure the amount of test compound in serum, the sample serum proteins are first separated using 50% Acetonitrile (4° C. overnight) followed by centrifugation at 14000 rpm for 30 minutes. The supernatant is then analyzed by the RP-HPLC and the compound concentration calculated based on a calibration curve of known standard. According to this procedure, reverse phase HPLC is employed to detect a candidate compound in a linear range of 1.5-800 ng (R2=1) using a spiked test samples (not shown). When the above analytical technique is applied to blood serum from animals receiving candidate compounds, circulating concentrations of candidate compounds are quantitatively measured.

With the development of the above methods, it is possible to evaluate the efficacy of different routes of compound administration and to characterize bioactivity. To test time dependent serum bioavailability, animals are treated with candidate compounds by intraperitoneal injection (i.p.), and orally by gavage.

In Vivo Inhibition of MIF

The purpose for the following in vivo experiments is to confirm initial in vitro assay results using candidate compounds to inhibit MIF. LPS-induced toxicity appears to be related to an overproduction of MIF as well as TNF-$\alpha$ and IL-1$\beta$. Since animals can be protected from endotoxin shock by neutralizing or inhibiting these inflammation mediators. The present model was chosen because it provides reproducible and rapid lethal models of sepsis and septic shock.

Doses of lipopolysacchraride (LPS) are made fresh prior to each experiment. LPS (*Escherichia Coli* 0111:B4, Sigma) is reconstituted by adding 0.5% TEA (1 ml USP water+5 ml Triethylamine (Pierce)) to a vial of 5 mg endotoxin. Once reconstituted, the solution is incubated at 37° C. for 30 minutes. Subsequently, the solution is sonicated in a 56-60° C. bath sonicator for 30 seconds 3 times. Following sonication the mixture is vortexed for 3 minutes continuously. The stock solution of LPS is then ready for use.

Detection of IL-1$\beta$ and TNF-$\alpha$ and MIF in Blood

Ten 10-week-old (20±2 gram) female BALB/c mice (Charles River Laboratories, Kingston, N.Y.) are housed in a group of five per cage with free access to food and water and are acclimatized for at least one week prior to experimentation. On the day of experiment, mice are weighed and randomly distributed into groups of ten animals of equal mean body weight. Mice are injected i.p. with 200 µL of formulated candidate compounds or buffer alone immediately before the i.p. injection of LPS (*Escherichia coli* 0111:B4, 10 mg/kg or 5 mg/kg body weight) and $\beta$-D-galactosamine (50 mg/kg body weight). Each dose of LPS (0.2 ml for 20 gram mouse) is administered intraperitoneally and mixed with a final concentration of $\beta$-D-galactosamine of 50 mg per ml. Following collection of blood specimens taken from cardiac puncture, the animal is sacrificed. Typical collections are performed at 4 hours post LPS treatment. The serum is separated in a serum separator (Microtainer® Becton Dickinson, Minneapolis, N.J.) according to the manufacturer's protocol. Mouse serum Il-1$\beta$ and TNF-$\alpha$ are measured by ELISA using a "mouse IL 1$\beta$ immunoassay or mouse TNF-$\alpha$ immunoassay" kits (R&D System Minneapolis, Minn.) following manufacturer's direction. Serum MIF concentrations in mouse serum are quantified by a sandwich ELISA (ChemiKine MIF Kit, Chemicon, San Diego, Calif.). Samples are analyzed in duplicate, and results are averaged.

Murine LPS Model

Ten 8 to 10 week-old (20±2 gram) female BALB/c mice are housed and acclimatized as described above. On the day of the experiments, the mice are weighed and randomly distributed into groups of five animals of equal mean body weight. Mice are injected with 200 µl of formulated candidate compounds or their Buffer (average 20 mg/kg compound) following i.p. injection of LPS (*E. Coli* 055B5, Sigma) (40, 10, 5, 2 or 0.5 mg/kg body weight) and 50 mg/kg of $\beta$-D-galactosamine. Mice are observed every two hours during the first 18 hours and twice a day for seven days. For these studies Kaplan-Meier estimation methods are employed to assess animal survival.

For all in vivo studies, standard statistical comparisons among treatment groups are performed using the Fisher test for categorical data and the Mantel-Cox test for continuous variables. To determine if levels of serum IL-1 correlated to serum MIF, a Fisher's test is applied. The analyses are performed using Stat View 5.0 Software (Abacus Concepts, Berkeley, Calif.). All reported p values that are two-sided and of a value less than 0.05 are considered to indicate statistical significance.

An initial control experiment is conducted to determine the base line levels of endogenous MIF in the murine model system (female Balb/c mice), and further to determine the rate and extent of increase in endogenous MIF following treatment with LPS (10 mg/kg). Female Balb/c mice are treated with LPS (Sigma 0111:B1) admixed with 50 mg/kg $\beta$-D-galactosamine. The level of MIF in serum is measured by HPLC as described above at 0, 2, 5 and 6 hours following LPS/galactosamine treatment. At the initiation of this representative experiment, the baseline level of endogenous MIF is determined When mice are treated with candidate compounds (formulated in 50% aqueous solution) and 10 mg/kg of LPS there is a significant decrease in the level of circulating MIF that can be detected. In a further experiment, both MIF and IL-1$\beta$ are measured in mouse serum via ELISA. A direct and highly significant correlation between the two is observed in MIF and IL-1$\beta$. This correlation is also observed between MIF and TNF-$\alpha$. In a similar experiment, reductions in serum IL-1$\beta$ level and serum TNF-$\alpha$ level are observed following administration of 20 mg/kg of candidate compound.

Studies of experimental toxic shock induced by LPS have revealed a central role for MIF and TNF-$\alpha$. The fact that LPS stimulates macrophage-like cells to produce MIF, that in turn induce TNF-$\alpha$ secretion by macrophage like cells suggests a potential role for MIF in the pathogenesis of LPS. To test if candidate compounds can prevent LPS shock, a model of lethal LPS mediated shock in BALB/c mice sensitized with $\beta$-D-galactosamine is employed. Treatment with candidate compounds at the time of injection of a lethal dose of LPS (2, 5 and 10 mg/kg) increases survival. The effects are modulated by the concentration of LPS employed, demonstrating that when using a higher concentration of LPS, the effect of the candidate compound is saturable and hence specific.

MIF Overcomes the Effects of Candidate Compounds

Exogenous recombinant human MIF when administered with candidate compounds can reverse the beneficial effects of the compound, supporting the hypothesis that candidate compounds act to increase animal resistance to LPS by modulating MIF levels in mice serum. In this example, mice are treated with the standard LPS protocol except that in addition to 1 mg/kg LPS and 20 mg/kg of a candidate compound, some animals also receive 300 µg/kg human recombinant MIF. At 12 hours, significantly more mice survive the LPS with candidate compounds, but this survival is neutralized by the administration of MIF.

MIF Inhibitor in a Collagen Induced Arthritis Model

Twenty DBA/1LacJ mice, age 10 to 12 weeks, are immunized on Day 0 at base of the tail with bovine collagen type II (CII 100 µg) emulsified in Freunds complete adjuvant (FCA; GibcoBRL). On Day 7, a second dose of collagen is administrated via the same route (emulsified in Freunds incomplete adjuvant). On Day 14 mice are injected subcutaneously with 100 mg of LPS (055:B5). On Day 70 mice are injected 40 μg LPS (0111:B4) intraperitoneally. Groups are divided according paw thickness, which is measured by a caliper, after randomization, to create a balanced starting group. Candidate compound in buffer is given to mice on Days 71, 72, 73, and 74 (total eight doses at 0.4 mg/dose, approximately 20 mg/kg of body weight). Mice are then examined on Day 74 by two observers for paw thickness. In this experiment, subsided mice (decline of full-blown arthritis) are treated with a final i.p. injection of LPS on Day 70 to stimulate cytokine production as well as acute inflammation. Candidate compound treated mice develop mildly reduced edema of the paw compared with vehicle only treated controls. In the late time point, the animals in the treated group do not reach a full-blown expression of collagen induced arthritis as compared to its control.

In another experiment, fifteen DBA/IJ mice, age 10 to 12 weeks are immunized on Day 0 at the base of the tail with bovine collagen type II (CII 100 μg), emulsified in Freunds complete adjuvant (FCA; GibcoBRL). On Day 21, a second dose of collagen is administered via the same route, emulsified in Freunds incomplete adjuvant. On Day 28 the mice are injected subcutaneously with 100 μg of LPS (055:B5). On Day 71 the mice are injected i.p. with 40 μg LPS (0111:B4). Groups and treatment protocol are the same as described as above. On Day 74 blood samples are collected and cytokines were measured. Candidate compounds reduce serum MIF levels as compared to untreated CIA samples. An even more significant inhibition of serum TNF-α levels is detected.

Example 2

Inhibitors of MIF of certain embodiments may be prepared according to the following reaction schemes. Each of these MIF inhibitors belongs to one of the classes of compounds described above. The variables $R_1$, $R_2$, $R_3$, $R_4$, Z, and n are as defined above.

General Methods for the Synthesis of the Compounds of the Inventions

The compounds were synthesized starting from substituted or unsubstituted isatoic anhydrides. The strategies to introduce $R_2$ and/or $R_3$ groups into the compounds of structures (1a) and (1b) described above involved preparation of substituted isatoic anhydrides as precursor compounds from substituted anthranilic acids. The substituted anthranilic acids were prepared from substituted nitrobenzoic acids. In some cases, the nitro benzoic acids were obtained by nitration of appropriate benzoic acid, as shown in Reaction Scheme 1, however, any suitable method for preparation of nitrobenzoic acids may be employed.

Reaction Scheme 1

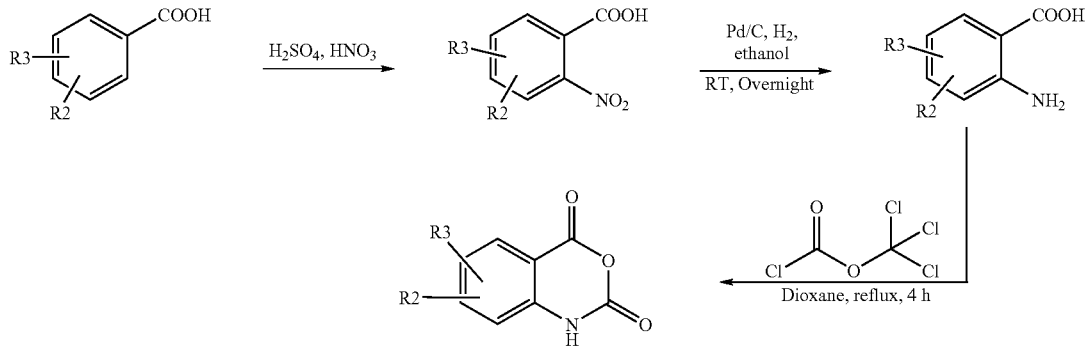

Two different methods were employed to introduce the $R_1$ group into the compounds of structures (1a) and (1b) as described above. In one method, the substituted isatoic anhydrides prepared as described in Reaction Scheme 1 were alkylated in the N-1 position, then converted to the substituted quinolinone intermediate of structure i (depicted in Reaction Scheme 2 below). Amination of intermediate i yielded amide intermediate of structure ii which was reacted with phosphorousoxychloride to yield an intermediate of type iii as depicted in Reaction Scheme 2.

Reaction Scheme 2

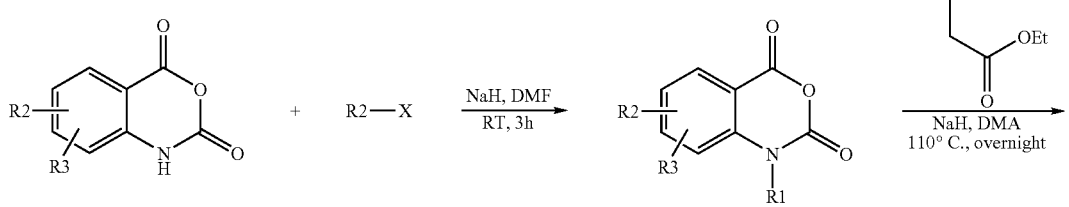

-continued

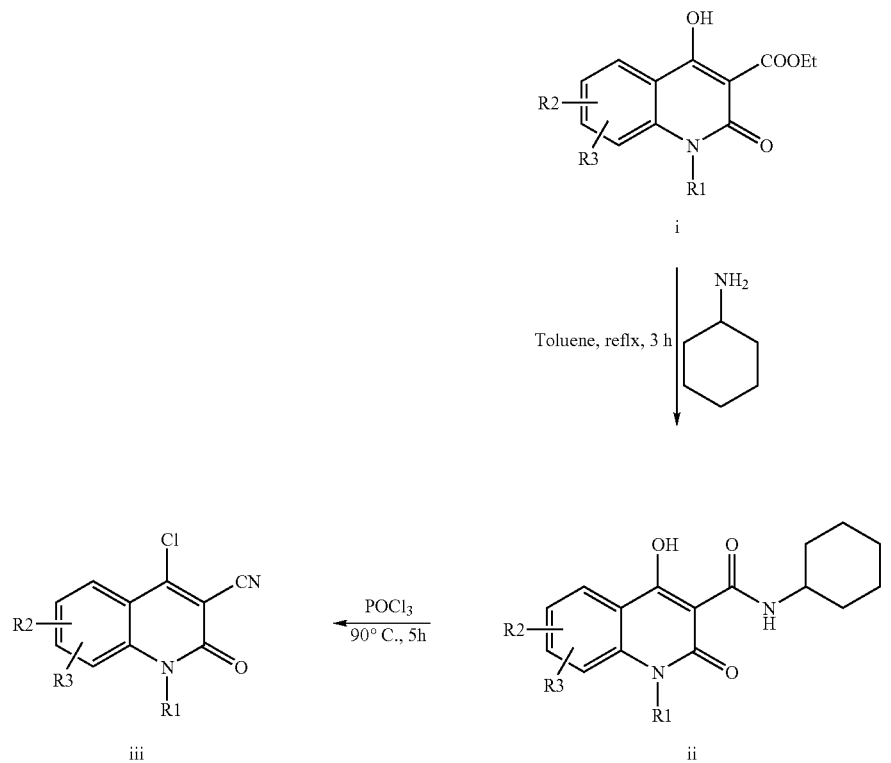

To introduce the $R_4$ group into the compounds of structures (1a) and (1b), the chloro intermediate of structure iii was either reacted with acylated piperazine or reacted first with excess piperazine to yield an intermediate of structure iv, and then acylated to yield the target compound as depicted in Reaction Scheme 3. Acylation of intermediate iv was carried out by treating the intermediate with either commercially available acyl chloride or a freshly prepared acyl chloride prepared from the reaction of the corresponding carboxylic acid and oxalyl chloride as shown in Reaction Scheme 3.

Reaction Scheme 3

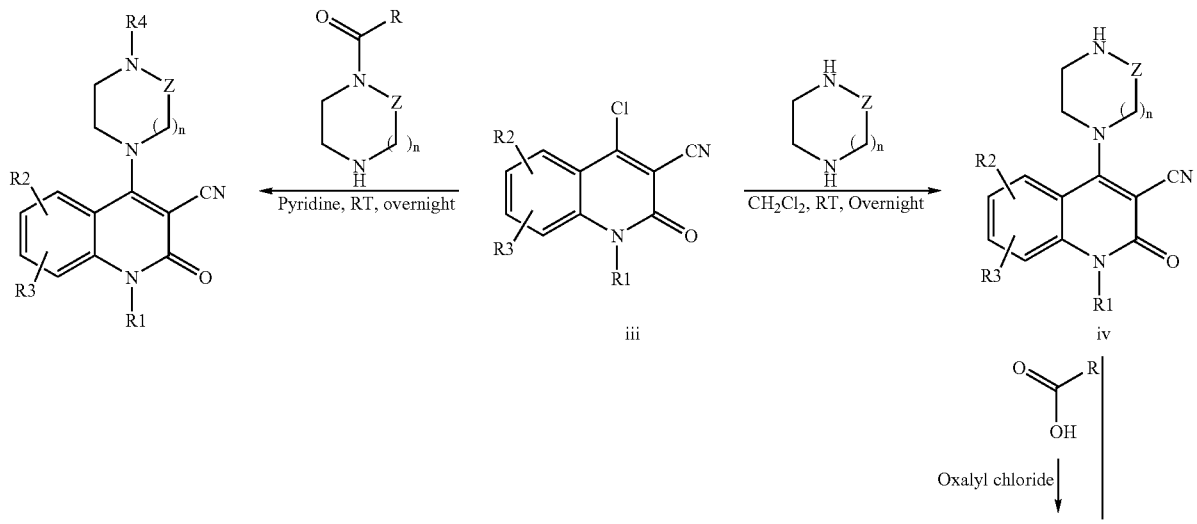

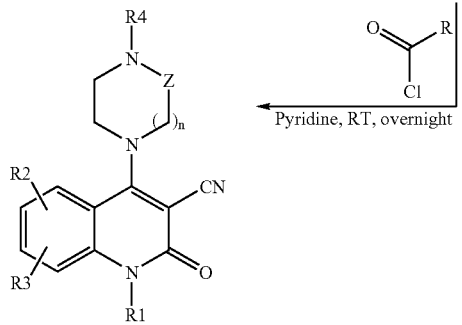

In an alternate method for introducing the $R_1$ group into the compounds of structures (1a) and (1b), the intermediate of structure ix was prepared from isatoic anhydrides and alkylated at the N-1 position in a final step. The isatoic anhydride was converted into the intermediate of structure v by treating it with diethyl malonate. The amination, followed by reaction with hot phosphorous oxychloride, of intermediate v yielded the dichloroquinolinone intermediate of structure vii. The reaction of intermediate vii with ammonium acetate in acetic acid gave intermediate of structure viii, which was treated with acyl piperazine to yield the intermediate of structure ix as depicted in Reaction Scheme 4.

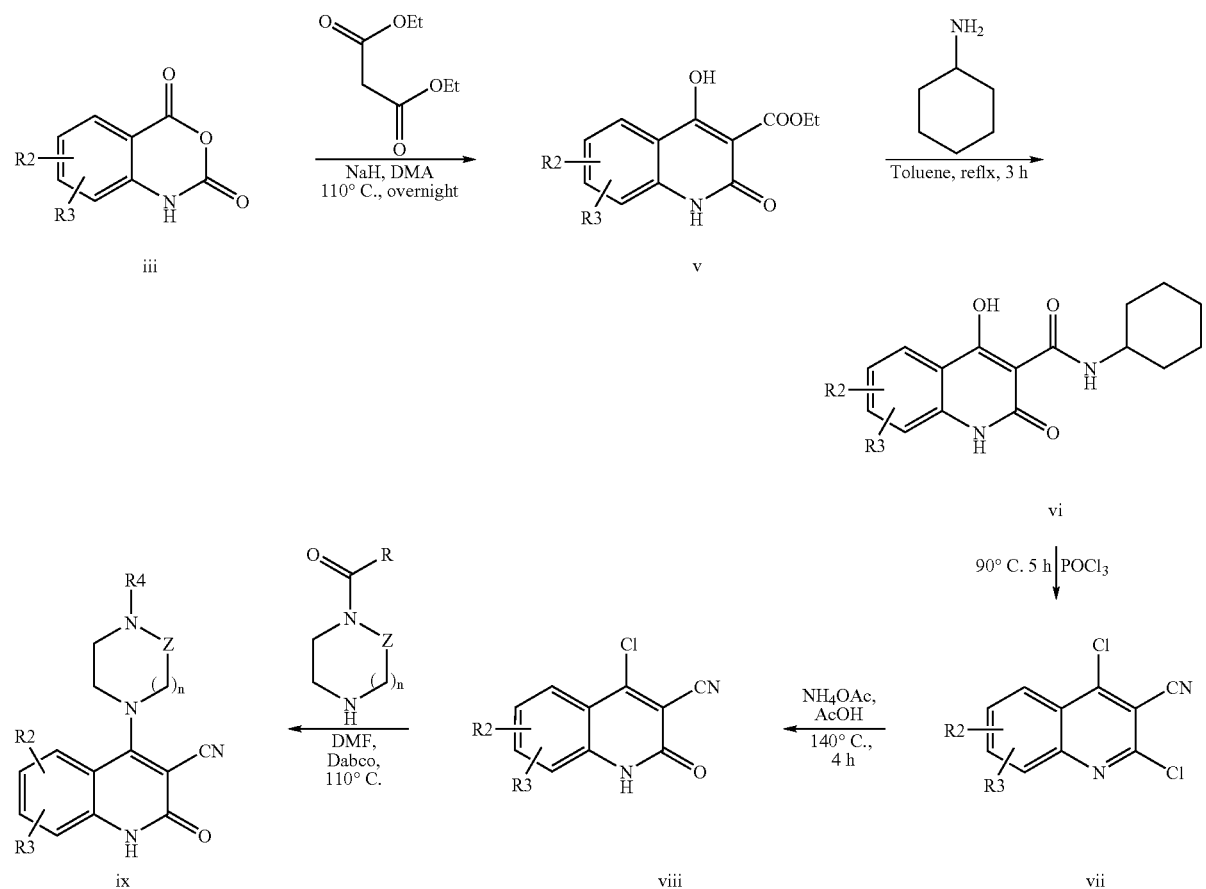

The alkylation of the N-1 position of intermediate ix yielded the desired compounds with a different $R_1$ substitution. The alkylation was carried out by either heating intermediate ix with potassium carbonate and the corresponding alkyl halide, or by treating the intermediate with sodium hydride and alkyl halide at room temperature, as depicted in Reaction Scheme 5.

Reaction Scheme 5

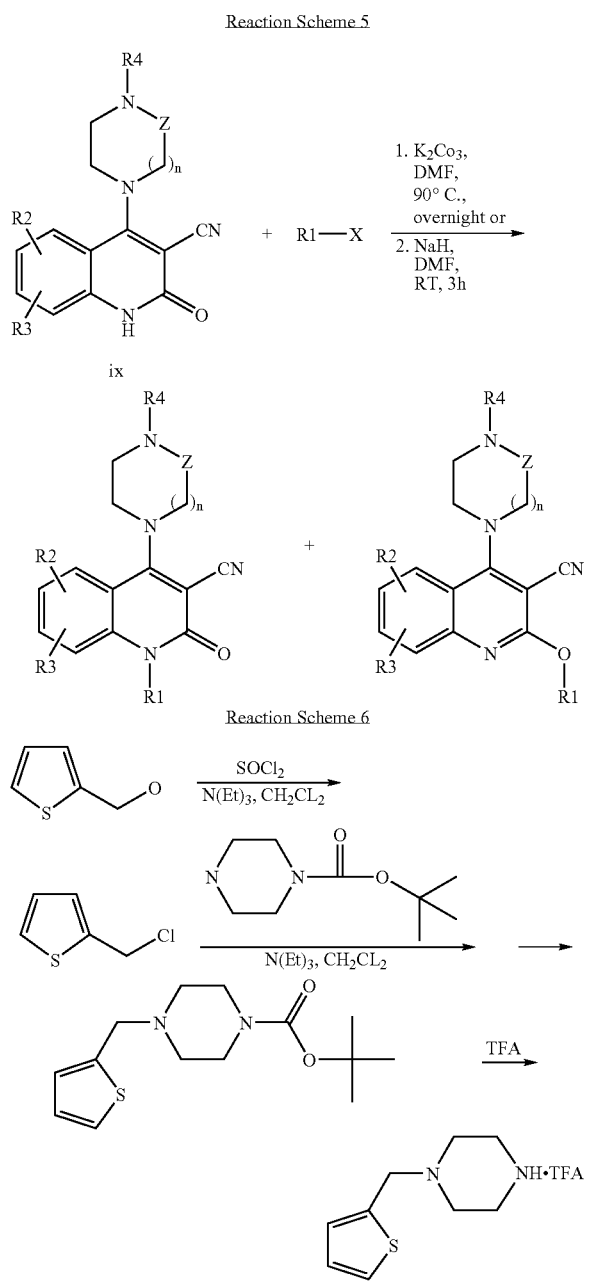

Reaction Scheme 6

Acyl and alkylpiperazines suitable for use as intermediates may be synthesized as follows. A solution of freshly distilled thionyl chloride (3.9 ml; 0.053 mol) in methylene dichloride (5 ml) was added dropwise to a stirreed solution of 2-thiophenemethanol (4.2 ml; 0.044 mol) and triethylamine (7.4 ml; 0.05 mol) in methylene dichloride (25 ml) at a temperature kept below 20° C. The temperature was then raised to 40° C. over 1 h, and the solution poured onto crushed ice. The $CH_2Cl_2$ phase was separated and dried over $MgSO_4$, then added dropwise to a stirred solution of N-Boc-piperazine (2 g; 0.011 mol) and triethylamine (1.5 ml; 0.011 mol) in $CH_2Cl_2$ (45 ml). See, e.g., Meanwell et al., *J. Med. Chem.* (1993) Vol. 36., pp. 3251-3264; Carceller et al., *J. Med. Chem.* (1993) No. 36, pp. 2984-2997. The mixture was stirred overnight at room temperature. The solvent was then removed under reduced pressure, and the residue was extracted with ether. The ether solution was evaporated under reduced pressure, and the residue was dissolved in trifluoroacetic acid (TFA) (3.3 ml; 0.043 mol) and kept during 30 min. TFA was removed under reduced pressure, the residue was triturated with ether, the precipitate was filtered off and dried in air to yield 1-(2-thienylmethyl)piperazine ditrifluoroacetate (3.16 g; 72%). See, e.g., Archer et al., *J. Chem. Soc. Perkin Trans. II.* (1983) pp. 813-819.

Reaction Scheme 7

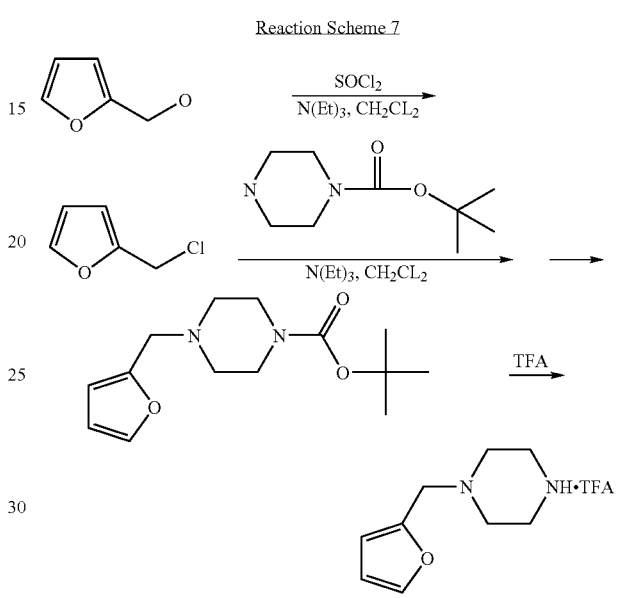

A solution of freshly distilled thionyl chloride (3.9 ml; 0.053 mol) in methylene dichloride (5 ml) was added dropwise to a stirred solution of furfuryl alcohol (3.8 ml; 0.044 mol) and triethylamine (7.4 ml; 0.05 mol) in methylene dichloride (25 ml); the temperature was maintained below 20° C. The mixture was stirred for 1 h, then the solvent was evaporated, and the residue was dissolved in $CH_2Cl_2$ (150 ml). The solution obtained was added dropwise to a stirred solution of N-Boc-piperazine (2 g; 0.011 mol) and triethylamine (4 ml; 0.029 mol) in $CH_2Cl_2$ (45 ml). The mixture was stirred overnight at room temperature, the solvent was removed under reduced pressure, and the residue was extracted with ether. The ether solution was evaporated under reduced pressure, the residue was dissolved in TFA (3.3 ml; 0.043 mol) and maintained for 30 min. TFA was removed under reduced pressure, the residue was triturated with ether, and the black precipitate obtained was filtered off. Then, the precipitate was dissolved in 200 ml of MeOH, activated charcoal was added, and the mixture was heated under reflux for 30 min. Charcoal was filtered off, the solvent was evaporated, the residue was triturated with ether. The white precipitate obtained was filtered off and dried on the air to yield 1-(2-furylmethyl)piperazine ditrifluoroacetate (1.64 g; 40%). See, e.g., Lukes et al., *Collection Czechoslov. Chem. Commun.* (1954) Vol. 19, pp. 609-610.

Preparation of 4-(Thiophene-2-carbonyl)-piperazine-1-carboxylic acid tert-butyl ester (Compound 595-03)

2-Thiophenecarbonylchloride (2.04 g, 1.49 mL) was added to a solution of tert-butyl-1-piperazinecarboxylate (2.5 g, 13.4 mmol) and DMAP (20 mg) in pyridine (15 mL) at 0° C. under $N_2$ atmosphere and stirred at room temperature for overnight. The mixture was poured into ice water, the precipitate was filtered, washed several times with water, and dried to yield white solids (3.5 g, 88%). M.P. 76° C. $^1$H NMR (DMSO-d$_6$): δ 1.42 (s, 12H), 3.40 (m, 4H), 3.61 (m, 4H), 7.12 (m, 1H), 7.43 (d, J=4.1 Hz, 1H), 7.77 (d, J=4.8 Hz, 1H). EIMS m/z 297 (M+1), 319 (M+23). Anal. (C$_{14}$H$_{20}$N$_2$O$_3$S) C, H, N.

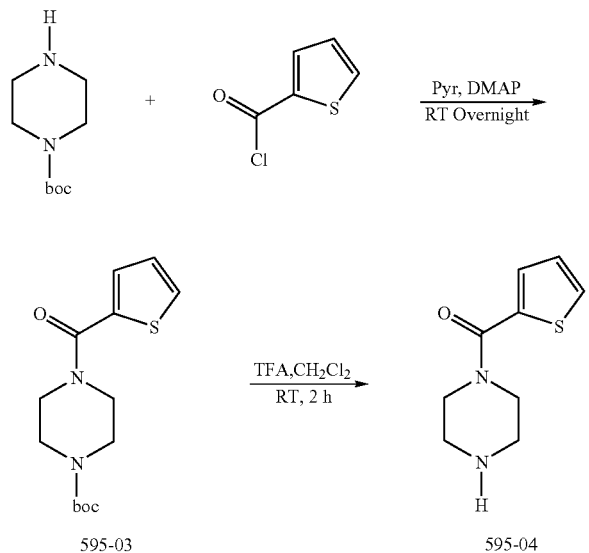

Preparation of piperazine-1-yl-thiophen-2-yl-methanone (Compound 595-04)

To a solution of 595-03 (3.5 g, 11.8 mmol) in dichloromethane (50 mL) was added trifluoroacetic acid (10 mL). The solution was stirred at room temperature for 3 h. The solvent was evaporated under vacuum and the residue was dissolved in chloroform. The organic phase was washed by saturated solution of sodium bicarbonate, dried over Na$_2$SO$_4$ and evaporated to get 2.20 g (94%) of brown viscous oil. $^1$H NMR (DMSO-d$_6$): δ 2.78 (m, 4H), 3.59 (m, 4H), 7.12 (t, J=4.1, 1H), 7.38 (d, J=4.1 Hz, 1H), 7.74 (d, J=4.8 Hz, 1H). EIMS m/z 197 (M+1).

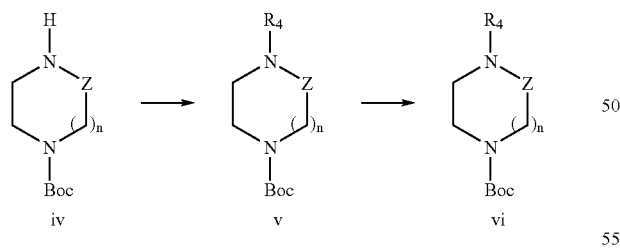

N-substituted piperazines of structure vi are useful intermediates in the preparation of MIF inhibitors. They may be prepared by deprotection of protected intermediate v (in this case, protected with N-tert-butyloxycarbonyl or "Boc" for purpose of illustration). The protected intermediate may be made from the N-protected piperazine iv by addition of the desired R$_4$ group. In the above reaction scheme, Z is —CH$_2$— or —C(=O)—; n is 0, 1 or 2, with the proviso that when n is 0, Z is —C(=O)—; R$_4$ is selected from the group consisting of —CH$_2$R$_7$, —C(=O)NR$_5$R$_6$, —C(=O)OR$_7$, —C(=O)R$_7$, R$_8$, and

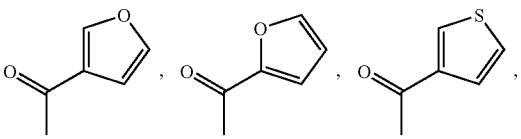

R$_5$ and R$_6$ are independently selected from the group consisting of hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ is selected from the group consisting of alkyl, substituted alkyl, aryl, substituted aryl, arylalkyl, substituted arylalkyl, heterocycle, substituted heterocycle, heterocyclealkyl, and substituted heterocyclealkyl; and R$_8$ is selected from the group consisting of hydrogen, alkyl, substituted alkyl, aryl, substituted aryl, arylalkyl, substituted arylalkyl, heterocycle, substituted heterocycle, heterocyclealkyl, and substituted heterocyclealkyl.

Example 3

The following describes the synthesis of a library of compounds of general structure 1'(a) and 1'(b) as depicted below. Compounds including "M" in the designation incorporate the CN moiety. Numerical designations in Table 1 are as given below.

In compounds that have designations including "+i", R$_{13}$ is a substituent on the oxygen atom of the quinolone group rather than the nitrogen atom, i.e., a compound of structure 1'(b), as depicted below. The designation "i" appears elsewhere in the preferred embodiments, and refers to a substituent on the oxygen atom of the quinolone group rather than the nitrogen atom.

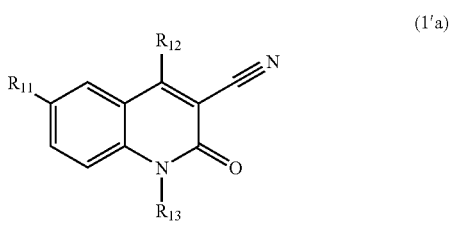

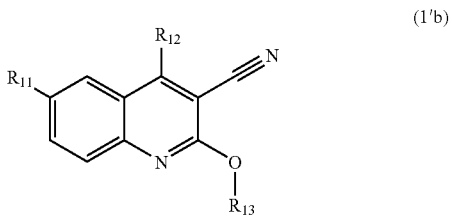

Numerical Designations for $R_{11}$ Functional Groups
| Hydrogen | Methyl | Chlorine |
|---|---|---|
| 1 | 2 | 3 |
Numerical Designations for $R_{12}$ Functional Groups
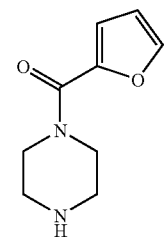
1
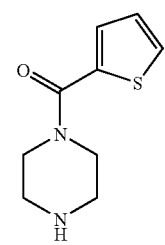
2
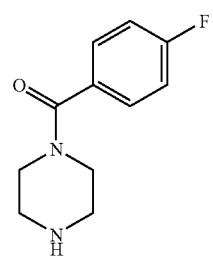
3
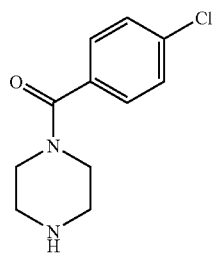
4
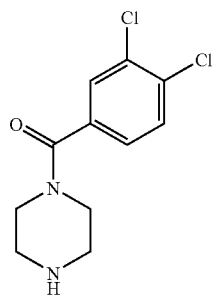
5
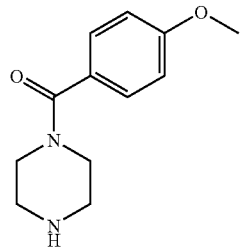
6
Numerical Designations for $R_{\_3}$ Functional Groups
Me
1
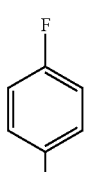
2
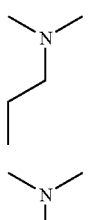
3
4
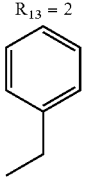
5
The numerical designations of the MIF inhibitors prepared are provided in Table 1.
TABLE 1
| $R_{13} = 1$ Methyl | $R_{13} = 2$ | $R_{13} = 4$ F | $R_{13} = 5$ | $R_{13} = 6$ |
|---|---|---|---|---|
| 1M11 | 1M12 | 1M13 | 1M14 | 1M15 + i |
| 1M21 | 1M22 | 1M23 | 1M24 | 1M25 + i |
| 1M31 | 1M32 | 1M33 | 1M34 | 1M35 + i |

TABLE 1-continued

| $R_{13} = 1$ Methyl | $R_{13} = 2$ (benzyl) | $R_{13} = 4$ (4-F-benzyl) | $R_{13} = 5$ (dimethylaminopropyl) | $R_{13} = 6$ (dimethylaminobutyl) |
|---|---|---|---|---|
| 1M41 | 1M42 | 1M43 | 1M44 | 1M45 + i |
| 1M51 | 1M52 | 1M53 | 1M54 | 1M55 |
| 1M61 | 1M62 | 1M63 | 1M64 | 1M65 |
| 2M11 | 2M12 | 2M13 | 2M14 | 2M15 |
| 2M21 | 2M22 | 2M23 | 2M24 | 2M25 + i |
| 2M31 | 2M32 | 2M33 | 2M34 | 2M35 + i |
| 2M41 | 2M42 | 2M43 | 2M44 | 2M45 + i |
| 2M51 | 2M52 | 2M53 | 2M54 | 2M55 |
| 2M61 | 2M62 | 2M63 | 2M64 | 2M65 + i |
| 3M11 | 3M12 | 3M13 | 3M14 | 3M15 + i |
| 3M21 | 3M22 | 3M23 | 3M24 | 3M25 |
| 3M31 | 3M32 | 3M33 | 3M34 | 3M35 + i |
| 3M41 | 3M42 | 3M43 | 3M44 | 3M45 + i |
| 3M51 | 3M52 | 3M53 | 3M54 | 3M55 + i |
| 3M61 | 3M62 | 3M63 | 3M64 | 3M65 + i |

Details of reaction schemes for preparing intermediates or MIF inhibitors are provided below.

Synthesis of Representative Compounds

Preparation of 4-Hydroxy-1-methyl-2-oxo-1,2-dihydro-quinoline-3-carboxylic acid ethyl ester (Compound 1)

A solution of diethyl malonate (8.16 g, 51 mmol) was added slowly to a suspension of sodium hydride (60% in mineral oil, 2.24 g, 56 mmol) in dimethylacetamide under $N_2$ atmosphere. The mixture was stirred at room temperature until the evolution of hydrogen gas ceased, then heated to 90° C. for 30 min. and cooled to room temperature. A solution of N-methylisatoic anhydride (10 g, 56 mmol) in dimethylacetamide was added slowly and the mixture was heated overnight at 120° C. The mixture was then cooled to room temperature, poured into ice water, and acidified by cold 10% HCl. The solids formed were filtered and washed several times by water to yield 8.47 g (67%) of white solids. M.P. 67° C. $^1$H NMR (DMSO-$d_6$): δ 1.30 (t, J=7.0 Hz, 3H), 3.53 (s, 3H), 4.32 (q, J=7.0 Hz, 2H), 7.30 (t, J=7.5 Hz, 1H), 7.52 (d, J=8.5 Hz, 1H), 7.75 (t, J=8.4 Hz, 1H), 8.04 (d, J=7.8 Hz, 1H), 13.03 (s, 1H). EIMS m/z 248 (M+1), 270 (M+23). Anal. ($C_{13}H_{13}NO_4$) C, H, N.

Preparation of 4-Hydroxy-1-methyl-2-oxo-1,2-dihydro-quinoline-3-carboxylic acid cyclohexylamide (Compound 2)

Cyclohexylamine (2.0 mL, 18.20 mmol) was added to a solution of Compound 1 (2.25 g, 9.1 mmol) in toluene (20 mL) and refluxed for 4 h. The solution was cooled and the solvent was evaporated under vacuum. The residue obtained was suspended in water, briefly sonicated, and filtered to yield 1.9 g (70%) of white solids. M.P. 145° C. $^1$H NMR (DMSO-$d_6$): δ 1.26 (m, 1H), 1.38 (m, 4H), 1.54 (m, 1H), 1.68 (m, 2H), 1.86 (m, 2H), 3.62 (s, 3H), 3.87 (m, 1H), 7.37 (t, J=7.5 Hz, 1H), 7.63 (d, J=8.5 Hz, 1H), 7.80 (t, J=8.4 Hz, 1H), 8.09 (d, J=7.8 Hz, 1H), 10.46 (s, 1H), 17.46 (s, 1H). EIMS m/z 301 (M+1), 323 (M+23). Anal. ($C_{17}H_{20}N_2O_3$) C, H, N.

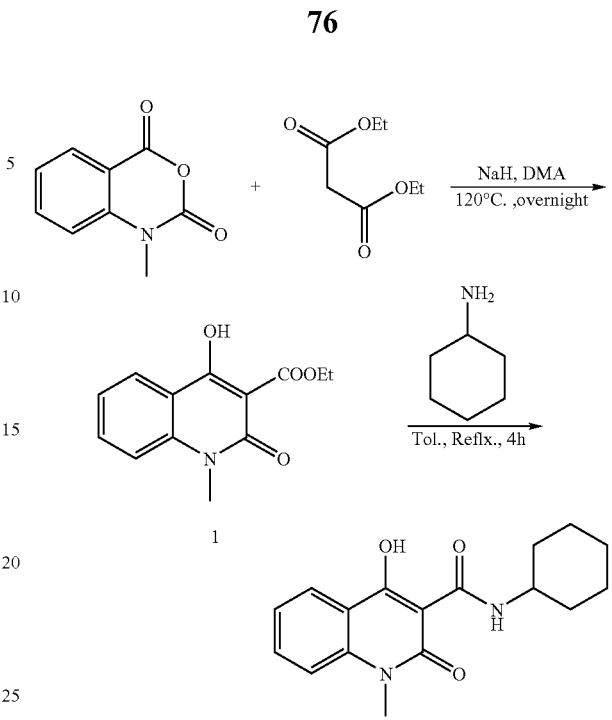

Preparation of 4-Chloro-1-methyl-2-oxo-1,2-dihydro-quinoline-3-carbonitrile (Compound 3)

A solution of Compound 2 (1.5 g, 5 mmol) in 20 mL phosphorus oxychloride was heated at 90° C. for 2 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 903 mg (82%) of white solids. M.P. 235° C. $^1$H NMR (DMSO-$d_6$): 3.66 (s, 3H), 7.50 (t, J=7.7 Hz, 1H), 7.74 (d, J=8.6 Hz, 1H), 7.91 (t, J=8.7 Hz, 1H), 8.08 (d, J=7.6 Hz, 1H). EIMS m/z 219 (M+1), 241 (M+23). Anal. ($C_{11}H_7ClN_2O$) C, H, N.

Preparation of 1-Methyl-2-oxo-4-[4-(thiophene-2-carbonyl)-piperazin-1-yl]-1,2-dihydro-quinolin-3-carbonitrile (Compound 4)

Piperazine-1-yl-thiophen-2-yl-methanone (600 mg, 3.06 mmol) was added to a solution of Compound 3 (319 mg, 1.46 mmol) in toluene (40 mL) and heated overnight at 120° C. The solvent was removed under vacuum. The residue was suspended in water, sonicated, and filtered to yield 540 mg (98%) of white solids. M.P. 247° C. $^1$H NMR (DMSO-$d_6$): δ 3.58 (s, 3H), 3.63 (m, 4H), 3.92 (m, 4H), 7.16 (t, J=4.8 Hz, 1H), 7.33 (t, J=7.5 Hz, 1H), 7.48 (d, J=3.5 Hz, 1H), 7.59 (d, J=8.5 Hz, 1H), 7.75 (t, J=7.25, 2H), 7.79 (d, J=4.8 Hz, 1H) 7.92 (d, J=7.5 Hz, 1H). EIMS m/z 379 (M+1), 401 (M+23). Anal. ($C_{20}H_{18}N_4O_2S$) C, H, N.

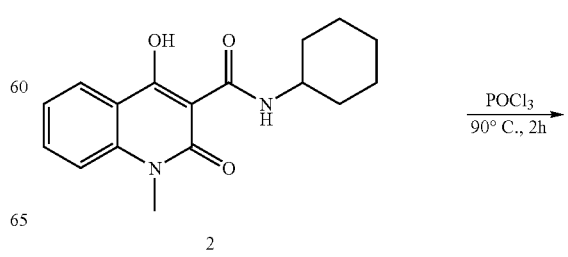

-continued

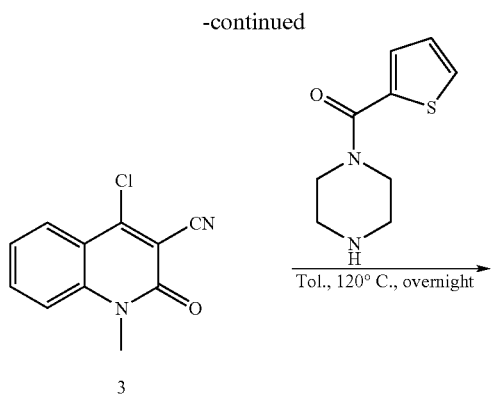

3

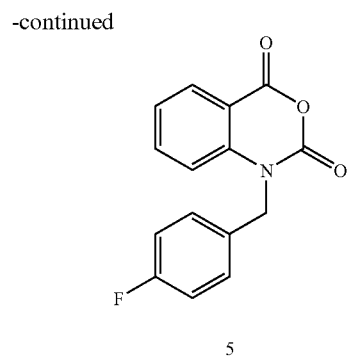

5

Preparation of 1-(4-Fluorobenzyl)-4-hydroxy-2-oxo-1,2-dihydro-quinoline-3-carboxylic acid ethyl ester (Compound 6)

A solution of diethyl malonate (8.0 g, 51 mmol) was added slowly to a suspension of sodium hydride (60% in mineral oil, 2.21 g, 55 mmol) in dimethylacetamide under $N_2$ atmosphere. The mixture was stirred at room temperature until the evolution of hydrogen gas ceased, then heated to 90° C. for 30 min. and cooled to room temperature. A solution of Compound 5 (15 g, 53 mmol) in dimethylacetamide was added slowly to the mixture, which was heated overnight at 120° C. The mixture was cooled to room temperature, poured into ice water, and acidified by cold 10% HCl. The solids formed were filtered and washed several times by water to yield 13.37 g (78%) of white solids. M.P. 116-120° C. $^1$H NMR (DMSO-$d_6$): δ 1.31 (t, J=7.0 Hz, 3H), 4.36 (q, J=7.0 Hz, 2H), 5.43 (s, 2H), 7.13 (m, 2H), 7.23-7.30 (m, 3H), 7.37 (d, J=8.5 Hz, 1H), 7.63 (t, J=7.0 Hz, 1H), 8.08 (d, J=7.6 Hz, 1H), 13.20 (s, 1H). EIMS m/z 342 (M+1), 364 (M+23). Anal. ($C_{19}H_{16}FNO_4$) C, H, N.

4

Preparation of 1-(4-Fluorobenzyl)-1H-benzo[d][1,3]oxazine-2,4-dione (Compound 5)

A solution of isatoic anhydride (20 g, 122 mmol) in dimethylformamide (DMF) was added to a suspension of NaH (60% in mineral oil, 5.39 g, 135 mmol) in DMF and stirred at room temperature for 1 h. Then, 4-fluorobenzyl bromide (16.8 mL, 135 mmol) was added and the mixture stirred at room temperature for 4 h. The solution was poured into water and the solids formed were filtered, washed several times by water and dried. The solids were suspended in hexane, sonicated briefly, filtered, and washed by hexane to yield 30 g (90%) of white solids. M.P. 167° C. $^1$H NMR (DMSO-$d_6$): δ 5.27 (s, 2H), 7.17 (t, J=8.8 Hz, 2H), 7.25 (d, J=8.4 Hz, 1H), 7.31 (t, J=7.4 Hz, 1H), 7.47 (m, 2H), 7.74 (t, J=7.0 Hz, 1H), 8.02 (d, J=7.8 Hz, 1H). Anal. ($C_{15}H_{10}FNO_3$) C, H, N.

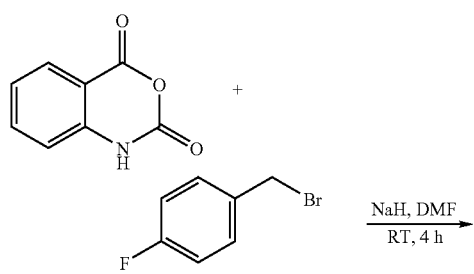

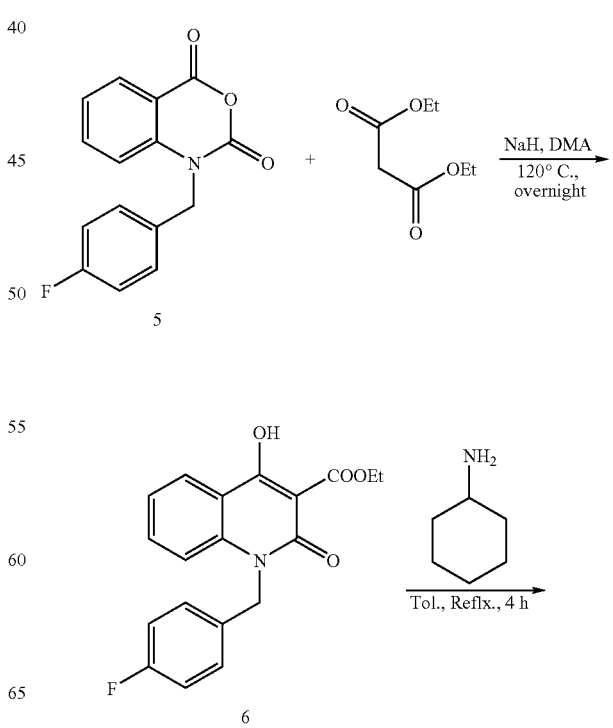

6

-continued

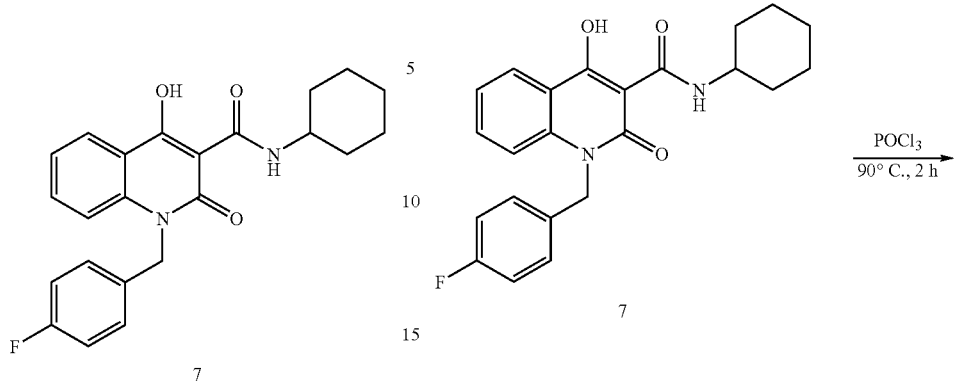

Preparation of 1-(4-Fluorobenzyl)-4-hydroxy-2-oxo-1,2-dihydro-quinoline-3-carboxylic acid cyclohexylamide (Compound 7)

Cyclohexylamine (0.67 mL, 5.85 mmol) was added to a solution of Compound 6 (1.0 g, 2.92 mmol) in toluene (20 mL) and refluxed for 4 h. The solution was cooled and the solvent was evaporated under vacuum. The residue obtained was suspended in water, briefly sonicated, and filtered. The crude product was recrystalized by ether to yield 1.0 g (87%) of white solids. M.P. 168° C. $^1$H NMR (DMSO-d$_6$): δ 1.26 (m, 1H), 1.36 (m, 4H), 1.55 (m, 1H), 1.68 (m, 2H), 1.89 (m, 2H), 3.88 (m, 1H), 5.51 (s, 2H), 7.13 (m, 2H), 7.25 (m, 2H), 7.33 (t, J=7.5 Hz, 1H), 7.45 (d, J=8.5 Hz, 1H), 7.70 (t, J=8.4 Hz, 1H), 8.12 (d, J=7.9 Hz, 1H), 10.35 (s, 1H), 17.66 (s, 1H). EIMS m/z 395 (M+1), 417 (M+23). Anal. ($C_{23}H_{23}FN_2O_3$) C, H, N.

Preparation of 4-Chloro-1-(4-fluorobenzyl)-2-oxo-1,2-dihydro-quinoline-3-carbonitrile (Compound 8)

A solution of Compound 7 (0.7 g, 1.77 mmol) in 20 mL neat phosphorus oxychloride was heated at 90° C. for 2 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 420 mg (76%) of white solids. M.P. 231° C. $^1$H NMR (DMSO-d$_6$): δ 5.54 (s, 2H), 7.13 (m, 2H), 7.34 (m, 2H), 7.46 (t, J=7.5 Hz, 1H), 7.55 (d, J=8.5 Hz, 1H), 7.80 (t, J=8.4 Hz, 1H), 8.12 (d, J=7.9 Hz, 1H). EIMS m/z 335 (M+23). Anal. ($C_{17}H_{10}ClFN_2O$) C, H, N.

Preparation of 1-(4-Fluorobenzyl)-2-oxo-4-[4-(thiophene-2-carbonyl)-piperazin-1-yl]-1,2-dihydro-quinolin-3-carbonitrile (Compound 9)

Piperazine-1-yl-thiophen-2-yl-methanone (234 mg, 1.19 mmol) was added to a solution of Compound 8 (170 mg, 0.54 mmol) in toluene (40 mL) and heated overnight at 120° C. The solvent was removed under vacuum. The residue was suspended in water, sonicated, and filtered to yield 247 mg (97%) of white solids. M.P. 258° C. $^1$H NMR (DMSO-d$_6$): δ 3.69 (m, 4H), 3.94 (m, 4H), 5.47 (s, 2H), 7.16 (m, 3H), 7.28 (m, 3H), 7.43 (d, J=8.5 Hz, 1H), 7.50 (d, J=3.3 Hz, 1H), 7.64 (t, J=7.25, 2H), 7.81 (d, J=4.8 Hz, 1H) 7.95 (d, J=7.5 Hz, 1H). EIMS m/z 473 (M+1), 495 (M+23). Anal. ($C_{26}H_{21}FN_4O_2S$) C, H, N.

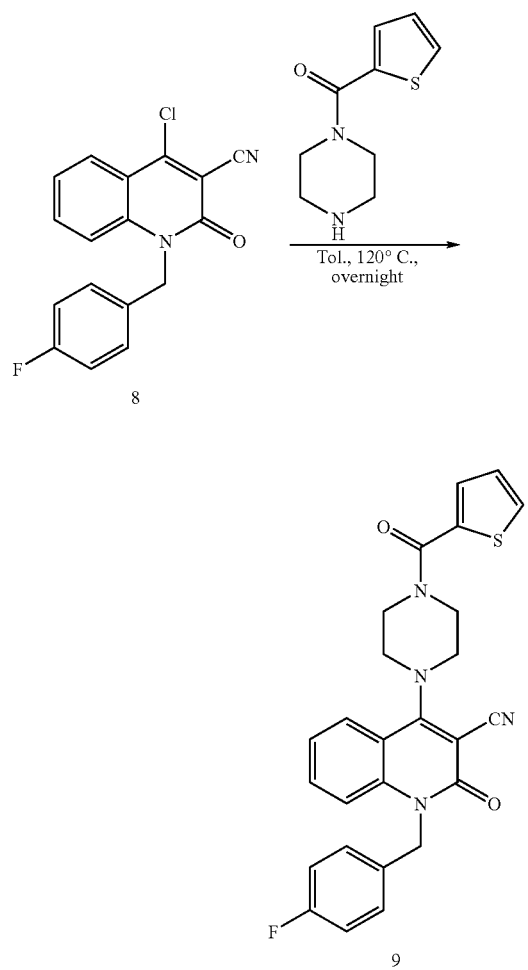

Preparation of 2-Amino-5-methyl benzoic acid (Compound 10)

To a solution of 5-methyl-2-nitrobenzoic acid (20 g, 110 mmol) in ethanol was added 10% Pd/C (1 g). The mixture was stirred overnight at room temperature under hydrogen atmosphere. The solution was filtered through celite and evaporated under reduced pressure to yield 16 g (96%) of white solids. M.P. 162° C. $^1$H NMR (DMSO-d$_6$): δ 2.13 (s, 3H), 6.65 (d, J=8.6 Hz, 1H), 7.06 (dd, J=8.6, 1.8 Hz, 1H), 7.48 (d, J=1.1, 1H). EIMS m/z 174 (M+1), 152 (M+23).

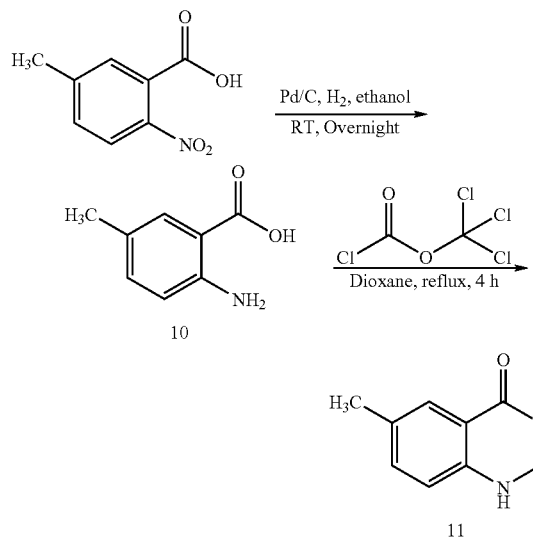

Preparation of 6-Methyl-1H-benzo[d][1,3]oxazine-2,4-dione (Compound 11)

Trichloromethyl chloroformate (36.27 mL, 300 mmol) was added to a stirred solution of Compound 10 (41.3 g, 273 mmol) in dry dioxane at room temperature and the solution was refluxed for 4 h. The solution was cooled in ice bath and the solids formed were filtered. The solids were washed by ether and dried under vacuum at room temperature to yield 45.5 g (94%) of white solids. M.P. 257° C. $^1$H NMR (DMSO-$d_6$): δ 2.32 (s, 3H), 7.06 (d, J=8.6 Hz, 1H), 7.56 (dd, J=8.6, 1.8 Hz, 1H), 7.71 (d, J=1.1, 1H), 11.63 (s, 1H). EIMS (neg. mode) m/z 176 (M−1), 152 (M+23). Anal. ($C_9H_7NO_3$) C, H, N.

Preparation of 1-Benzyl-6-methyl-1H-benzo[d][1,3]oxazine-2,4-dione (Compound 12)

A solution of Compound 11 (25 g, 141 mmol) in DMF was added slowly to a suspension of NaH (60% in mineral oil, 6.21 g, 155 mmol) in DMF and further stirred at room temperature for 1 h. Then, neat benzyl bromide (19.53 mL, 155 mmol) was added and the solution further stirred at room temperature for 3 h. The solution was poured into ice water, and the solids formed were filtered, washed several times by water, and dried. The solid was suspended in hexane, sonicated briefly, filtered, and washed by hexane to yield 36.5 g (97%) of white solids. M.P. 150° C. $^1$H NMR (DMSO-$d_6$): δ 2.32 (s, 3H), 5.27 (s, 2H), 7.15 (d, J=8.7 Hz, 1H), 7.26-7.39 (m, 5H), 7.54 (dd, J=1.5, 8.7 Hz, 1H), 7.83 (d, J=1.5 Hz, 1H). Anal. ($C_{16}H_{13}NO_3$) C, H, N.

Preparation of 1-(4-Fluorobenzyl-6-methyl-1H-benzo[d][1,3]oxazine-2,4-dione (Compound 13)

A solution of Compound 11 (5 g, 28 mmol) in DMF was added slowly to a suspension of NaH (60% in mineral oil, 1.24 g, 31 mmol) in DMF and further stirred at room temperature for 1 h. Then, neat 4-fluorobenzyl bromide (3.81 mL, 31 mmol) was added, and the solution further stirred at room temperature for 3 h. The solution was poured into ice water and the solids formed were filtered, washed several times by water, and dried. The solids were suspended in hexane, sonicated briefly, filtered, and washed by hexane to yield 6.3 g (79%) of white solids. M.P. 153° C. $^1$H NMR (DMSO-$d_6$): δ 2.32 (s, 3H), 5.24 (s, 2H), 7.14-7.17 (m, 3H), 7.44 (m, 2H), 7.54 (dd, J=1.7, 8.2 Hz, 1H), 7.83 (d, J=1.2 Hz, 1H). Anal. ($C_{16}H_{12}FNO_3$) C, H, N.

Preparation of 1,6-Dimethyl-1H-benzo[d][1,3]oxazine-2,4-dione (Compound 14)

A solution of Compound 11 (5 g, 28 mmol) in DMF was added slowly to a suspension of NaH (60% in mineral oil, 1.24 g, 31 mmol) in DMF and further stirred at room temperature for 1 h. Then, methyl iodide (1.92 mL, 31 mmol) was added and further stirred at room temperature for 3 h. The solution was poured into ice water and the solids formed were filtered, washed several times by water, and dried. The solids were suspended in hexane, sonicated briefly, filtered, and washed by hexane to yield 4.9 g (74%) of white solids. M.P. 153° C. $^1$H NMR (DMSO-$d_6$): δ 2.32 (s, 3H), 3.52 (s, 3H), 7.38 (d, J=8.6 Hz, 1H), 7.54 (dd, J=1.7, 8.2 Hz, 1H), 7.83 (d, J=1.2 Hz, 1H).

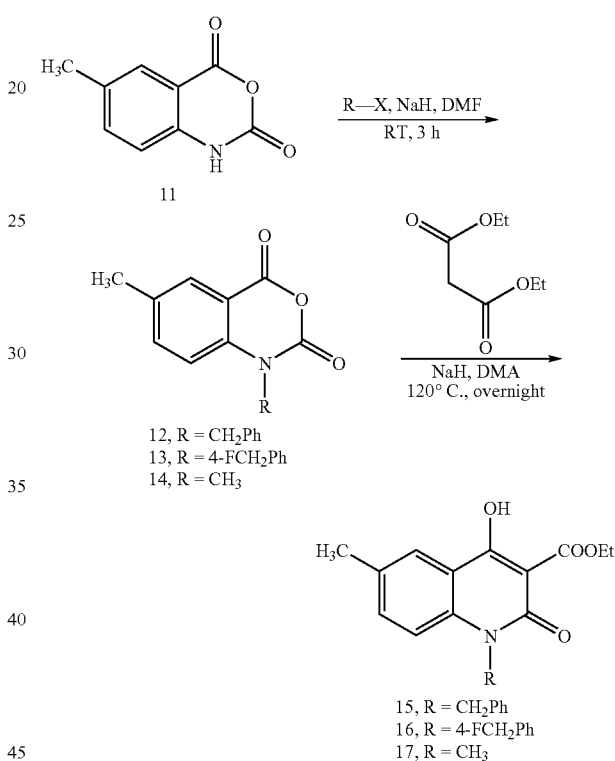

Preparation of 1-Benzyl-4-hydroxy-6-methyl-2-oxo-1,2-dihydro-quinoline-3-carboxylic acid ethyl ester (Compound 15)

Neat diethyl malonate (19.07 mL, 125 mmol) was added slowly to a suspension of sodium hydride (60% in mineral oil, 5.52 g, 138 mmol) in dimethylacetamide under $N_2$ atmosphere. The mixture was stirred at room temperature until the evolution of hydrogen gas ceased, then heated to 90° C. for 30 min and cooled to room temperature. A solution of Compound 12 (36.8 g, 138 mmol) in dimethylacetamide was added slowly and the mixture was heated overnight at 110° C. The mixture was cooled to room temperature, poured into ice water, and acidified by cold 10% HCl. The solids formed were filtered, washed several times by water, and dried at room temperature under vacuum to yield 41 g (97%) of white solids. M.P. 113° C. $^1$H NMR (DMSO-$d_6$): δ 1.31 (t, J=7.5 Hz, 3H), 2.33 (s, 3H), 4.35 (q, J=7.5 Hz, 2H), 5.43 (s, 2H), 7.15-7.30 (m, 6H), 7.43 (dd, J=1.6, 8.7 Hz, 1H), 7.85 (d, J=1.5 Hz, 1H). EIMS m/z 338 (M+1), 360 (M+23). Anal. ($C_{20}H_{19}NO_4$) C, H, N.

Preparation of 1-(4-Fluoro-benzyl)-4-hydroxy-6-methyl-2-oxo-1,2-dihydro-quinoline-3-carboxylic acid ethyl ester (Compound 16)

Neat diethyl malonate (3.04 mL, 20 mmol) was added slowly to a suspension of sodium hydride (60% in mineral oil, 0.88 g, 22 mmol) in dimethylacetamide under $N_2$ atmosphere. The mixture was stirred at room temperature until the evolution of hydrogen gas ceased, then the mixture was heated to 90° C. for 30 min and cooled to room temperature. A solution of Compound 13 (6.3 g, 22 mmol) in dimethylacetamide was added slowly and the mixture heated overnight at 110° C. The mixture was cooled to room temperature, poured into ice water, and acidified by cold 10% HCl. The solids formed were filtered, washed several times by water, and dried at room temperature under vacuum to yield 5.1 g (71%) of white solids. M.P. 130° C. $^1$H NMR (DMSO-$d_6$): δ 1.31 (t, J=7.0 Hz, 3H), 2.34 (s, 3H), 4.37 (q, J=7.5 Hz, 2H), 5.94 (s, 2H), 7.09-7.32 (m, 5H), 7.45 (dd, J=1.6, 8.7 Hz, 1H), 7.86 (d, J=1.5 Hz, 1H). EIMS m/z 356 (M+1), 378 (M+23). Anal. ($C_{20}H_{18}FNO_4$) C, H, N.

Preparation of 4-Hydroxy-1,6-dimethyl-2-oxo-1,2-dihydro-quinoline-3-carboxylic acid ethyl ester (Compound 17)

Neat diethyl malonate (2.28 g, 14.26 mmol) was added slowly to a suspension of sodium hydride (60% in mineral oil, 628 mg, 15.69 mmol) in dimethylacetamide under $N_2$ atmosphere. The mixture was stirred at room temperature until the evolution of hydrogen gas ceased, then the mixture was heated to 90° C. for 30 min. and cooled to room temperature. A solution of Compound 14 (10 g, 56 mmol) in dimethylacetamide was added slowly and the mixture heated overnight at 120° C. The mixture was cooled to room temperature, poured into ice water, and acidified by cold 10% HCl. The solids formed were filtered and washed several times by water to yield 3.26 g (87%) of white solids. M.P. 132° C. $^1$H NMR (DMSO-$d_6$): δ 1.30 (t, J=6.9 Hz, 3H), 2.50 (s, 3H), 3.50 (s, 3H), 4.33 (q, J=6.9 Hz, 2H), 7.41 (d, J=8.6 Hz, 1H), 7.56 (dd, J=1.7, 8.5 Hz, 1H), 7.82 (d, J=1.7 Hz, 1H), 13.03 (s, 1H). EIMS m/z 262 (M+1), 284 (M+23).

Preparation of 1-Benzyl-4-hydroxy-6-methyl-2-oxo-1,2-dihydro-quinoline-3-carboxylic acid cyclohexylamide (Compound 18)

Cyclohexylamine (3.41 mL, 29.64 mmol) was added to a solution of Compound 15 (5.0 g, 14.82 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 5.5 g (95%) of white solids. M.P. 87° C. $^1$H NMR (DMSO-$d_6$): δ 1.22 (m, 1H), 1.36 (m, 4H), 1.56 (m, 1H), 1.67 (m, 2H), 1.88 (m, 2H), 2.36 (s, 3H), 3.87 (m, 1H), 5.51 (s, 2H), 7.14-7.33 (m, 6H), 7.47 (d, J=8.6 Hz, 1H), 7.90 (s, 1H), 10.44 (s, 1H). EIMS m/z 391 (M+1).

Preparation of 1-(4-Fluorobenzyl)-4-hydroxy-6-methyl-2-oxo-1,2-dihydro-quinoline-3-carboxylic acid cyclohexylamide (Compound 19)

Cyclohexylamine (3.22 mL, 28.14 mmol) was added to a solution of Compound 16 (5.0 g, 14.07 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 5.3 g (93%) of yellow solids. M.P. 156° C. $^1$H NMR (DMSO-$d_6$): δ 1.24 (m, 1H), 1.37 (m, 4H), 1.57 (m, 1H), 1.68 (m, 2H), 1.88 (m, 2H), 2.36 (s, 3H), 3.87 (m, 1H), 5.49 (s, 2H), 7.11 (m, 2H), 7.22 (m, 2H), 7.36 (d, J=8.7 Hz, 1H), 7.51 (dd, J=1.6, 8.7 Hz, 1H), 7.90 (d, J=1.6 Hz, 1H), 10.39 (s, 1H). EIMS m/z 409 (M+1), 431 (M+23).

Preparation of 4-Hydroxy-1,6-dimethyl-2-oxo-1,2-dihydro-quinoline-3-carboxylic acid cyclohexylamide (Compound 20)

Cyclohexylamine (2.85 mL, 24.95 mmol) was added to a solution of Compound 17 (3.26 g, 12.47 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 3.8 g (97%) of white solids. M.P. 218° C. $^1$H NMR (DMSO-$d_6$): δ 1.28 (m, 1H), 1.36 (m, 4H), 1.55 (m, 1H), 1.68 (m, 2H), 1.87 (m, 2H), 2.40 (s, 3H), 3.59 (s, 3H), 3.87 (m, 1H), 7.51 (d, J=8.7 Hz, 1H), 7.61 (d, J=8.7 Hz, 1H), 7.86 (s, 1H), 10.49 (s, 1H). EIMS m/z 315 (M+1), 337 (M+23).

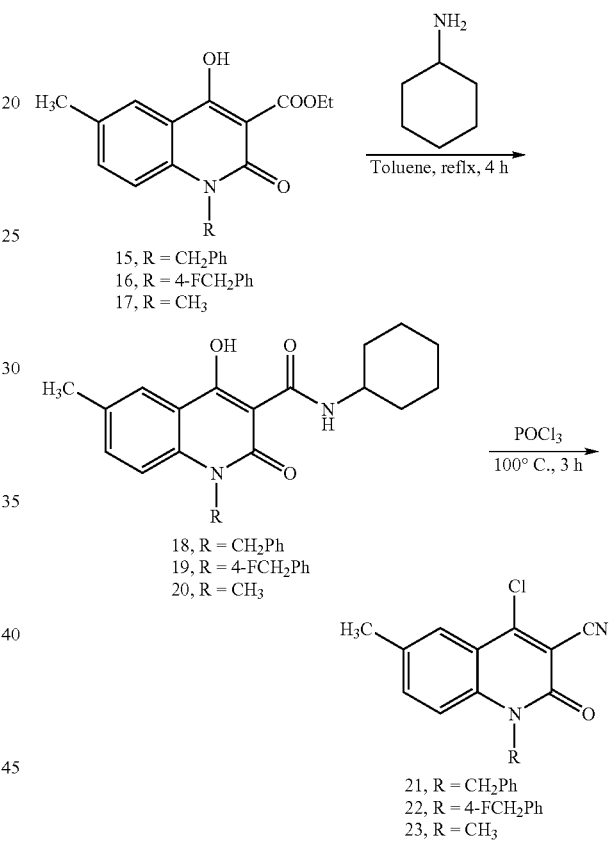

Preparation of 1-Benzyl-4-chloro-6-methyl-2-oxo-1,2-dihydro-quinoline-3-carbonitrile (Compound 21)

A solution of Compound 18 (5 g, 12.80 mmol) in 30 mL neat phosphorus oxychloride was heated at 100° C. for 3 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 1.51 g (38%) of yellow solids. M.P. 219° C. $^1$H NMR (DMSO-$d_6$): δ 2.40 (s, 3H), 5.54 (s, 2H), 7.23-7.26 (m, 3H), 7.29-7.32 (m, 2H), 7.45 (d, J=8.8 Hz, 1H), 7.61 (dd, J=1.5, 8.8 Hz, 1H), 7.89 (d, J=1.5 Hz, 1H). EIMS m/z 309 (M+1), 331 (M+23).

Preparation of 4-Chloro-1-(4-fluorobenzyl)-6-methyl-2-oxo-1,2-dihydro-quinoline-3-carbonitrile (Compound 22)

A solution of Compound 19 (5 g, 12.24 mmol) in 30 mL neat phosphorus oxychloride was heated at 100° C. for 3 h.

The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 1.90 g (47%) of yellow solids. M.P. 206° C. $^1$H NMR (DMSO-$d_6$): δ 2.40 (s, 3H), 5.52 (s, 2H), 7.12-7.15 (m, 2H), 7.30-7.33 (m, 2H), 7.46 (d, J=8.7 Hz, 1H), 7.64 (dd, J=1.2, 8.7 Hz, 1H), 7.89 (d, J=1.2 Hz, 1H). EIMS m/z 327 (M+1).

Preparation of 4-Chloro-1,6-dimethyl-2-oxo-1,2-dihydro-quinoline-3-carbonitrile (Compound 23)

A solution of Compound 20 (3 g, 9.5 mmol) in 30 mL neat phosphorus oxychloride was heated at 100° C. for 3 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 1.2 g (54%) of yellow solids. M.P. 241° C. $^1$H NMR (DMSO-$d_6$): δ 2.44 (s, 3H), 3.64 (s, 3H), 7.62 (d, J=8.7 Hz, 1H), 7.73 (dd, J=1.5, 8.7 Hz, 1H), 7.85 (d, J=1.5 Hz, 1H). EIMS m/z 255 (M+1).

Preparation of 1-Benzyl-6-methyl-2-oxo-4-[4-(thiophene-2-carbonyl)-piperazin-1-yl]-1,2-dihydro-quinolin-3-carbonitrile (Compound 24)

piperazine-1-yl-thiophen-2-yl-methanone (490 mg, 2.5 mmol) was added to a solution of Compound 20 (309 mg, 1 mmol) in toluene (20 mL) and heated overnight at 110° C. The solvent was removed under vacuum. The residue was suspended in water, sonicated, and filtered. The crude product was purified by flash chromatography eluting with 0-2% methanol in dichloromethane gradient to yield 362 mg (77%) of white solids. M.P. 183° C. $^1$H NMR (DMSO-$d_6$): δ 2.36 (s, 3H), 3.69 (m, 4H), 3.94 (m, 4H), 5.47 (s, 2H), 7.16-7.20 (m, 4H), 7.23-7.33 (m, 3H), 7.44 (d, J=8.8 Hz, 1H), 7.50 (d, J=3.8 Hz, 1H), 7.70 (s, 1H), 7.81 (d, J=4.8 Hz, 1H). EIMS m/z 491 (M+23). Anal. ($C_{27}H_{24}N_4O_2S$) C, H, N.

Preparation of 1-(4-Fluoro-benzyl)-6-methyl-2-oxo-4-[4-(thiophene-2-carbonyl)-piperazin-1-yl]-1,2-dihydro-quinolin-3-carbonitrile (Compound 25)

piperazine-1-yl-thiophen-2-yl-methanone (490 mg, 2.5 mmol) was added to a solution of Compound 21 (327 mg, 1 mmol) in toluene (20 mL) and heated overnight at 110° C. The solvent was removed under vacuum. The residue was suspended in water, sonicated, and filtered. The crude product was purified by flash chromatography eluting with 0-2% methanol in dichloromethane gradient to yield 210 mg (43%) of white solids. M.P. 274° C. $^1$H NMR (DMSO-$d_6$): δ 2.37 (s, 3H), 3.68 (m, 4H), 3.94 (m, 4H), 5.45 (s, 2H), 7.12-7.18 (m, 3H), 7.24-7.27 (m, 2H), 7.33 (d, J=8.6 Hz, 1H), 7.45 (d, J=8.8 Hz, 1H), 7.50 (d, J=3.5 Hz, 1H), 7.70 (s, 1H), 7.81 (d, J=4.8 Hz, 1H). EIMS m/z 509 (M+23). Anal. ($C_{27}H_{23}FN_4O_2S$) C, H, N.

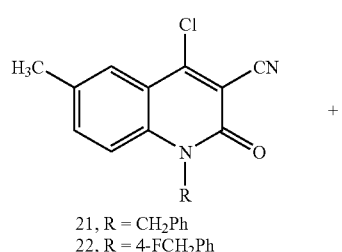

21, R = CH$_2$Ph
22, R = 4-FCH$_2$Ph

+

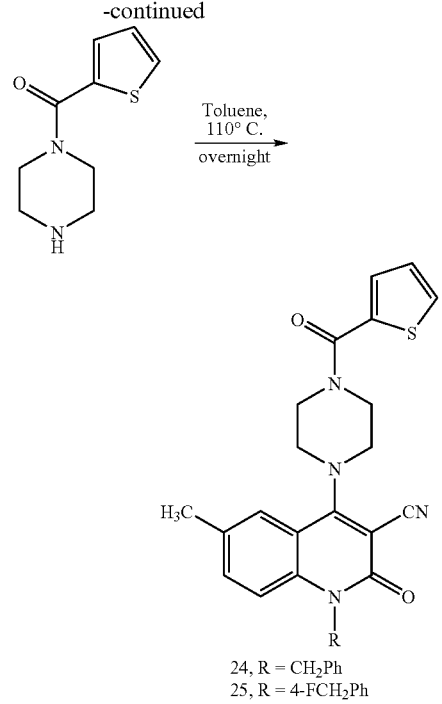

24, R = CH$_2$Ph
25, R = 4-FCH$_2$Ph

Preparation of 1-Benzyl-6-methyl-2-oxo-4-(piperazin-1-yl)-1,2-dihydro-quinolin-3-carbonitrile (Compound 26)

A solution of Compound 21 (1.2 g, 3.9 mmol) in dichloromethane was added slowly to a stirred solution of piperazine (1.67 g, 19.4 mmol) in dichloromethane at room temperature. The solution was stirred overnight at room temperature. The solvent was removed under reduced pressure. The residue was taken in water, sonicated briefly, and filtered. The solids were dissolved in ethyl acetate and washed by water. The organic layer was dried over Na$_2$SO$_4$ and concentrated to yield 1.34 g (96%) of yellow solids. M.P. 152° C. $^1$H NMR (DMSO-$d_6$): δ 2.34 (s, 3H), 2.94 (m, 4H), 3.54 (m, 4H), 5.44 (s, 2H), 7.16-7.20 (m, 2H), 7.22 (d, J=7.6 Hz, 1H), 7.28-7.31 (m, 3H), 7.40 (d, J=8.8 Hz, 1H), 7.64 (s, 1H). EIMS m/z 359 (M+1).

Preparation of 1-(4-Fluoro-benzyl)-6-methyl-2-oxo-4-(piperazin-1-yl)-1,2-dihydro-quinolin-3-carbonitrile (Compound 27)

A solution of Compound 22 (1.6 g, 4.9 mmol) in dichloromethane was added slowly to a stirred solution of piperazine (2.2 g, 24.5 mmol) in CH$_2$Cl$_2$ at room temperature and further stirred overnight. The solvent was removed under reduced pressure. The residue was taken in water, sonicated briefly, and filtered. The solids were dissolved in ethyl acetate and washed by water. The organic layer was dried over Na$_2$SO$_4$ and concentrated to yield 1.30 g (72%) of yellow solids. M.P. 121° C. $^1$H NMR (DMSO-$d_6$): δ 2.35 (s, 3H), 2.96 (m, 4H), 3.54 (m, 4H), 5.42 (s, 2H), 7.11-7.17 (m, 2H), 7.23-7.26 (m, 2H), 7.44 (dd, J=1.2, 8.6 Hz, 1H), 7.64 (s, 1H). EIMS m/z 377 (M+1).

Preparation of 1,6-Dimethyl-2-oxo-4-(piperazin-1-yl)-1,2-dihydro-quinolin-3-carbonitrile (Compound 28)

A solution of Compound 23 (1 g, 4.3 mmol) in dichloromethane was added slowly to a stirred solution of piperazine (1.1 g, 12.9 mmol) in dichloromethane at room temperature. The solution was stirred overnight at room temperature. The solvent was removed under reduced pressure. The residue was taken in water, sonicated briefly, and filtered. The solids were dissolved in ethyl acetate and washed by water. The organic layer was dried over $Na_2SO_4$ and concentrated to yield 1.07 g (88%) yellow solids. M.P. 274° C. $^1$H NMR (DMSO-$d_6$): δ 2.39 (s, 3H), 2.94 (m, 4H), 3.48 (m, 4H), 3.54 (s, 3H), 7.45 (d, J=8.6 Hz, 1H), 7.56 (dd, J=1.3, 8.6 Hz, 1H), 7.64 (s, 1H). EIMS m/z 283 (M+1).

(d, J=7.3 Hz, 2H), 7.23 (d, J=7.4 Hz, 1H), 7.29-7.33 (m, 3H), 7.44 (d, J=1.3, 8.7 Hz, 1H), 7.71 (s, 1H), 7.89 (s, 1H). EIMS m/z 475 (M+23). Anal. ($C_{27}H_{24}N_4O_3$) C, H, N.

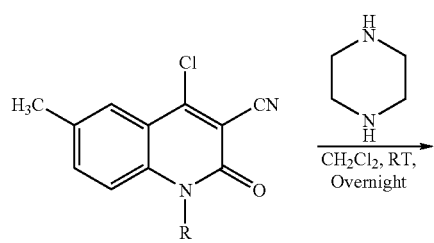

21, R = CH$_2$Ph
22, R = 4-FCH$_2$Ph
23, R = CH$_3$

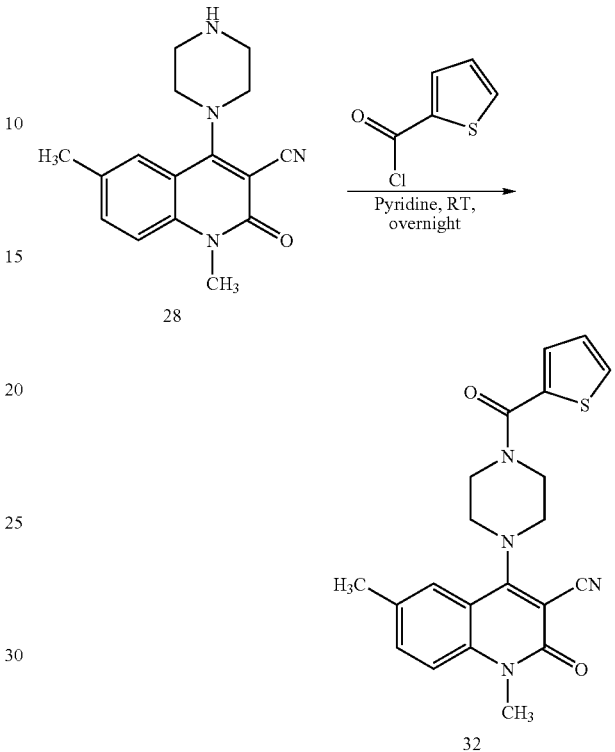

28

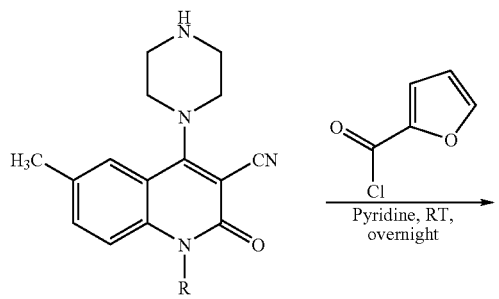

26, R = CH$_2$Ph
27, R = 4-FCH$_2$Ph
28, R = CH$_3$

32

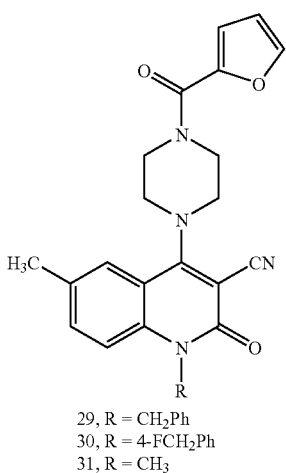

29, R = CH$_2$Ph
30, R = 4-FCH$_2$Ph
31, R = CH$_3$

Preparation of 1-Benzyl-4-[4-(furan-2-carbonyl)-piperazin-1-yl]-6-methyl-2-oxo-1,2-dihydro-quinolin-3-carbonitrile (Compound 29)

2-Furoyl chloride (118 μL, 1.2 mmol) was added to a stirred solution of Compound 26 (287 mg, 0.8 mmol) in pyridine (5 mL) under argon at 0° C. The solution was allowed to come to room temperature and further stirred overnight. The solution was poured into ice water and the solids formed were filtered. The solids were washed by excess water, dried and recrystallized by hexane and ether to yield 340 mg (90%) of white solids. M.P. 146° C. $^1$H NMR (DMSO-$d_6$): δ 2.36 (s, 3H), 3.69 (m, 4H), 3.97 (m, 4H), 5.47 (s, 2H), 6.66 (t, J=2.5 Hz, 1H), 7.09 (d, J=3.4 Hz, 1H), 7.18

Preparation of 1-(4-Fluorob-enzyl)-4-[4-(furan-2-carbonyl)-piperazin-1-yl]-6-methyl-2-oxo-1,2-dihydro-quinolin-3-carbonitrile (Compound 30)

2-Furoyl chloride (118 μL, 1.2 mmol) was added to a stirred solution of Compound 27 (300 mg, 0.8 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by hexane and ether to yield 320 mg (85%) of white solids. M.P. 276° C. $^1$H NMR (DMSO-$d_6$): δ 2.37 (s, 3H), 3.69 (m, 4H), 3.97 (m, 4H), 5.45 (s, 2H), 6.67 (dd, J=1.7, 3.7 Hz, 1H), 7.09 (d, J=3.4 Hz, 1H), 7.12 (m, 2H), 7.26 (m, 2H), 7.35 (d, J=8.7 Hz, 1H), 7.45 (d, J=8.8 Hz, 1H), 7.71 (s, 1H), 7.89 (s, 1H). EIMS m/z 493 (M+23). Anal. ($C_{27}H_{23}FN_4O_3$) C, H, N.

Preparation of 4-[4-(Furan-2-carbonyl)-piperazin-1-yl]-1,6-dimethyl-2-oxo-1,2-dihydro-quinolin-3-carbonitrile (Compound 31)

2-Furoyl chloride (148 μL, 1.5 mmol) was added to a stirred solution of Compound 28 (282 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 221 mg (59%) of white solids. M.P. 231° C. $^1$H NMR (DMSO-$d_6$): δ 2.41 (s, 3H), 3.56 (s, 3H), 3.63 (m, 4H), 3.95 (m, 4H), 6.66 (dd, J=1.5, 3.6 Hz, 1H), 7.08 (d, J=3.4 Hz, 1H), 7.48 (d, J=8.7 Hz, 1H), 7.59 (dd, J=1.2, 8.8 Hz, 1H), 7.69 (s, 1H), 7.88 (s, 1H). EIMS m/z 399 (M+23). Anal. ($C_{21}H_{20}N_4O_3$) C, H, N.

Preparation of 1,6-Dimethyl-2-oxo-4-[4-(thiophene-2-carbonyl)-piperazin-1-yl]-1,2-dihydro-quinolin-3-carbonitrile (Compound 32)

2-Thiophene carbonyl chloride (160 μL, 1.5 mmol) was added to a stirred solution of Compound 28 (282 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 277 mg (70%) of white solids. M.P. 214° C. $^1$H NMR (DMSO-$d_6$): δ 2.41 (s, 3H), 3.55 (s, 3H), 3.63 (m,4H), 3.92 (m, 4H), 7.16 (t, J=4.1 Hz, 1H), 7.47 (m, 2H), 7.56 (d, J=8.7 Hz, 1H), 7.68 (s, 1H), 7.80 (d, J=4.9 Hz, 1H). EIMS m/z 393 (M+1), 415 (M+23). Anal. ($C_{21}H_{20}N_4O_2S$) C, H, N.

Preparation of 5-Fluoro-2-nitrobenzoic acid (Compound 33)

3-Fluorobenzoic acid (1 g, 7.13 mmol) was dissolved in concentrated $H_2SO_4$ (2 ml) by warming slightly above room temperature. The solution was cooled to 0° C. Fuming nitric acid (539 mg, 8.56 mmol) was added slowly to the solution while keeping the temperature below 0° C. The solution was stirred at 0° C. for 3 h. The solution was poured into ice water, the solid formed were filtered, washed by cold water, and dried to yield 1.2 g (92%) of white solids. M.P. 122° C. $^1$H NMR (DMSO-$d_6$): 7.60 (dt, J=2.9, 8.5 Hz, 1H), 7.71 (dd, J=2.9, 8.6 Hz, 1H), 8.13 (dd, J=4.8, 8.8 Hz, 1H). EIMS m/z 186 (M+1).

Preparation of 2-Amino-5-fluoro benzoic acid (Compound 34)

A solution of Compound 33 (10 g, 54 mmol) in ethanol (100 mL) was stirred under hydrogen in the presence of 10% Pd/C (0.5 g) at room temperature for 4 h. The solution was filtered through celite. The solvent was evaporated under reduced pressure to yield 8.2 g (98%) of white solids. M.P. 142° C. $^1$H NMR (DMSO-$d_6$): 6.71 (dd, J=4.9, 8.9 Hz, 1H), 7.15 (dt, J=2.9, 8.4 Hz, 1H), 7.37 (dd, J=2.9, 9.8 Hz, 1H), 8.60 (s, 1H). EIMS m/z 156 (M+1).

Preparation of 6-Fluoro-1H-benzo[d][1,3]oxazine-2,4-dione (Compound 35)

Trichloromethyl chloroformate (7.01 mL, 58.13 mmol) was added to a stirred solution of Compound 34 (8.2 g, 52.85 mmol) in dry dioxane at room temperature and the solution was refluxed for 4 h. The solution was cooled in an ice bath and the solids formed were filtered. The solids were washed by ether and dried under vacuum at room temperature to yield 9.1 g (96%) of white solids. M.P. 240° C. $^1$H NMR (DMSO-$d_6$): δ 7.19 (dd, J=4.2, 8.9 Hz, 1H), 7.63-7.71 (m, 1H), 11.77 (s, 1H). EIMS (neg. mode) m/z 180 (M-1). Anal. ($C_8H_4FNO_3$) C, H, N.

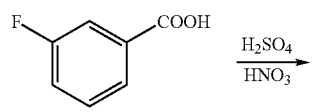

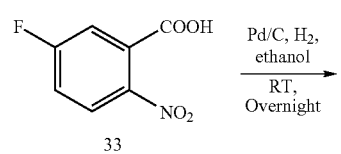

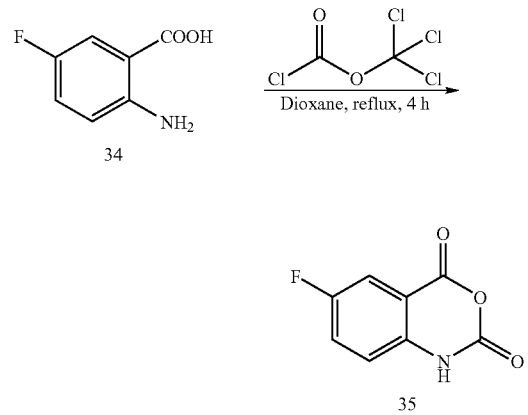

Preparation of 1-Benzyl-6-fluoro-1H-benzo[d][1,3]oxazine-2,4-dione (Compound 36)

A solution of Compound 35 (3 g, 16.57 mmol) in DMF was added slowly to a suspension of NaH (60% in mineral oil, 729 mg, 18.23 mmol) in DMF and further stirred at room temperature for 1 h. Then, neat benzyl bromide (2,17 mL, 18.23 mmol) was added and the solution was further stirred at room temperature for 3 h. The solution was poured into ice water and the solids formed were filtered, washed several times by water, and dried. The solids were suspended in hexane, sonicated briefly, filtered, and washed by hexane to yield 1.88 g (42%) of white solids. M.P. 95° C. $^1$H NMR (DMSO-$d_6$): δ 5.29 (s, 2H), 7.26 (m, 2H), 7.35 (m, 5H), 7.40 (m, 2H), 7.64 (dt, J=2.9, 8.4 Hz, 1H), 7.82 (dd, J=3.2, 8.0 Hz, 1H). Anal. ($C_{16}H_{13}NO_3$) C, H, N.

Preparation of 6-Fluoro-1-(4-fluorobenzyl)-1H-benzo [d][1,3]oxazine-2,4-dione (Compound 37)

A solution of Compound 35 (3 g, 16.57 mmol) in DMF was added slowly to a suspension of NaH (60% in mineral oil, 729 mg, 18.22 mmol) in DMF and further stirred at room temperature for 1 h. Then, neat 4-fluorobenzyl bromide (2.28 mL, 18.23 mmol) was added and the solution further stirred at room temperature for 3 h. The solution was poured into ice water and the solids formed were filtered, washed several times by water, and dried. The solids were suspended in hexane, sonicated briefly, filtered, and washed by hexane to yield 3.23 g (67%) of white solids. M.P. 107° C. $^1$H NMR (DMSO-$d_6$): δ 5.27 (s, 2H), 7.19 (m, 2H), 7.29 (dd, J=3.9, 9.0 Hz, 1H), 7.47 (m, 2H), 7.65 (td, J=5.5, 9.0 Hz, 1H), 7.81 (dd, J=2.9, 7.9 Hz, 1H). Anal. ($C_{15}H_9F_2NO_3$) C, H, N.

Preparation of 6-Fluoro-1-methyl-1H-benzo[d][1,3]oxazine-2,4-dione (Compound 38)

A solution of Compound 35 (3 g, 16.57 mmol) in DMF was added slowly to a suspension of NaH (60% in mineral oil, 0.729 g, 18.23 mmol) in DMF and further stirred at room temperature for 1 h. Then, neat methyl iodide (1.14 mL, 18.23 mmol) was added and the solution further stirred at room temperature for 3 h. The solution was poured into ice water and the solids formed were filtered, washed several times by water, and dried. The solids were suspended in hexane, sonicated briefly, filtered, and washed by hexane to yield 1.84 g (57%) of white solids. M.P. 133° C. $^1$H NMR (DMSO-$d_6$): δ 3.90 (s, 3H), 7.51 (dd, J=4.0, 8.8 Hz, 1H), 7.77 (m, 12). Anal. ($C_9H_6FNO_3$) C, H, N.

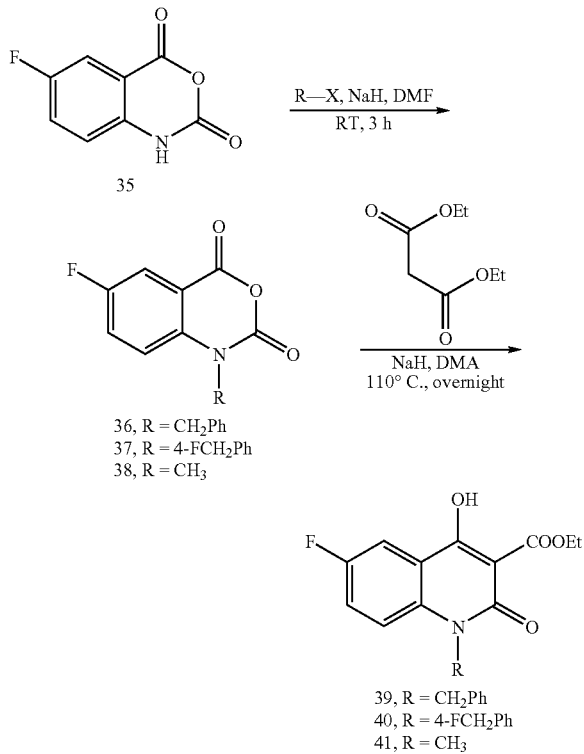

Preparation of 1-Benzyl-6-fluoro-4-hydroxy-2-oxo-1,2-dihydro-quinoline-3-carboxylic acid ethyl ester (Compound 39)

Neat diethyl malonate (0.89 mL, 5.8 mmol) was added slowly to a suspension of sodium hydride (60% in mineral oil, 256 mg, 6.41 mmol) in dimethylacetamide under $N_2$ atmosphere. The mixture was stirred at room temperature until the evolution of hydrogen gas ceased, then the mixture was heated to 90° C. for 30 min and cooled to room temperature. A solution of Compound 36 (1.74 g, 6.41 mmol) in dimethylacetamide was added slowly to the mixture, which was heated overnight at 110° C. The mixture was cooled to room temperature, poured into ice water, and acidified by cold 10% HCl. The solids formed were filtered, washed several times by water, and dried at room temperature under vacuum to yield 1.4 g (64%) of white solids. M.P. 129° C. $^1$H NMR (DMSO-$d_6$): δ 1.30 (t, J=6.9 Hz, 3H), 4.34 (q, J=6.9 Hz, 2H), 5.46 (s, 2H), 7.17-7.24 (m, 5H), 7.38 (dd, J=4.6, 9.6 Hz, 1H), 7.50 (td, J=2.9, 8.3 Hz, 1H), 7.80 (dd, J=3.1, 9.4 Hz, 1H). EIMS m/z 342 (M+1), 364 (M+23). Anal. ($C_{19}H_{16}FNO_4$) C, H, N.

Preparation of 6-Fluoro-1-(Fluoro-benzyl)-4-hydroxy-2-oxo-1,2-dihydro-quinoline-3-carboxylic acid ethyl ester (Compound 40)

Neat diethyl malonate (1.2 mL, 8.0 mmol) was added slowly to a suspension of sodium hydride (60% in mineral oil, 352 mg, 8.8 mmol) in dimethylacetamide under $N_2$ atmosphere. The mixture was stirred at room temperature until the evolution of hydrogen gas ceased, then the mixture was heated to 90° C. for 30 min and cooled to room temperature. A solution of Compound 37 (2.5 g, 8.8 mmol) in dimethylacetamide was added slowly and heated overnight at 110° C. The mixture was cooled to room temperature, poured into ice water, and acidified by cold 10% HCl. The solids formed were filtered, washed several times by water, and dried at room temperature under vacuum to yield 2.5 g (87%) of white solids. M.P. 123° C. $^1$H NMR (DMSO-$d_6$): δ 1.31 (t, J=7.0 Hz, 3H), 4.37 (q, J=7.5 Hz, 2H), 5.43 (s, 2H), 7.19 (m, 2H), 7.29 (dd, J=3.9, 9.0 Hz, 1H), 7.47 (m, 2H), 7.65 (td, J=5.5, 9.0 Hz, 1H), 7.81 (dd, J=2.9, 7.9 Hz, 1H). EIMS m/z 360 (M+1), 382 (M+23). Anal. ($C_{19}H_{15}F_2NO_4$) C, H, N.

Preparation of 6-Fluoro-4-hydroxy-1-methyl-2-oxo-1,2-dihydro-quinoline-3-carboxylic acid ethyl ester (Compound 41)

Neat diethyl malonate (1.27 g, 8.4 mmol) was added slowly to a suspension of sodium hydride (60% in mineral oil, 372 mg, 9.3 mmol) in dimethylacetamide under $N_2$ atmosphere. The mixture was stirred at room temperature until the evolution of hydrogen gas ceased, then the mixture was heated to 90° C. for 30 min. and cooled to room temperature. A solution of Compound 38 (1.8 g, 9.3 mmol) in dimethylacetamide was added slowly and the mixture heated overnight at 120° C. The mixture was cooled to room temperature, poured into ice water, and acidified by cold 10% HCl. The solids formed were filtered and washed several times by water to yield 1.3 g (53%) of white solids. M.P. 131° C. $^1$H NMR (DMSO-$d_6$): δ 1.30 (t, J=6.9 Hz, 3H), 3.54 (s, 3H), 4.31 (q, J=6.9 Hz, 2H), 7.56 (dd, J=4.6, 9.3 Hz, 1H), 7.64 (dd, J=2.9, 9.1 Hz, 1H), 7.76 (dd, J=2.9, 9.3 Hz, 1H), 12.80 (s, 1H). EIMS m/z 266 (M+1), 288 (M+23).

Preparation of 1-Benzyl-6-fluoro-4-hydroxy-2-oxo-1,2-dihydro-quinoline-3-carboxylic acid cyclohexylamide (Compound 42)

Cyclohexylamine (2.95 mL, 25.78 mmol) was added to a solution of Compound 39 (4.4 g, 12.89 mmol) in toluene (50 mL) and refluxed for 3 h. The solution was cooled and the solvent was evaporated under vacuum. The residue obtained was suspended in water, briefly sonicated, and filtered. The crude product was recrystallized by ether to yield 4.0 g (78%) of white solids. M.P. 130-134° C. $^1$H NMR (DMSO-$d_6$): δ 1.37 (m, 5H), 1.56 (m, 1H), 1.67 (m, 2H), 1.88 (m, 2H), 3.87 (m, 1H), 5.29 (s, 2H), 7.17 (m, 2H), 7.23 (m, 1H), 7.33 (m, 1H), 7.46 (dd, J=3.9, 9.1 Hz, 1H), 7.57 (td, J=2.9, 8.3 Hz, 1H), 7.81 (dd, J=2.9, 8.8 Hz, 1H). EIMS m/z 394 (M+1).

Preparation of 6-Fluoro-1-(4-fluorobenzyl)-4-hydroxy-2-oxo-1,2-dihydro-quinoline-3-carboxylic acid cyclohexylamide (Compound 43)

Cyclohexylamine (3.25 mL, 28.38 mmol) was added to a solution of Compound 40 (5.1 g, 14.19 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 5.0 g (86%) of white solids. M.P. 118° C. $^1$H NMR (DMSO-$d_6$): δ 1.18 (m, 2H), 1.35 (m, 3H), 1.57 (m, 1H), 1.67 (m, 2H), 1.88 (m, 2H), 3.86 (m, 1H), 5.48 (s, 2H), 7.13 (m, 2H), 7.24 (m, 2H), 7.35 (dd, J=3.9, 9.0 Hz, 1H), 7.53 (td, J=5.5, 9.0 Hz, 1H), 7.80 (dd, J=2.9, 7.9 Hz, 1H). EIMS m/z 413 (M+1).

Preparation of 6-Fluoro-4-hydroxy-1-methyl-2-oxo-1,2-dihydro-quinoline-3-carboxylic acid cyclohexylamide (Compound 44)

Cyclohexylamine (1.98 mL, 17.34 mmol) was added to a solution of Compound 41 (2.3 g, 8.67 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 2.38 g (97%) of white solids. M.P. 193° C. $^1$H NMR (DMSO-$d_6$): δ 1.28 (m, 1H), 1.36 (m, 4H), 1.55 (m, 1H), 1.68 (m, 2H), 1.87 (m, 2H), 3.62 (s, 3H), 3.90 (m, 1H), 7.70 (m, 3H), 7.77 (d, J=8.0 Hz, 1H), 10.41 (s, 1H). EIMS m/z 341 (M+23).

Preparation of 1-Benzyl-4-chloro-6-fluoro-2-oxo-1,2-dihydro-quinoline-3-carbonitrile (Compound 45)

A solution of Compound 42 (3.5 g, 8.86 mmol) in 30 mL neat phosphorus oxychloride was heated at 90° C. for 5 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 1.29 g (47%) of yellow solids. M.P. 228° C. $^1$H NMR (DMSO-$d_6$): δ 5.29 (s, 2H), 7.27 (m, 4H), 7.32 (m, 2H), 7.58 (dd, J=4.3, 9.3 Hz, 1H), 7.71 (td, J=2.4, 8.0 Hz, 1H), 7.91 (dd, J=2.9, 8.9 Hz, 1H). EIMS m/z 335 (M+23).

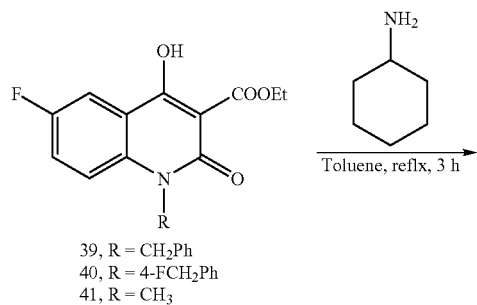

39, R = CH$_2$Ph
40, R = 4-FCH$_2$Ph
41, R = CH$_3$

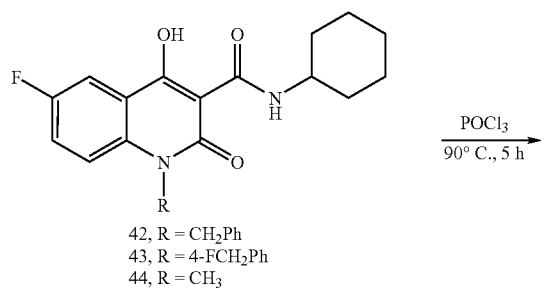

42, R = CH$_2$Ph
43, R = 4-FCH$_2$Ph
44, R = CH$_3$

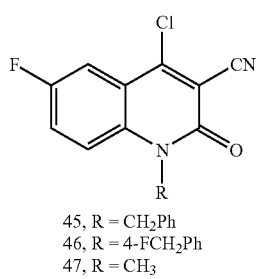

45, R = CH$_2$Ph
46, R = 4-FCH$_2$Ph
47, R = CH$_3$

Preparation of 4-Chloro-6-fluoro-1-(4-fluorobenzyl)-2-oxo-1,2-dihydro-quinoline-3-carbonitrile (Compound 46)

A solution of Compound 43 (5.1 g, 12.36 mmol) in 20 ml neat phosphorus oxychloride was heated at 100° C. for 5 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 2.05 g (50%) of yellow solids. M.P. 236° C. $^1$H NMR (DMSO-$d_6$): δ 5.54 (s, 2H), 7.14 (m, 2H), 7.33 (m, 2H), 7.59 (dd, J=4.0, 9.1 Hz, 1H), 7.72 (td, J=2.8, 7.9 Hz, 1H), 7.91 (dd, J=2.8, 8.9 Hz, 1H). EIMS m/z 331 (M+1).

Preparation of 4-Chloro-6-fluoro-1-methyl-2-oxo-1,2-dihydro-quinoline-3-carbonitrile (Compound 47)

A solution of Compound 44 (2 g, 6.28 mmol) in 20 ml neat phosphorus oxychloride was heated at 90° C. for 5 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 0.80 g (56%) of yellow solids. M.P. 258° C. $^1$H NMR (DMSO-$d_6$): δ 3.67 (s, 3H), 7.78-7.89 (m, 3H). EIMS m/z 259 (M+23).

Preparation of 1-Benzyl-6-fluoro-2-oxo-4-(piperazin-1-yl)-1,2-dihydro-quinolin-3-carbonitrile (Compound 48)

A solution of Compound 45 (1.0 g, 3.2 mmol) in dichloromethane was added slowly to a stirred solution of piperazin (826 mg g, 9.59 mmol) in dichloromethane at room temperature. The solution was stirred overnight at room temperature. The solvent was removed under reduced pressure. The residue was taken in water sonicated briefly and filtered. The solid was dissolved in ethyl acetate and washed by water. The organic layer was dried over Na$_2$SO$_4$ and concentrated to yield 1.1 g (96%) yellow solids. M.P. 162° C. $^1$H NMR (DMSO-$d_6$): δ 2.70 (s, 1H), 2.94 (m, 4H), 3.53 (m, 4H), 5.47 (s, 2H), 7.19-7.25 (m, 3H), 7.42 (m, 2H), 7.51 (dd, J=4.3, 9.3 Hz, 1H), 7.54 (td, J=2.4, 8.0 Hz, 1H), 7.58 (dd, J=2.9, 8.9 Hz, 1H). EIMS m/z 363 (M+1).

Preparation of 6-Fluoro-1-(4-Fluoro-benzyl)-2-oxo-4-(piperazin-1-yl)-1,2-dihydro-quinolin-3-carbonitrile (Compound 49)

A solution of Compound 46 (2.0 g, 6.04 mmol) in dichloromethane was added slowly to a stirred solution of piperazine (1.56 g, 18.21 mmol) in dichloromethane at room temperature. The solution was stirred overnight at room temperature. The solvent was removed under reduced pressure. The residue was taken in water, sonicated briefly, and filtered. The solids were dissolved in ethyl acetate and washed by water. The organic layer was dried over Na$_2$SO$_4$ and concentrated to yield 2.18 g (95%) yellow solids. M.P. 240° C. $^1$H NMR (DMSO-$d_6$): δ 2.84 (s, 1H), 2.94 (m, 4H), 3.54 (m, 4H), 5.45 (s, 2H), 7.15 (m, 2H), 7.27 (m, 2H), 7.44 (dd, J=4.4, 9.3 Hz, 1H), 7.53 (td, J=2.4, 8.0 Hz, 1H), 7.58 (dd, J=2.9, 8.9 Hz, 1H). EIMS m/z 381 (M+1).

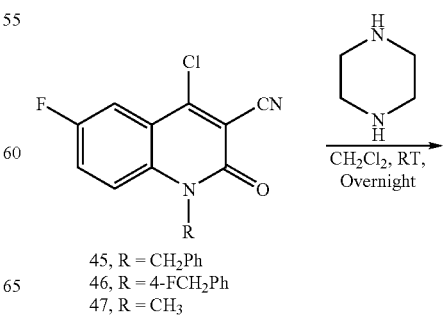

45, R = CH$_2$Ph
46, R = 4-FCH$_2$Ph
47, R = CH$_3$

-continued

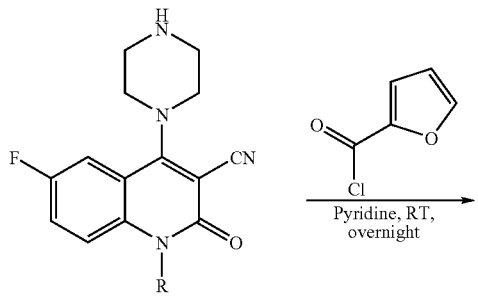

48, R = CH₂Ph
49, R = 4-FCH₂Ph
50, R = CH₃

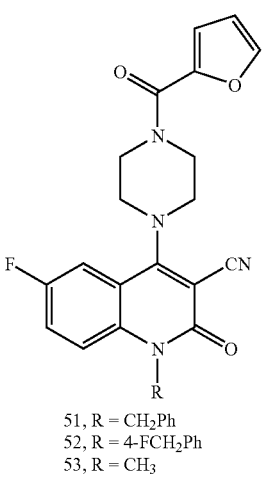

51, R = CH₂Ph
52, R = 4-FCH₂Ph
53, R = CH₃

Preparation of 6-Fluoro-1-methyl-2-oxo-4-(piperazin-1-yl)-1,2-dihydro-quinolin-3-carbonitrile (Compound 50)

A solution of Compound 47 (750 mg, 3.17 mmol) in dichloromethane was added slowly to a stirred solution of piperazine (819 mg, 9.50 mmol) in dichloromethane at room temperature. The solution was stirred overnight at room temperature. The solvent was removed under reduced pressure. The residue was taken in water, sonicated briefly, and filtered. The solids were dissolved in ethyl acetate and washed by water. The organic layer was dried over $Na_2SO_4$ and concentrated to yield 780 mg (86%) of yellow solids. M.P. 211° C. $^1$H NMR (DMSO-$d_6$): δ 2.91 (m, 4H), 3.47 (m, 4H), 3.56 (s, 3H), 7.54 (m, 1H), 7.63 (m, 2H). EIMS m/z 287 (M+1).

Preparation of 1-Benzyl-6-fluoro-4-[4-(furan-2-carbonyl)-piperazin-1-yl]-2-oxo-1,2-dihydro-quinolin-3-carbonitrile (Compound 51)

2-Furoyl chloride (148 μL, 1.5 mmol) was added to a stirred solution of Compound 48 (363 mg, 1 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 332 mg (73%) of white solids. M.P. 209° C. $^1$H NMR (DMSO-$d_6$): δ 3.69 (m, 4H), 3.97 (m, 4H), 5.49 (s, 2H), 6.66 (m, 1H), 7.09 (d, J=3.3 Hz, 1H), 7.22 (m, 3H), 7.32 (m, 2H), 7.45 (dd, J=4.7, 9.5 Hz, 1H), 7.55 (m, 1H), 7.69 (dd, J=2.8, 9.7 Hz, 1H), 7.88 (s, 1H). EIMS m/z 479 (M+23). Anal. ($C_{26}H_{21}FN_4O_3$) C, H, N.

Preparation of 6-Fluoro-1-(4-fluoro-benzyl)-4-[4-(furan-2-carbonyl)-piperazin-1-yl]-2-oxo-1,2-dihydro-quinolin-3-carbonitrile (Compound 52)

2-Furoyl chloride (148 μL, 1.5 mmol) was added to a stirred solution of Compound 49 (380 mg, 1 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethylacetate to yield 282 mg (85%) of white solids. M.P. 248° C. $^1$H NMR (DMSO-$d_6$): δ 3.68 (m, 4H), 3.96 (m, 4H), 5.47 (s, 2H), 6.66 (dd, J=1.6, 3.6 Hz, 1H), 7.08 (d, J=3.4 Hz, 1H), 7.15 (m, 2H), 7.28 (m, 2H), 7.47 (dd, J=4.7, 9.6 Hz, 1H), 7.55 (m, 1H), 7.69 (dd, J=2.8, 9.7 Hz, 1H), 7.88 (s, 1H). EIMS m/z 497 (M+23). Anal. ($C_{26}H_{20}F_2N_4O_3$) C, H, N.

Preparation of 6-Fluoro-4-[4-(furan-2-carbonyl)-piperazin-1-1-yl]-1-methyl-2-oxo-1,2-dihydro-quinolin-3-carbonitrile (Compound 53)

2-Furoyl chloride (148 μL, 1.5 mmol) was added to a stirred solution of Compound 50 (286 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 333 mg (87%) of white solids. M.P. 263° C. $^1$H NMR (DMSO-$d_6$): δ 3.58 (s, 3H), 3.62 (m, 4H), 3.95 (m, 4H), 6.66 (d, J=3.6 Hz, 1H), 7.08 (d, J=3.4 Hz, 1H), 7.65 (m, 3H), 7.88 (s, 1H). EIMS m/z 403 (M+23). Anal. ($C_{20}H_{17}FN_4O_3$) C, H, N.

Preparation of 1-Benzyl-6-fluoro-2-oxo-4-[4-(thiophene-2-carbonyl)-piperazin-1-yl]-1,2-dihydro-quinolin-3-carbonitrile (Compound 54)

2-Thiophene carbonyl chloride (160 μL, 1.5 mmol) was added to a stirred solution of Compound 48 (362 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 359 mg (76%) of white solids. M.P. 246° C. $^1$H NMR (DMSO-$d_6$): δ 3.67 (m, 4H), 3.94 (m, 4H), 5.49 (s, 2H), 7.16 (m, 1H), 7.20-7.26 (m, 3H), 7.45 (dd, J=4.6, 9.4 Hz, 1H), 7.50 (d, J=3.9 Hz, 1H), 7.55 (td, J=2.7, 9.2 Hz, 1H), 7.66 (dd, J=2.8, 9.7 Hz, 1H), 7.80 (d, J=5.1 Hz, 1H). EIMS m/z 473 (M+1). Anal. ($C_{26}H_{21}FN_4O_2S$) C, H, N.

Preparation of 6-Fluoro-1-(fluoro-benzyl)-2-oxo-4-[4-(thiophene-2-carbonyl)-piperazin-1-yl]-1,2-dihydro-quinolin-3-carbonitrile (Compound 55)

2-Thiophene carbonyl chloride (160 μL, 1.5 mmol) was added to a stirred solution of Compound 49 (380 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 294 mg (60%) of white solids. M.P. 211° C. $^1$H NMR (DMSO-$d_6$): δ 3.67 (m, 4H), 3.94 (m, 4H), 5.47 (s, 2H), 7.15

(m, 3H), 7.27 (m, 2H), 7.46 (m, 2H), 7.54 (td, J=2.6, 9.2 Hz, 1H), 7.67 (dd, J=2.8, 9.7 Hz, 1H), 7.80 (d, J=5.1 Hz, 1H). EIMS m/z 491 (M+1). Anal. ($C_{26}H_{20}F_2N_4O_2S$) C, H, N.

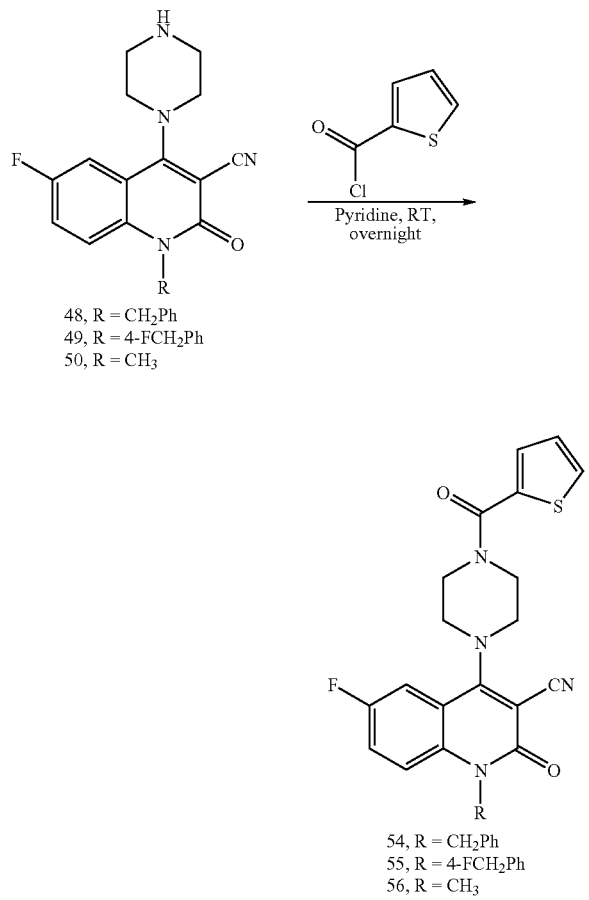

48, R = CH$_2$Ph
49, R = 4-FCH$_2$Ph
50, R = CH$_3$

54, R = CH$_2$Ph
55, R = 4-FCH$_2$Ph
56, R = CH$_3$

Preparation of 6-Fluoro-1-methyl-2-oxo-4-[4-(thiophene-2-carbonyl)-piperazin-1-yl]-1,2-dihydro-quinolin-3-carbonitrile (Compound 56)

2-Thiophene carbonyl chloride (160 μL, 1.5 mmol) was added to a stirred solution of Compound 50 (286 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 390 mg (98%) of white solids. M.P. 286° C. $^1$H NMR (DMSO-d$_6$): δ 3.58 (s, 3H), 3.62 (m, 4H), 3.92 (m, 4H), 7.16 (dd, J=3.5, 5.0, 1H), 7.50 (d, J=3.2 Hz, 1H), 7.63-7.68 (m, 3H), 7.80 (d, J=4.8 Hz, 1H). EIMS m/z 397 (M+1). Anal. ($C_{20}H_{17}FN_4O_2S$) C, H, N.

Preparation of 2-Amino-5-chloro benzoic acid (Compound 57)

To a solution of 5-chloro-2-nitrobenzoic acid (20 g, 110 mmol) in ethanol was added freshly activated raney nickel (2 g). The mixture was stirred overnight at room temperature under hydrogen atmosphere. The solution was filtered through celite and evaporated under reduced pressure to yield 16 g (96%) of white solids. $^1$H NMR (DMSO-d$_6$): δ 6.77 (d, J=8.9 Hz, 1H), 7.24 (dd, J=2.9, 8.9 Hz, 1H), 7.62 (d, J=2.9 Hz, 1H), 8.7 (b, 3H); EIMS: 170 (M–H).

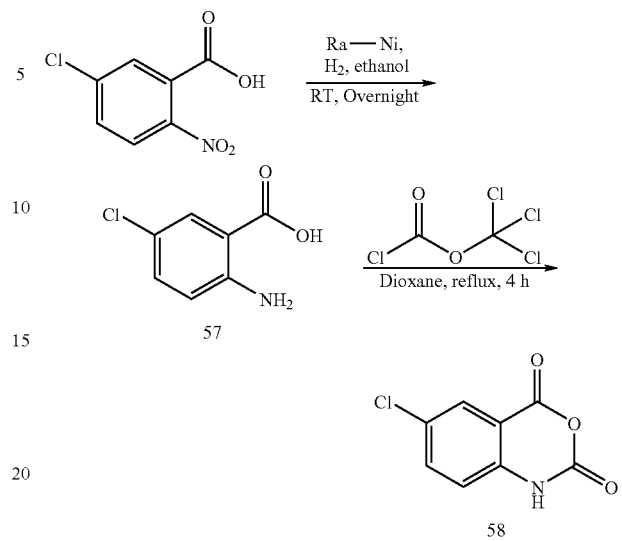

Preparation of 6-Chloro-1H-benzo[d][1,3]oxazine-2,4-dione (Compound 58)

Trichloromethyl chloroformate (4.8 mL, 300 mmol) was added to a stirred solution of Compound 57 (6.84 g, 40 mmol) in dry dioxane at room temperature and the solution was refluxed for 4 h. The solution was cooled in an ice bath and the solids formed were filtered. The solids were washed by ether and dried under vacuum at room temperature to yield 7.3 g (92%) of white solids. $^1$H NMR (DMSO-d$_6$): δ 7.47 (d, J=8.6 Hz, 1H), 7.70 (dd, J=8.6, 1.8 Hz, 1H), 7.82 (d, J=1.1, 1H), 11.63 (s, 1H).

Preparation of 1-Benzyl-6-chloro-1H-benzo [d][1,3]oxazine-2,4-dione (Compound 59)

A solution of Compound 58 (4.9 g, 25 mmol) in DMF was added slowly to a suspension of NaH (60% in mineral oil, 1.2 g, 30 mmol) in DMF and further stirred at room temperature for 1 h. Then, neat benzyl bromide (3.78 mL, 30 mmol) was added and the solution further stirred at room temperature for 3 h. The solution was poured into ice water and the solids formed were filtered, washed several times by water, and dried. The solids were suspended in hexane, sonicated briefly, filtered, and washed by hexane to yield 6.5 g (90%) of white solids. $^1$H NMR (DMSO-d$_6$): δ 5.45 (s, 2H), 7.17 (d, J=8.7 Hz, 1H), 7.26-7.39 (m, 5H), 7.65 (dd, J=1.5, 8.7 Hz, 1H), 8.02 (d, J=1.5 Hz, 1H).

Preparation of 6-Chloro-1-(4-Fluorobenzyl)-1H-benzo[d][1,3]oxazine-2,4-dione (Compound 60)

A solution of Compound 58 (5 g, 25 mmol) in DMF was added slowly to a suspension of NaH (60% in mineral oil, 1.24 g, 31 mmol) in DMF and further stirred at room temperature for 1 h. Then, neat 4-fluorobenzyl bromide (3.81 mL, 31 mmol) was added and the solution further stirred at room temperature for 3 h. The solution was poured into ice water and the solids formed were filtered, washed several times by water, and dried. The solids were suspended in hexane, sonicated briefly, filtered, and washed by hexane to yield 7.3 g (96%) of white solids. $^1$H NMR (DMSO-d$_6$): δ 5.45 (s, 2H), 7.14-7.17 (m, 3H), 7.44 (m, 2H), 7.64 (dd, J=1.7, 8.2 Hz, 1H), 7.80 (d, J=1.2 Hz, 1H).

Preparation of 1,6-Dimethyl-1H-benzo[d][1,3]oxazine-2,4-dione (Compound 61)

A solution of Compound 58 (5 g, 25 mmol) in DMF was added slowly to a suspension of NaH (60% in mineral oil, 1.24 g, 31 mmol) in DMF, and the solution was further stirred at room temperature for 1 h. Then, methyl iodide (1.92 mL, 31 mmol) was added and the solution was further stirred at room temperature for 3 h. The solution was poured into ice water and the solids formed were filtered, washed several times by water, and dried. The solids were suspended in hexane, sonicated briefly, filtered, and washed by hexane to yield 4.6 g (75%) of white solids. $^1$H NMR (DMSO-d$_6$): δ 3.52 (s, 3H), 7.54 (d, J=8.2 Hz, 1H), 7.74 (dd, J=1.7, 8.2 Hz, 1H), 7.80 (d, J=1.2 Hz, 1H).

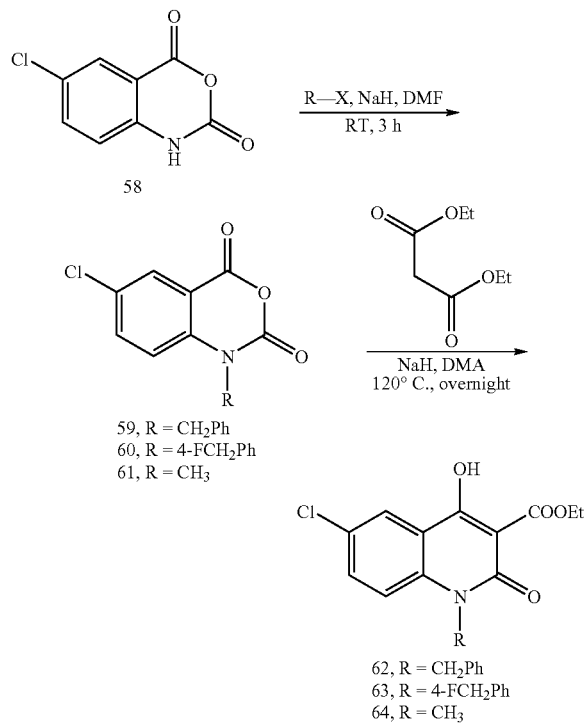

Preparation of 1-Benzyl-6-chloro-4-hydroxy-2-oxo-1,2-dihydro-quinoline-3-carboxylic acid ethyl ester (Compound 62)

Neat diethyl malonate (19.07 mL, 125 mmol) was added slowly to a suspension of sodium hydride (60% in mineral oil, 5.52 g, 138 mmol) in dimethylacetamide under N$_2$ atmosphere. The mixture was stirred at room temperature until the evolution of hydrogen gas ceased, then the mixture was heated to 90° C. for 30 min then cooled to room temperature. A solution of Compound 59 (39.88 g, 138 mmol) in dimethylacetamide was added slowly and the mixture heated overnight at 110° C. The mixture was cooled to room temperature, poured into ice water, and acidified by cold 10% HCl. The solids formed were filtered, washed several times by water, and dried at room temperature under vacuum to yield 38 g (86%) of white solids. $^1$H NMR (DMSO-d$_6$): δ 1.31 (t, J=7.2 Hz, 3H), 4.32 (q, J=7.2 Hz, 2H), 5.45 (s, 2H), 7.17 (d, J=7.2 Hz, 2H), 7.2 (m, 2H), 7.31 (t, J=6.8 Hz, 1H), 7.37 (d, J=9.2 Hz, 1H), 7.65 (dd, J=2.8, 9.2 Hz, 1H), 8.02 (d, J=2.4 Hz, 1H), 12.90 (b, 1H); EIMS: 358 (M+H).

Preparation of 6-Chloro-1-(4-Fluoro-benzyl)-4-hydroxy-2-oxo-1,2-dihydro-quinoline-3-carboxylic acid ethyl ester (Compound 63)

Neat diethyl malonate (3.04 mL, 20 mmol) was added slowly to a suspension of sodium hydride (60% in mineral oil, 0.88 g, 22 mmol) in dimethylacetamide under N$_2$ atmosphere. The mixture was stirred at room temperature until the evolution of hydrogen gas ceased, then the mixture was heated to 90° C. for 30 min and cooled to room temperature. A solution of Compound 60 (6.7 g, 22 mmol) in dimethylacetamide was added slowly and the mixture heated overnight at 110° C. The mixture was cooled to room temperature, poured into ice water, and acidified by cold 10% HCl. The solids formed were filtered, washed several times by water, and dried at room temperature under vacuum to yield 6.4 g (85%) of white solids. $^1$H NMR (DMSO-d$_6$): δ 1.31 (t, J=6.8 Hz, 3H), 4.34 (q, J=6.8 Hz, 2H), 5.43 (s, 2H), 7.1 (m, 2H), 7.2 (m, 2H), 7.40 (d, J=9.2, 1H), 7.66 (dd, J=2.4, 9.2 Hz, 1H), 8.02 (d, J=2.8 Hz, 1H), 13.00 (b, 1H); EIMS: 376 (M+H).

Preparation of 6-Chloro-4-Hydroxy-1-methyl-2-oxo-1,2-dihydro-quinoline-3-carboxylic acid ethyl ester (Compound 64)

Neat diethyl malonate (2.28 g, 14.26 mmol) was added slowly to a suspension of sodium hydride (60% in mineral oil, 628 mg, 15.69 mmol) in dimethylacetamide under N$_2$ atmosphere. The mixture was stirred at room temperature until the evolution of hydrogen gas ceased, then the mixture was heated to 90° C. for 30 min. then cooled to room temperature. A solution of Compound 61 (12 g, 56 mmol) in dimethylacetamide was added slowly and the mixture heated overnight at 120° C. The mixture was cooled to room temperature, poured into ice water, and acidified by cold 10% HCl. The solids formed were filtered and washed several times by water to yield 3.96 g (97%) of white solids. $^1$H NMR (DMSO-d$_6$): δ 1.29 (t, J=6.9 Hz, 3H), 3.52 (s, 3H), 4.30 (q, J=6.9 Hz, 2H), 7.54 (d, J=9.1 Hz, 1H), 7.74 (dd, J=1.6, 8.9 Hz, 1H), 8.0 (m, 1H), 12.80 (b, 1H); EIMS: 282 (M+H).

Preparation of 1-Benzyl-6-chloro-4-hydroxy-2-oxo-1,2-dihydro-quinoline-3-carboxylic acid cyclohexylamide (Compound 65)

Cyclohexylamine (1.27 mL, 11.17 mmol) was added to a solution of Compound 62 (2.0 g, 5.6 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 2.23 g (96%) of white solids. M.P. 158° C. $^1$H NMR (DMSO-d$_6$): δ 1.22 (m, 2H), 1.35 (m, 3H), 1.56 (m, 1H), 1.67 (m, 2H), 1.88 (m, 2H), 3.87 (m, 1H), 5.51 (s, 2H), 7.16 (m, 2H), 7.24 (m, 1H), 7.32 (m, 2H), 7.42 (d, J=9.0 Hz, 1H), 7.70 (d, J=9.0 Hz, 1H), 7.80 (d, J=2.1 Hz, 1H), 10.36 (s, 1H). EIMS m/z 411 (M+1).

Preparation of 6-Chloro-1-(4-fluorobenzyl)-4-hydroxy-6-methyl-2-oxo-1,2-dihydro-quinoline-3-carboxylic acid cyclohexylamide (Compound 66)

Cyclohexylamine (1.83 mL, 16 mmol) was added to a solution of Compound 63 (3.0 g, 8 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 3.1 g (90%) of white solids. M.P. 157° C. $^1$H NMR (DMSO-d$_6$): δ 1.21 (m, 2H), 1.35 (m, 3H), 1.55 (m, 1H), 1.67 (m, 2H), 1.88 (m, 2H), 2.36 (s, 3H), 3.87 (m, 1H), 5.49 (s, 2H), 7.13 (m, 2H), 7.23 (m, 2H), 7.44 (d, J=9.3 Hz, 1H), 7.70 (dd, J=2.6, 9.4 Hz, 1H), 7.80 (d, J=2.8 Hz, 1H), 10.33 (s, 1H).

Preparation of 4-Chloro-6-hydroxy-1-methyl-2-oxo-1,2-dihydro-quinoline-3-carboxylic acid cyclohexylamide (Compound 67)

Cyclohexylamine (1.62 mL, 14.2 mmol) was added to a solution of Compound 64 (2.0 g, 7.1 mmol) in toluene (50 mL) and refluxed for 4 h. The solution was cooled and the solvent was evaporated under vacuum. The residue obtained was suspended in water, briefly sonicated, and filtered. The crude product was recrystallized by ether to yield 2.27 g (67%) of white solids. M.P. 186° C. $^1$H NMR (DMSO-$d_6$): δ 1.28 (m, 1H), 1.38 (m, 4H), 1.54 (m, 1H), 1.69 (m, 2H), 1.87 (m, 2H), 3.60 (s, 3H), 3.87 (m, 1H), 7.66 (d, J=9.0 Hz, 1H), 7.83 (d, J=9.0 Hz, 1H), 7.98 (s, 1H), 10.39 (s, 1H). EIMS m/z 335 (M+1).

Preparation of 1-Benzyl-4,6-dichloro-2-oxo-1,2-dihydro-quinoline-3-carbonitrile (Compound 68)

A solution of Compound 65 (2 g, 4.86 mmol) in 20 mL neat phosphorus oxychloride was heated to 90° C. for 5 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 810 mg (51%) of yellow solids. M.P. 243° C. $^1$H NMR (DMSO-$d_6$): δ 5.55 (s, 2H), 7.25 (m, 3H), 7.32 (m, 2H), 7.56 (d, J=9.0 Hz, 1H), 7.85 (dd, J=2.1, 9.0 Hz, 1H), 7.89 (d, J=2.1 Hz, 1H). EIMS m/z 352 (M+23).

Preparation of 4,6-Dichloro-1-(4-fluorobenzyl)-2-oxo-1,2-dihydro-quinoline-3-carbonitrile (Compound 69)

A solution of Compound 66 (3 g, 7 mmol) in 30 mL neat phosphorus oxychloride was heated at 90° C. for 5 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 1.2 g (50%) of yellow solids. M.P. 252° C. $^1$H NMR (DMSO-$d_6$): δ 5.53 (s, 2H), 7.15 (m, 2H), 7.33 (m, 2H), 7.56 (d, J=9.0 Hz, 1H), 7.86 (dd, J=2.1, 9.0 Hz, 1H), 8.08 (d, J=2.1 Hz, 1H).

Preparation of 4,6-Dichloro-1-methyl-2-oxo-1,2-dihydro-quinoline-3-carbonitrile (Compound 70)

A solution of Compound 67 (2.2 g, 6.57 mmol) in 20 mL neat phosphorus oxychloride was heated at 90° C. for 5 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 0.8 g (48%) of yellow solids. M.P. 256° C. $^1$H NMR (DMSO-$d_6$): δ 3.65 (s, 3H), 7.60 (d, J=9.0 Hz, 1H), 7.94 (dd, J=2.1, 9.0 Hz, 1H), 8.06 (d, J=2.1 Hz, 1H). EIMS m/z 254 (M+1).

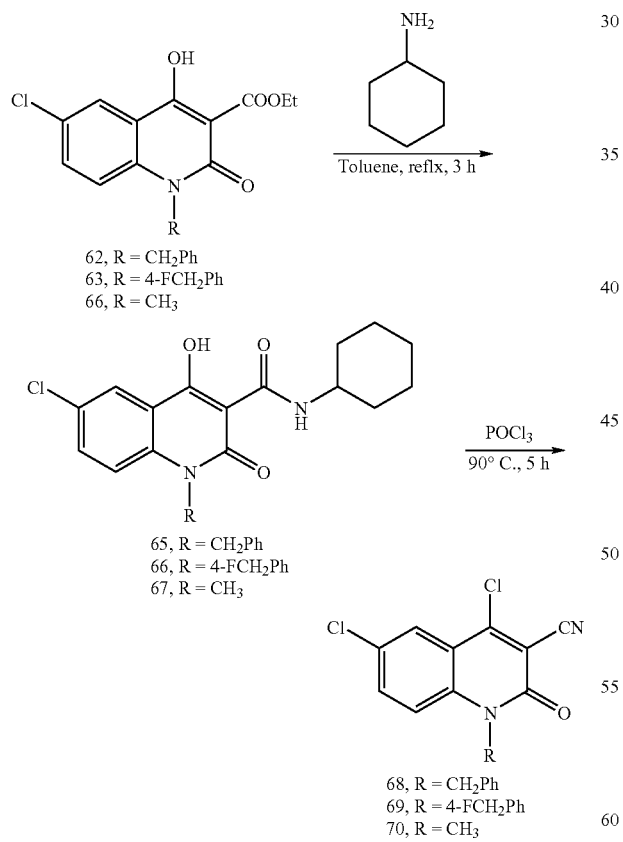
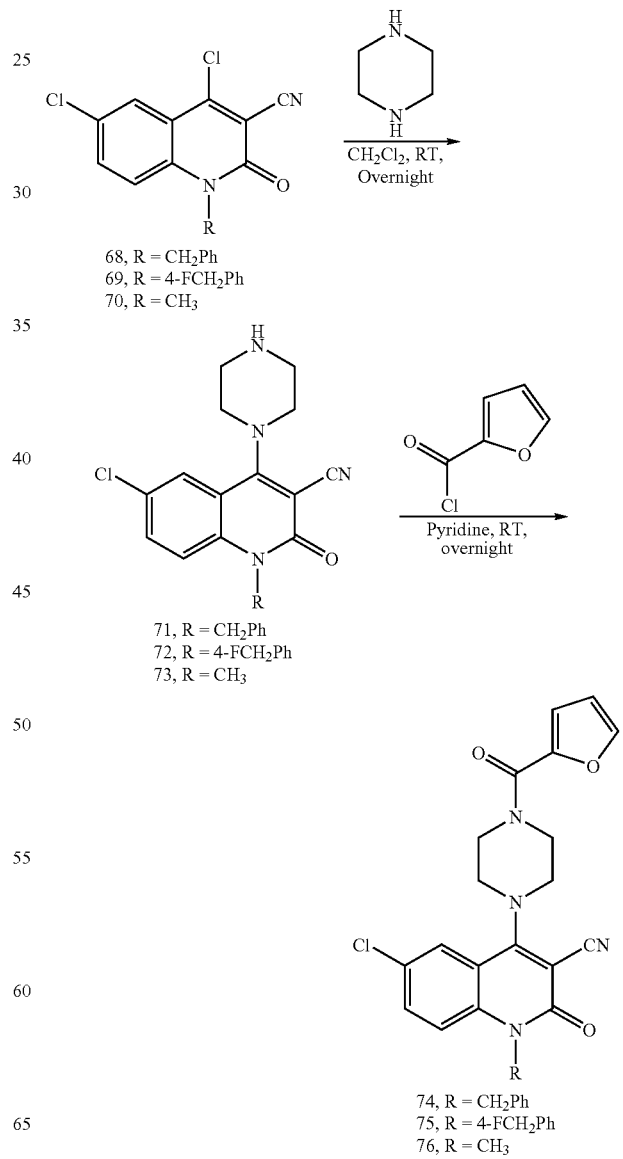

Preparation of 1-Benzyl-6-chloro-2-oxo-4-(piperazin-1-yl)-1,2-dihydro-quinolin-3-carbonitrile (Compound 71)

A solution of Compound 68 (0.8 g, 2.43 mmol) in dichloromethane was added slowly to a stirred solution of piperazine (628 mg g, 7.29 mmol) in dichloromethane at room temperature. The solution was stirred overnight at room temperature. The solvent was then removed under reduced pressure. The residue was taken in water, sonicated briefly, and filtered. The solids were dissolved in ethyl acetate and washed by water. The organic layer was dried over $Na_2SO_4$ and concentrated to yield 0.9 g (98%) of yellow solids. M.P. 156° C. $^1$H NMR (DMSO-$d_6$): δ 2.94 (m, 4H), 3.55 (m, 4H), 5.47 (s, 2H), 7.19 (m, 2H), 7.24 (m, 1H), 7.31 (m, 2H), 7.39 (d, J=8.9 Hz, 1H), 7.64 (dd, J=2.6, 8.9 Hz, 1H), 7.81 (d, J=2.6 Hz, 1H). EIMS m/z 379 (M+1).

Preparation of 6-Chloro-1-(4-fluoro-benzyl)-2-oxo-4-(piperazin-1-yl)-1,2-dihydro-quinolin-3-carbonitrile (Compound 72)

A solution of Compound 69 (1.2 g, 3.48 mmol) in dichloromethane was added slowly to a stirred solution of piperazine (0.9 g, 10.45 mmol) in dichloromethane at room temperature. The solution was stirred overnight at room temperature. The solvent was then removed under reduced pressure. The residue was taken in water, sonicated briefly, and filtered. The solids were dissolved in ethyl acetate and washed by water. The organic layer was dried over $Na_2SO_4$ and concentrated to yield 1.36 (98%) of yellow solids. M.P. 189° C. $^1$H NMR (DMSO-$d_6$): δ 2.94 (m, 4H), 3.54 (m, 4H), 5.43 (s, 2H), 7.14 (m, 2H), 7.26 (m, 2H), 7.43 (d, J=9.0 Hz, 1H), 7.67 (dd, J=2.5, 9.0 Hz, 1H), 7.81 (d, J=2.5 Hz, 1H). EIMS m/z 397 (M+1).

Preparation of 6-Chloro-1-methyl-2-oxo-4-(piperazin-1-yl)-1,2-dihydro-quinolin-3-carbonitrile (Compound 73)

A solution of Compound 70 (0.8 g, 3.16 mmol) in dichloromethane was added slowly to a stirred solution of piperazine (819 mg, 9.50 mmol) in dichloromethane at room temperature. The solution was stirred overnight at room temperature. The solvent was then removed under reduced pressure. The residue was taken in water, sonicated briefly, and filtered. The solids were dissolved in ethyl acetate and washed by water. The organic layer was dried over $Na_2SO_4$ and concentrated to yield 950 mg (99%) of yellow solids. M.P. 223° C. $^1$H NMR (DMSO-$d_6$): δ 2.92 (m, 4H), 3.48 (m, 4H), 3.55 (s, 3H), 7.60 (d, J=8.8 Hz, 1H), 7.77 (m, 2H). EIMS m/z 303 (M+1).

Preparation of 1-Benzyl-6-chloro-4-[4-(furan-2-carbonyl)-piperazin-1-yl]-2-oxo-1,2-dihydro-quinolin-3-carbonitrile (Compound 74)

2-Furoyl chloride (148 μL, 1.5 mmol) was added to a stirred solution of Compound 71 (379 mg, 1 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 361 mg (76%) of white solids. M.P. 221° C. $^1$H NMR (DMSO-$d_6$): δ 3.70 (m, 4H), 3.97 (m, 4H), 5.48 (s, 2H), 6.67 (dd, J=2.0, 3.6 Hz, 1H), 7.10 (d, J=3.6 Hz, 1H), 7.20 (m, 2H), 7.25 (m, 1H), 7.27 (m, 2H), 7.42 (d, J=9.2 Hz, 1H), 7.70 (dd, J=2.4, 9.2 Hz), 7.90 (s, 1H). EIMS m/z 496 (M+23). Anal. ($C_{26}H_{21}ClN_4O_3$) C, H, N.

Preparation of 6-Chloro-1-(4-fluoro-benzyl)-4-[4-(furan-2-carbonyl)-piperazin-1-yl]-2-oxo-1,2-dihydro-quinolin-3-carbonitrile (Compound 75)

2-Furoyl chloride (148 μL, 1.5 mmol) was added to a stirred solution of Compound 72 (397 mg, 1 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethylacetate to yield 212 mg (43%) of white solids. M.P. 253° C. $^1$H NMR (DMSO-$d_6$): δ 3.69 (m, 4H), 3.96 (m, 4H), 5.45 (s, 2H), 6.66 (m, 1H), 7.08 (d, J=3.6 Hz, 1H), 7.20 (m, 2H), 7.27 (m, 2H), 7.46 (d, J=9.0 Hz, 1H), 7.69 (dd, J=2.4, 9.0 Hz), 7.89 (s, 1H). EIMS m/z 514 (M+23). Anal. ($C_{26}H_{20}ClFN_4O_3$) C, H, N.

Preparation of 6-Chloro-4-[4-(furan-2-carbonyl)-piperazin-1-yl]-1-methyl-2-oxo-1,2-dihydro-quinolin-3-carbonitrile (Compound 76)

2-Furoyl chloride (148 μL, 1.5 mmol) was added to a stirred solution of Compound 73 (303 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to get 271 mg (68%) of white solids. M.P. 228° C. $^1$H NMR (DMSO-$d_6$): δ 3.56 (s, 3H), 3.64 (m, 4H), 3.94 (m, 4H), 6.65 (m, 1H), 7.08 (d, J=3.4 Hz, 1H), 7.60 (d, J=9.0 Hz, 1H), 7.79 (dd, J=1.9, 9.0 Hz, 1H), 7.86 (m, 2H). EIMS m/z 419 (M+23). Anal. ($C_{20}H_{17}ClN_4O_3$) C, H, N.

Preparation of 1-Benzyl-6-chloro-2-oxo-4-[4-(thiophene-2-carbonyl)-piperazin-1-yl]-1,2-dihydro-quinolin-3-carbonitrile (Compound 77)

2-Thiophene carbonyl chloride (160 μL, 1.5 mmol) was added to a stirred solution of Compound 71 (379 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 398 mg (82%) of white solids. M.P. 266° C. $^1$H NMR (DMSO-$d_6$): δ 3.70 (m, 4H), 3.93 (m, 4H), 5.48 (s, 2H), 7.15 (m, 1H), 7.19-7.26 (m, 3H), 7.32 (m, 2H), 7.42 (d, J=8.9 Hz, 1H), 7.51 (d, J=4.0 Hz, 1H), 7.68 (dd, J=2.6, 8.9 Hz, 1H), 7.80 (d, J=4.0 Hz, 1H), 7.88 (s, 1H). EIMS m/z 512 (M+23). Anal. ($C_{26}H_{21}ClN_4O_2S$) C, H, N.

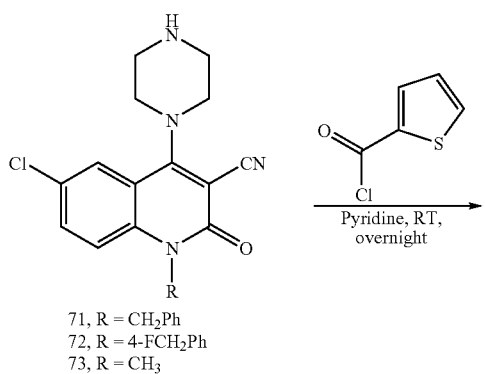

71, R = $CH_2Ph$
72, R = 4-F$CH_2Ph$
73, R = $CH_3$

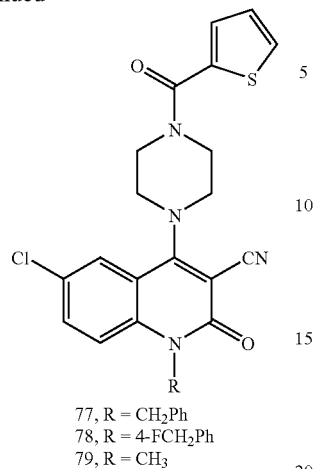

77, R = CH₂Ph
78, R = 4-FCH₂Ph
79, R = CH₃

Preparation of 6-Chloro-1-(4-fluoro-benzyl)-2-oxo-4-[4-(thiophene-2-carbonyl)-piperazin-1-yl]-1,2-dihydro-quinolin-3-carbonitrile (Compound 78)

2-Thiophene carbonyl chloride (160 µL, 1.5 mmol) was added to a stirred solution of Compound 72 (397 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 280 mg (55%) of white solids. M.P. 253° C. $^1$H NMR (DMSO-d$_6$): δ 3.70 (m, 4H), 3.93 (m, 4H), 5.46 (s, 2H), 7.13-7.17 (m, 3H), 7.27 (m, 2H), 7.44 (d, J=9.0 Hz, 1H), 7.51 (d, J=4.0 Hz, 1H), 7.68 (dd, J=2.6, 9.0 Hz, 1H), 7.79 (d, J=4.0 Hz, 1H), 7.89 (s, 1H). EIMS m/z 508 (M+1). Anal. ($C_{26}H_{20}FClN_4O_2S$) C, H, N.

Preparation of 6-Chloro-1-methyl-2-oxo-4-[4-(thiophene-2-carbonyl)-piperazin-1-yl]-1,2-dihydro-quinolin-3-carbonitrile (Compound 79)

2-Thiophene carbonyl chloride (160 µL, 1.5 mmol) was added to a stirred solution of Compound 73 (303 mg, 1.0 mmol) in pyridine (5 mL) under argon at 0° C. The solution was allowed to come to room temperature and further stirred overnight. The solution was poured into ice water and the solids formed were filtered. The solids were washed by excess water, dried, and recrystallized by ethyl acetate to yield 341 mg (83%) of white solids. M.P. 262° C. $^1$H NMR (DMSO-d$_6$): δ 3.57 (s, 3H), 3.64 (m, 4H), 3.91 (m, 4H), 7.16 (m, 1H), 7.50 (d, J=3.2 Hz, 1H), 7.62 (d, J=9.0 Hz, 1H), 7.79 (m, 2H), 7.86 (s, 1H). EIMS m/z 414 (M+1). Anal. ($C_{20}H_{17}ClN_4O_2S$) C, H, N.

Preparation of 1-(4-Fluoro-benzyl)-2-oxo-4-(piperazin-1-yl)-1,2-dihydro-quinolin-3-carbonitrile (Compound 80)

A solution of Compound 8 (15 g, 48 mmol) in dichloromethane was added slowly to a stirred solution of piperazine (12 g, 144 mmol) in dichloromethane at room temperature. The solution was stirred overnight at room temperature. The solvent was removed under reduced pressure. The residue was taken in water, sonicated briefly, and filtered. The solid was dissolved in ethyl acetate and washed by water. The organic layer was dried over Na$_2$SO$_4$ and concentrated to yield 17.17 g (98%) of yellow solids. $^1$H NMR (DMSO-d$_6$): δ 2.8 (m, 2H), 3.0 (m, 2H), 3.6 (m, 2H), 3.7 (m, 2H), 5.45 (s, 2H), 7.1 (m, 2H), 7.3 (m, 3H), 7.4 (m, 1H), 7.6 (m, 1H), 7.90 (t, J=8.2 Hz, 1H); EIMS: 363 (M+H).

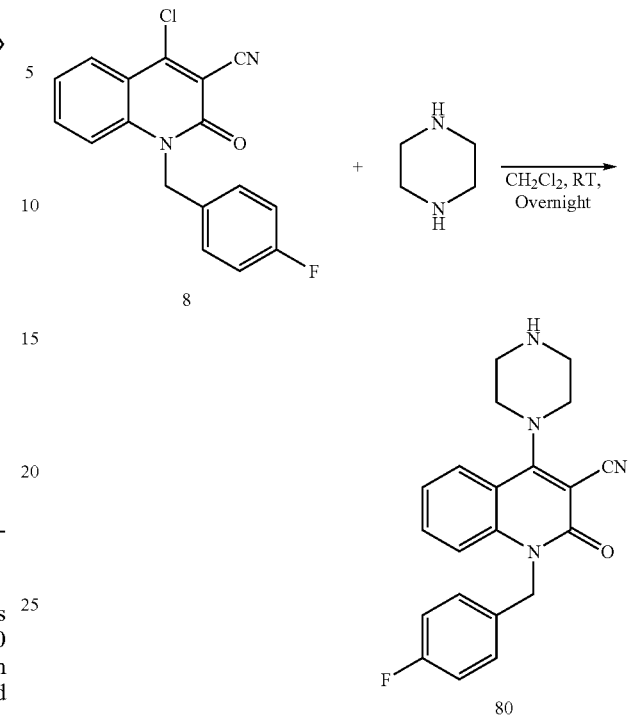

Acylation at Piperazine Moiety

The compounds referred to as Compound 81 through 102 were prepared by applying either General Procedure A or General Procedure B as described below. General Procedure A was employed to prepare the title compounds from the commercially available corresponding acid chlorides, whereas General Procedure B was employed to prepare the title compounds from commercially available acids.

General Procedure A

The corresponding acid chloride (1.25 mmol) was added to a stirred solution of Compound 80 (300 mg, 0.82 mmol) in pyridine (5 mL) under argon at 0° C. The solution was allowed to come to room temperature and further stirred overnight. The solution was poured into ice water and the solids formed were filtered. The solids were washed by excess water, dried, and purified by flash chromatography eluting with 0-2% MeOH in a CH$_2$Cl$_2$ gradient.

General Procedure B

Oxalyl chloride (1.66 mmol) and DMF (2 drops) were added sequentially to a stirred solution of the corresponding acid (1.25 mmol) in CH$_2$Cl$_2$ at room temperature, then further stirred for 2 h under argon atmosphere. The solvent was removed under vacuum at room temperature to yield the dry corresponding acid chloride. A solution of Compound 80 (300 mg, 0.82 mmol) in dry pyridine was added to the residue under argon atmosphere and briefly sonicated. The solution was stirred overnight at room temperature under argon atmosphere. The solution was poured into ice water and the solids formed were filtered. The solids were washed by excess water, dried, and purified by flash chromatography eluting with 0-2% MeOH in a CH$_2$Cl$_2$ gradient.

Preparation of 4-(4-Benzoyl-piperazin-1-yl)-1-(4-fluoro-benzyl)-2-oxo-1,2-dihydro-quinolin-3-carbonitrile (Compound 81)

The title compound was prepared by applying General Procedure A to yield 269 mg (72%) of white solids. M.P.

242° C. $^1$H NMR (DMSO-d$_6$): δ 3.66 (m, 4H), 3.92 (m, 4H), 5.46 (s, 2H), 7.14 (m, 3H), 7.28 (m, 3H), 7.42 (d, J=9.0 Hz, 1H), 7.48 (m, 5H), 7.63 (m, 1H), 7.94 (dd, J=1.5, 9.0 Hz, 1H). EIMS m/z 467 (M+1). Anal. (C$_{28}$H$_{23}$FN$_4$O$_2$) C, H, N.

Preparation of 4-(4-Cyclopentanecarbonyl-piperazin-1-yl)-1-(4-fluoro-benzyl)-2-oxo-1,2-dihydro-quinolin-3-carbonitrile (Compound 82)

The title compound was prepared by General Procedure A to yield 216 mg (58%) of white solids. M.P. 233° C. $^1$H NMR (DMSO-d$_6$): δ 1.56-1.75 (m, 8H), 3.07 (m, 1H), 3.56 (m, 4H), 3.80 (m, 4H), 5.46 (s, 2H), 7.14 (m, 2H), 7.28 (m, 3H), 7.42 (d, J=9.0 Hz, 1H), 7.64 (m, 1H), 7.94 (dd, J=1.5, 9.0 Hz, 1H). EIMS m/z 459 (M+1). Anal. (C$_{27}$H$_{27}$FN$_4$O$_2$) C, H, N.

Preparation of 1-(4-Fluoro-benzyl)-2-oxo-4-[4-(2-thiophen-2-yl-acetyl)-piperazin-1-yl]-1,2-dihydro-quinolin-3-carbonitrile (Compound 83)

The title compound was prepared by applying General Procedure A to yield 72 mg (18%) of white solids. M.P. 199° C. $^1$H NMR (DMSO-d$_6$): δ 3.58 (m, 4H), 3.82 (m, 4H), 4.05 (s, 2H), 5.46 (s, 2H), 6.97 (m, 2H), 7.14 (m, 2H), 7.28 (m, 3H), 7.40 (m, 2H), 7.48 (m, 5H), 7.63 (m, 1H), 7.92 (dd, J=1.5, 9.0 Hz, 1H). EIMS m/z 487.4 (M+1). Anal. (C$_{27}$H$_{23}$FN$_4$O$_2$S) C, H, N.

Preparation of 1-(4-Fluoro-benzyl)-4-[4-(isoxazole-5-carbonyl)-piperazin-1-yl]-2-oxo-1,2-dihydro-quinolin-3-carbonitrile (Compound 84)

The title compound was prepared by applying General Procedure A to yield 213 mg (58%) of white solids. M.P. 253° C. $^1$H NMR (DMSO-d$_6$): δ 3.70 (m, 4H), 3.84 (m, 4H), 5.47 (s, 2H), 7.03 (d, J=2.0 Hz, 1H), 7.13 (m, 2H), 7.27 (m, 3H), 7.45 (d, J=8.4 Hz, 1H). 7.64 (m, 1H), 7.93 (dd, J=1.5, 8.0 Hz, 1H), 8.79 (d, J=2.0 Hz, 1H). EIMS m/z 458 (M+1). Anal. (C$_{25}$H$_{20}$FN$_5$O$_3$) C, H, N.

Preparation of 4-[4-(4-Fluorobenzoyl)-piperazin-1-yl]-1-(4-fluoro-benzyl)-2-oxo-1,2-dihydro-quinolin-3-carbonitrile (Compound 85)

The title compound was prepared by applying General Procedure A to yield 341 mg (88%) of white solids. M.P. 272° C. $^1$H NMR (DMSO-d$_6$): δ 3.66 (m, 4H), 3.84 (m, 4H), 5.46 (s, 2H), 7.13 (m, 2H), 7.31 (m, 5H), 7.42 (d, J=8.0 Hz, 1H), 7.55 (m, 2H), 7.65 (m, 1H), 7.93 (dd, J=1.2, 8.4 Hz, 1H). EIMS m/z 485 (M+1). Anal. (C$_{28}$H$_{22}$F$_2$N$_4$O$_2$) C, H, N.

Preparation of 1-(4-Fluoro-benzyl)-2-oxo-4-[4-(pyridine-4-carbonyl)-piperazine-1-yl]-1,2-dihydro-quinolin-3-carbonitrile (Compound 86)

The title compound was prepared by applying General Procedure A to yield 273 mg (73%) of white solids. M.P. 274° C. $^1$H NMR (DMSO-d$_6$): δ 3.60 (m, 4H), 3.86 (m, 4H), 5.46 (s, 2H), 7.12 (m, 2H), 7.28 (m, 3H), 7.42 (d, J=8.0 Hz, 1H), 7.47 (m, 2H), 7.61 (m, 1H), 7.90 (d, J=7.2 Hz, 1H), 8.71 (dd, J=1.2, 4.4 Hz, 1H). EIMS m/z 468 (M+1). Anal. (C$_{27}$H$_{22}$FN$_5$O$_2$) C, H, N.

Preparation of 1-(4-Fluoro-benzyl)-2-oxo-4-[4-(piperidine-1-carbonyl)-piperazine-1-yl]-1,2-dihydro-quinolin-3-carbonitrile (Compound 87)

The title compound was prepared by applying General Procedure B to yield 243 mg (62%) of white solids. M.P. 223° C. $^1$H NMR (DMSO-d$_6$): δ 1.51 (m, 6H), 3.19 (m, 4H), 3.40 (m, 4H), 3.62 (m, 4H), 5.46 (s, 2H), 7.12 (m, 2H), 7.28 (m, 3H), 7.41 (d, J=8.8 Hz, 1H), 7.64 (m, 2H), 7.92 (d, J=8.0 Hz, 1H). EIMS m/z 474 (M+1). Anal. (C$_{27}$H$_{28}$FN$_5$O$_2$) C, H, N.

Preparation of 1-(4-Fluoro-benzyl)-2-oxo-4-[4-(Pyrrolidine-1-carbonyl)-piperazine-1-yl]-1,2-dihydro-quinolin-3-carbonitrile (Compound 88)

The title compound was prepared by applying General Procedure B to yield 252 mg (67%) of white solids. M.P. 232° C. $^1$H NMR (DMSO-d$_6$): δ 1.78 (m, 4H), 3.44 (m, 4H), 3.61 (m, 4H), 5.46 (s, 2H), 7.12 (m, 2H), 7.27 (m, 3H), 7.42 (d, J=8.8 Hz, 1H), 7.62 (m, 2H), 7.93 (d, J=8.0 Hz, 1H). EIMS m/z 459 (M+1). Anal. (C$_{26}$H$_{26}$FN$_5$O$_2$) C, H, N.

Preparation of 1-(4-Fluoro-benzyl)-2-oxo-4-[4-(thiophene-2-sulfonyl)-piperazine-1-yl]-1,2-dihydro-quinolin-3-carbonitrile (Compound 89)

The title compound was prepared by applying General Procedure B to yield 332 mg (79%) of yellow solids. M.P. 226° C. $^1$H NMR (DMSO-d$_6$): δ 3.25 (m, 4H), 3.73 (m, 4H), 5.44 (s, 2H), 7.13 (m, 2H), 7.26 (m, 3H), 7.41 (d, J=8.4 Hz, 1H), 7.61 (m, 2H), 7.71 (m, 1H), 7.80 (d, J=8.0 Hz, 1H), 8.12 (d, J=4.5 Hz, 1H). EIMS m/z 509 (M+1). Anal. (C$_{25}$H$_{21}$FN$_4$O$_3$S$_2$) C, H, N.

Preparation of 1-(4-Fluoro-benzyl)-4-[4-(furan-3-carbonyl)-piperazine-1-yl]-2-oxo-1,2-dihydro-quinolin-3-carbonitrile (Compound 90)

The title compound was prepared by applying General Procedure B to yield 183 mg (48%) of white solids. M.P. 261° C. $^1$H NMR (DMSO-d$_6$): δ 3.65 (m, 4H), 3.86 (m, 4H), 5.47 (s, 2H), 6.73 (s, 1H), 7.13 (m, 2H), 7.28 (m, 3H), 7.43 (d, J=8.4 Hz, 1H), 7.64 (m, 1H), 7.78 (s, 1H), 7.92 (dd, J=1.2, 8.4 Hz, 1H), 8.12 (s, 1H). EIMS m/z 457 (M+1). Anal. (C$_{26}$H$_{21}$FN$_4$O$_3$) C, H, N.

Preparation of 1-(4-Fluoro-benzyl)-4-[4-(1-methyl-1-H-pyrrole-2-carbonyl)-piperazine-1-yl]-2-oxo-1,2-dihydro-quinolin-3-carbonitrile (Compound 91)

The title compound was prepared by applying General Procedure B to yield 233 mg (60%) of white solids. M.P. 236° C. $^1$H NMR (DMSO-d$_6$): δ 3.66 (m, 4H), 3.92 (m, 4H), 5.47 (s, 2H), 6.06 (dd, J=2.4, 3.6 Hz, 1H), 6.40 (d, J=4.0 Hz, 1H), 6.93 (s, 1H), 7.15 (m, 2H), 7.29 (m, 3H), 7.43 (d, J=8.4 Hz, 1H), 7.62 (m, 1H), 7.94 (dd, J=1.2, 8.0 Hz, 1H). EIMS m/z 470 (M+1). Anal. (C$_{27}$H$_{24}$FN$_5$O$_2$) C, H, N.

Preparation of 4-[4-(5-Acetyl-thiophene-2-carbonyl)-piperazine-1-yl]-1-(4-fluoro-benzyl)-2-oxo-1,2-dihydro-quinolin-3-carbonitrile (Compound 92)

The title compound was prepared by applying General Procedure B to yield 259 mg (60%) of white solids. M.P. 269° C. $^1$H NMR (DMSO-d$_6$): δ 3.70 (m, 4H), 3.90 (m, 4H), 5.47 (s, 2H), 7.12 (m, 2H), 7.29 (m, 3H), 7.44 (d, J=8.4 Hz, 1H), 7.53 (d, J=3.6 Hz, 1H), 7.64 (m, 1H), 7.94 (m, 2H). EIMS m/z 515 (M+1). Anal. (C$_{28}$H$_{23}$FN$_4$O$_3$S) C, H, N.

Preparation of 1-(4-Fluoro-benzyl)-2-oxo-4-[4-(thiophene-3-carbonyl)-piperazine-1-yl]-1,2-dihydro-quinolin-3-carbonitrile (Compound 93)

The title compound was prepared by applying General Procedure B to yield 312 mg (79%) of white solids. M.P. 251° C. $^1$H NMR (DMSO-d$_6$): δ 3.66 (m, 4H), 3.82 (m, 4H), 5.46 (s, 2H), 7.12 (m, 2H), 7.28 (m, 3H), 7.48 (d, J=8.4 Hz, 1H), 7.61 (m, 2H), 7.87 (m, 1H), 7.92 (d, J=8.4 Hz, 1H). EIMS m/z 473 (M+1). Anal. (C$_{26}$H$_{21}$FN$_4$O$_2$S) C, H, N.

Preparation of 1-(4-Fluoro-benzyl)-2-oxo-4-[4-(pyridine-2-carbonyl)-piperazine-1-yl]-1,2-dihydro-quinolin-3-carbonitrile (Compound 94)

The title compound was prepared by applying General Procedure B to yield 123 mg (32%) of white solids. M.P. 231° C. $^1$H NMR (DMSO-d$_6$): δ 3.63 (m, 2H), 3.72 (m, 4H), 3.96 (m, 2H), 5.47 (s, 2H), 6.73 (s, 1H), 7.14 (m, 2H), 7.28 (m, 3H), 7.42 (d, J=8.4 Hz, 1H), 7.50 (m, 1H), 7.68 (m, 2H), 7.96 (m, 2H), 8.64 (dd, J=0.8, 4.8 Hz, 1H). EIMS m/z 468 (M+1). Anal. (C$_{27}$H$_{22}$FN$_5$O$_2$) C, H, N.

Preparation of 1-(4-Fluoro-benzyl)-2-oxo-4-[4-(pyrazine-2-carbonyl)-piperazin-1-yl]-1,2-dihydro-quinoline-3-carbonitrile (Compound 95)

The title compound was prepared by applying General Procedure B. MP: 145-156° C.; $^1$H-NMR (DMSO-$d_6$): 3.8 (m, 8H), 5.47 (s, 2H), 7.15 (t, J=8.8 Hz, 2H), 7.3 (m, 3H), 7.44 (d, J=8.4 Hz, 1H), 7.64 (t, J=7.8 Hz, 1H), 7.95 (dd, J=1.2, 8.4 Hz, 1H), 8.7 (m, 1H), 8.78 (d, J=2.4 Hz, 1H), 8.94 (d, J=1.6 Hz, 1H); EIMS: 469 (M+H).

Preparation of 1-(4-Fluoro-benzyl)-2-oxo-4-[4-(quinoline-2-carbonyl)-piperazin-1-yl]-1,2-dihydro-quinoline-3-carbonitrile (Compound 96)

The title compound was prepared by applying General Procedure B. MP: 144-157° C.; $^1$H-NMR (DMSO-$d_6$): 3.7 (m, 6H), 4.0 (m, 2H), 5.47 (s, 2H), 7.1 (m, 2H), 7.3 (m, 3H), 7.43 (d, J=8.4 Hz, 1H), 7.63 (t, J=7.2 Hz, 1H), 7.71 (t, J=7.6 Hz, 1H), 7.78 (d, J=8.4 Hz, 1H), 7.86 (t, J=7.6 Hz, 1H), 7.97 (dd, J=1.2, 8.4 Hz, 1H), 8.07 (d, J=9.2 Hz, 2H), 8.55 (d, J=8.4 Hz, 1H); EIMS: 518 (M+H).

Preparation of 1-(4-Fluoro-benzyl)-4-[4-(5-methyl-isoxazole-3-carbonyl)-piperazin-1-yl]-2-oxo-1,2-dihydro-quinoline-3-carbonitrile (Compound 97)

The title compound was prepared by applying General Procedure B. MP: 130-137° C.; $^1$H-NMR (DMSO-$d_6$): 2.48 (s, 3H), 3.7 (m, 4H), 3.9 (m, 4H), 5.47 (s, 2H), 6.53 (s, 1H), 7.15 (t, J=9.2 Hz, 2H), 7.3 (m, 3H), 7.44 (d, J=8.4 Hz, 1H), 7.64 (t, J=7.8 Hz, 1H), 7.94 (dd, J=1.2, 8.4 Hz, 1H); EIMS: 472 (M+H).

Preparation of 1-(4-Fluoro-benzyl)-2-oxo-4-[4-(tetrahydro-furan-2-carbonyl)-piperazin-1-yl]-1,2-dihydro-quinoline-3-carbonitrile (Compound 98)

The title compound was prepared by applying General Procedure B. MP: 123-135° C.; $^1$H-NMR (DMSO-$d_6$): 1.8 (m, 2H), 2.1 (m, 2H), 3.6 (m, 4H), 3.8 (m, 6H), 4.7 (m, 1H), 5.47 (s, 2H), 7.15 (d, J=8.8 Hz, 2H), 7.3 (m, 3H), 7.43 (d, J=8.4 Hz, 1H), 7.64 (t, J=7.8 Hz, 1H), 7.93 (dd, J=1.2, 8.4 Hz, 1H); EIMS: 461 (M+H).

Preparation of 4-[4-(Benzo[1,3]dioxole-5-carbonyl)-piperazin-1-yl]-1-(4-fluoro-benzyl)-2-oxo-1,2-dihydro-quinoline-3-carbonitrile (Compound 99)

The title compound was prepared by applying General Procedure B. MP: 140-160° C.; $^1$H-NMR (DMSO-$d_6$): 3.7 (m, 8H), 5.47 (s, 2H), 6.09 (s, 2H), 7.00 (s, 2H), 7.1 (m, 1H), 7.15 (t, J=7.8 Hz, 2H), 7.3 (m, 3H), 7.43 (d, J=8.4 Hz, 1H), 7.63 (t, J=7.8 Hz, 1H), 7.92 (dd, J=1.2, 8.0 Hz, 1H); EIMS: 511 (M+H).

Preparation of 1-(4-Fluoro-benzyl)-2-oxo-4-[4-(4-trifluoromethyl-benzoyl)-piperazin-1-yl]-1,2-dihydro-quinoline-3-carbonitrile (Compound 100)

The title compound was prepared by applying General Procedure B. MP: 181-185° C.; $^1$H-NMR (DMSO-$d_6$): 3.7 (m, 8H), 5.47 (s, 2H), 7.1 (m, 2H), 7.3 (m, 3H), 7.43 (d, J=8.4 Hz, 1H), 7.6 (m, 1H), 7.7 (m, 1H), 7.8 (m, 1H), 7.9 (m, 2H), 7.91 (dd, J=1.2, 8.4 Hz, 1H); EIMS: 535 (M+H).

Preparation of 1-(4-Fluoro-benzyl)-4-[4-(1H-imidazole-4-carbonyl)-piperazin-1-yl]-2-oxo-1,2-dihydro-quinoline-3-carbonitrile (Compound 101)

The title compound was prepared by applying General Procedure B. MP: 176-183° C.; $^1$H-NMR (DMSO-$d_6$): 3.67 (s, 4H), 4.3 (m, 4H), 5.47 (s, 2H), 7.2 (m, 2H), 7.3 (m, 3H), 7.45 (d, J=8.4 Hz, 1H), 7.6 (m, 2H), 7.76 (d, J=1.2 Hz, 1H), 7.97 (dd, J=1.2, 8.0 Hz, 1H); EIMS: 457 (M+H).

Preparation of 1-(4-Fluoro-benzyl)-2-oxo-4-[4-(tetrahydro-thiophene-2-carbonyl)-piperazin-1-yl]-1,2-dihydro-quinoline-3-carbonitrile (Compound 102)

The title compound was prepared by applying General Procedure B. MP: 133-140° C.; $^1$H-NMR (DMSO-$d_6$): 1.9 (m, 1H), 2.0 (m, 1H), 2.1 (m, 1H), 2.3 (m, 1H), 2.9 (m, 2H), 3.7 (m, 8H), 4.32 (t, J=5.6 Hz, 1H), 5.47 (s, 2H), 7.15 (t, J=8.0 Hz, 2H), 7.3 (m, 3H), 7.43 (d, J=8.4 Hz, 1H), 7.64 (t, J=7.6 Hz, 1H), 7.93 (d, J=8.0 Hz, 1H); EIMS: 477 (M+H).

Preparation of 4-Hydroxy-6-methyl-2-oxo-1,2-dihydro-quinoline-3-carboxylic acid ethyl ester (Compound 103)

Neat diethyl malonate (18.05 g, 112.7 mmol) was added slowly to a suspension of sodium hydride (60% in mineral oil, 4.96 mg, 124 mmol) in dimethylacetamide under $N_2$ atmosphere. The mixture was stirred at room temperature until the evolution of hydrogen gas ceased, then the mixture was heated to 90° C. for 30 min. then cooled to room temperature. A solution of Compound 11 (22 g, 124 mmol) in dimethylacetamide was added slowly and the solution heated overnight at 110° C. The mixture was cooled to room temperature, poured into ice water, and acidified by cold 10% HCl. The solids formed were filtered and washed several times by water to yield 10.2 g (36%) of white solids. M.P. 242° C. $^1$H NMR (DMSO-$d_6$): δ 1.30 (t, J=7.2 Hz, 3H), 2.35 (s, 3H), 4.34 (q, J=7.2 Hz, 2H), 7.19 (d, J=8.4 Hz, 1H), 7.46 (dd, J=1.6, 8.4 Hz, 1H), 7.72 (d, J=1.6 Hz, 1H), 11.35 (s, 1H), 13.03 (s, 1H). EIMS m/z 248 (M+1).

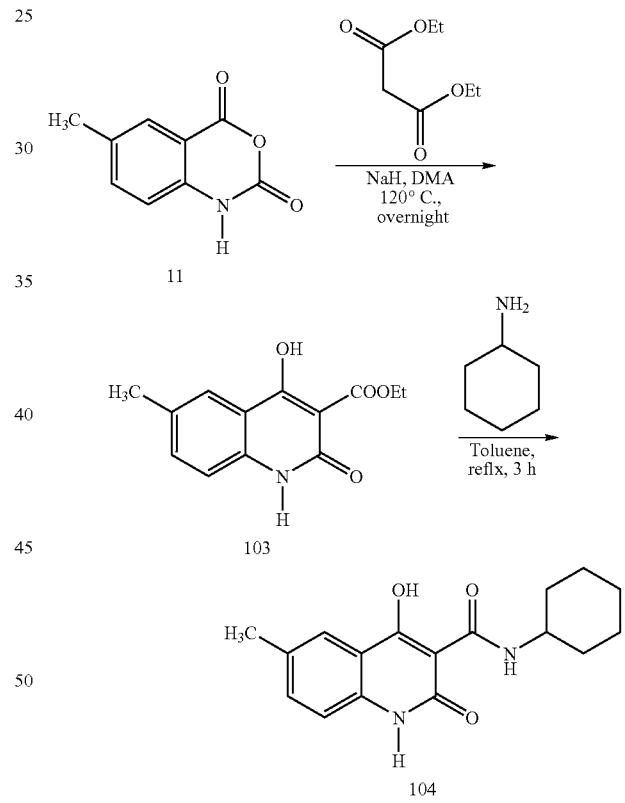

Preparation of 4-Hydroxy-6-methyl-2-oxo-1,2-dihydro-quinoline-3-carboxylic acid cyclohexylamide (Compound 104)

Cyclohexylamine (13.88 mL, 121.33 mmol) was added to a solution of Compound 102 (10 g, 40.44 mmol) in toluene (200 mL) and refluxed for 4 h. The solution was cooled and the solvent was evaporated under vacuum. The residue obtained was suspended in water, briefly sonicated, and filtered. The crude product was recrystallized by ether to yield 12 g (98%) of white solids. M.P. 269° C. $^1$H NMR (DMSO-$d_6$): δ 1.28 (m, 5H), 1.32 (m, 1H), 1.67 (m, 2H), 1.88 (m, 2H), 2.37 (s, 3H), 3.90 (m, 1H), 7.26 (d, J=8.7 Hz, 1H), 7.51 (d, J=8.7 Hz, 1H), 7.74 (s, 1H), 10.49 (s, 1H), 11.80 (s, 1H). EIMS m/z 301 (M+1).

Preparation of 2,4-Dichloro-6-methyl-quinoline-3-carbonitrile (Compound 105)

A solution of Compound 104 (12 g, 39.95 mmol) in 40 mL neat phosphorus oxychloride was heated at 90° C. for 3 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 7.2 g (76%) of white solids. M.P. 159° C. $^1$H NMR (DMSO-$d_6$): δ 2.28 (s, 3H), 7.93 (dd, J=2.0, 8.8 Hz, 1H), 8.02 (d, J=8.8 Hz, 1H), 8.07 (s, 1H). EIMS m/z 237 (M+1).

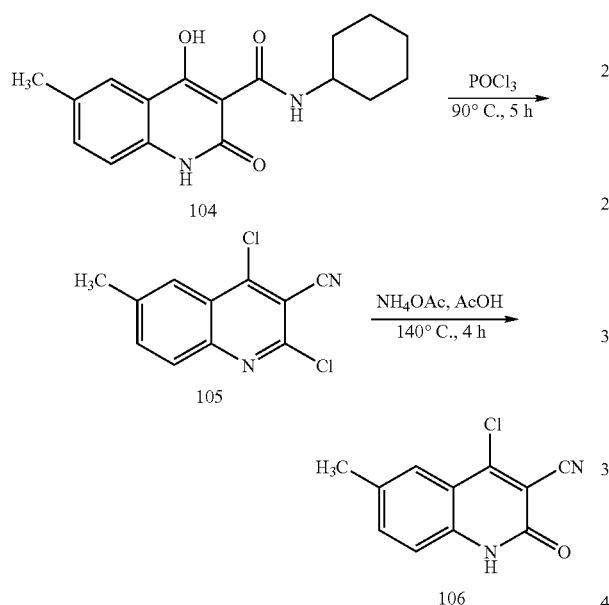

Preparation of 4-Chloro-6-methyl-2-oxo-1,2-dihydro-quinoline-3-carbonitrile (Compound 106)

Ammonium acetate was added to a suspension of Compound 105 (7.1 g, 29.95 mmol) in glacial acetic acid and heated at 140° C. for 4 h. The solution was cooled and poured into ice water. The solids formed were filtered, washed by water, and dried under vacuum to yield 4.5 g (69%) of white solids. M.P. 264° C. $^1$H NMR (DMSO-$d_6$): δ 2.32 (s, 3H), 7.34 (d, J=8.4 Hz, 1H), 7.63 (dd, J=1.5, 8.4 Hz, 1H), 7.75 (s, 1H). EIMS m/z 219 (M+1).

Preparation of 6-Methyl-2-oxo-4-[4-(thiophene-2-carbonyl)-piperazin-1-yl]-1,2-dihydro-quinolin-3-carbonitrile (Compound 107)

Piperazine-1-yl-thiophen-2-yl-methanone (8.73 g, 41.16 mmol) was added to a solution of Compound 106 (4.5 g, 20.08 mmol) in toluene (50 mL) and heated overnight at 110° C. The solvent was removed under vacuum. The residue was suspended in water, sonicated, and filtered. The crude product was purified by flash chromatography eluting with 0-2% methanol in dichloromethane gradient to yield 7.0 g (92%) of white solids. M.P. 269° C. $^1$H NMR (DMSO-$d_6$): δ 2.34 (s, 3H), 3.65 (m, 4H), 3.92 (m, 4H), 7.14 (m, 1H), 7.23 (d, J=8.4 Hz, 1H), 7.43 (d, J=8.6 Hz, 1H), 7.49 (d, J=3.5 Hz, 1H), 7.51 (s, 1H), 7.81 (d, J=4.8 Hz, 1H). EIMS m/z 379 (M+1).

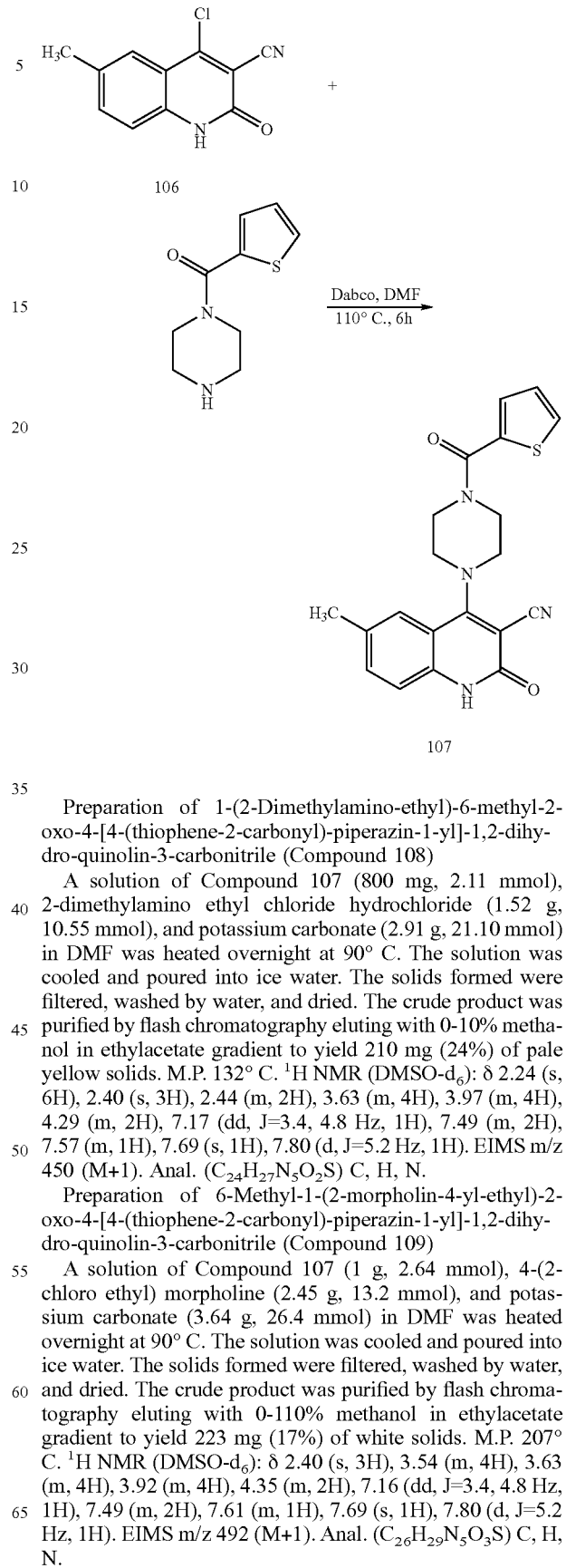

Preparation of 1-(2-Dimethylamino-ethyl)-6-methyl-2-oxo-4-[4-(thiophene-2-carbonyl)-piperazin-1-yl]-1,2-dihydro-quinolin-3-carbonitrile (Compound 108)

A solution of Compound 107 (800 mg, 2.11 mmol), 2-dimethylamino ethyl chloride hydrochloride (1.52 g, 10.55 mmol), and potassium carbonate (2.91 g, 21.10 mmol) in DMF was heated overnight at 90° C. The solution was cooled and poured into ice water. The solids formed were filtered, washed by water, and dried. The crude product was purified by flash chromatography eluting with 0-10% methanol in ethylacetate gradient to yield 210 mg (24%) of pale yellow solids. M.P. 132° C. $^1$H NMR (DMSO-$d_6$): δ 2.24 (s, 6H), 2.40 (s, 3H), 2.44 (m, 2H), 3.63 (m, 4H), 3.97 (m, 4H), 4.29 (m, 2H), 7.17 (dd, J=3.4, 4.8 Hz, 1H), 7.49 (m, 2H), 7.57 (m, 1H), 7.69 (s, 1H), 7.80 (d, J=5.2 Hz, 1H). EIMS m/z 450 (M+1). Anal. ($C_{24}H_{27}N_5O_2S$) C, H, N.

Preparation of 6-Methyl-1-(2-morpholin-4-yl-ethyl)-2-oxo-4-[4-(thiophene-2-carbonyl)-piperazin-1-yl]-1,2-dihydro-quinolin-3-carbonitrile (Compound 109)

A solution of Compound 107 (1 g, 2.64 mmol), 4-(2-chloro ethyl) morpholine (2.45 g, 13.2 mmol), and potassium carbonate (3.64 g, 26.4 mmol) in DMF was heated overnight at 90° C. The solution was cooled and poured into ice water. The solids formed were filtered, washed by water, and dried. The crude product was purified by flash chromatography eluting with 0-110% methanol in ethylacetate gradient to yield 223 mg (17%) of white solids. M.P. 207° C. $^1$H NMR (DMSO-$d_6$): δ 2.40 (s, 3H), 3.54 (m, 4H), 3.63 (m, 4H), 3.92 (m, 4H), 4.35 (m, 2H), 7.16 (dd, J=3.4, 4.8 Hz, 1H), 7.49 (m, 2H), 7.61 (m, 1H), 7.69 (s, 1H), 7.80 (d, J=5.2 Hz, 1H). EIMS m/z 492 (M+1). Anal. ($C_{26}H_{29}N_5O_3S$) C, H, N.

Preparation of 1-(2-Dimethylamino-ethyl)-6-methyl-2-oxo-4-[4-(thiophene-2-carbonyl)-piperazin-1-yl-1,2-dihydro-quinolin-3-carbonitrile (Compound 110)

A solution of Compound 107 (1 g., 2.64 mmol), 2-(diisopropylamino) ethyl chloride hydrochloride (2.64 g, 13.2 mmol), and potassium carbonate (3.64 g, 26.4 mmol) in DMF was heated overnight at 90° C. The solution was cooled and poured into ice water. The solids formed were filtered, washed by water, and dried. The crude product was purified by flash chromatography eluting with 0-10% methanol in ethylacetate gradient to yield 409 mg (30%) of pale yellow solids. M.P. 110-117° C. $^1$H NMR (DMSO-d$_6$): δ 0.93 (s, 12H), 2.40 (s, 3H), 2.59 (m, 2H), 3.01 (m, 2H), 3.61 (m, 4H), 3.91 (m, 4H), 4.15 (m, 2H), 7.16 (dd, J=3.4, 4.8 Hz, 1H), 7.49 (m, 2H), 7.58 (m, 1H), 7.69 (s, 1H), 7.80 (d, J=5.2 Hz, 1H). EIMS m/z 506 (M+1). Anal. ($C_{28}H_{35}N_5O_2S$) C, H, N.

Preparation of 6-Methyl-2-oxo-1-(2-pyrrolidin-1-yl-ethyl)-4-[4-(thiophene-2-carbonyl)-piperazin-1-yl]-1,2-dihydro-quinolin-3-carbonitrile (Compound 111)

A solution of Compound 107 (1 g., 2.64 mmol), 1-(2-chloroethyl) pyrrolidine hydrochloride (2.24 g, 13.2 mmol), and potassium carbonate (3.64 g, 26.4 mmol) in DMF was heated overnight at 90° C. The solution was cooled and poured into ice water. The solids formed were filtered, washed by water, and dried. The crude product was purified by flash chromatography eluting with 0-10% methanol in ethylacetate gradient to yield 236 mg (19%) of pale yellow solids. M.P. 139-143° C. $^1$H NMR (DMSO-d$_6$): δ 1.67 (m, 4H), 2.41 (s, 3H), 2.53 (m, 4H), 2.61 (m, 2H), 3.01 (m, 2H), 3.62 (m, 4H), 3.93 (m, 4H), 4.30 (m, 2H), 7.16 (dd, J=3.4, 4.8 Hz, 1H), 7.49 (m, 2H), 7.60 (m, 1H), 7.69 (s, 1H), 7.80 (d, J=5.2 Hz, 1H). EIMS m/z 476 (M+1). Anal. ($C_{26}H_{29}N_5O_2S$) C, H, N.

Preparation of 4-Hydroxy-2-oxo-1,2-dihydro-quinoline-3-carboxylic acid ethyl ester (Compound 112)

Neat diethyl malonate (18.05 g, 112.7 mmol) was added slowly to a suspension of sodium hydride (60% in mineral oil, 4.96 mg, 124 mmol) in dimethylacetamide under $N_2$ atmosphere. The mixture was stirred at room temperature until the evolution of hydrogen gas ceased, then the mixture was heated to 90° C. for 30 min. and cooled to room temperature. A solution of isatoic anhydride (20 g, 124 mmol) in dimethylacetamide was added slowly and the mixture heated overnight at 110° C. The mixture was cooled to room temperature, poured into ice water, and acidified by cold 10% HCl. The solids formed were filtered and washed several times by water to yield 8.7 g (30%) of white solids. M.P. 173° C. $^1$H NMR (DMSO-d$_6$): δ 1.31 (t, J=6.6 Hz, 3H), 4.34 (q, J=6.6 Hz, 2H), 7.20 (t, J=8.0 Hz, 1H), 7.27 (d, J=8.4 Hz, 1H), 7.62 (t, J=7.2 Hz, 1H), 7.93 (d, J=8.0 Hz, 1H), 11.50 (b, 1H); EIMS: 234 (M+H).

Preparation of 4-Hydroxy-2-oxo-1,2-dihydro-quinoline-3-carboxylic acid cyclohexylamide (Compound 113)

Cyclohexylamine (13.88 mL, 121.33 mmol) was added to a solution of Compound 112 (9.4 g, 40.44 mmol) in toluene (200 mL) and refluxed for 4 h. The solution was cooled and the solvent was evaporated under vacuum. The residue obtained was suspended in water, briefly sonicated, and filtered. The crude product was recrystallized by ether to yield 10.1 g (87%) of white solids. M.P. 223° C. $^1$H NMR (DMSO-d$_6$): δ 1.3 (m, 4H), 1.6 (m, 2H), 1.7 (m, 2H), 1.9 (m, 2H), 3.8 (m, 1H), 7.25 (t, J=7.7 Hz, 1H), 7.35 (d, J=8.3 Hz, 1H), 7.65 (t, J=7.2 Hz, 1H), 7.95 (d, J=7.7 Hz, 1H), 10.44 (b, 1H); EIMS (neg. mode): 285 (M–H).

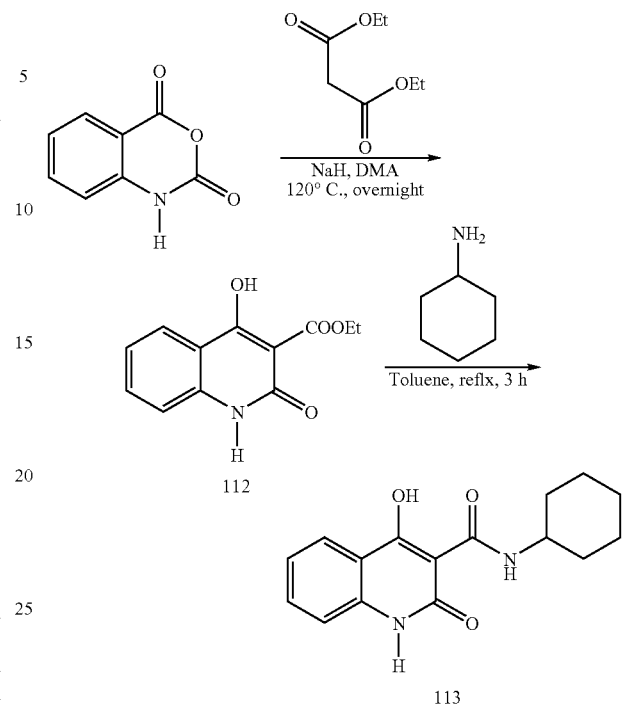

Preparation of 2,4-Dichloro-quinoline-3-carbonitrile (Compound 114)

A solution of Compound 113 (8.5 g, 30 mmol) in 40 mL neat phosphorus oxychloride was heated at 90° C. for 3 h. The solvent was evaporated under reduced pressure. The residue was suspended in ice water and neutralized by solid sodium bicarbonate. The solids formed were filtered, washed by water, and purified by flash chromatography eluting with 1% methanol in dichloromethane to yield 6.0 g (91%) of white solids. M.P. 157° C. $^1$H NMR (DMSO-d$_6$): δ $^1$H-NMR (DMSO-d$_6$): 7.9 (m, 1H), 8.09 (d, J=4.3 Hz, 2H), 8.28 (d, J=8.8 Hz, 1H); EIMS: 223 (M+H).

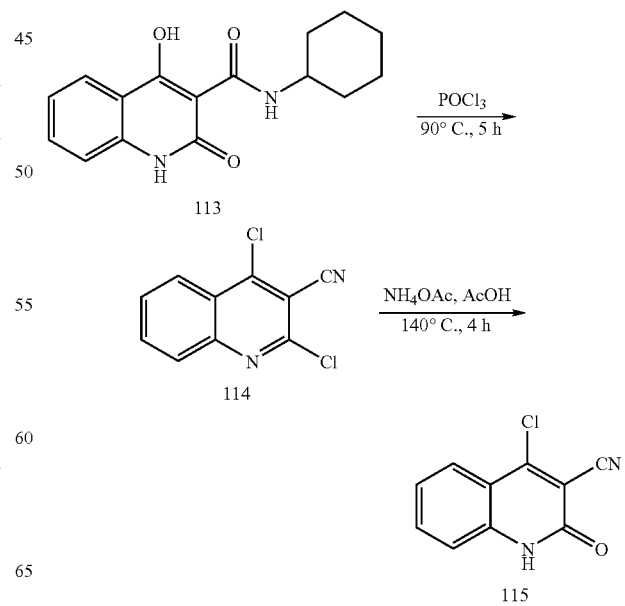

Preparation of 4-Chloro-2-oxo-1,2-dihydro-quinoline-3-carbonitrile (Compound 115)

Ammonium acetate (2.1 g, 27 mmol) was added to a suspension of Compound 114 (6.0 g, 27 mmol) in glacial acetic acid and heated at 140° C. for 4 h. The solution was cooled and poured into ice water. The solids formed were filtered, washed by water, and dreid under vacuum to yield 5.2 g (94%) of white solids. M.P. 302° C. $^1$H NMR (DMSO-$d_6$): δ$^1$H-NMR (DMSO-$d_6$): 7.4 (m, 2H), 7.79 (t, J=7.6 Hz, 1H), 7.96 (d, J=8.0 Hz, 1H); EIMS: 205 (M+H).

Preparation of 2-Oxo-4-[4-(thiophene-2-carbonyl)-piperazin-1-yl]-1,2-dihydro-quinolin-3-carbonitrile (Compound 116)

Piperazine-1-yl-thiophen-2-yl-methanone (8.0 g, 41 mmol) was added to a solution og Compound 115 (4.1 g, 20 mmol) in toluene (50 mL) and heated overnight at 110° C. The solvent was removed under vacuum. The residue was suspended in water, sonicated, and filtered. The crude product was purified by flash chromatography eluting with 0-2% methanol in dichloromethane gradient to yield 6.4 g (88%) of white solids. M.P. 264° C. $^1$H NMR (DMSO-$d_6$): δ 3.7 (m, 4H), 3.9 (m, 4H), 7.16 (t, J=4.8 Hz, 1H), 7.23 (t, J=5.9 Hz, 1H), 7.31 (d, J=8.6 Hz, 1H), 7.49 (d, J=4.0 Hz, 1H), 7.61 (t, J=8.3 Hz, 1H), 7.8 (m, 2H), 11.90 (b, 1H); EIMS: 364 (M+H).

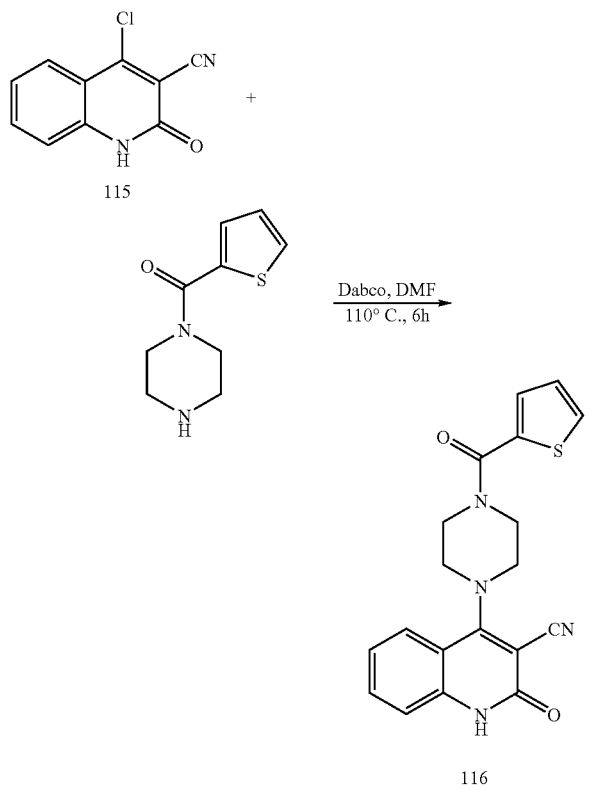

Preparation of Alkylation at N–1 position of quinolinone moiety

The compounds referred to as Compound 117-158 were prepared by applying either General Procedure C or General Procedure D.

General Procedure C

A solution of Compound 116 (364 mg, 1 mmol) and potassium carbonate (691 g, 5 mmol) with 2.5 mmol of the corresponding alkyl halide (chloro, bromo or iodo) in DMF was heated overnight at 90° C. The solution was cooled and poured into ice water. The solids formed were filtered, washed by water, and dried. In cases where solids were not formed, the product was extracted with either dichloromethane or n-butanol and concentrated under vacuum. The crude product was purified by flash chromatography eluting with 0-5% methanol in dichloromethane gradient.

General Procedure D

A solution of Compound 116 (364 mg, 1 mmol) in DMF was added to a stirred suspension of NaH (60% in mineral oil, 44 mg, 1.1 mmol) in DMF at room temperature under argon atmosphere. The solution was stirred at room temperature for 1 h and the corresponding alkyl halide was added via syringe. The solution was further stirred at room temperature for 3 to 48 h (TLC control). The reaction was worked up as described in General Procedure C.

Preparation of 1-(2-Dimethylamino-ethyl)-2-oxo-4-[4-(thiophene-2-carbonyl)-piperazin-1-yl]-1,2-dihydro-quinolin-3-carbonitrile (Compound 117)

The compound was prepared from the corresponding alkyl halide according to General Procedure D to yield white solids. Yield 211 mg (48%). M.P. 96-99° C. $^1$H NMR (DMSO-$d_6$): δ 2.20 (s, 6H), 2.46 (m, 1H), 2.71 (s, 1H), 3.68 (m, 4H), 3.93 (m, 4H), 4.30 (m, 1H), 4.55(m, 1H), 7.16 (dd, J=3.4, 4.8 Hz, 1H), 7.32 (m, 1H), 7.49 (m, 1H), 7.59 (d, J=8.4 Hz, 1H), 7.71 (m, 2H), 8.02 (d, J=5.2 Hz, 1H). EIMS m/z 436 (M+1). Anal. ($C_{23}H_{25}N_5O_2S$) C, H, N.

Preparation of 1-Isobutyl-2-oxo-4-[4-(thiophene-2-carbonyl)-piperazin-1-yl]-1,2-dihydro-quinolin-3-carbonitrile (Compound 118)

The compound was prepared from the corresponding alkyl halide according to General Procedure D to yield white solids. Yield 89 mg (21%). M.P. 209° C. $^1$H NMR (DMSO-$d_6$): δ 0.89 (s, 6H), 2.12 (m, 1H), 3.65 (m, 4H), 3.93 (m, 4H), 4.11 (d, J=7.6 Hz, 2H), 7.16 (dd, J=3.6, 4.8 Hz, 1H), 7.32 (m, 1H), 7.49 (dd, J=0.8, 3.6 Hz, 1H), 7.60 (d, J=8.8 Hz, 1H), 7.70 (m, 1H), 7.79 (dd, J=1.2, 4.8 Hz, 1H), 7.93 (dd, J=1.2, 8.0 Hz, 1H). EIMS m/z 421 (M+1). Anal. ($C_{23}H_{24}N_4O_2S$) C, H, N.

Preparation of 1-(4-Methoxybenzyl)-2-oxo-4-[4-(thiophene-2-carbonyl)-piperazin-1-yl]-1,2-dihydro-quinolin-3-carbonitrile (Compound 119)

The compound was prepared from the corresponding alkyl halide according to General Procedure D to yield white solids. Yield 127 mg (26%). M.P. 246° C. $^1$H NMR (DMSO-$d_6$): δ 3.68 (m, 4H), 3.70 (s, 3H), 3.93 (m, 4H), 5.41 (s, 2H), 6.86 (m, 2H), 7.16 (m, 3H), 7.29 (m, 1H), 7.49 (m, 2H), 7.63 (m, 1H), 7.80 (d, J=4.8, 2H), 7.93 (d, J=5.2 Hz, 1H). EIMS m/z 485 (M+1). Anal. ($C_{27}H_{24}N_4O_3S$) C, H, N.

Preparation of 1-(2-Cyclohexyl-ethyl)-2-oxo-4-[4-(thiophene-2-carbonyl)-piperazin-1-yl]-1,2-dihydro-quinoline-3-carbonitrile (Compound 120)

The compound was prepared from the corresponding alkyl halide according to General Procedure C. MP: 213-215° C.; $^1$H-NMR (DMSO-$d_6$): 0.9 (m, 2H), 1.2 (m, 3H), 1.4 (m, 3H), 1.6 (m, 3H), 1.7 (m, 2H), 3.6 (m, 4H), 3.92 (s, 4H), 4.22 (t, J=7.2 Hz, 2H), 7.2 (m, 1H), 7.33 (t, J=7.6 Hz, 1H), 7.49 (dd, J=0.8, 3.6 Hz, 1H), 7.55 (d, J=8.4 Hz, 1H), 7.7 (m, 1H), 7.81 (dd, J=1.2, 5.2 Hz, 1H), 7.93 (dd, J=1.2, 8.0 Hz, 1H); EIMS: 498 (M+Na).

Preparation of 2-(2-Cyclohexyl-ethoxy)-4-[4-(thiophene-2-carbonyl)-piperazin-1-yl]-quinoline-3-carbonitrile (Compound 121)

The compound was prepared from the corresponding alkyl halide according to General Procedure C. MP: 170-173° C.; $^1$H-NMR (DMSO-$d_6$): 1.0 (m, 2H), 1.2 (m, 3H), 1.5 (m, 1H), 1.7 (m, 7H), 3.7 (m, 4H), 3.94 (b, 4H), 4.48 (t, J=6.8 Hz, 2H), 7.2 (m, 1H), 7.4 (m, 1H), 7.50 (dd, J=1.2, 3.6 Hz, 1H), 7.7 (m, 2H), 7.81 (dd, J=0.8, 4.8 Hz, 1H), 8.01 (d, J=8.4 Hz, 1H); EIMS: 475 (M+H).

Preparation of 2-Oxo-4-[4-(thiophene-2-carbonyl)-piperazin-1-yl]-1-(4-trifluoromethyl-benzyl)-1,2-dihydro-quinoline-3-carbonitrile (Compound 122)

The compound was prepared from the corresponding alkyl halide according to General Procedure C. MP: 248° C.; $^1$H-NMR (DMSO-d$_6$): 3.72 (s, 4H), 3.95 (s, 4H), 5.59 (s, 2H), 7.2 (m, 1H), 7.32 (t, J=8.0 Hz, 1H), 7.39 (d, J=8.4 Hz, 1H), 7.43 (d, J=8.0 Hz, 2H), 7.51 (dd, J=1.2, 3.6 Hz, 1H), 7.6 (m, 1H), 7.69 (d, J=8.0 Hz, 2H), 7.82 (dd, J=1.2, 5.2 Hz, 1H), 7.97 (dd, J=1.2, 8.4 Hz, 1H); EIMS: 545 (M+Na).

Preparation of 1-Cyclohexylmethyl-2-oxo-4-[4-(thiophene-2-carbonyl)-piperazin-1-yl]-1,2-dihydro-quinoline-3-carbonitrile (Compound 123)

The compound was prepared from the corresponding alkyl halide according to General Procedure C. MP: 122-127° C.; $^1$H-NMR (DMSO-d$_6$): 1.1 (m, 5H), 1.6 (m, 6H), 3.6 (m, 4H), 3.93 (b, 4H), 4.11 (b, 2H), 7.2 (m, 1H), 7.32 (t, J=7.6 Hz, 1H), 7.49 (dd, J=0.8, 3.6 Hz, 1H), 7.61 (d, J=8.4 Hz, 1H), 7.7 (m, 1H), 7.80 (dd, J=1.2, 5.2 Hz, 1H), 7.9 (m, 1H); EIMS: 461 (M+H).

Preparation of 2-Cyclohexylmethoxy-4-[4-(thiophene-2-carbonyl)-piperazin-1-yl]-quinoline-3-carbonitrile (Compound 124)

The compound was prepared from the corresponding alkyl halide according to General Procedure C. M.P. 166° C.; $^1$H-NMR (DMSO-d$_6$): 1.4 (m, 5H), 1.7 (m, 6H), 3.68 (b, 4H), 3.94 (b, 4H), 4.25 (d, J=6.0 Hz, 2H), 7.2 (m, 1H), 7.4 (m, 1H), 7.50 (dd, J=0.8, 3.6 Hz, 1H), 7.7 (m, 2H), 7.81 (dd, J=1.2, 5.2 Hz, 1H), 8.01 (d, 8.0 Hz, 1H); EIMS: 461 (M+H).

Preparation of 2-Oxo-1-phenethyl-4-[4-(thiophene-2-carbonyl)-piperazin-1-yl]-1,2-dihydro-quinoline-3-carbonitrile (Compound 125)

The compound was prepared from the corresponding alkyl halide according to General Procedure C. M.P. 258-260° C.; $^1$H-NMR (DMSO-d$_6$): 2.8 (m, 2H), 3.65 (b, 4H), 3.93 (b, 4H), 4.4 (m, 2H), 7.2 (m, 1H), 7.3 (m, 6H), 7.50 (dd, J=1.2, 3.6 Hz, 1H), 7.7 (m, 2H), 7.81 (dd, J=1.2, 5.2 Hz, 1H), 7.95 (dd, J=1.2, 8.4 Hz, 1H); EIMS: 469 (M+H).

Preparation of 2-Phenethyloxy-4-[4-(thiophene-2-carbonyl)-piperazin-1-yl]-quinoline-3-carbonitrile (Compound 126)

The compound was prepared from the corresponding alkyl halide according to General Procedure C. M.P. 145-147° C.; $^1$H-NMR (DMSO-d$_6$): 3.09 (t, J=6.8 Hz, 2H), 3.68 (b, 4H), 3.93 (b, 4H), 4.62 (t, J=6.8 Hz, 2H), 7.1 (m, 1H), 7.2 (m, 1H), 7.31 (t, J=7.2 Hz, 2H), 7.4 (m, 2H), 7.5 (m, 1H), 7.51 (dd, J=1.2, 3.6 Hz, 1H), 7.7 (m, 2H), 7.81 (dd, J=0.8, 4.8 Hz, 1H), 8.01 (d, J=8.4 Hz, 1H); EIMS: 469 (M+H).

Preparation of 2-(4-Methoxy-benzyloxy)-4-[4-(thiophene-2-carbonyl)-piperazin-1-yl]-quinoline-3-carbonitrile (Compound 127)

The compound was prepared from the corresponding alkyl halide according to General Procedure C. M.P. 192-194° C.; $^1$H-NMR (DMSO-d$_6$): 3.69 (b, 4H), 3.76 (s, 3H), 3.94 (b, 4H), 5.47 (s, 2H), 6.96 (d, J=8.4 Hz, 2H), 7.2 (m, 1H), 7.5 (m, 4H), 7.78 (d, J=3.6 Hz, 2H), 7.81 (dd, J=1.2, 5.2 Hz, 1H), 8.03 (d, J=8.4 Hz, 1H); EIMS: 485 (M+H).

Preparation of 2-Oxo-1-(2-oxo-2-phenyl-ethyl)-4-[4-(thiophene-2-carbonyl)-piperazin-1-yl]-1,2-dihydro-quinoline-3-carbonitrile (Compound 128)

The compound was prepared from the corresponding alkyl halide according to General Procedure C. M.P. 260-261° C.; $^1$H-NMR (DMSO-d$_6$): 3.71 (b, 4H), 3.96 (b, 4H), 5.90 (s, 2H), 7.17 (m, 1H), 7.33 (m, 1H), 7.45 (d, J=8.8 Hz, 1H), 7.51 (dd, J=1.2, 4.0 Hz, 1H), 7.6 (m, 3H), 7.75 (t, J=7.6 Hz, 1H), 7.81 (dd, J=0.8, 4.8 Hz, 1H), 7.97 (dd, J=1.2, 8.0 Hz, 1H), 8.14 (d, J=7.2 Hz, 2H); EIMS: 483 (M+H).

Preparation of 1-Naphthalen-2-ylmethyl-2-oxo-4-[4-(thiophene-2-carbonyl)-piperazin-1-yl]-1,2-dihydro-quinoline-3-carbonitrile (Compound 129)

The compound was prepared from the corresponding alkyl halide according to General Procedure C. M.P. 276-279° C.; $^1$H-NMR (DMSO-d$_6$): 3.71 (b, 4H), 3.96 (b, 4H), 5.65 (b, 2H), 7.2 (m, 1H), 7.3 (m, 1H), 7.41 (dd, J=1.6, 8.4 Hz, 1H), 7.5 (m, 3H), 7.51 (dd, J=1.2, 3.6 Hz, 1H), 7.6 (m, 1H), 7.7 (s, 1H), 7.8 (m, 2H), 7.9 (m, 2H), 7.96 (d, J=9.2 Hz, 1H); EIMS: 505 (M+H).

Preparation of 2-(Naphthalen-2-ylmethoxy)-4-[4-(thiophene-2-carbonyl)-piperazin-1-yl]-quinoline-3-carbonitrile (Compound 130)

The compound was prepared from the corresponding alkyl halide according to General Procedure C. M.P. 250° C.; $^1$H-NMR (DMSO-d$_6$): 3.7 (m, 4H), 3.95 (b, 4H), 5.72 (s, 2H), 7.2 (m, 1H), 7.5 (m, 4H), 7.67 (dd, J=1.6, 8.4 Hz, 1H), 7.8 (m, 3H), 7.9 (m, 3H), 8.1 (m, 2H); EIMS: 505 (M+H).

Preparation of 1-(3-Dimethylamino-propyl)-2-oxo-4-[4-(thiophene-2-carbonyl)-piperazin-1-yl]-1,2-dihydro-quinoline-3-carbonitrile (Compound 131)

The compound was prepared from the corresponding alkyl halide according to General Procedure C. M.P. 203-204° C.; $^1$H-NMR (DMSO-d$_6$): 1.7 (m, 2H), 2.24 (s, 6H), 2.4 (m, 2H), 3.64 (b, 4H), 3.93 (b, 4H), 4.23 (t, J=7.2 Hz; 2H), 7.2 (m, 1H), 7.34 (m, 1H), 7.50 (dd, J=1.2, 3.6 Hz, 1H), 7.67 (d, J=8.4 Hz, 1H), 7.7 (m, 1H), 7.81 (dd, J=1.2, 5.2 Hz, 1H), 7.95 (dd, J=1.2, 8.0 Hz, 1H); EIMS: 450 (M+H).

Preparation of 2-(3-Dimethylamino-propoxy)-4-[4-(thiophene-2-carbonyl)-piperazin-1-yl]-quinoline-3-carbonitrile (Compound 132)

The compound was prepared from the corresponding alkyl halide according to General Procedure C. M.P. 130° C.; $^1$H-NMR (DMSO-d$_6$): 1.9 (m, 2H), 2.17 (s, 6H), 2.43 (t, J=6.8 Hz, 2H), 3.7 (m, 4H), 3.95 (b, 4H), 4.47 (t, J=6.8 Hz, 2H), 7.2 (m, 1H), 7.5 (m, 1H), 7.52 (dd, J=0.8, 3.6 Hz, 1H), 7.7 (m, 2H), 7.81 (dd, J=1.2, 5.2 Hz, 1H), 8.02 (d, J=8.0 Hz, 1H); EIMS: 450 (M+H).

Preparation of 1-(2,2-Dimethyl-propyl)-2-oxo-4-[4-(thiophene-2-carbonyl)-piperazin-1-yl]-1,2-dihydro-quinoline-3-carbonitrile (Compound 133)

The compound was prepared from the corresponding alkyl halide according to General Procedure C. M.P. 111-116° C.; $^1$H-NMR (DMSO-d$_6$): 0.9 (s, 9H), 3.65 (b, 4H), 3.93 (b, 4H), 4.20 (b, 2H), 7.2 (m, 1H), 7.30 (t, J=7.6 Hz, 1H), 7.50 (dd, J=0.8, 3.6 Hz, 1H), 7.7 (m, 1H), 7.8 (m, 2H), 7.91 (dd, J=1.6, 8.4 Hz, 1H); EIMS: 457 (M+Na).

Preparation of 2-Oxo-4-[4-(thiophene-2-carbonyl)-piperazin-1-yl]-1-(2,2,2-trifluoro-ethyl)-1,2-dihydro-quinoline-3-carbonitrile (Compound 134)

The compound was prepared from the corresponding alkyl halide according to General Procedure C. M.P. 242° C.; $^1$H-NMR (DMSO-d$_6$): 3.71 (b, 4H), 3.93 (b, 4H), 5.2 (m, 2H), 7.2 (m, 1H), 7.4 (m, 1H), 7.50 (dd, J=0.8, 3.6 Hz, 1H), 7.7 (m, 2H), 7.81 (dd, J=0.8, 4.8 Hz, 1H), 7.95 (d, J=8.0 Hz, 1H); EIMS: 447 (M+H).

Preparation of 4-[4-(Thiophene-2-carbonyl)-piperazin-1-yl]-2-(2,2,2-trifluoro-ethoxy)-quinoline-3-carbonitrile (Compound 135)

The compound was prepared from the corresponding alkyl halide according to General Procedure C. M.P. 204° C.; $^1$H-NMR (DMSO-$d_6$): 3.70 (b, 4H), 3.95 (b, 4H), 5.2 (m, 2H), 7.2 (m, 1H), 7.5 (m, 2H), 7.8 (m, 3H), 8.1 (m, 1H); EIMS: 447 (M+H).

Preparation of 2-Oxo-4-[4-(thiophene-2-carbonyl]piperazin-1-yl-1-(4-trifluoromethoxy-benzyl)-1,2-dihydro-quinoline-3-carbonitrile (Compound 136)

The compound was prepared from the corresponding alkyl halide according to General Procedure C. M.P. 150-160° C.; $^1$H-NMR (DMSO-$d_6$): 3.7 (m, 4H), 3.9 (m, 4H), 5.52 (s, 2H), 7.2 (m, 1H), 7.3 (m, 5H), 7.44 (d, J=8.3 Hz, 1H), 7.51 (d, J=3.8 Hz, 1H), 7.64 (t, J=7.1 Hz, 1H), 7.81 (dd, J=1.0, 5.0 Hz, 1H), 7.96 (J=1.3, 8.3 Hz, 1H); EIMS: 539 (M+H).

Preparation of 4-[4-(Thiophene-2-carbonyl]piperazin-1-yl]-2-(4-trifluoromethoxy-benzyloxy)-quinol-3-carbonitrile (Compound 137)

The compound was prepared from the corresponding alkyl halide according to General Procedure C. M.P. 170-172° C.; $^1$H-NMR (DMSO-$d_6$): 3.7 (m, 4H), 3.98 (b, 4H), 5.63 (s, 2H), 7.2 (m, 1H), 7.46 (d, J=8.0 Hz, 2H), 7.5 (m, 2H), 7.70 (d, J=8.8 Hz, 2H), 7.8 (m, 2H), 7.85 (dd, J=0.8, 4.8 Hz, 1H), 8.08 (d, 8.4 Hz, 1H); EIMS: 539 (M+H).

Preparation of 1-(3-Fluoro-benzyl)-2-oxo-4-[4-(thiophene-2-carbonyl)-piperazin-1-yl]-1,2-dihydro-quinoline-3-carbonitrile (Compound 138)

The compound was prepared from the corresponding alkyl halide according to General Procedure C. M.P. 261-263° C.; $^1$H-NMR (DMSO-$d_6$): 3.7 (m, 4H), 3.94 (b, 4H), 5.50 (s, 2H), 7.1 (m, 3H), 7.2 (m, 1H), 7.3 (m, 2H), 7.41 (d, J=8.4 Hz, 1H), 7.51 (dd, J=0.8, 3.6 Hz, 1H), 7.6 (m, 1H), 7.81 (dd, J=1.2, 5.2 Hz, 1H), 7.9 (m, 1H); EIMS: 473 (M+H).

Preparation of 1-(2-Fluoro-benzyl)-2-oxo-4-[4-(thiophene-2-carbonyl)-piperazin-1-yl]-1,2-dihydro-quinoline-3-carbonitrile (Compound 139)

The compound was prepared from the corresponding alkyl halide according to General Procedure C. M.P. 203-205° C.; $^1$H-NMR (DMSO-$d_6$): 3.7 (m, 4H), 3.9 (m, 4H), 5.50 (s, 2H), 6.86 (t, J=6.7 Hz, 1H), 7.07 (t, J=7.5 Hz, 1H), 7.2 (m, 1H), 7.3 (m, 4H), 7.50 (dd, J=0.9, 3.6 Hz, 1H), 7.7 (m, 1H), 7.81 (dd, J=0.9, 5.0 Hz, 1H), 7.97 (dd, J=1.2, 8.2 Hz, 1H); EIMS: 473 (M+H).

Preparation of 2-Oxo-1-propyl-4-[4-(thiophene-2-carbonyl)-piperazin-1-yl]-1,2-dihydro-quinoline-3-carbonitrile (Compound 140)

The compound was prepared from the corresponding alkyl halide according to General Procedure C. M.P. 210-212° C.; $^1$H-NMR (DMSO-$d_6$): 0.97 (t, J=7.2 Hz, 3H), 1.6 (m, 2H), 3.6 (m, 4H), 3.9 (m, 4H), 4.16 (t, J=7.6 Hz, 2H), 7.1 (m, 1H), 7.33 (t, J=7.6 Hz, 1H), 7.49 (dd, J=0.8, 3.6 Hz, 1H), 7.63 (d, J=8.4 Hz, 1H), 7.7 (m, 1H), 7.79 (dd, J=1.2, 5.2 Hz, 1H), 7.94 (dd, J=1.2, 8.4 Hz, 1H); EIMS: 407 (M+H).

Preparation of 2-Propoxy-4-[4-(thiophene-2-carbonyl)-piperazin-1-yl]-quinoline-3-carbonitrile (Compound 141)

The compound was prepared from the corresponding alkyl halide according to General Procedure C. M.P. 198-199° C.; $^1$H-NMR (DMSO-$d_6$): 1.01 (t, J=7.6 Hz, 3H), 1.8 (m, 2H), 3.69 (b, 4H), 3.94 (b, 4H), 4.41 (t, J=6.4 Hz, 2H), 7.2 (m, 1H), 7.4 (m, 1H), 7.50 (d, J=3.6 Hz, 1H), 7.7 (m, 2H), 7.80 (d, J=4.8 Hz, 1H), 8.02 (d, J=8.4 Hz, 1H); EIMS: 407 (M+H).

Preparation of 1-Butyl-2-oxo-4-[4-(thiophene-2-carbonyl)-piperazin-1-yl]-1,2-dihydro-quinoline-3-carbonitrile (Compound 142)

The compound was prepared from the corresponding alkyl halide according to General Procedure C. M.P. 155-157° C.; $^1$H-NMR (DMSO-$d_6$): 0.93 (t, J=7.2 Hz, 3H), 1.4 (m, 2H), 1.6 (m, 2H), 3.6 (m, 4H), 3.92 (b, 4H), 4.20 (t, J=7.6 Hz, 2H), 7.2 (m, 1H), 7.33 (t, J=7.6 Hz, 1H), 7.50 (d, J=3.2 Hz, 1H), 7.61 (d, J=8.4 Hz, 1H), 7.75 (t, J=7.2 Hz, 1H), 7.80 (d, J=5.2 Hz, 1H), 7.94 (d, J=7.6 Hz, 1H); EIMS: 421 (M+H).

Preparation of 2-Butoxy-4-[4-(thiophene-2-carbonyl)-piperazin-1-yl]-quinoline-3-carbonitrile (Compound 143)

The compound was prepared from the corresponding alkyl halide according to General Procedure C. M.P. 190-191° C.; $^1$H-NMR (DMSO-$d_6$): 0.96 (t, J=7.2 Hz, 3H), 1.5 (m, 2H), 1.8 (m, 2H), 3.68 (b, 4H), 3.94 (b, 4H), 4.46 (t, J=6.4 Hz, 2H), 7.2 (m, 1H), 7.4 (m, 1H), 7.50 (dd, J=0.8, 3.6 Hz, 1H), 7.7 (m, 2H), 7.80 (dd, J=1.2, 5.2 Hz, 1H), 8.02 (d, J=8.4 Hz, 1H); EIMS: 421 (M+H).

Preparation of 1-(3-Hydroxy-propyl)-2-oxo-4-[4-(thiophene-2-carbonyl)-piperazin-1-yl]-1,2-dihydro-quinoline-3-carbonitrile (Compound 144)

The compound was prepared from the corresponding alkyl halide according to General Procedure C. M.P. 209-210° C.; $^1$H-NMR (DMSO-$d_6$): 1.7 (m, 2H), 3.5 (m, 2H), 3.6 (m, 4H), 3.9 (m, 4H), 4.26 (t, J=7.2 Hz, 2H), 4.65 (t, J=5.2 Hz, 1H), 7.1 (m, 1H), 7.34 (t, J=7.2 Hz, 1H), 7.49 (d, J=3.2 Hz, 1H), 7.64 (d, J=8.8 Hz, 1H), 7.76 (t, J=7.2 Hz, 1H), 7.80 (d, J=5.2 Hz, 1H), 7.94 (d, J=7.6 Hz, 1H); EIMS: 423 (M+H).

Preparation of 1-Cyclopropylmethyl-2-oxo-4-[4-(thiophene-2-carbonyl)-piperazin-1-yl]-1,2-dihydro-quinoline-3-carbonitrile (Compound 145)

The compound was prepared from the corresponding alkyl halide according to General Procedure C. M.P. 198° C.; $^1$H-NMR (DMSO-$d_6$): 0.45 (d, J=6.4 Hz, 4H), 1.2 (m, 1H), 3.6 (m, 4H), 3.9 (m, 4H), 4.17 (d, J=6.8 Hz, 2H), 7.1 (m, 1H), 7.3 (m, 1H), 7.49 (dd, J=1.2, 3.6 Hz, 1H), 7.7 (m, 2H), 7.79 (dd, J=1.2, 4.8 Hz, 1H), 7.94 (d, J=7.6 Hz, 1H); EIMS: 419 (M+H).

Preparation of 2-Cyclopropylmethoxy-4-[4-(thiophene-2-carbonyl)-piperazin-1-yl]-quinoline-3-carbonitrile (Compound 146)

The compound was prepared from the corresponding alkyl halide according to General Procedure C. M.P. 200-203° C.; $^1$H-NMR (DMSO-$d_6$): 0.5 (m, 2H), 0.6 (m, 2H), 1.3 (m, 1H), 3.69 (b, 4H), 3.94 (b, 4H), 4.31 (d, J=6.8 Hz, 2H), 7.2 (m, 1H), 7.5 (m, 1H), 7.49 (dd, J=0.8, 3.6 Hz, 1H), 7.7 (m, 2H), 7.8 (dd, J=0.8, 4.8 Hz, 1H), 8.02 (d, J=8.4 Hz, 1H); EIMS: 419 (M+H).

Preparation of 1-(4-Cyano-benzyl)-2-oxo-4-[4-(thiophene-2-carbonyl)-piperazin-1-yl]-1,2-dihydro-quinoline-3-carbonitrile (Compound 147)

The compound was prepared from the corresponding alkyl halide according to General Procedure C. M.P. 260-263° C.; $^1$H-NMR (DMSO-$d_6$): 3.72 (b, 4H), 3.95 (b, 4H), 5.58 (s, 2H), 7.2 (m, 1H), 7.31 (t, J=7.6 Hz, 1H), 7.34 (d, J=8.8 Hz, 1H), 7.40 (d, J=8.4 Hz, 2H), 7.50 (dd, J=0.8, 3.6 Hz, 1H), 7.63 (t, J=7.2 Hz, 1H), 7.8 (m, 3H), 7.96 (d, J=7.2 Hz, 1H); EIMS: 480 (M+H).

Preparation of 2-(4-Cyano-benzyloxy)₄-[4-(thiophene-2-carbonyl)-piperazin-1-yl]-quinoline-3-carbonitrile (Compound 148)

The compound was prepared from the corresponding alkyl halide according to General Procedure C. M.P. 214-218° C.; ¹H-NMR (DMSO-d₆): 3.71 (b, 4H), 3.95 (b, 4H), 5.58 (s, 2H), 7.17 (t, J=2.8 Hz, 1H), 7.31 (t, J=7.2 Hz, 1H), 7.35 (d, J=8.8 Hz, 1H), 7.40 (d, J=8.0 Hz, 2H), 7.50 (d, J=3.6 Hz, 1H), 7.63 (t, J=7.2 Hz, 1H), 7.8 (m, 3H), 7.96 (d, J=8.0 Hz, 1H); EIMS: 480 (M+H).

Preparation of 2-Oxo-1-pentvil-4-[4-(thiophene-2-carbonyl)-piperazin-1-yl]-1,2-dihydro-quinoline-3-carbonitrile (Compound 149)

The compound was prepared from the corresponding alkyl halide according to General Procedure C. M.P. 201-202° C.; ¹H-NMR (DMSO-d₆): 0.88 (t, J=6.8 Hz, 3H), 1.3 (m, 4H), 1.6 (m, 2H), 3.6 (m, 4H), 3.92 (b, 4H), 4.19 (t, J=7.6 Hz, 2H), 7.2 (m, 1H), 7.33 (t, J=7.6 Hz, 1H), 7.49 (dd, J=0.8, 3.6 Hz, 1H), 7.61 (d, J=8.4 Hz, 1H), 7.75 (t, J=7.2 Hz, 1H), 7.8 (dd, J=0.8, 4.8 Hz, 1H), 7.94 (d, J=0.8, 8.0 Hz, 1H); EIMS: 435 (M+H).

Preparation of 2-Pentyloxy-4-[4-(thiophene-2-carbonyl)-piperazin-1-yl]-quinoline-3-carbonitrile (Compound 150)

The compound was prepared from the corresponding alkyl halide according to General Procedure C. M.P. 152-155° C.; ¹H-NMR (DMSO-d₆): 0.91 (t, J=7.2 Hz, 3H), 1.4 (m, 4H), 1.7 (m, 2H), 3.7 (m, 4H), 3.94 (b, 4H), 4.45 (t, J=6.8 Hz, 2H), 7.17 (t, J=4.4 Hz, 1H), 7.4 (m, 1H), 7.50 (d, J=3.6 Hz, 1H), 7.7 (m, 2H), 7.80 (d, J=4.8 Hz, 1H), 8.02 (d, J=8.4 Hz, 1H); EIMS: 435 (M+H).

Preparation of 1-(4-Methyl-benzyl)-2-oxo-4-[4-(thiophene-2-carbonyl)-piperazin-1-yl]-1,2-dihydro-quinoline-3-carbonitrile (Compound 151)

The compound was prepared from the corresponding alkyl halide according to General Procedure C. M.P. 236-238° C.; ¹H-NMR (DMSO-d₆): 2.25 (s, 3H), 3.7 (m, 4H), 3.9 (m, 4H), 5.44 (s, 2H), 7.12 (s, 4H), 7.2 (m, 1H), 7.29 (t, J=7.8 Hz, 1H), 7.41 (d, J=8.4 Hz, 1H), 7.50 (dd, J=1.2, 4.0 Hz, 1H), 7.6 (m, 1H), 7.81 (dd, J=0.8, 4.8 Hz, 1H), 7.94 (dd, J=1.2, 8.4 Hz, 1H); EIMS: 469 (M+H).

Preparation of 2-(4-Methyl-benzyloxy)-4-[4-(thiophene-2-carbonyl)-piperazin-1-yl]-quinoline-3-carbonitrile (Compound 152)

The compound was prepared from the corresponding alkyl halide according to General Procedure C. M.P. 188-191° C.; ¹H-NMR (DMSO-d₆): 2.31 (s, 3H), 3.7 (m, 4H), 3.9 (m, 4H), 5.50 (s, 2H), 7.2 (m, 1H), 7.21 (d, J=7.6 Hz, 2H), 7.41 (d, J=8.0 Hz, 2H), 7.5 (m, 2H), 7.77 (d, J=4.0 Hz, 2H), 7.80 (dd, J=1.2, 5.2 Hz, 1H), 8.03 (d, J=8.4 Hz, 1H); EIMS: 469 (M+H).

Preparation of 2-Oxo-1-propyl-4-[4-(thiophene-2-carbonyl)-piperazin-1-yl]-1,2-dihydro-[1,8]naphthyridine-3-carboxylic acid ethyl ester (Compound 153)

The compound was prepared from the corresponding alkyl halide according to General Procedure C. M.P. 92-96° C.; ¹H-NMR (DMSO-d₆): 0.91 (t, J=7.2 Hz, 3H), 1.30 (t, J=7.2 Hz, 3H), 1.6 (m, 2H), 3.13 (s, 4H), 3.88 (s, 4H), 4.3 (m, 4H), 7.1 (m, 1H), 7.4 (m, 1H), 7.45 (dd, J=1.2, 3.6 Hz, 1H), 7.79 (dd, J=0.8, 4.8 Hz, 1H), 8.34 (dd, J=1.6, 8.0 Hz, 1H), 8.70 (dd, J=1.6, 4.4 Hz, 1H); EIMS: 455 (M+H).

Preparation of 1-Butyl-2-oxo-4-[4-(thiophene-2-carbonyl)-piperazin-1-yl]-1,2-dihydro-[1,8]naphthyridine-3-carboxylic acid ethyl ester (Compound 154)

The compound was prepared from the corresponding alkyl halide according to General Procedure C. M.P. 90-96° C.; ¹H-NMR (DMSO-d₆): 0.92 (t, J=7.2 Hz, 3H), 1.3 (m, 5H), 1.6 (m, 2H), 3.13 (s, 4H), 3.88 (s, 4H), 4.32 (m, 4H), 7.15 (m, 1H), 7.38 (m, 1H), 7.45 (dd, J=1.2, 3.6, 1H), 7.79 (dd, J=1.2, 5.2 Hz, 1H), 8.34 (dd, J=1.6, 8.0 Hz, 1H), 8.70 (dd, J=1.6, 4.4 Hz, 1H); EIMS: 469 (M+H).

Preparation of 1-Allyl-2-oxo-4-[4-(thiophene-2-carbonyl)-piperazin-1-yl]-1,2-dihydro-[1,8]naphthyridine-3-carboxylic acid ethyl ester (Compound 155)

The compound was prepared from the corresponding alkyl halide according to General Procedure C. M.P. 89-96° C.; ¹H-NMR (DMSO-d₆): 1.30 (t, J=7.2 Hz, 3H), 3.15 (s, 4H), 3.89 (s, 4H), 4.31 (t, J=7.2 Hz, 2H), 5.0 (m, 4H), 5.9 (m, 1H), 7.15 (m, 1H), 7.39 (dd, J=4.8, 8.0 Hz, 1H), 7.46 (dd, J=0.8, 3.6 Hz), 7.79 (dd, J=0.8, 4.8 Hz, 1H), 8.34 (dd, J=1.6, 8.0 Hz, 1H), 8.68 (dd, J=1.6, 4.8 Hz, 1H); EIMS: 453 (M+H).

Preparation of 1-(2-Fluoro-benzyl)-2-oxo-4-[4-(thiophene-2-carbonyl)-piperazin-1-yl]-1,2-dihydro-[1,8]naphthyridine-3-carboxylic acid ethyl ester (Compound 156)

The compound was prepared from the corresponding alkyl halide according to General Procedure C. M.P. 105-110° C.; ¹H-NMR (DMSO-d₆): 1.29 (t, J=7.2 Hz, 3H), 3.19 (s, 4H), 3.91 (s, 4H), 4.30 (q, J=7.2 Hz, 2H), 5.60 (s, 2H), 6.81 (m, 1H), 7.04 (m, 1H), 7.2 (m, 3H), 7.39 (m, 1H), 7.46 (dd, J=0.8, 3.6 Hz, 1H), 7.80 (dd, J=0.8, 4.8 Hz, 1H), 8.38 (dd, J=1.6, 8.0 Hz, 1H), 8.63 (dd, J=1.6, 4.4 Hz, 1H); EIMS: 521 (M+H).

Preparation of 1-(3-Fluoro-benzyl)-2-oxo-4-[4-(thiophene-2-carbonyl)-piperazin-1-yl]-1,2-dihydro-[1,8]naphthyridine-3-carboxylic acid ethyl ester (Compound 157)

The compound was prepared from the corresponding alkyl halide according to General Procedure C. M.P. 105-110° C.; ¹H-NMR (DMSO-d₆): 1.29 (t, J=6.8 Hz, 3H), 3.18 (s, 4H), 3.89 (s, 4H), 4.31 (q, J=6.8 Hz, 2H), 5.56 (s, 2H), 7.1 (m, 4H), 7.4 (m, 3H), 7.79 (d, J=4.4 Hz, 1H), 8.36 (d, J=7.6 Hz, 1H), 8.67 (d, J=3.2 Hz, 1H); EIMS: 521 (M+H).

Preparation of 1-(3-Dimethylamino-propyl)-2-oxo-4-[4-(thiophene-2-carbonyl)-piperazin-1-yl]-1,2-dihydro-[1,8]naphthyridine-3-carboxylic acid ethyl ester (Compound 158)

The compound was prepared from the corresponding alkyl halide according to General Procedure C. M.P. 84-94° C.; ¹H-NMR (DMSO-d₆): 1.30 (t, J=7.2 Hz, 3H), 1.7 (m, 2H), 2.14 (s, 6H), 2.30 (t, J=6.8 Hz, 2H), 3.13 (b, 4H), 3.88 (b, 4H), 4.3 (m, 4H), 7.2 (m, 1H), 7.3 (m, 1H), 7.45 (dd, J=1.2, 3.6 Hz, 1H), 7.79 (dd, J=0.8, 4.8 Hz, 1H), 8.34 (dd, J=2.0, 8.0 Hz, 1H), 8.70 (dd, J=2.0, 4.8 Hz, 1H); EIMS: 498 (M+H).

Preparation of 2-Oxo-1-phenyl-4-[4-(thiophene-2-carbonyl)-piperazin-1-yl]-1,2-dihydro-quinolin-3-carbonitrile (Compound 159)

Cupric acetate (497 mg, 2.74 mmol), triethylamine (380 μL, 2.74 mmol), and phenyl boronic acid (335 mg, 2.74 mmol) were added successively to a solution of Compound 116 (500 mg, 1.37 mmol) in dichloromethane. The solution was stirred at room temperature for 48 h. The solution was filtered through celite and washed successively by saturated NaHCO₃ solution, water, and brine. The organic phase was dried over Na₂SO₄ and evaporated to yield a residue which was purified by flash chromatography eluting with 0-1% MeOH in dichloromethane gradient to get 187 mg (31%) of white solids. M.P. 289° C. ¹H NMR (DMSO-d₆): δ 3.78 (m, 4H), 4.02 (m, 4H), 6.60 (d, J=7.6 Hz, 1H), 7.22 (m, 1H), 7.38 (m, 3H), 7.57-7.71 (m, 5H), 7.88 (dd, J=0.8, 4.8 Hz, 1H), 8.02 (d, J=7.2 Hz, 1H). EIMS m/z 441 (M+1). Anal. ($C_{25}H_{20}N_4O_2S$) C, H, N.

exhibit particularly high levels of inhibition of MIF activity. These MIF inhibitors were each active at concentrations of from 0.01 nM to 50 μM.

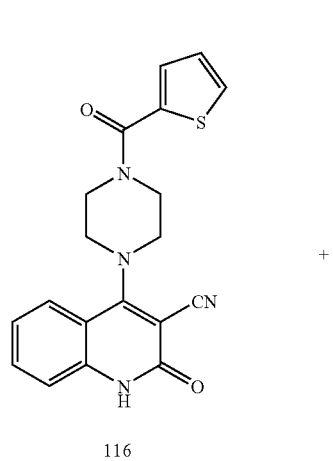

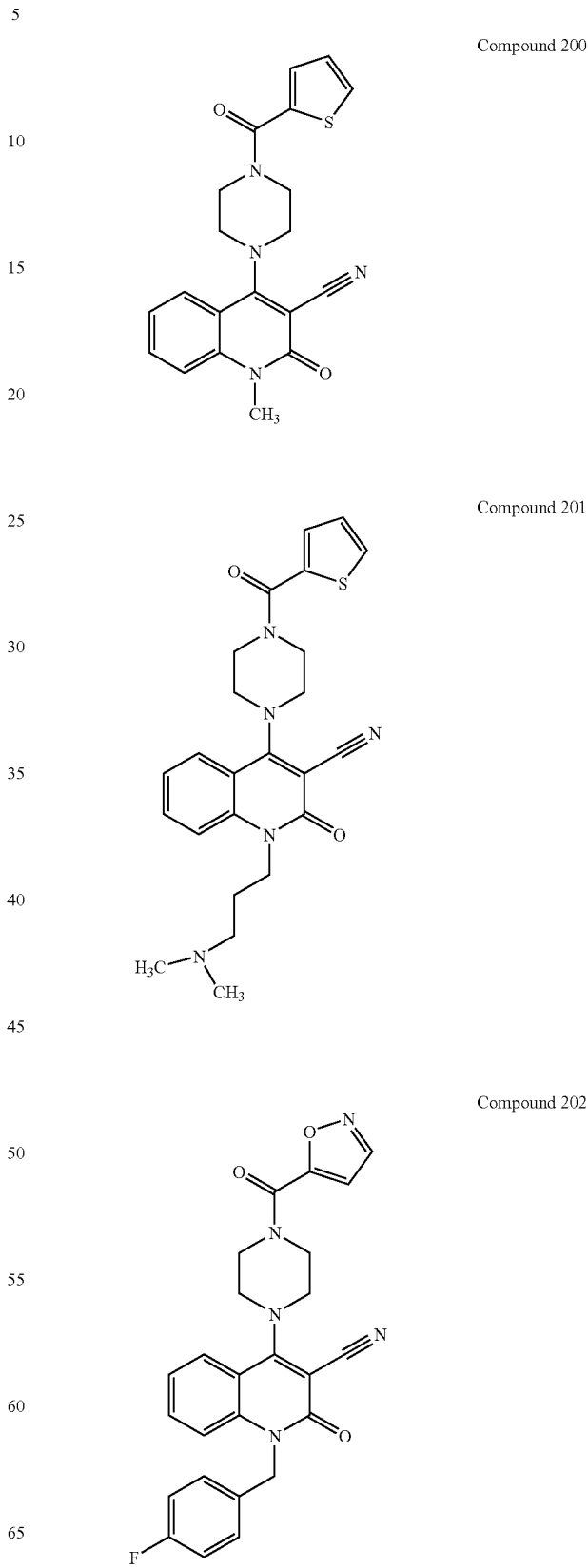

Example 4

The following inhibitors of MIF were prepared by the methods described in the examples. Each of these MIF inhibitors belongs to the class of compounds of structure 1(a) described above. Results of tautomerase assays indicated that each of the following candidate compounds Compound 203
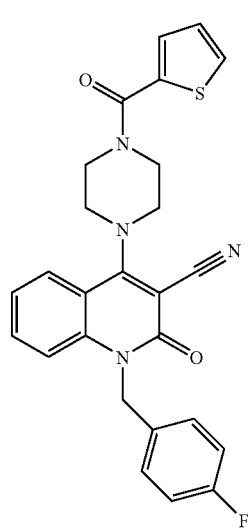
Compound 204
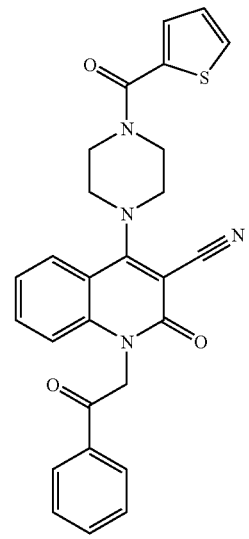
Compound 205
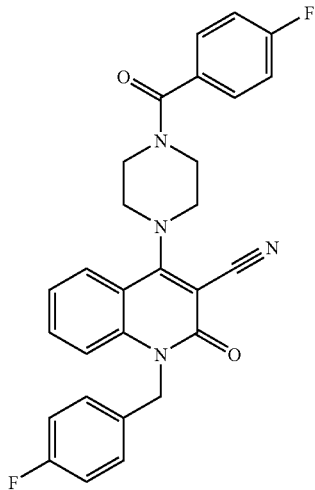
Compound 206
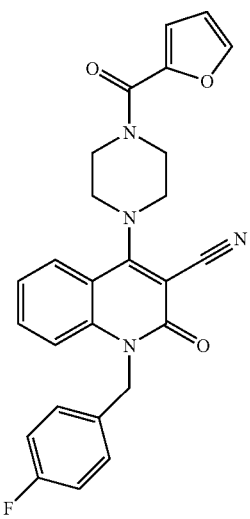
Compound 207
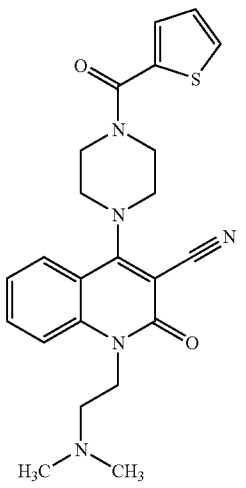
Compound 208
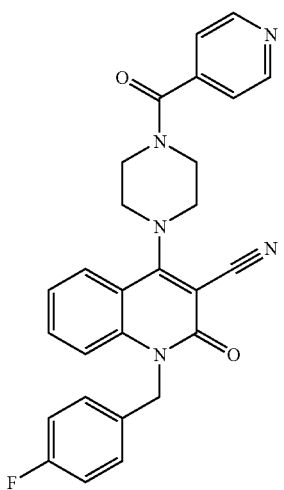

-continued
Compound 209
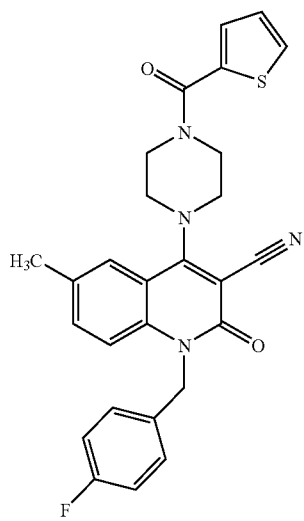
Compound 210
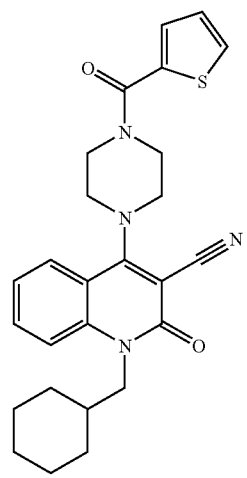
Compound 211
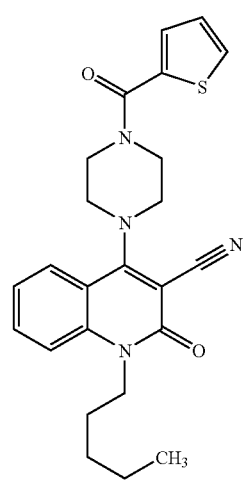
-continued
Compound 212
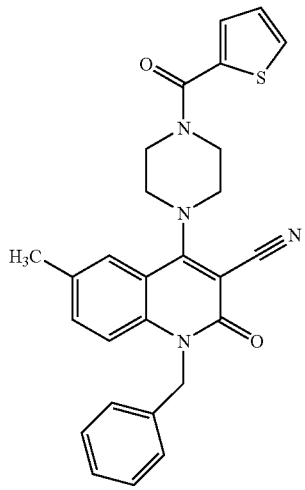
Compound 213
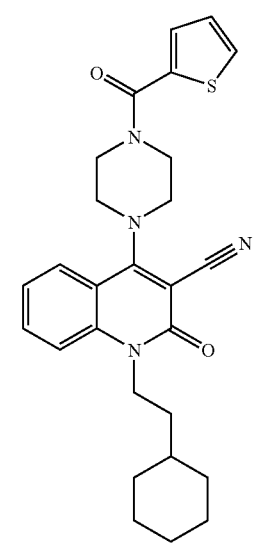
Compound 214
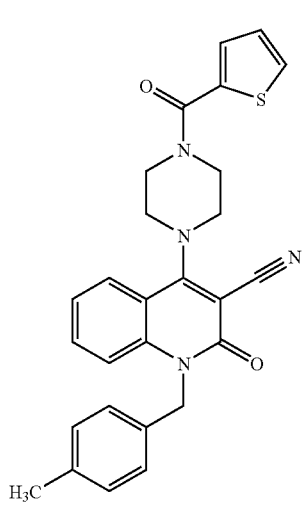

-continued
Compound 215
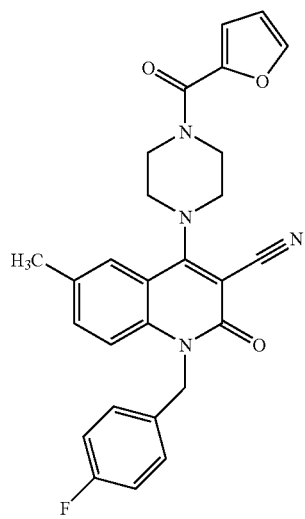
Compound 216
Compound 217
-continued
Compound 218
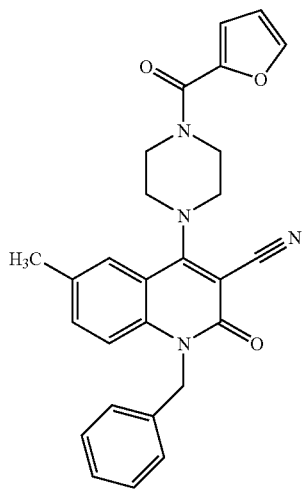
Compound 219
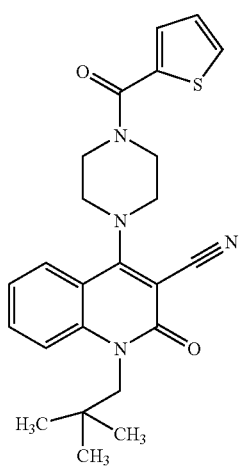
Compound 220
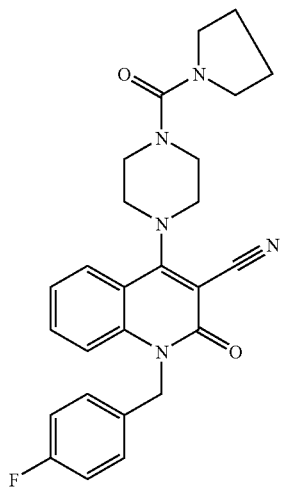

Compound 221
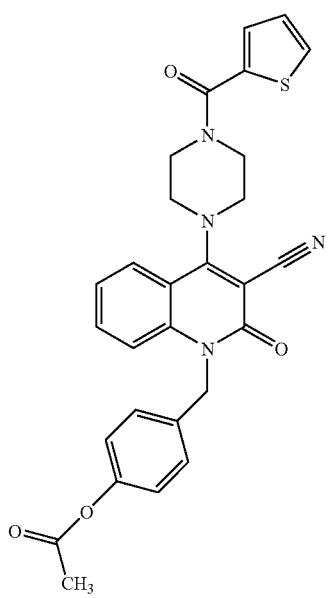
Compound 222
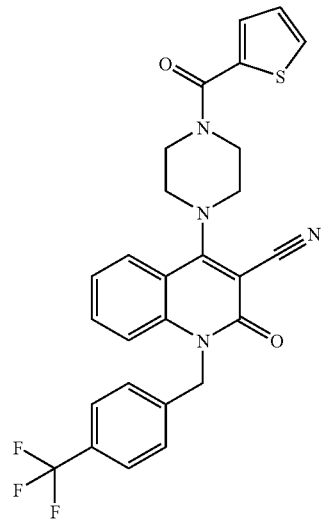
Compound 223
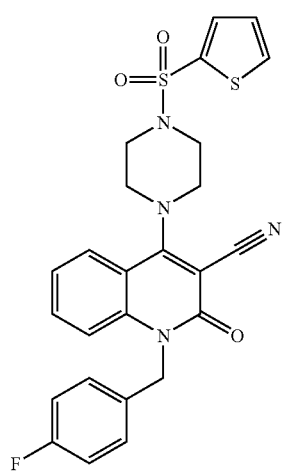
Compound 224
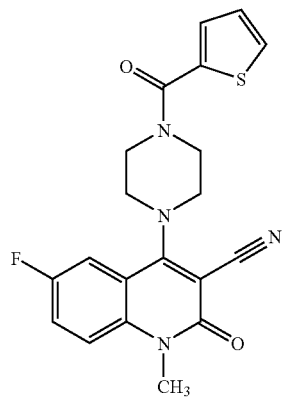
Compound 225
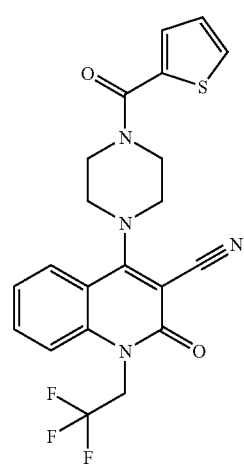
Compound 226
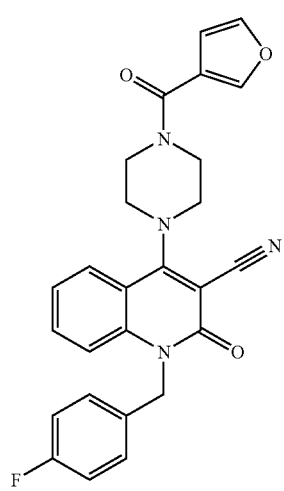

-continued
Compound 227
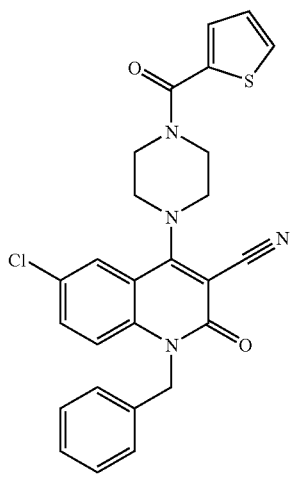
Compound 228
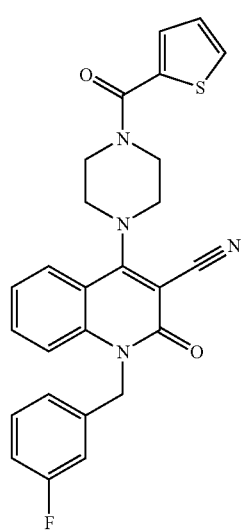
Compound 229
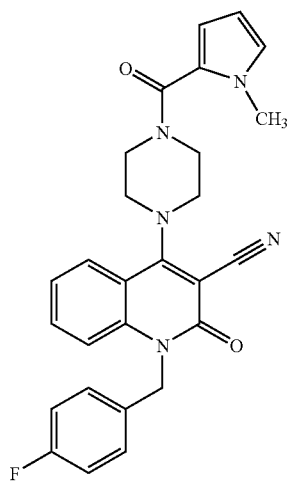
-continued
Compound 230
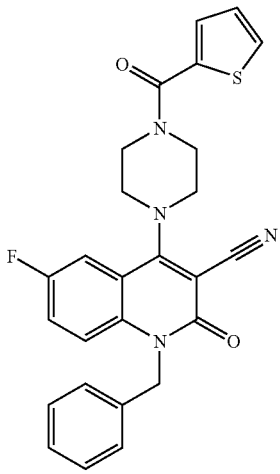
Compound 231
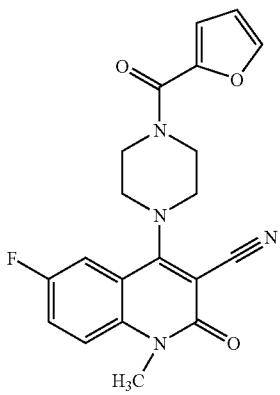
Compound 232
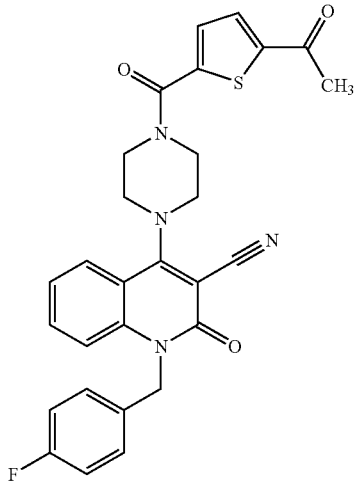

Compound 233
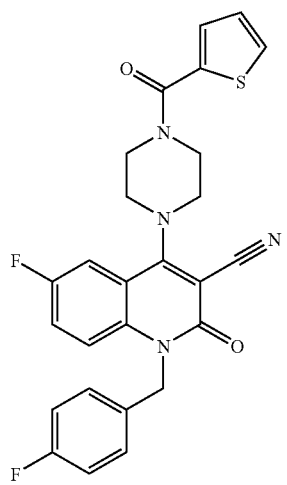
Compound 234
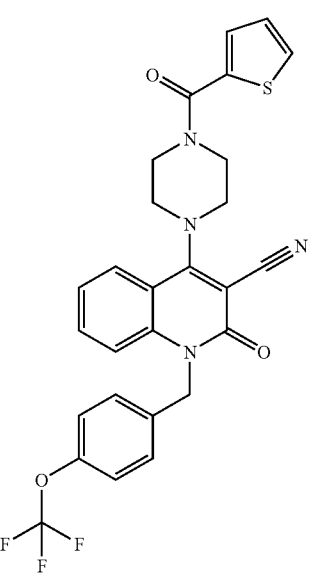
Compound 235
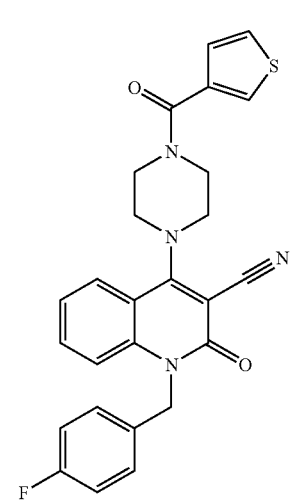
Compound 236
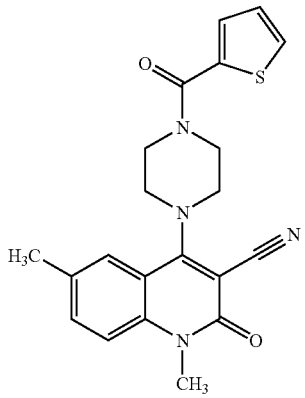
Compound 237
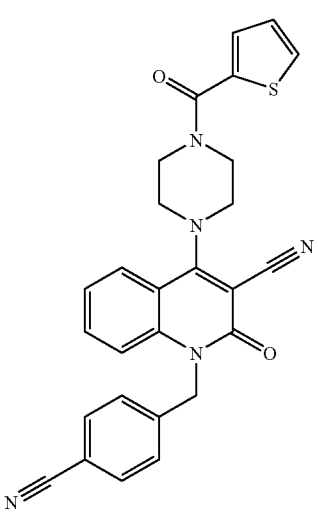
Compound 238
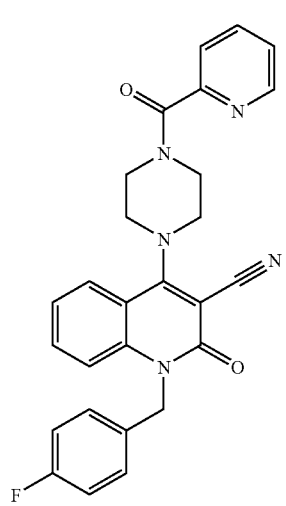

Compound 239
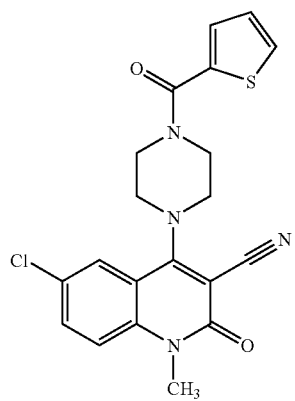
Compound 240
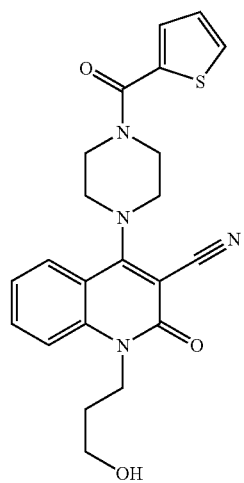
Compound 241
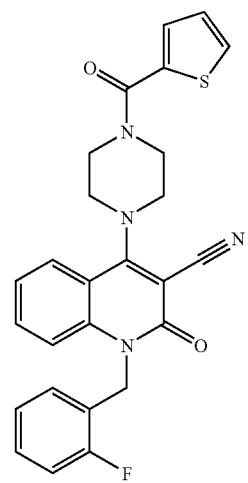
Compound 242
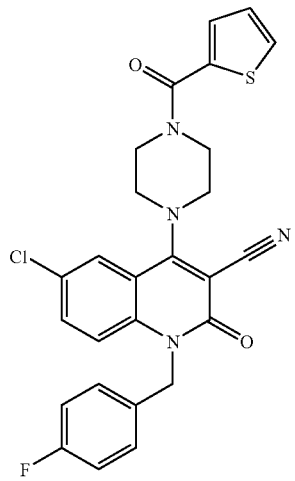
Compound 243
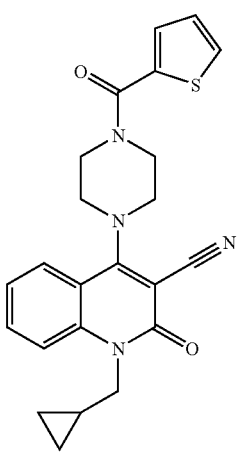
Compound 244

Compound 245
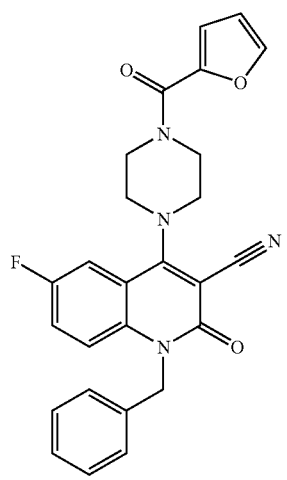
Compound 248
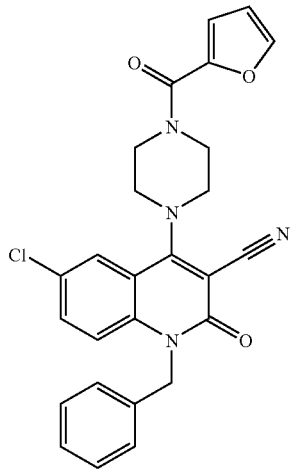
Compound 246
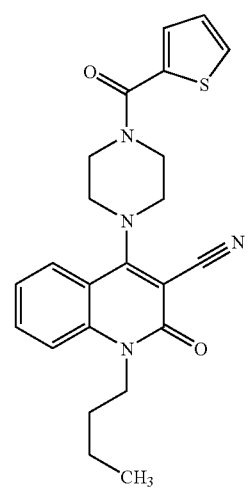
Compound 249
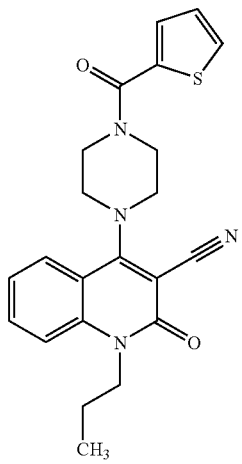
Compound 247
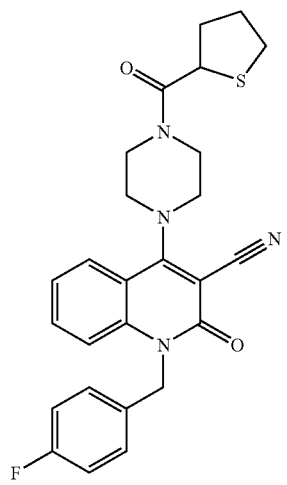
Compound 250
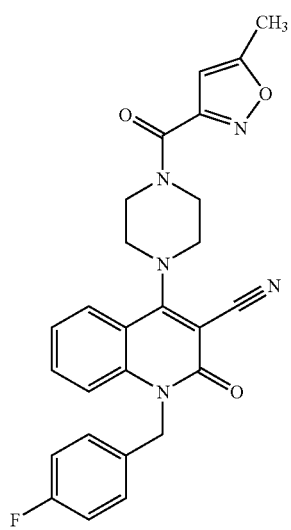

Compound 251
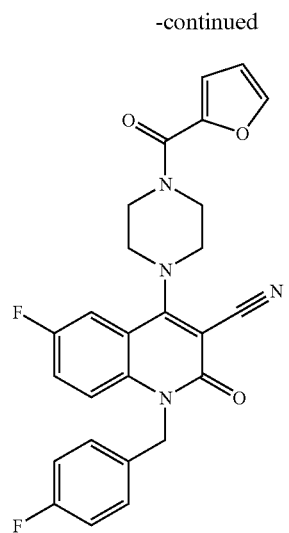
Compound 252
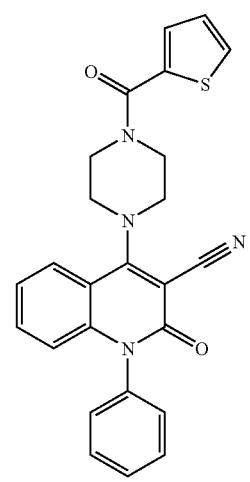
Compound 253
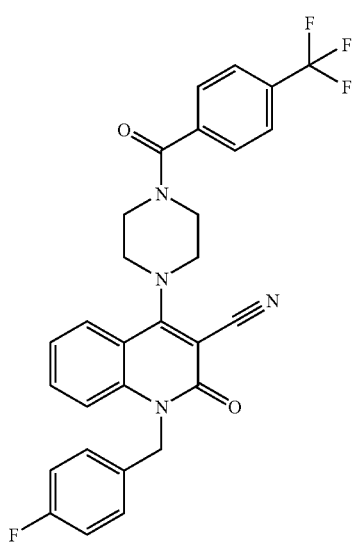
Compound 254
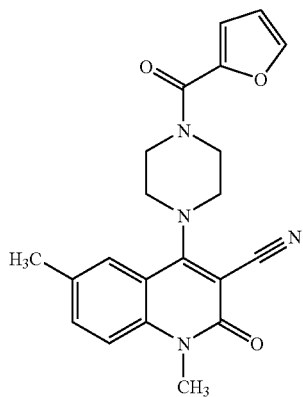
Compound 255
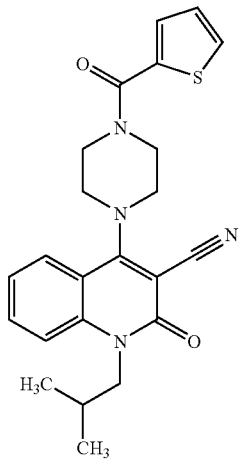
Compound 256
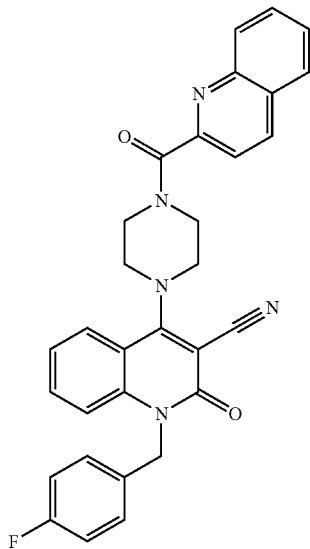

-continued
Compound 257
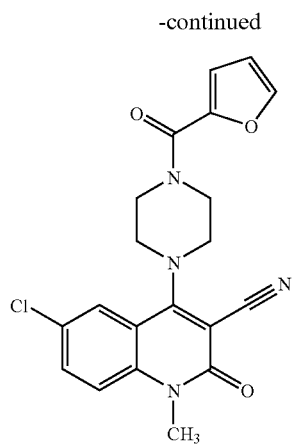
Compound 258
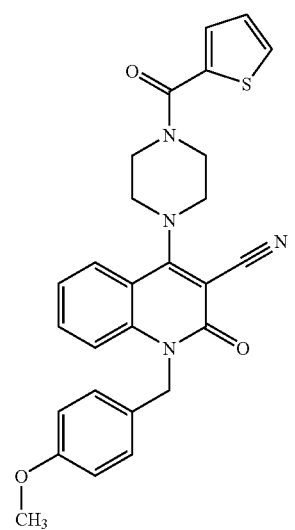
Compound 259
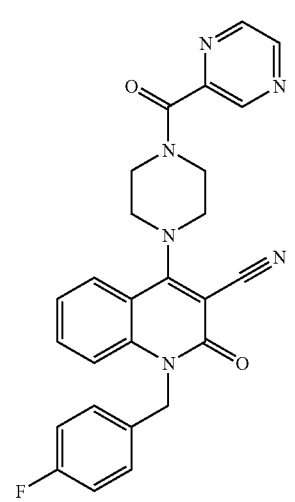
-continued
Compound 260
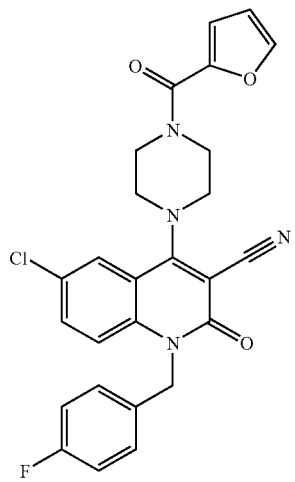
Compound 261
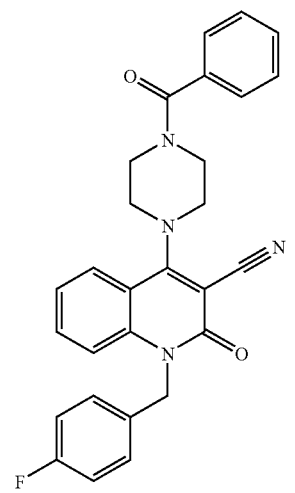
Compound 262
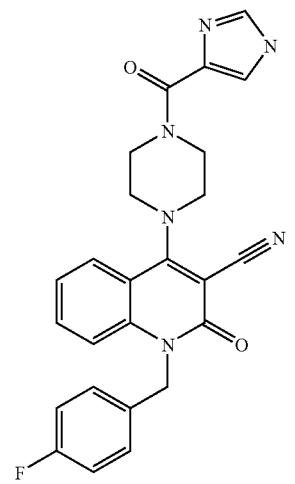

Compound 263
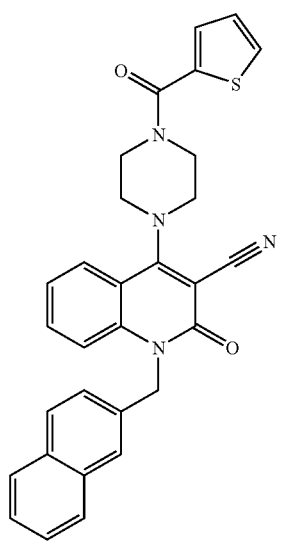
Compound 264
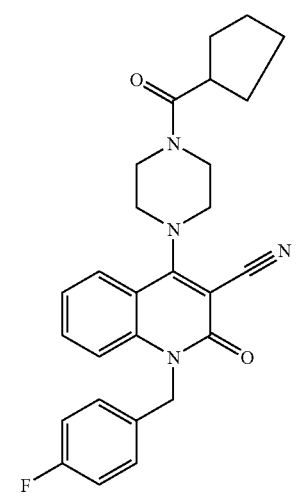
Compound 265
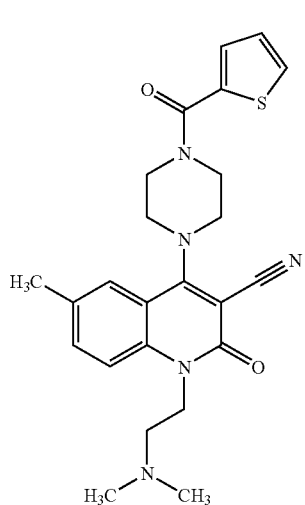
Compound 266
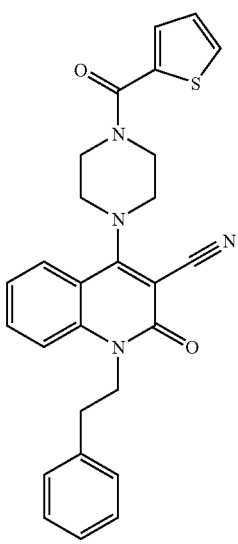
Compound 267
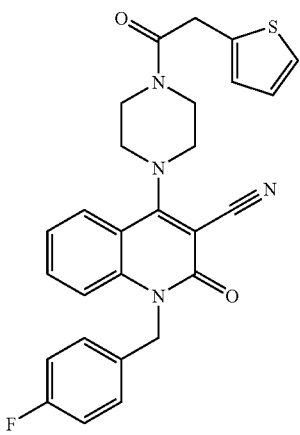
Compound 268
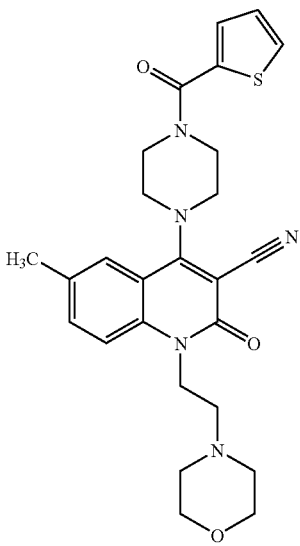

Compound 269
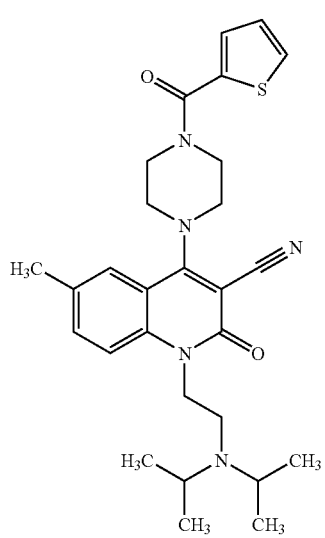
Compound 270
Compound 301
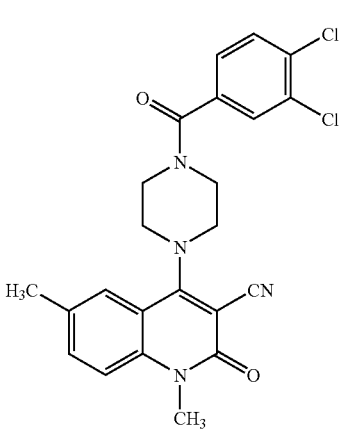
Compound 302
Example 5
The following inhibitors of MIF of preferred embodiments can be prepared by the methods described in the examples.
Compound 300
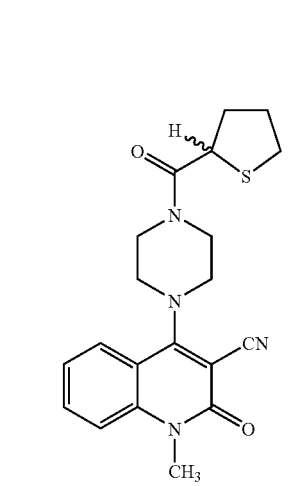
Compound 303
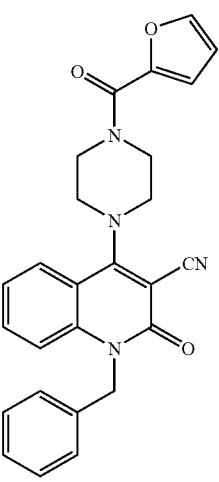

-continued
Compound 304
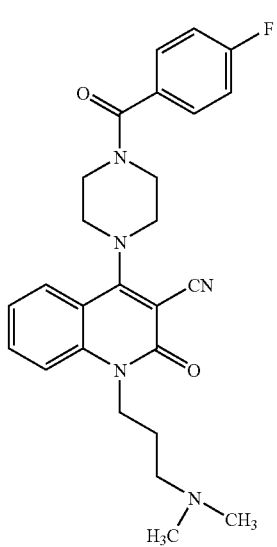
Compound 305
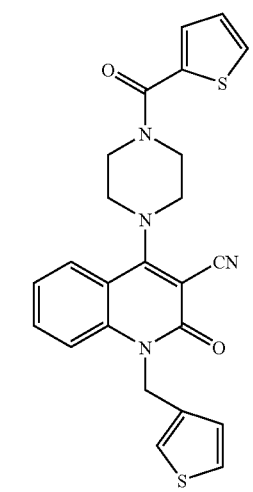
Compound 306
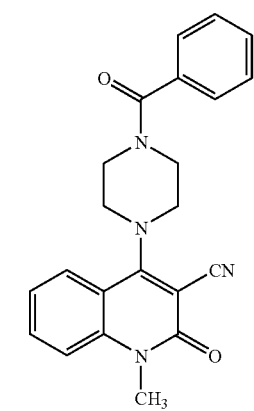
-continued
Compound 307
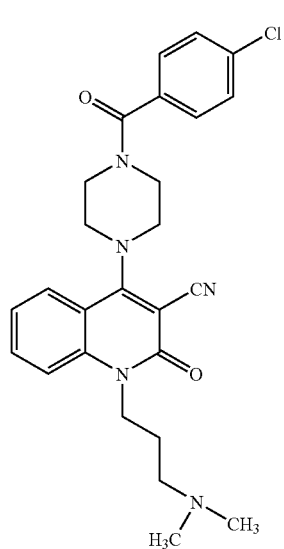
Compound 308
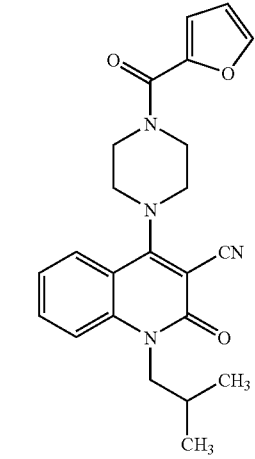
Compound 309
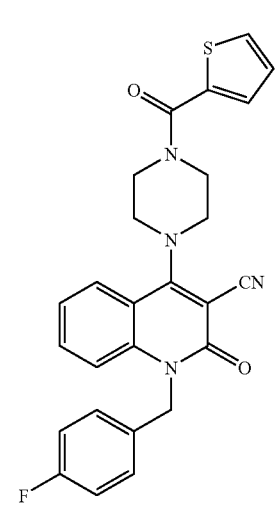

Compound 310
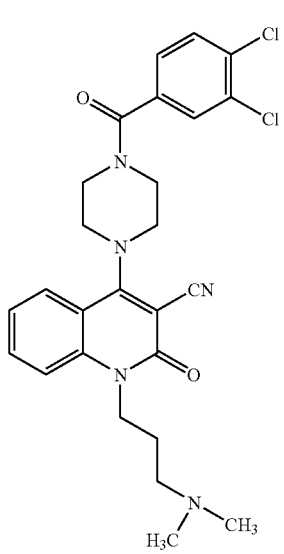
Compound 313
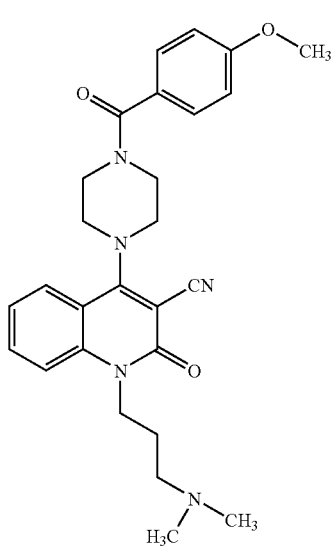
Compound 311
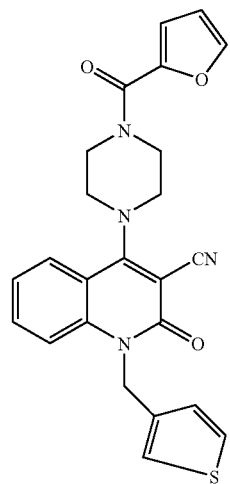
Compound 314
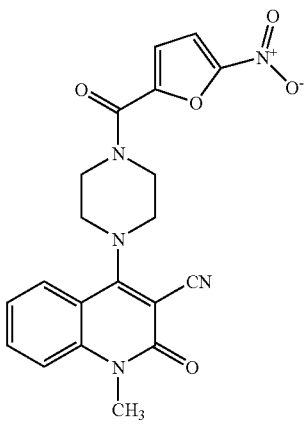
Compound 312
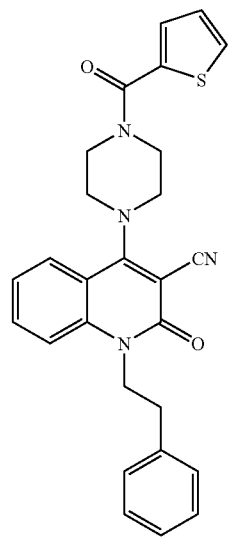
Compound 315
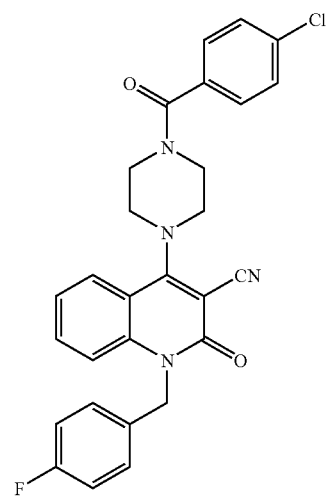

-continued
Compound 316
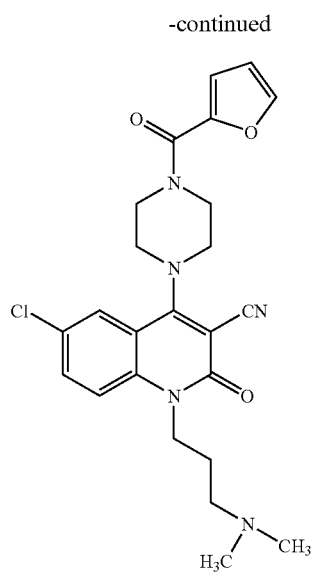
Compound 317
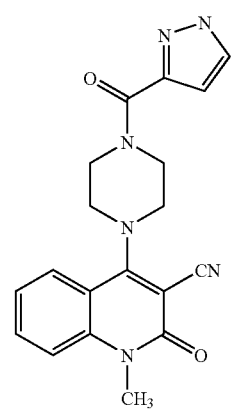
Compound 318
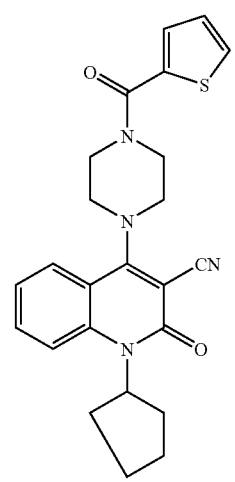
-continued
Compound 319
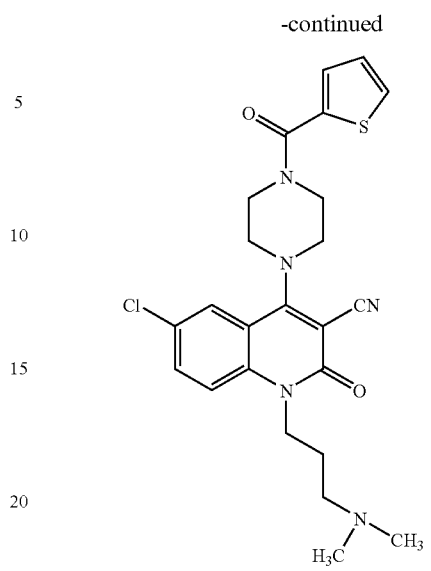
Compound 320
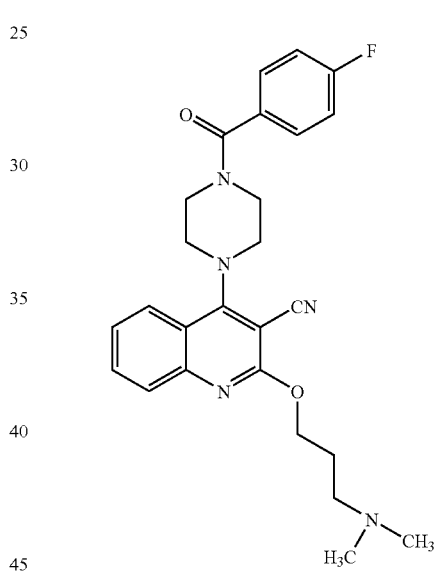
Compound 321
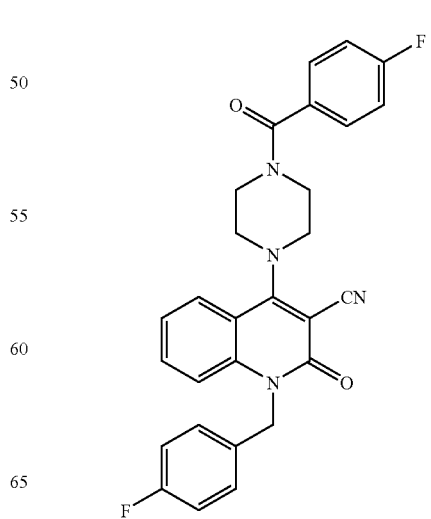

-continued
Compound 322
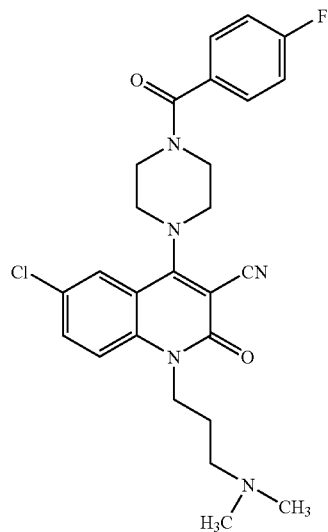
Compound 323
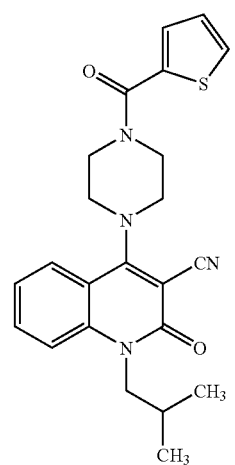
Compound 324
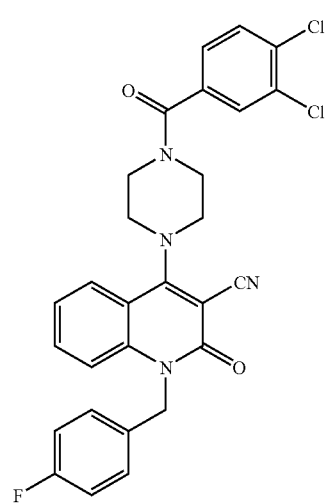
-continued
Compound 325
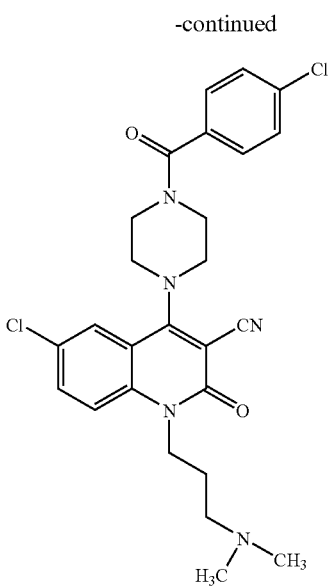
Compound 326
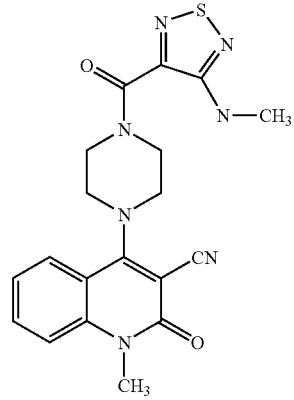
Compound 327
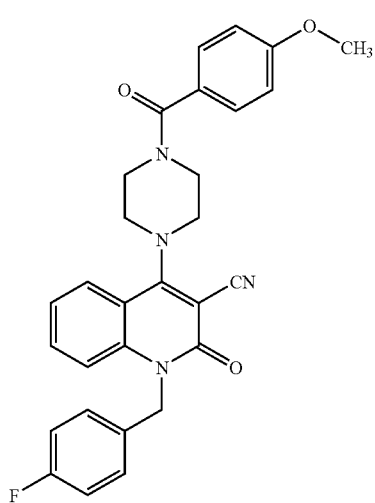

-continued
Compound 328
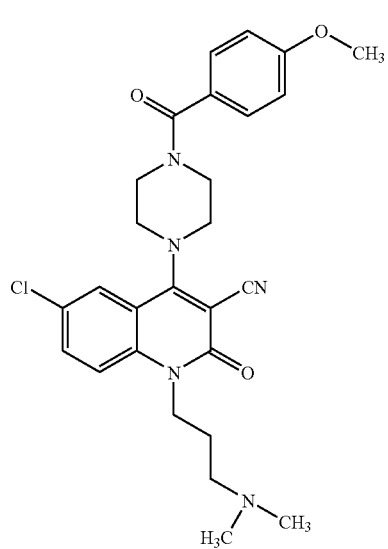
Compound 329
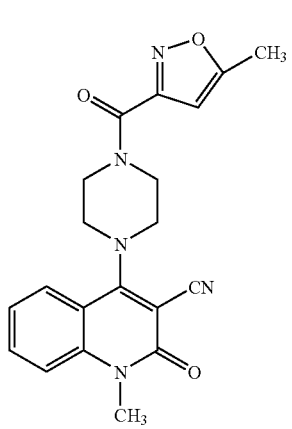
Compound 330
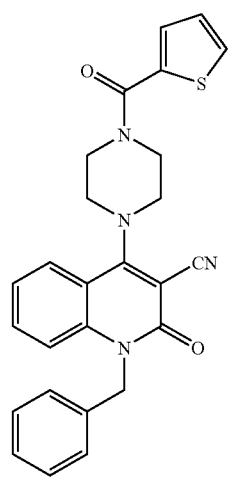
-continued
Compound 331
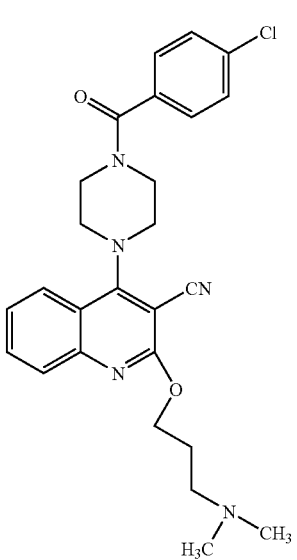
Compound 332
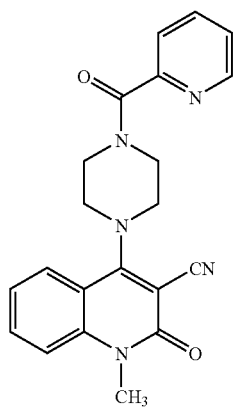
Compound 333
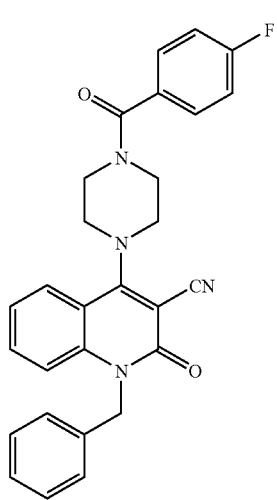

Compound 334
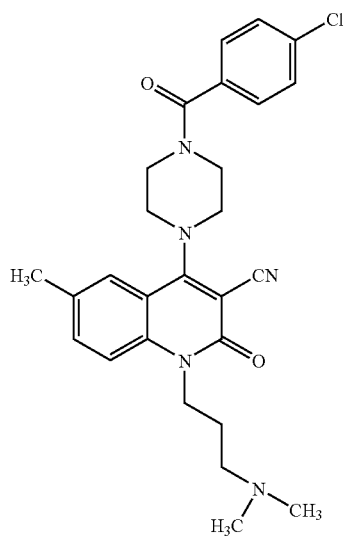
Compound 335
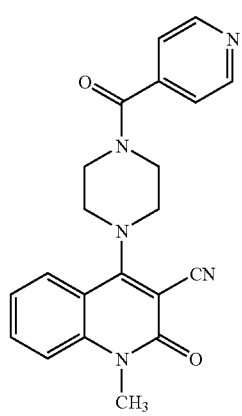
Compound 336
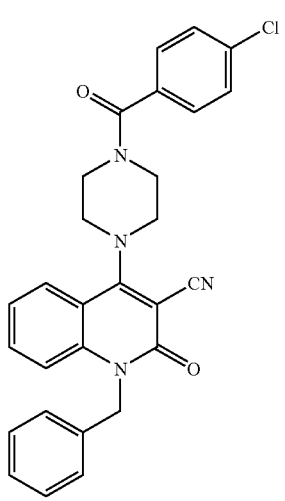
Compound 337
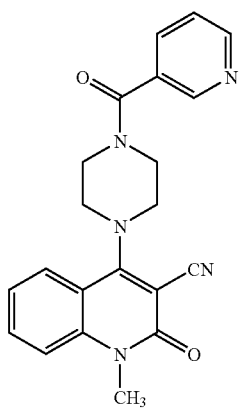
Compound 338
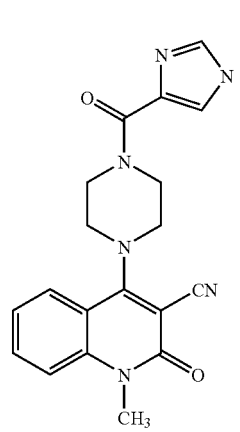
Compound 339
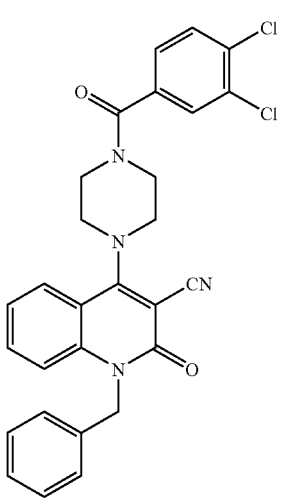

-continued
Compound 340
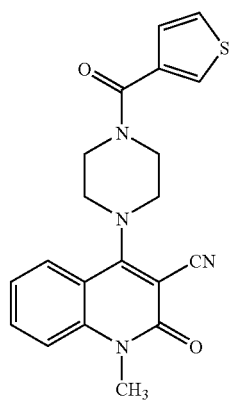
Compound 341
Compound 342
-continued
Compound 343
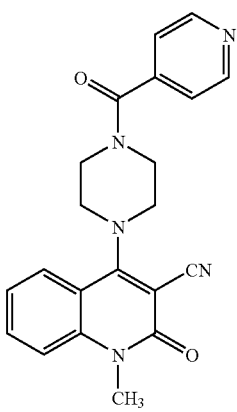
Compound 344
Compound 345
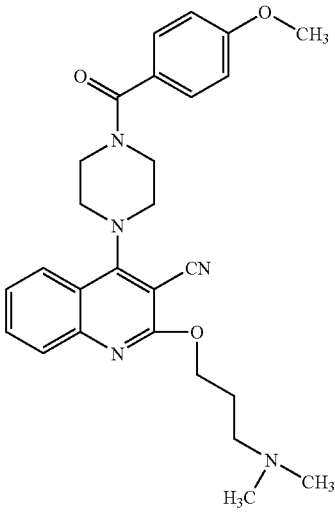

-continued
Compound 346
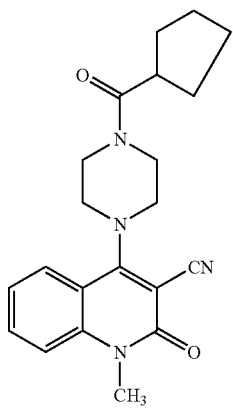
Compound 347
Compound 348
Compound 349
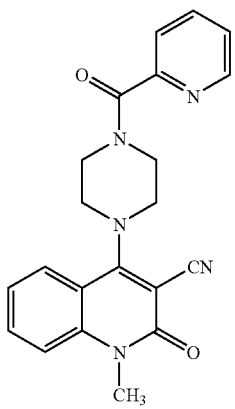
Compound 350
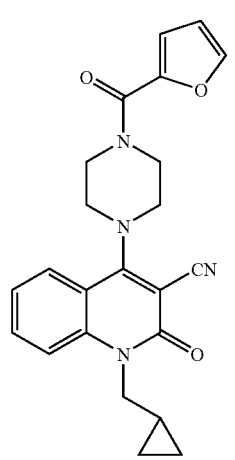
Compound 351
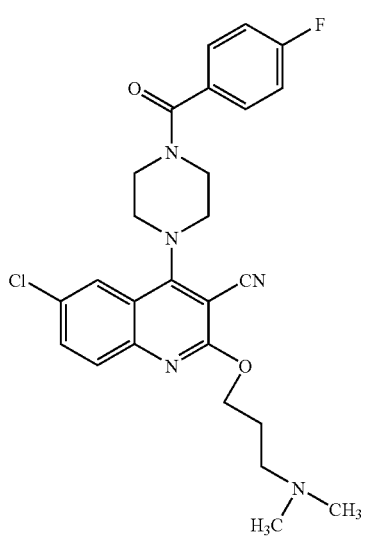

-continued
Compound 352
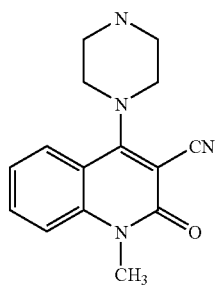
Compound 353
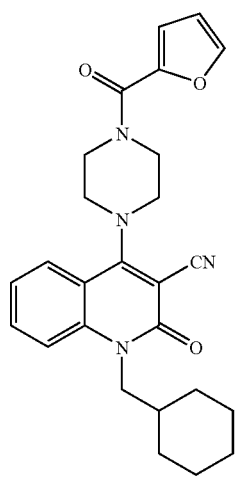
Compound 354
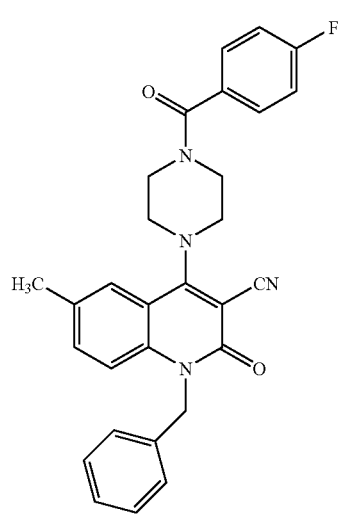
-continued
Compound 355
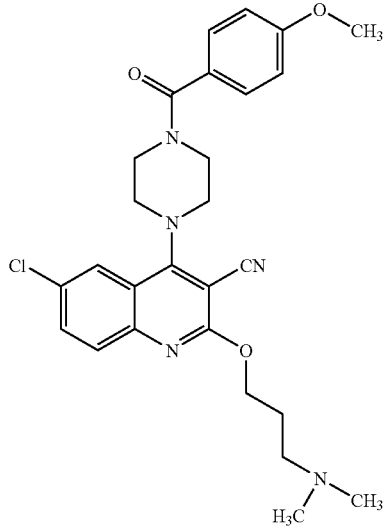
Compound 356
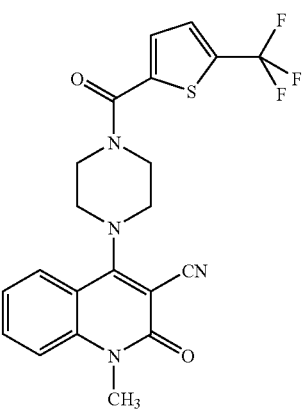
Compound 357
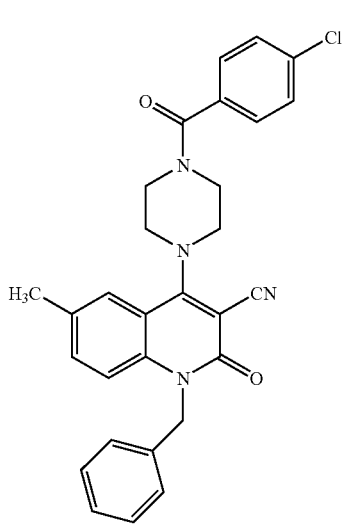

-continued
Compound 358
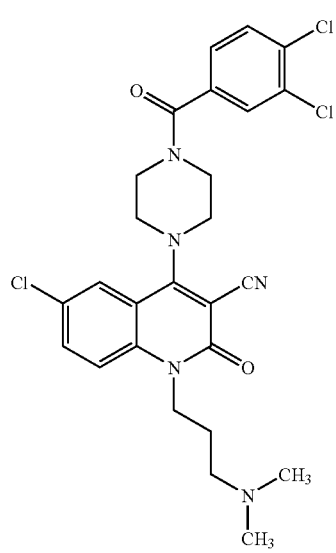
Compound 359
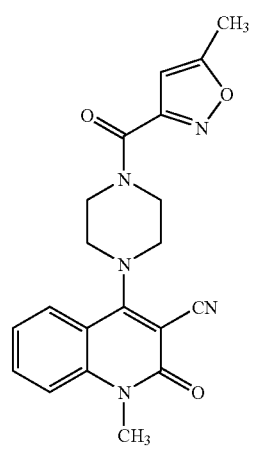
Compound 360
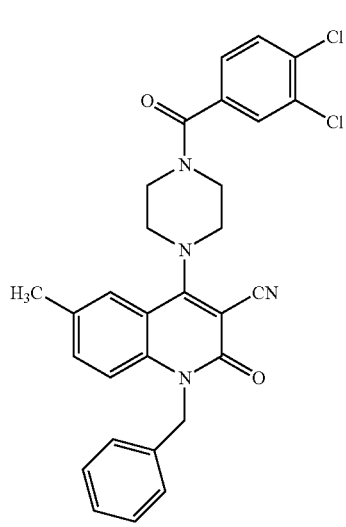
-continued
Compound 361
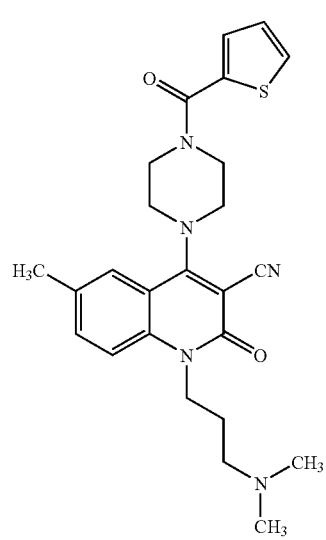
Compound 362
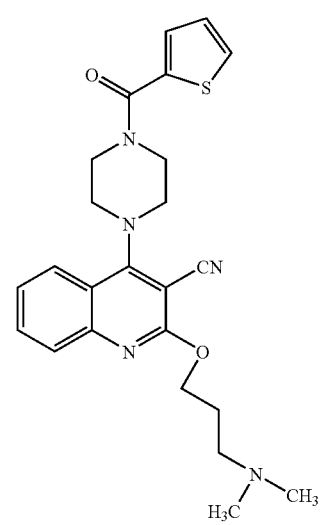
Compound 363
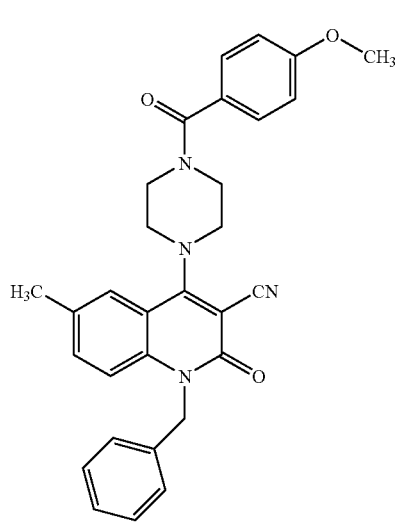

-continued
Compound 364
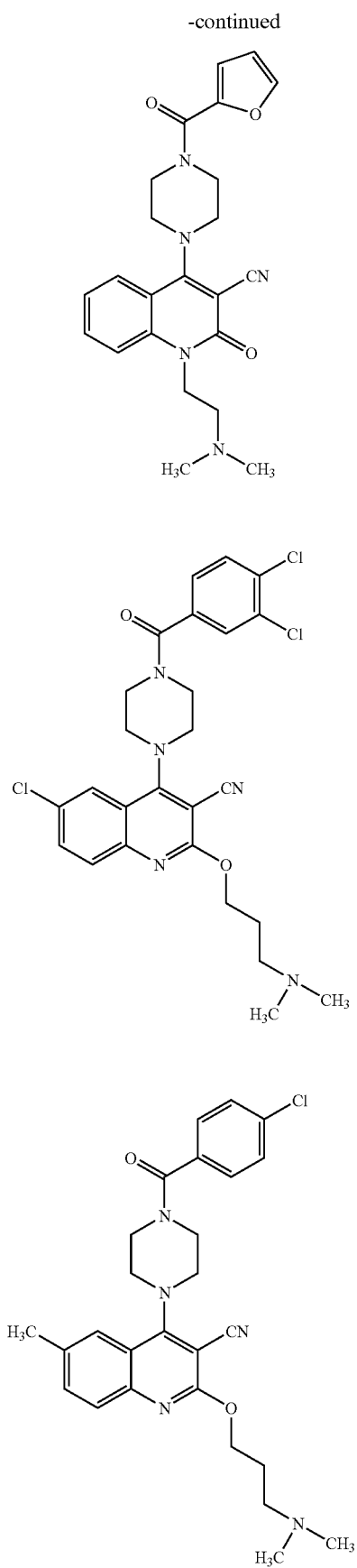
Compound 365
Compound 366
-continued
Compound 367
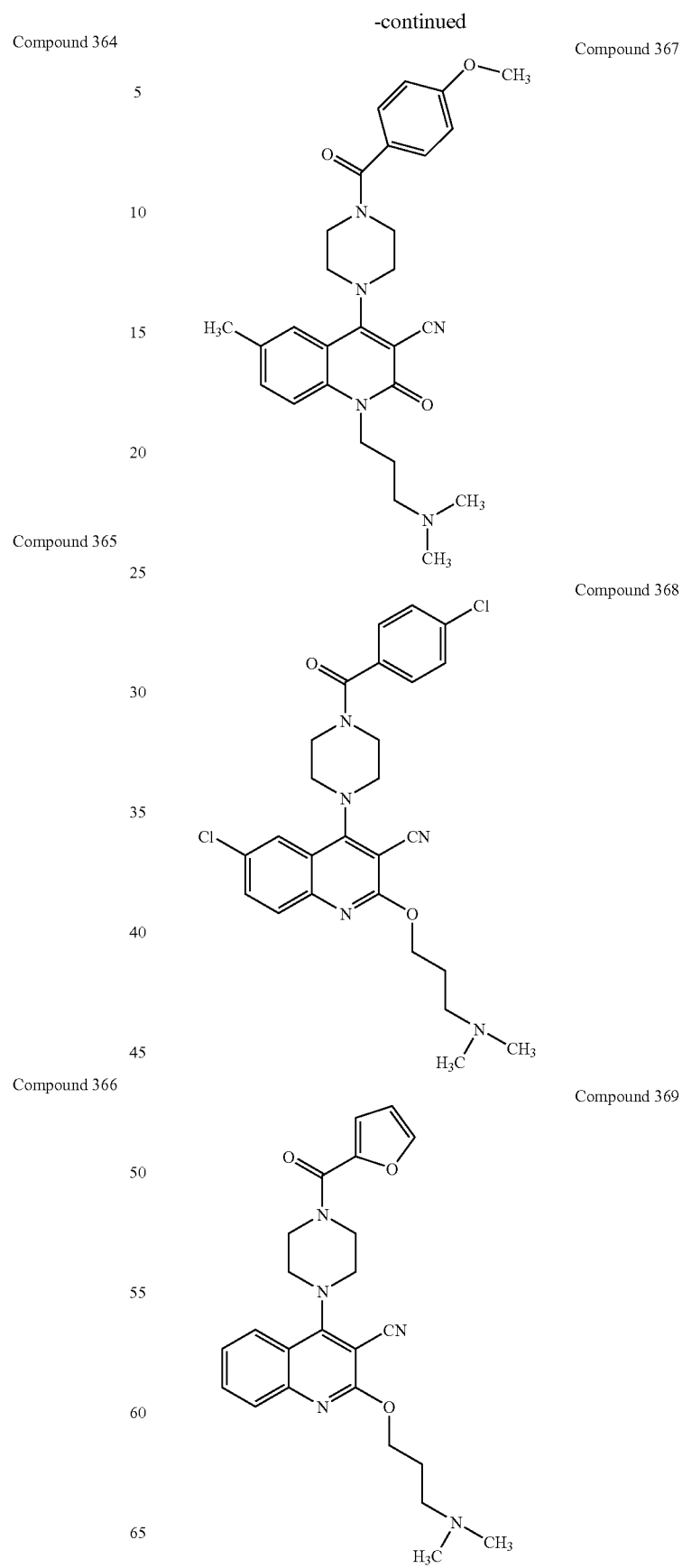
Compound 368
Compound 369

-continued
Compound 370
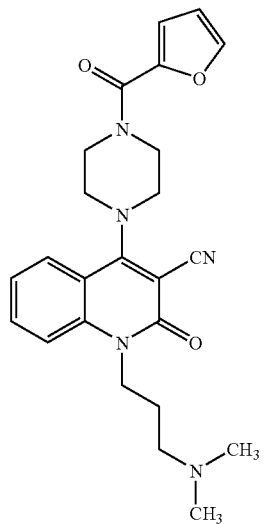
Compound 371
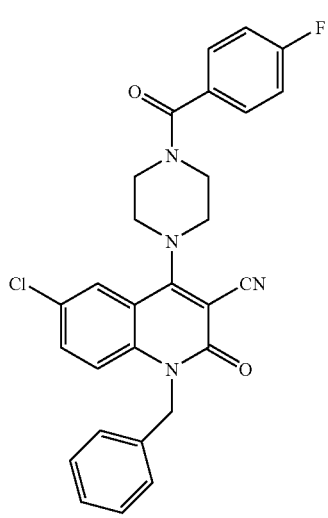
Compound 372
-continued
Compound 373
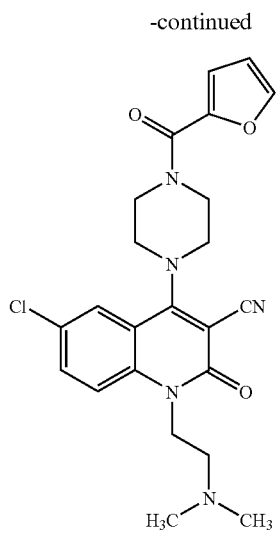
Compound 374
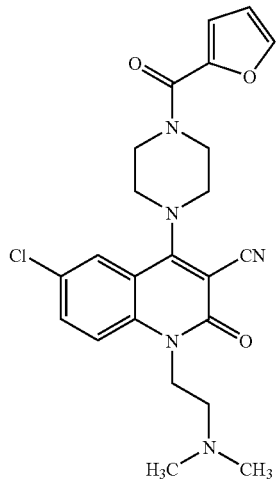
Compound 375
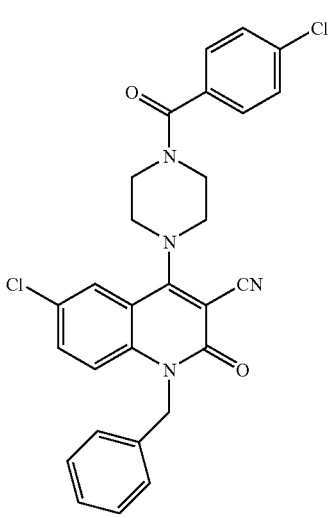

-continued
Compound 376
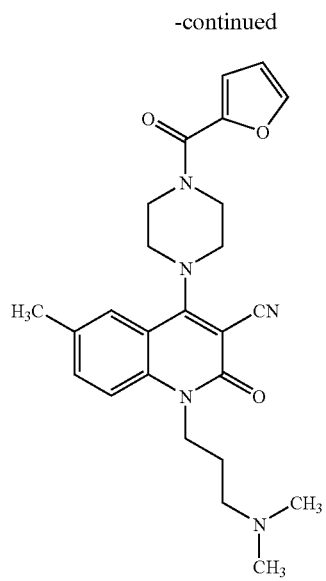
Compound 377
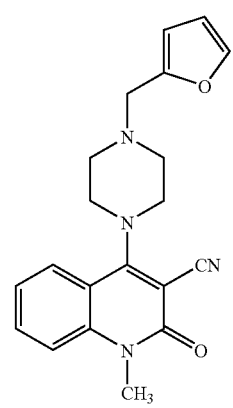
Compound 378
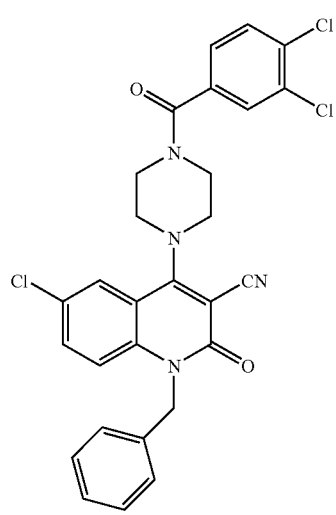
-continued
Compound 379
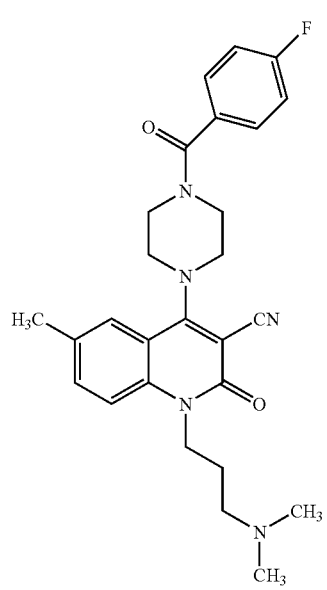
Compound 380
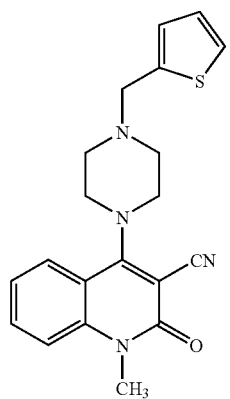
Compound 381
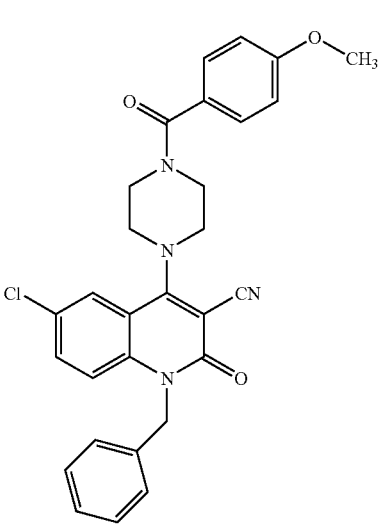

-continued
Compound 382
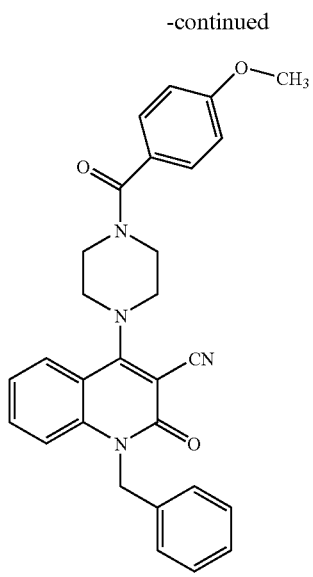
Compound 383
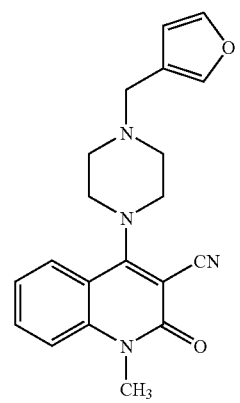
Compound 384
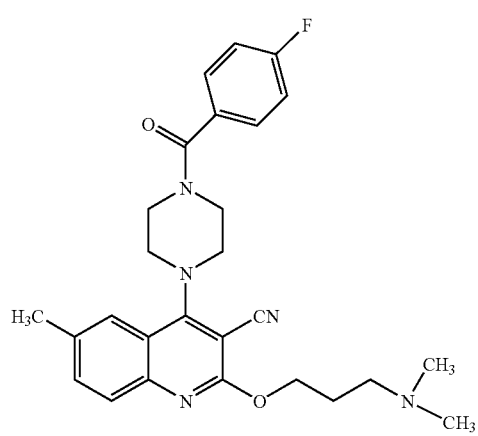
-continued
Compound 385
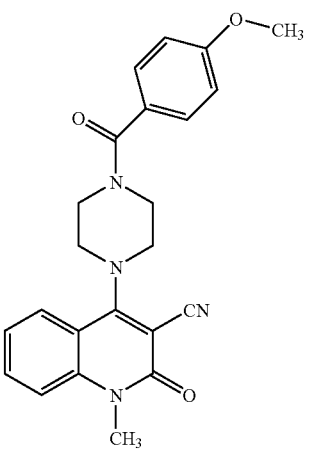
Compound 386
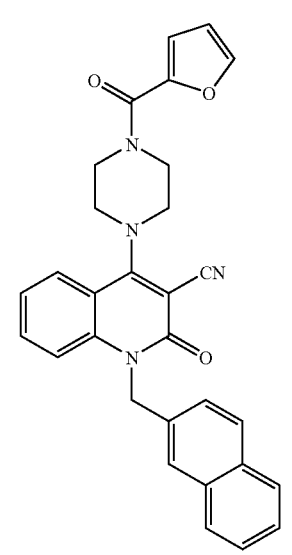
Compound 387
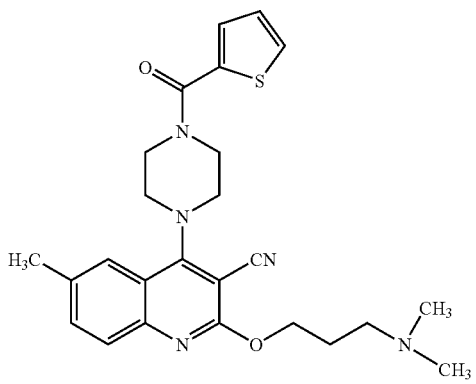

-continued
Compound 388
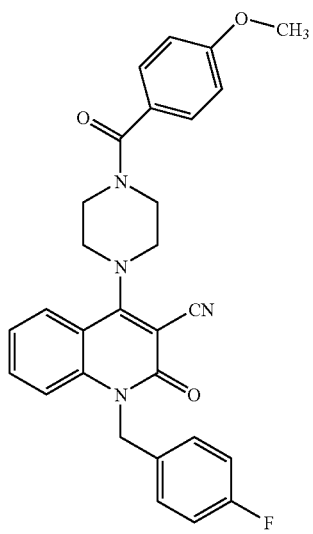
Compound 389
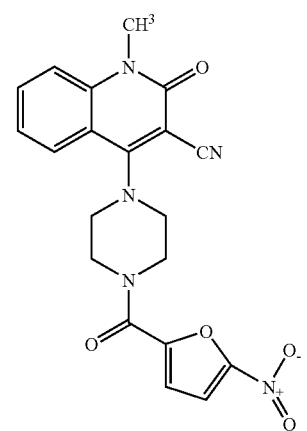
Compound 400
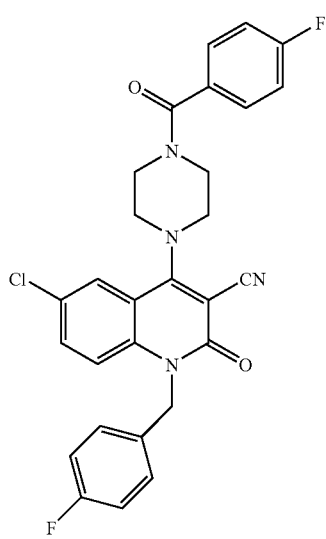
-continued
Compound 401
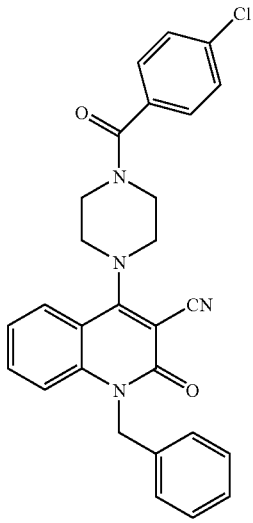
Compound 402
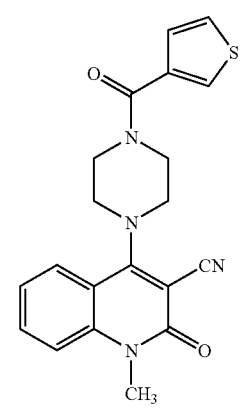
Compound 403
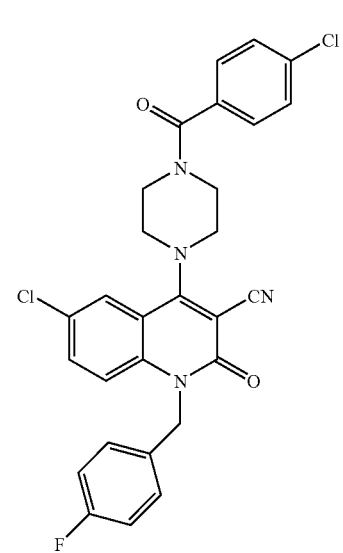

Compound 404
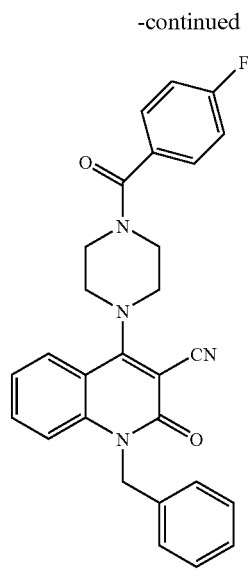
Compound 405
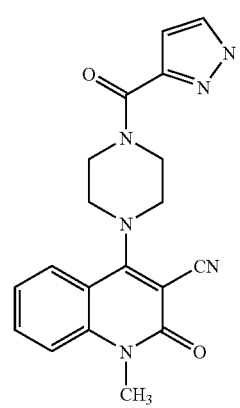
Compound 406
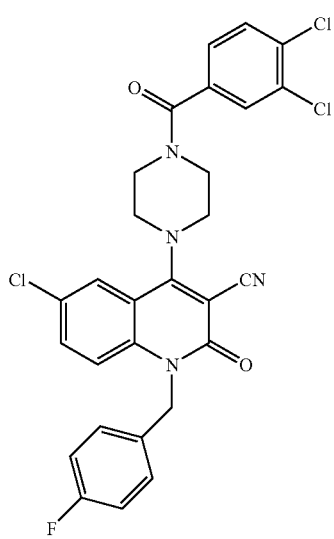
Compound 407
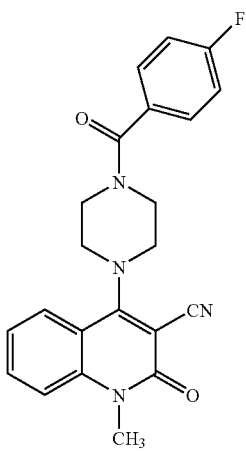
Compound 408
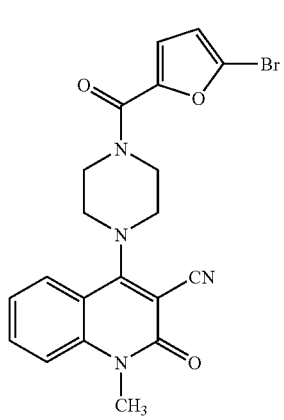
Compound 409
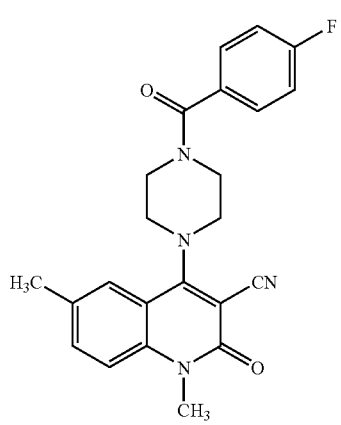

-continued
Compound 410
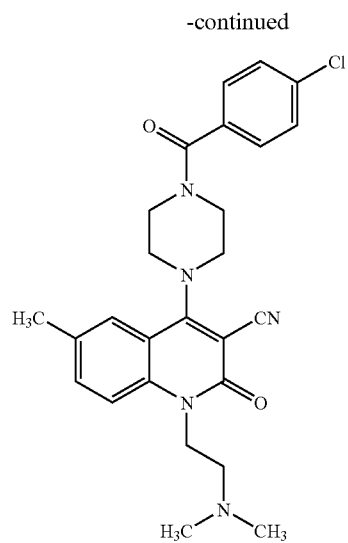
Compound 411
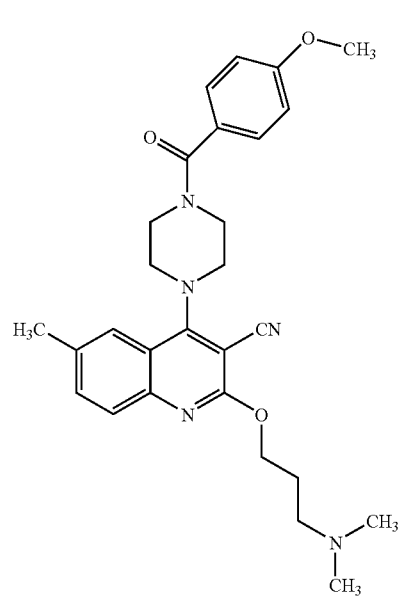
Compound 412
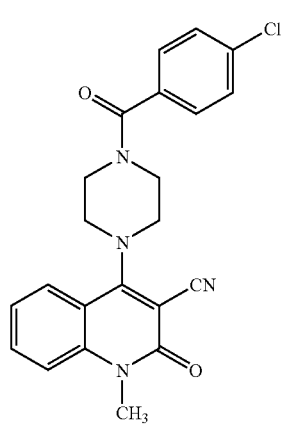
-continued
Compound 413
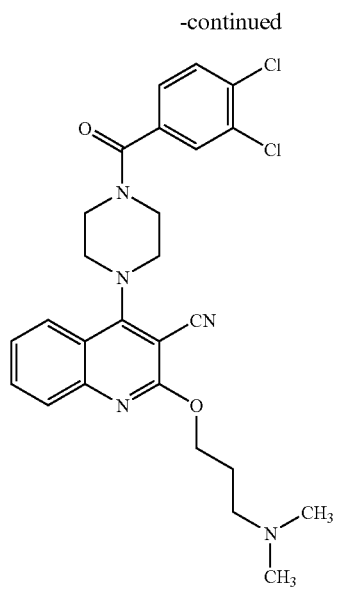
Compound 414
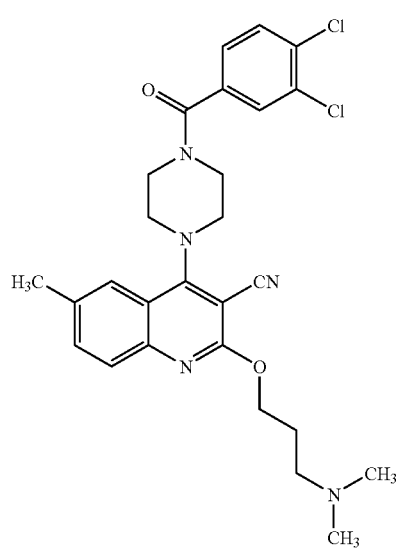
Compound 415
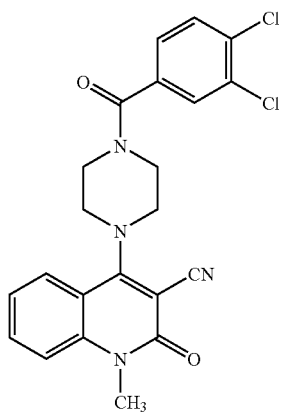

-continued
Compound 416
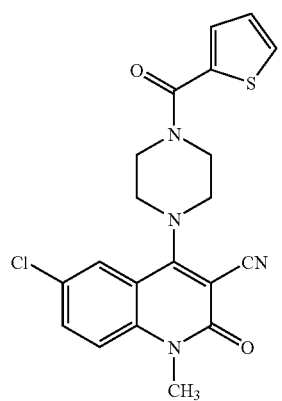
Compound 417
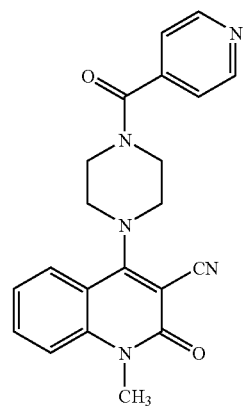
Compound 418
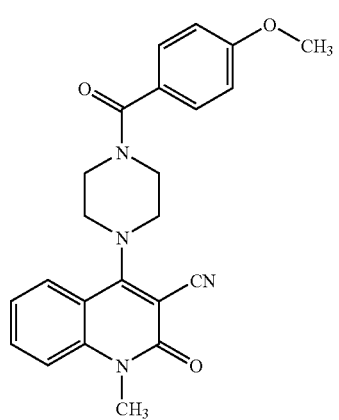
-continued
Compound 419
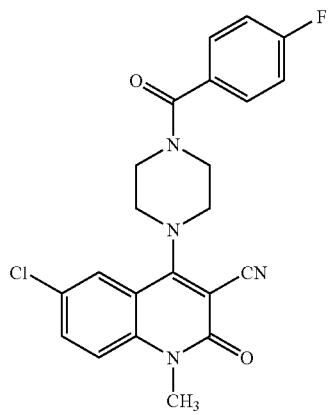
Compound 420
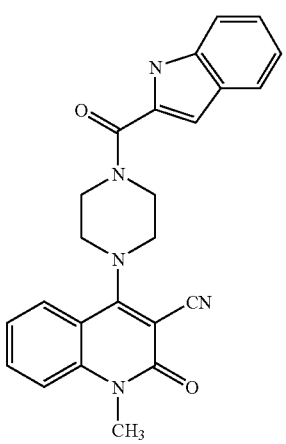
Compound 421

Compound 422
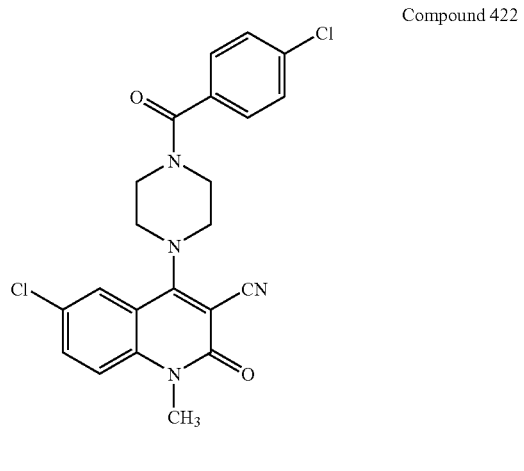
Compound 425
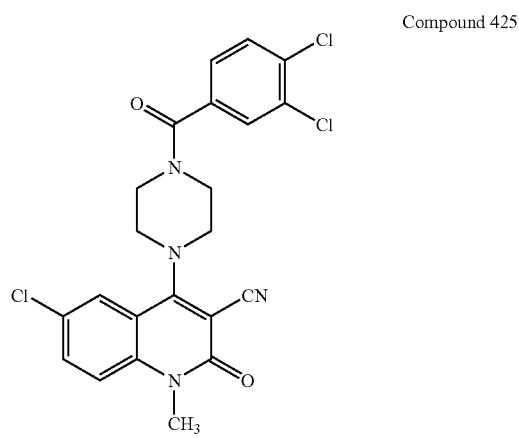
Compound 423
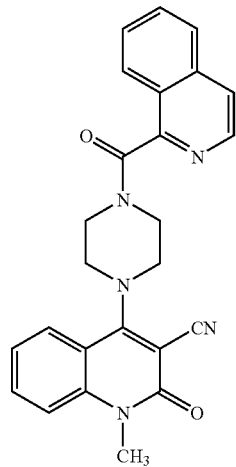
Compound 426
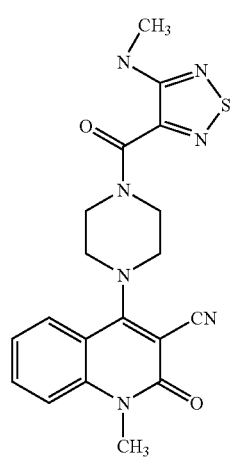
Compound 424
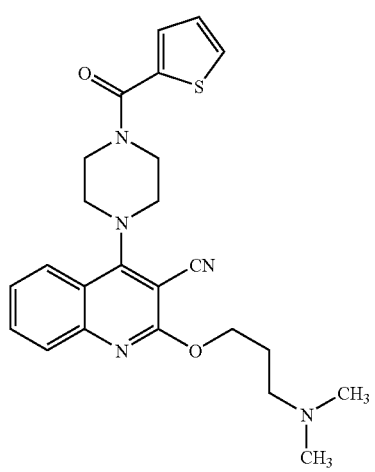
Compound 427
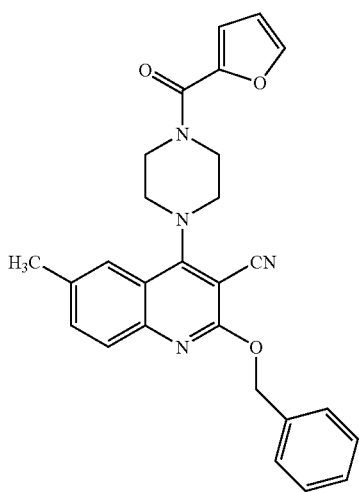

-continued
Compound 428
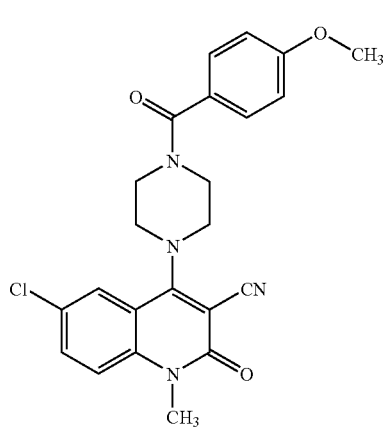
Compound 429
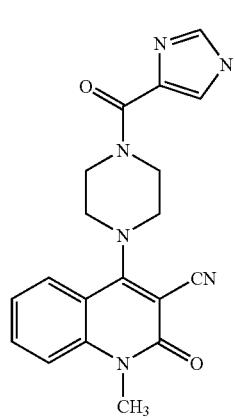
Compound 430
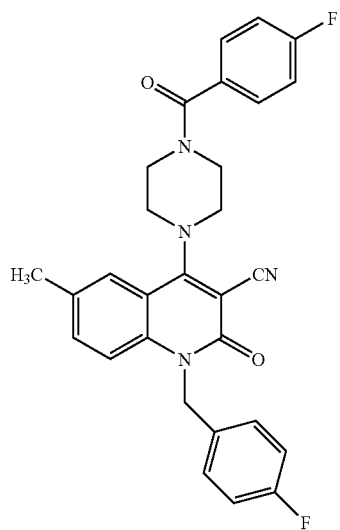
-continued
Compound 431
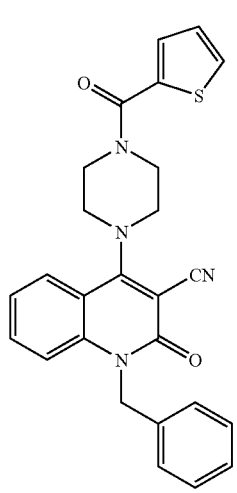
Compound 432
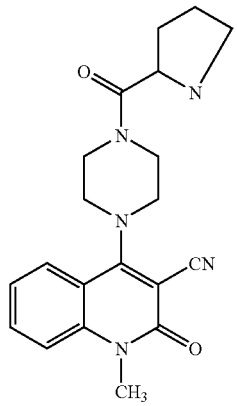
Compound 433
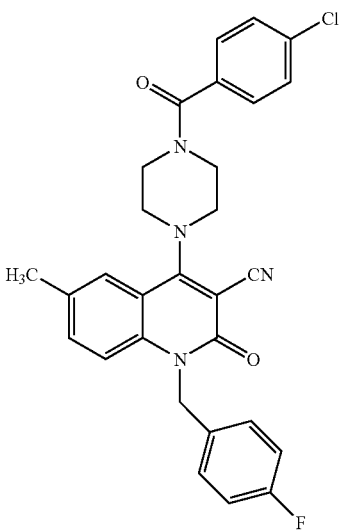

-continued
Compound 434
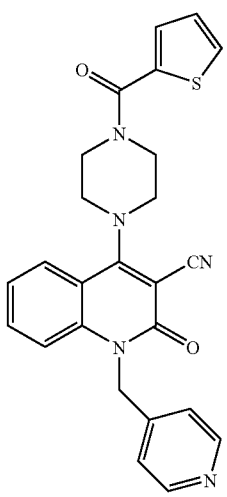
Compound 435
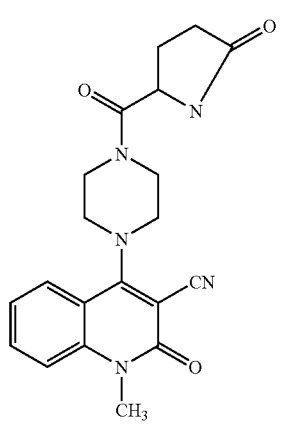
Compound 436
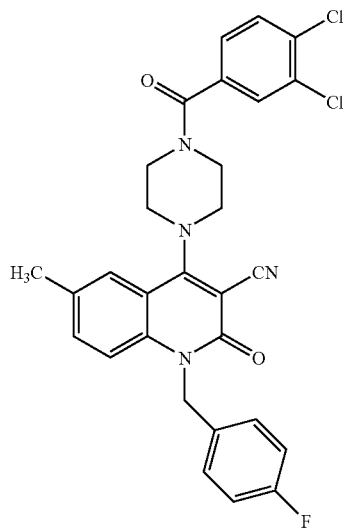
-continued
Compound 437
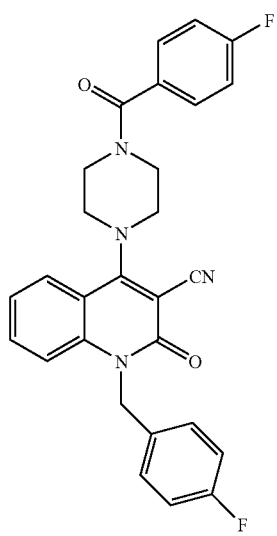
Compound 438
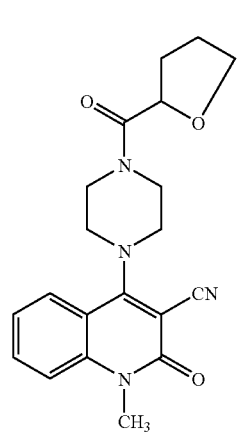
Compound 439
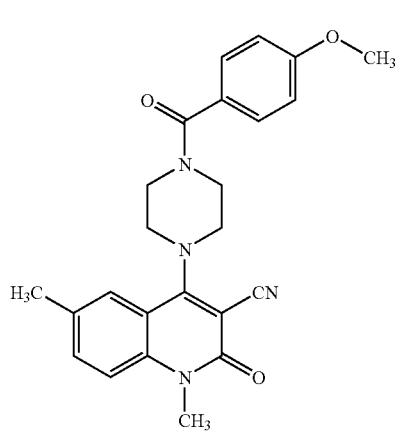

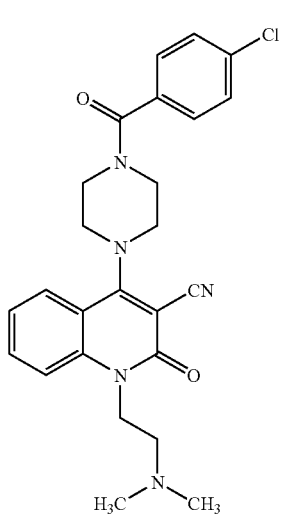
Compound 440
Compound 441
Compound 442
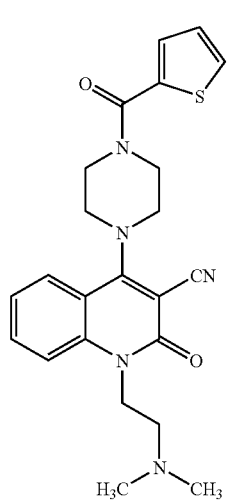
Compound 443
Compound 444
Compound 445

-continued

Compound 446

Compound 447

Compound 448

-continued

Compound 449

Compound 450

Compound 451

Compound 452
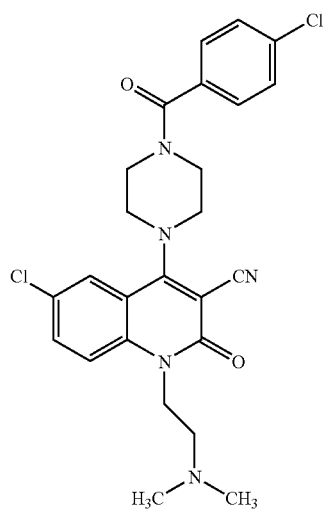
Compound 453
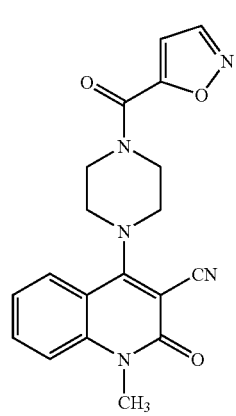
Compound 454
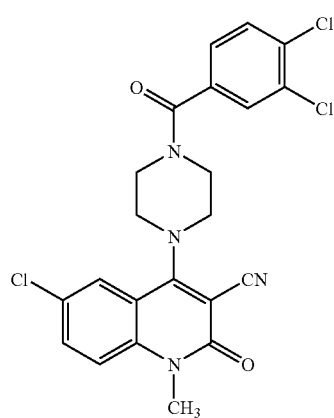
Compound 455
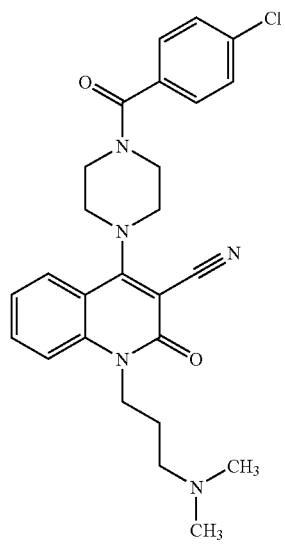
Compound 456
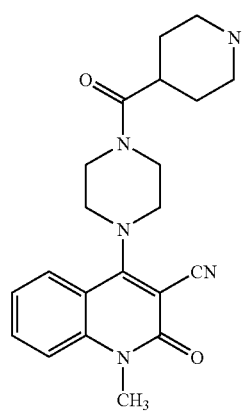
Compound 457
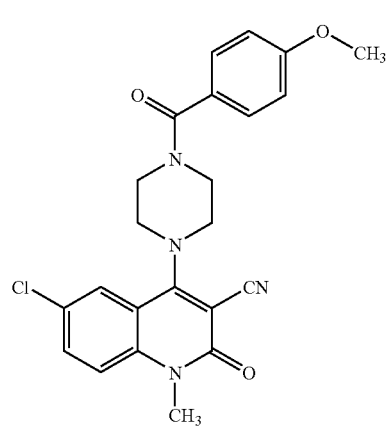

-continued
Compound 458
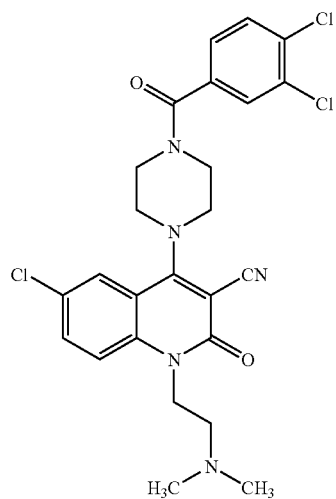
Compound 459
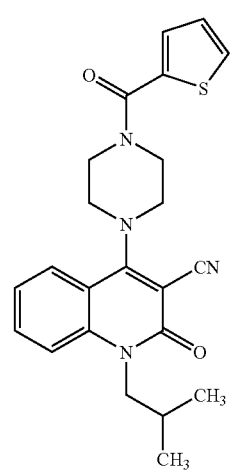
Compound 460
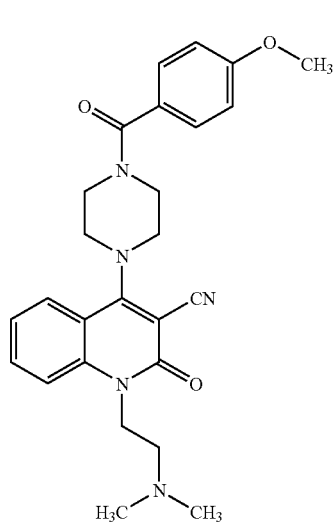
-continued
Compound 461
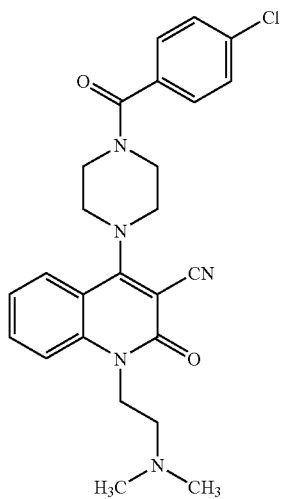
Compound 462
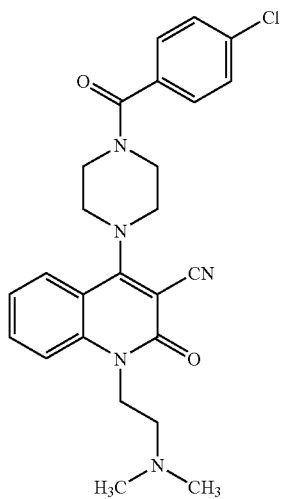
Compound 463
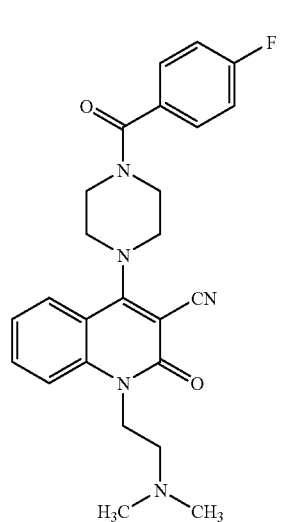

-continued
Compound 464
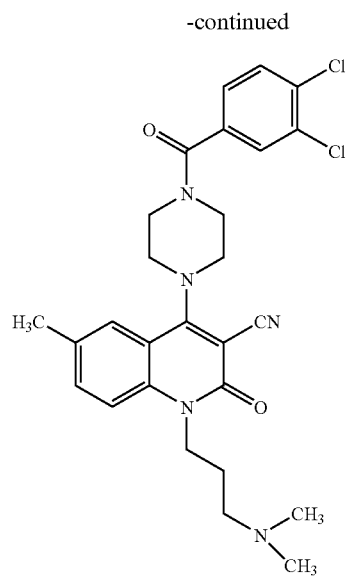
Compound 465
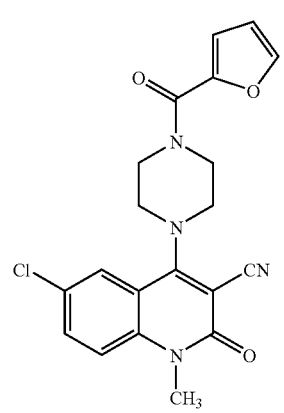
Compound 466
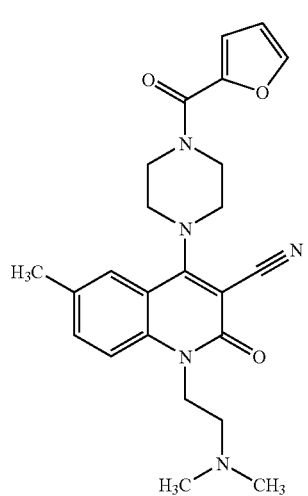
-continued
Compound 467
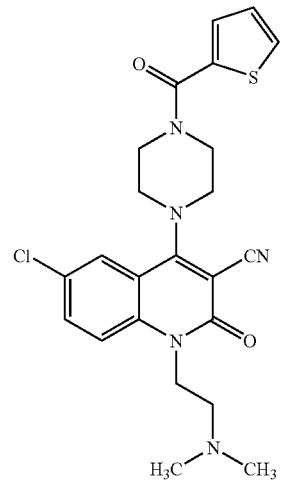
Compound 468
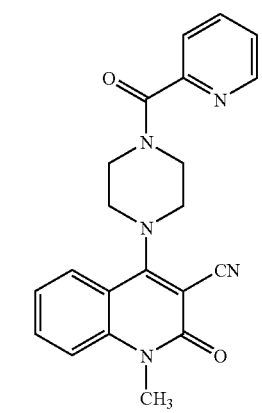
Compound 469
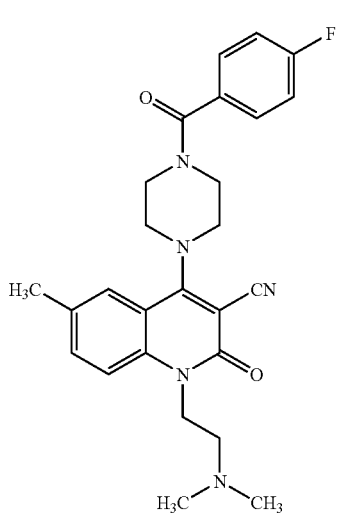

-continued
Compound 470
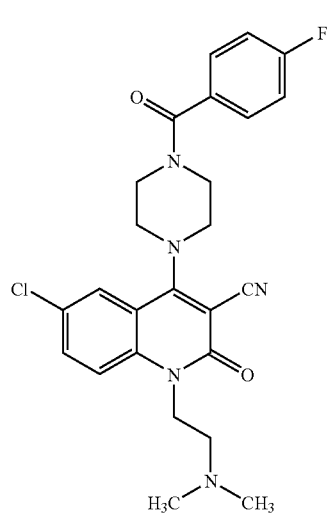
Compound 471
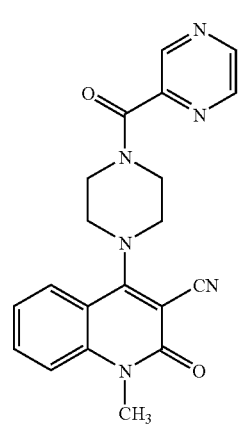
Compound 472
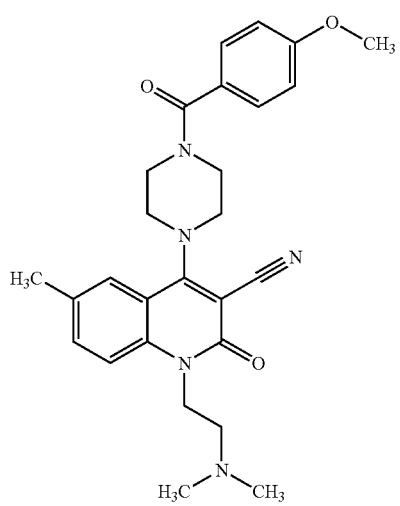
-continued
Compound 473
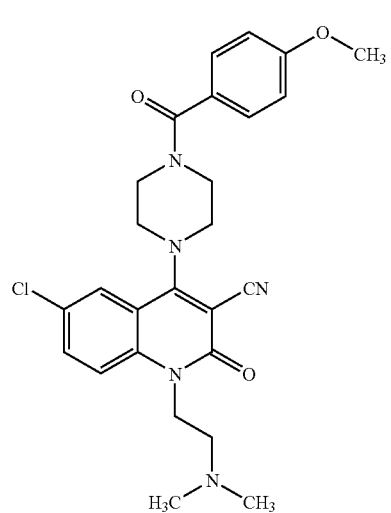
Compound 474
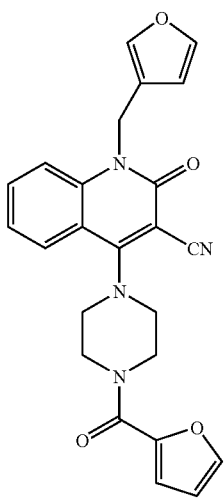
Compound 475
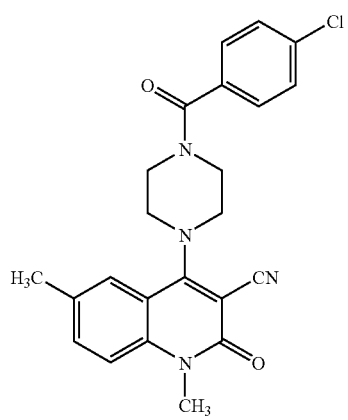

Compound 476
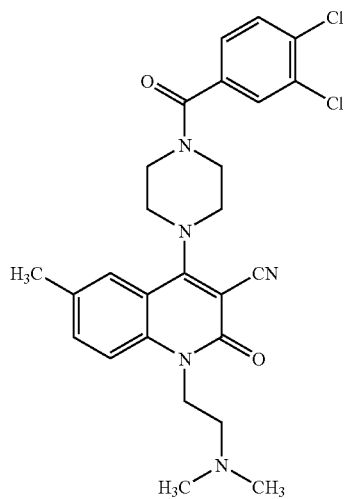
Compound 477
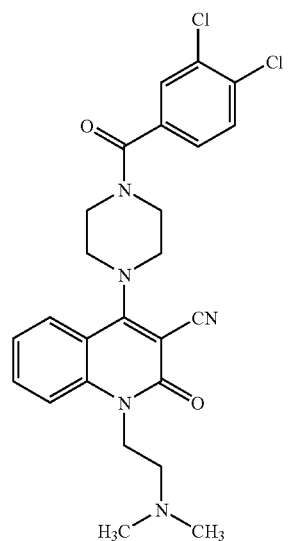
Compound 478
Compound 479
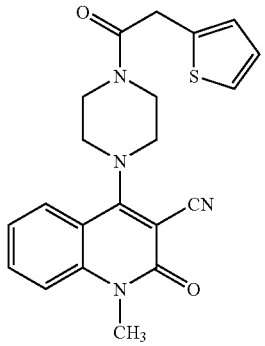
Compound 480
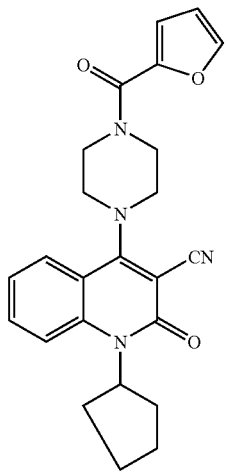
Compound 481
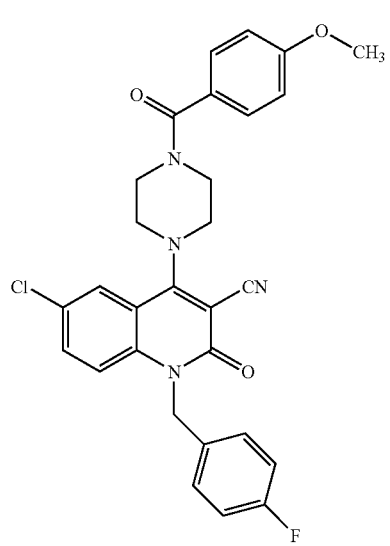

-continued

Compound 482

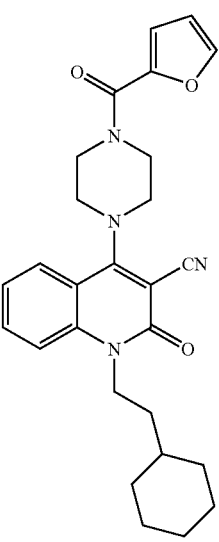

Compound 483

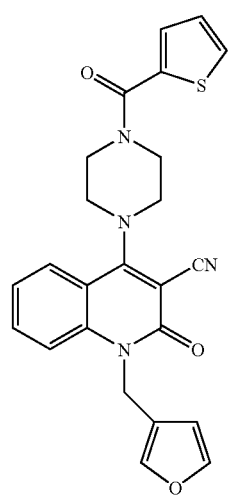

Compound 484

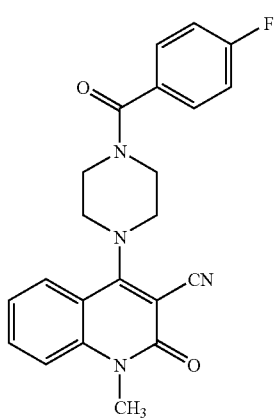

-continued

Compound 485

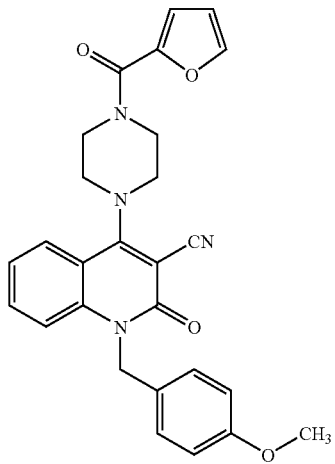

Compound 486

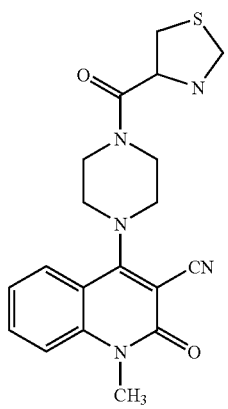

Example 6

Compound 200 was tested in the THP-1 Cell Assay at several different concentrations. Compound 200 exhibits MIF inhibitory activity, as shown in FIG. 1. Compound 200 exhibits MIF inhibitory activity Example 7

Figure 2:
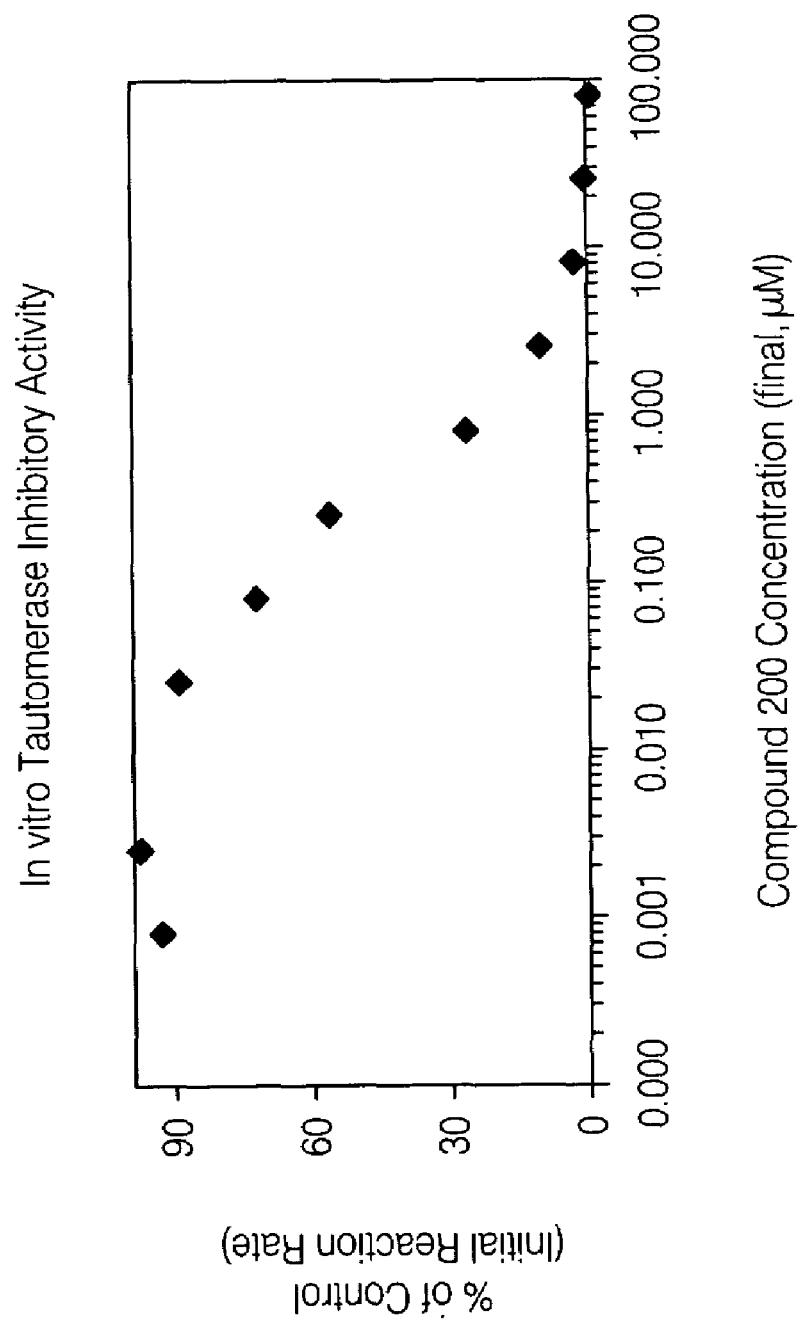
FIG. 2 provides in vitro tautomerase inhibitory activity data for Compound 200.

Compound 200 was tested for in vitro tautomerase inhibitory activity at several different concentrations. Compound 200 exhibits MIF inhibitory activity, as shown in FIG. 2.

Example 8

Figure 3:
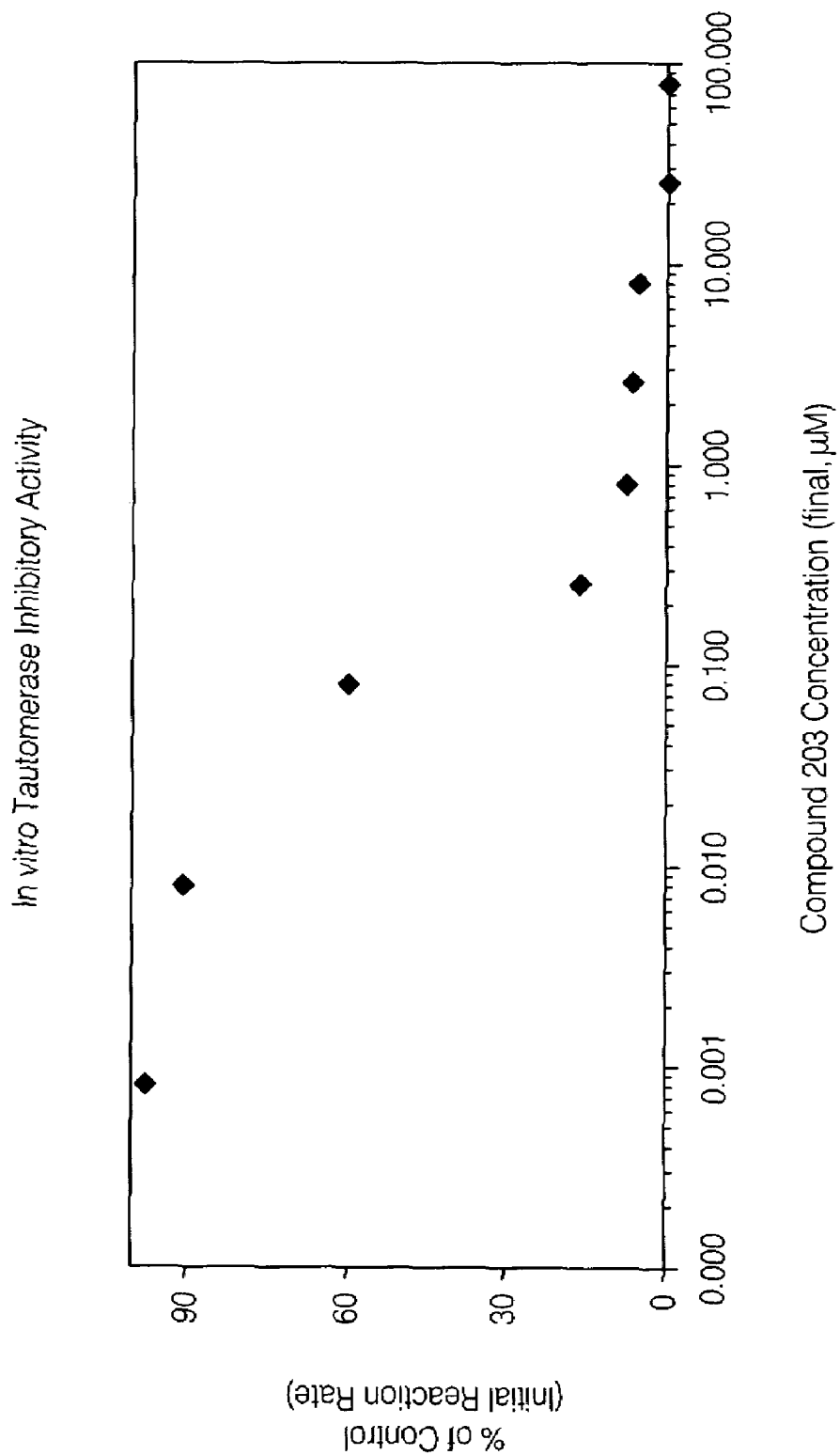
FIG. 3 provides in vitro tautomerase inhibitory activity data for Compound 203.

Compound 203 was tested for in vitro tautomerase inhibitory activity at several different concentrations. Compound 203 exhibits MIF inhibitory activity, as shown in FIG. 3.

Example 9

The MIF inhibitory activity of Compound 200 and Compound 203 were compared. Both exhibit satisfactory MIF inhibitory activity.

TABLE 2

| | In Vitro Activity of MIF Inhibitors (Inhibitory Concentration (IC) of 50 μm) | | | |
|---|---|---|---|---|
| Compound | Tautomerase Assay | Average IC 50 | THP-1/MIF Inhibition | Average IC 50 |
| 200 | 0.30 (0.23-0.4) | 0.32 | 0.023 (0.001-0.52) | 0.15 (0.13-0.17) |
| 200 | 0.34 (0.12-0.9) | — | 0.15 (0.13-0.17) | — |
| 200 | — | — | 0.15 (0.13-0.17) | — |
| 203 | 0.098 (0.071-0.134) | 0.098 | — | — |

The preferred embodiments have been described in connection with specific embodiments thereof. It will be understood that it is capable of further modification, and this application is intended to cover any variations, uses, or adaptations of the invention following, in general, the principles of the invention and including such departures from the present disclosure as come within known or customary practices in the art to which the invention pertains and as may be applied to the essential features hereinbefore set forth, and as fall within the scope of the invention and any equivalents thereof. Each reference cited herein, including but not limited to patents and technical literature, is hereby incorporated by reference in its entirety.

What is claimed is:

1. A method for treating endotoxic shock, the method comprising administering a drug for treating endotoxic shock that has no measurable macrophage migration inhibitory factor inhibiting activity, and further administering a macrophage migration inhibitory factor inhibiting compound having a structure selected from the group consisting of:

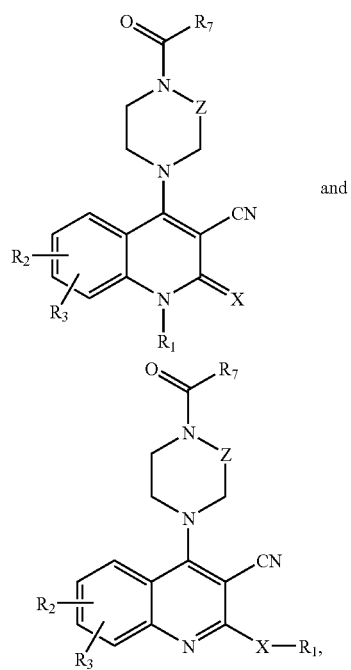

or a stereoisomer or a pharmaceutically acceptable salt thereof, wherein:

X is oxygen or sulfur;

Z is —$CH_2$— or —C(=O)—;

$R_1$ is selected from the group consisting of $C_{1-10}$ alkyl and aryl $C_{1-10}$ alkyl, wherein $R_1$ is unsubstituted or substituted with at least one substituent selected from the group consisting of halogen, alkoxy, alkylamino, dialkylamino, and keto;

$R_2$ and $R_3$ are independently selected from the group consisting of halogen, hydrogen, and $C_{1-6}$ alkyl; and $R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylarnino.

2. The method of claim 1, wherein the drug is a corticosteroid selected from the group consisting of cortisone, hydrocortisone, methyiprednisolone, prednisone, prednisolone, betamethesone, beclomethasone dipropionate, budesonide, dexamethasone sodium phosphate, flunisolide, fluticasone propionate, triameinolone acetonide, betamethasone, fluocinolone, fluocinonide, betamethasone dipropionate, betamethasone valerate, desonide, desoximetasone, fluocinolone, triameinolone, triameinolone acetonide, clobetasol propionate, and dexamethasone.

3. The method of claim 1, wherein the drug is an anti-infective agent selected from the group consisting of anthelmintics, aminoclyco sides, antifungal antibiotics, cephalosporins, beta-lactam antibiotics, chloramphenicol, macrolides, penicillins, tetracyclines, bacitracin, clindamycin, colistimethate sodium, polymyxin b sulfate, vancomycin, antivirals including acyclovir, amantadine, didanosine, efavirenz, fosearnet, ganciclovir, indinavir, lamivudine, nelfinavir, ritonavir, saquinavir, stavudine, valacyclovir, valganciclovir, zidovudine, quinolones, sulfonamides, sulfones, furazolidone, metronidazole, pentamidine, sulfanilamidum crystallinum, gatifloxacin, and sulfamethoxazole/trimethoprim.

4. The method of claim 1, wherein the drug is an anti-infective agent selected from the group consisting of mebendazole, gentamicin, neomycin, tobramycin, amphotericin b, fluconazole, griseoflulvin, itraconazole, ketoconazole, nystatin, micatin, tolnaftate, cefaclor, cefazolin, cefotaxime, ceftazidime, ceftriaxone, cefuroxime, cephalexin, cefotetan, meropenem, azithromycin, clarithromycin, erythromycin, penicillin G sodium salt, amoxicillin, ampicillin, dicloxacillin, nafcillin, piperacillin, ticarcillin, doxycycline, minocycline, tetracycline, ciprofloxacin, levofloxacin, sulfadiazine, sulfisoxazole, and dapsone.

5. The method of claim 1, wherein the compound has a structure:

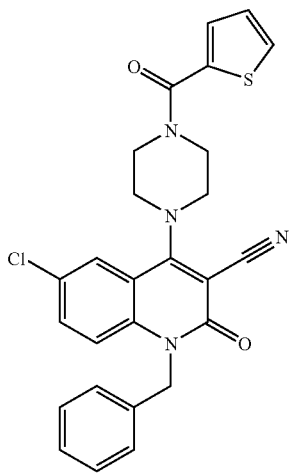

or a stereoisomer or a pharmaceutically acceptable salt thereof.

6. A method for treating arthritis, the method comprising administering a drug for treating arthritis that has no measurable macrophage migration inhibitory factor inhibiting activity, and further administering a macrophage migration inhibitory factor inhibiting compound having a structure selected from the group consisting of:

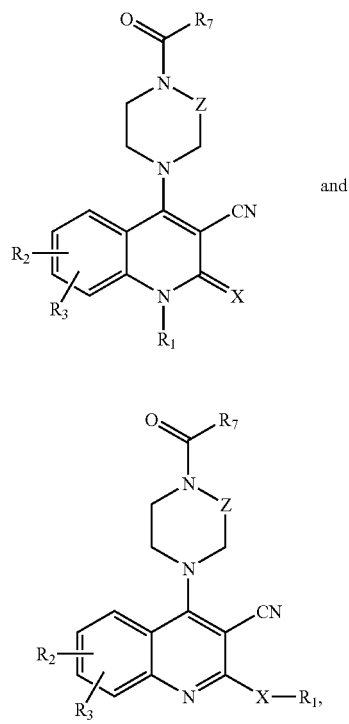

or a stereoisomer or a pharmaceutically acceptable salt thereof, wherein:

X is oxygen or sulfur;

Z is —$CH_2$— or —C(=O)—;

$R_1$ is selected from the group consisting of $C_{1-10}$ alkyl and aryl $C_{1-10}$ alkyl, wherein $R_1$ is unsubstituted or substituted with at least one substituent selected from the group consisting of halogen, alkoxy, alkylamino, dialkylamino, and keto;

$R_2$ and $R_3$ are independently selected from the group consisting of halogen, hydrogen, and $C_{1-6}$ alkyl; and $R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofitranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylamino.

7. The method of claim 6, wherein the arthritis is rheumatoid arthritis.

8. The method of claim 6, wherein the arthritis is osteoarthritis.

9. The method of claim 6, wherein the drug is a nonsteroidal anti-inflammatory drug selected from the group consisting of aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin.

10. The method of claim 6, wherein the drug is a corticosteroid selected from the group consisting of cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, dexamethasone, and rofecoxib.

11. The method of claim 6, wherein the compound has a structure:

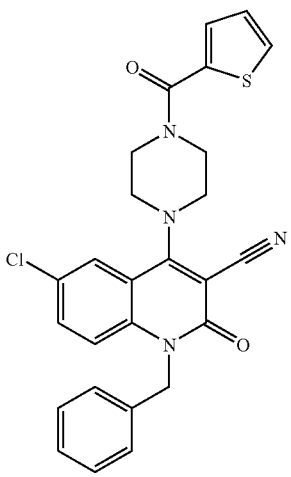

or a stereoisomer or a pharmaceutically acceptable salt thereof.

12. A method for treating diabetes; the method comprising administering a drug for treating diabetes that has no measurable macrophage migration inhibitory factor inhibiting activity, and further administering a macrophage migration inhibitory factor inhibiting compound having a structure selected from the group consisting of:

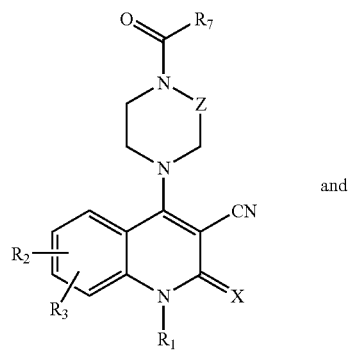

and

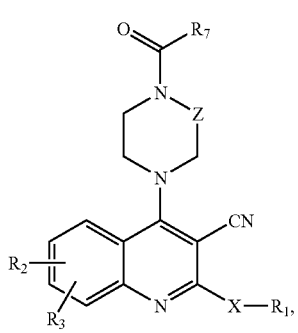

or a stereoisomer or a pharmaceutically acceptable salt thereof, wherein:

X is oxygen or sulfur;

Z is —$CH_2$— or —C(=O)—;

$R_1$ is selected from the group consisting of $C_{1-10}$ alkyl and aryl $C_{1-10}$ alkyl, wherein $R_1$ is unsubstituted or substituted with at least one substituent selected from the group consisting of halogen, alkoxy, alkylamino, dialkylamino, and keto;

$R_2$ and $R_3$ are independently selected from the group consisting of halogen, hydrogen, and $C_{1-6}$ alkyl; and $R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylamino.

13. The method of claim 12, wherein the compound has a structure:

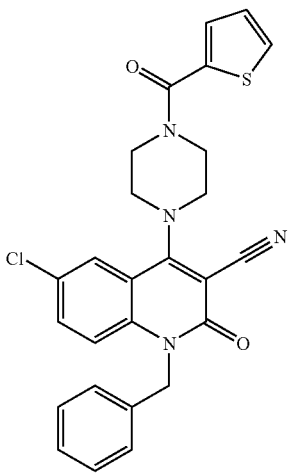

or a stereoisomer or a pharmaceutically acceptable salt thereof.

14. A method for treating psoriasis, the method comprising administering a drug for treating psoriasis that has no measurable macrophage migration inhibitory factor inhibiting activity, and further administering a macrophage migration inhibitory factor inhibiting compound having a structure selected from the group consisting of:

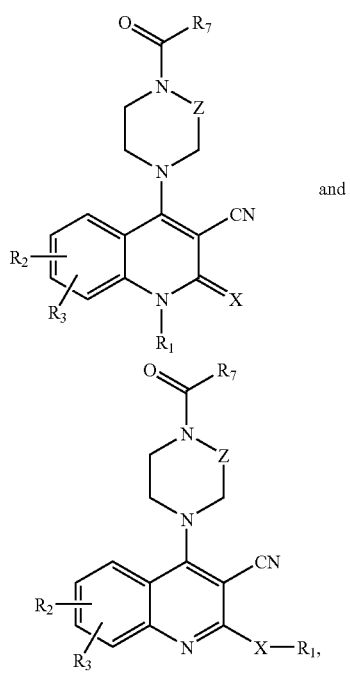

and

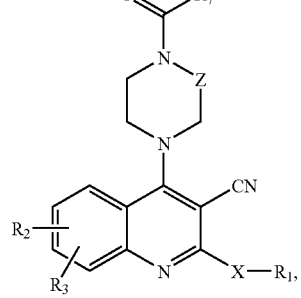

or a stereoisomer or a pharmaceutically acceptable salt thereof, wherein:

X is oxygen or sulfur;

Z is —$CH_2$— or —C(=O)—;

$R_1$ is selected from the group consisting of $C_{1-10}$ alkyl and aryl $C_{1-10}$ alkyl, wherein $R_1$ is unsubstituwd or substituted with at least one substituent selected from the group consisting of halogen, alkoxy, alkylamino, dialkylamino, and keto;

$R_2$ and $R_3$ are independently selected from the group consisting of halogen, hydrogen, and $C_{1-6}$ alkyl; and $R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylamino.

15. The method of claim 14, wherein the compound has a structure:

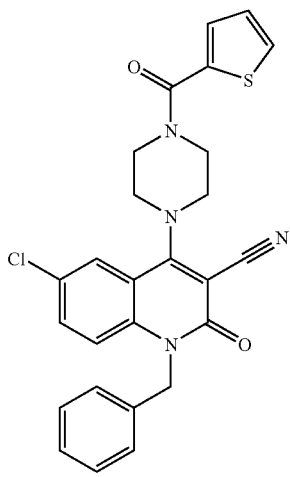

or a stereoisomer or a pharmaceutically acceptable salt thereof.

16. A method for treating glomerulonephritis, the method comprising administering a drug for treating glomerulonephritis that has no measurable macrophage migration inhibitory factor inhibiting activity, and further administering a macrophage migration inhibitory factor inhibiting compound having a structure selected from the group consisting of:

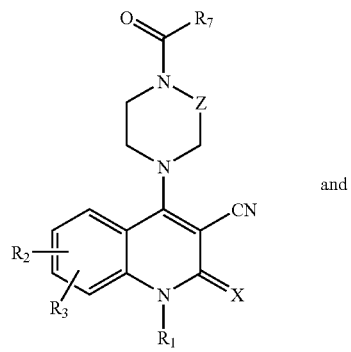

and

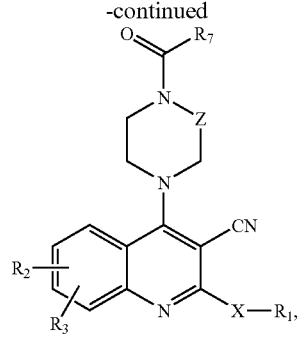

or a stereoisomer or a pharmaceutically acceptable salt thereof, wherein:

X is oxygen or sulfur;

Z is —$CH_2$— or —C(=O)—;

$R_1$ is selected from the group consisting of $C_{1-10}$ alkyl and aryl $C_{1-10}$ alkyl, wherein $R_1$ is unsubstituted or substituted with at least one substituent selected from the group consisting of halogen, alkoxy, alkylamino, dialkylamino, and keto;

$R_2$ and $R_3$ are independently selected from the group consisting of halogen, hydrogen, and $C_{1-6}$ alkyl; and $R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylamino.

17. The method of claim 16, wherein the compound has a structure:

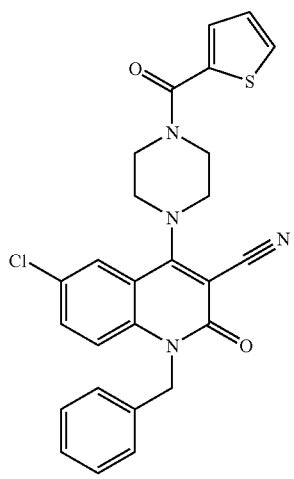

or a stereoisomer or a pharmaceutically acceptable salt thereof.

* * * * *